(12) United States Patent (10) Patent No.: US 8,067,412 B2
Winssinger et al. (45) Date of Patent: Nov. 29, 2011

(54) MACROCYCLIC COMPOUNDS USEFUL AS INHIBITORS OF KINASES AND HSP90

(75) Inventors: Nicolas Winssinger, Strasbourg (FR); Sofia Barluenga, Strasbourg (FR); Martin Karplus, Cambridge, MA (US)

(73) Assignees: Universite de Strasbourg, Strasbourg (FR); Le Centre National de la Recherche Scientifique, Paris Cedex (FR)

( * ) Notice: Subject to any disclaimer, the term of this patent is extended or adjusted under 35 U.S.C. 154(b) by 766 days.

(21) Appl. No.: 11/891,652

(22) Filed: Aug. 10, 2007

(65) Prior Publication Data
US 2008/0146545 A1 Jun. 19, 2008

Related U.S. Application Data

(60) Provisional application No. 60/837,154, filed on Aug. 11, 2006, provisional application No. 60/858,731, filed on Nov. 13, 2006.

(51) Int. Cl.
*A61K 31/5355* (2006.01)
*C07D 295/104* (2006.01)
(52) U.S. Cl. .................................. 514/233.5; 544/109
(58) Field of Classification Search ................ 514/233.5; 544/109
See application file for complete search history.

(56) References Cited

U.S. PATENT DOCUMENTS

| | | | |
|---|---|---|---|
| 3,196,019 A | 7/1965 | Andrews et al. |
| 3,239,346 A | 3/1966 | Hodge et al. |
| 3,373,038 A | 3/1968 | Hodge et al. |
| 3,453,367 A | 7/1969 | Bachman |
| 3,551,454 A | 12/1970 | Taub et al. |
| 3,586,701 A | 6/1971 | Urry et al. |
| 3,591,608 A | 7/1971 | Immer et al. |
| 3,621,036 A | 11/1971 | Jensen et al. |
| 3,631,179 A | 12/1971 | Urry et al. |
| 3,687,982 A | 8/1972 | Young |
| 3,704,249 A | 11/1972 | Czaja et al. |
| 3,751,431 A | 8/1973 | Wehrmeister et al. |
| 3,758,511 A | 9/1973 | Wendler et al. |
| 3,764,614 A | 10/1973 | Wehrmeister et al. |
| 3,810,918 A | 5/1974 | Urry et al. |
| 3,836,544 A | 9/1974 | Urry et al. |
| 3,852,307 A | 12/1974 | Urry et al. |
| 3,860,616 A | 1/1975 | Hoffsommer et al. |
| 3,887,583 A | 6/1975 | Wehrmeister et al. |
| 3,901,921 A | 8/1975 | Urry et al. |
| 3,901,922 A | 8/1975 | Urry et al. |
| 3,903,115 A | 9/1975 | Urry et al. |
| 3,925,423 A | 12/1975 | Hodge |
| 3,954,805 A | 5/1976 | Kavka |
| 3,957,825 A | 5/1976 | Urry et al. |
| 3,965,275 A | 6/1976 | Hidy et al. |
| 4,035,504 A | 7/1977 | Hidy et al. |
| 4,042,602 A | 8/1977 | Robertson et al. |
| 4,088,658 A | 5/1978 | Robertson |
| 4,228,079 A | 10/1980 | Calton |
| 4,670,249 A | 6/1987 | Ivy et al. |
| 4,751,239 A | 6/1988 | Hodge |
| 4,778,821 A | 10/1988 | Clough et al. |
| 4,849,447 A | 7/1989 | Jacobs |
| 4,902,711 A | 2/1990 | Hodge |
| 5,597,846 A | 1/1997 | Sugimura et al. |
| 5,650,430 A | 7/1997 | Sugimura et al. |
| 5,674,892 A | 10/1997 | Giese et al. |
| 5,710,174 A | 1/1998 | West et al. |
| 5,728,726 A | 3/1998 | Giese et al. |
| 5,731,343 A | 3/1998 | Feng et al. |
| 5,795,910 A | 8/1998 | Giese et al. |
| 5,977,165 A | 11/1999 | Agatsuma et al. |
| 6,239,168 B1 | 5/2001 | Ino et al. |
| 6,316,491 B1 | 11/2001 | Ino et al. |
| 6,617,348 B1 | 9/2003 | De Brabander et al. |
| 6,635,662 B2 | 10/2003 | Ino et al. |
| 6,635,671 B1 | 10/2003 | Kastelic et al. |
| 6,946,456 B2 | 9/2005 | Rosen et al. |
| 7,115,651 B2 | 10/2006 | Danishefsky et al. |
| 2001/0027208 A1 | 10/2001 | Ino et al. |
| 2003/0211469 A1 | 11/2003 | Waxman |
| 2003/0216369 A1 | 11/2003 | Rosen et al. |
| 2004/0053990 A1 | 3/2004 | Ino et al. |
| 2004/0063778 A1 | 4/2004 | De Brabander et al. |
| 2004/0102458 A1 | 5/2004 | Chiosis et al. |
| 2005/0074457 A1 | 4/2005 | Kamal et al. |
| 2005/0256183 A1 | 11/2005 | Kasibhatla et al. |

(Continued)

FOREIGN PATENT DOCUMENTS
EP 0248916 A1 12/1987
(Continued)

OTHER PUBLICATIONS

Author: Agatsuma et al. Title: Halohydrin and Oxime Derivatives of Radicicol: Synthesis and Antitumor Activities Publ: *Bioorganic & Medicinal Chemistry* vol. Iss: 10 pp. 3445-3454 Date: Jan. 1, 2002.
Author: Barluenga et al. Title: Solution- and Solid-Phase Synthesis of Radicicol (Monorden) and Pochonin C Publ: *European Journal of Chemistry* vol. Iss: 11 pp. 935-952 Date: Jan. 1, 2005.
Author: Barluenga et al. Title: Modular Asymmetric Synthesis of Pochonin C Publ: *Angewandte Chemie International* vol. Iss: 43 pp. 3467-3470 Date: Jan. 1, 2004.
Author: Hellwig et al. Title: Pochonins A-F, New Antiviral and Antiparasitic Resorcylic Acid Lactones from *Pochonia chlamydosporia* var. *catenulata* Publ: *Journal of Natural Products* vol. Iss: 66 pp. 829-837 Date: Jan. 1, 2003.

(Continued)

*Primary Examiner* — Taofiq A Solola
(74) *Attorney, Agent, or Firm* — Cooley LLP

(57) ABSTRACT

Disclosed are macrocyclic compounds of formulae I-V, which are analogs of the pochonin resorcylic acid lactones, and processes for the preparation of the compounds. The compounds disclosed are useful as inhibitors of kinases and Heat Shock Protein 90 (HSP 90). Also disclosed are pharmaceutical compositions comprising an effective kinase-inhibiting amount or an effective HSP90-inhibiting amount of the compounds and methods for the treatment of disorders that are mediated by kinases and HSP90.

36 Claims, 1 Drawing Sheet

U.S. PATENT DOCUMENTS

| | | |
|---|---|---|
| 2005/0261263 A1 | 11/2005 | Santi et al. |
| 2005/0267087 A1 | 12/2005 | Poulaki et al. |
| 2006/0073151 A1 | 4/2006 | Jay et al. |
| 2006/0247448 A1 | 11/2006 | Boivin et al. |
| 2006/0251574 A1 | 11/2006 | Kamal et al. |
| 2006/0269618 A1 | 11/2006 | Matrajt et al. |
| 2007/0004674 A1 | 1/2007 | Shiotsu et al. |
| 2007/0010432 A1 | 1/2007 | Workman et al. |

FOREIGN PATENT DOCUMENTS

| | | |
|---|---|---|
| EP | 1498104 A1 | 1/2005 |
| JP | 6-279279 A | 10/1994 |
| JP | 6-298764 A | 10/1994 |
| JP | 9-202781 A | 8/1997 |
| JP | 10-265381 A | 10/1998 |
| JP | 2000-236894 A | 9/2000 |
| JP | 2003-113183 A | 4/2003 |
| WO | WO 99/55689 A1 | 11/1999 |
| WO | WO 02/16362 A2 | 2/2002 |
| WO | WO 02/48135 A1 | 6/2002 |
| WO | WO 03/076424 A1 | 9/2003 |
| WO | WO 2005/061481 A1 | 7/2005 |
| WO | WO 2006/036941 A2 | 4/2006 |

OTHER PUBLICATIONS

Author: Immer et al. Title: Syntheses of Medium-Ring Benzoic Acid Lactones Publ: *The Journal of Organic Chemistry* vol. Iss: 33 (6) pp. 2457-2462 Date: Jun. 1, 1968.

Author: Moulin et al. Title: Diversity-Oriented Synthesis of Pochonins and Biological Evaluation against a Panel of Kinases Publ: *European Journal of Chemistry* vol. Iss: 12 pp. 8819-8834 Date: Jan. 1, 2006.

Author: Moulin et al. Title: Concise Synthesis of Pochonin A, An HSP90 Inhibitor Publ: *Organic Letters* vol. Iss: 7 (25) pp. 5637-5639 Date: Sep. 18, 2005.

Author: Moulin et al. Title: Design, Synthesis, and Biological Evaluation of HSP90 Inhibitors Based on Conformational Analysis of Radicichol and Its Analogues Publ: *Journal of the American Chemical Society* vol. Iss: 127 pp. 6999-7004 Date: Jan. 1, 2005.

Supplementary European Search Report based on European Patent Application No. EP 07811232, mailed on Sep. 23, 2010.

Crystal Structure of oxime a2-1 (E-isomer)

Crystal Structure of oxime a2-13 (E-isomer)

MACROCYCLIC COMPOUNDS USEFUL AS INHIBITORS OF KINASES AND HSP90

CROSS REFERENCE TO RELATED APPLICATIONS

This application claims priority to U.S. Provisional Patent Application Nos. 60/837,154, filed Aug. 11, 2006, and 60/858,731, filed Nov. 13, 2006.

FIELD OF THE INVENTION

The present invention is directed to novel derivatives, analogs and intermediates of the natural products radicicol and the pochonins, and to their syntheses. The present invention is further directed to use of these compounds as inhibitors of kinases and of the enzyme family known as heat shock protein 90 (HSP90).

BACKGROUND OF THE INVENTION

In the mid-1950's, it was discovered that phosphorylation can reversibly alter the function of enzymes by means of protein kinases which catalyze phosphorylation, or by protein phosphatases which are involved in the dephosphorylation step. These reactions play an essential role in regulating many cellular processes, especially signaling transduction pathways. In the late 1970's, the Rous sarcoma virus (v-Src)'s transforming factor was discovered to be a protein kinase, and also tumor-promoting phorbol esters were found to be potent activators of protein kinase C, revealing the first known connection between disease and abnormal protein phosphorylation. Since then transduction mechanistic defects have been found to cause numerous oncogenic processes and to have a role in diabetes, inflammatory disorders, and cardiovascular diseases. (T. Hunter, *Cell*, 100:113-127 (2000); P. Cohen, *Nat. Rev. Drug Discov.*, 1:309 (2002)). Thus selective kinase and phosphatase inhibitors have emerged as important drug targets, and inhibition of kinase phosphorylation activity is one of the most promising strategies for chemotherapy. Three kinase inhibitor drugs are already approved: Gleevec, which inhibits Abl, and Iressa and Tarceva, which both inhibit EGFR.

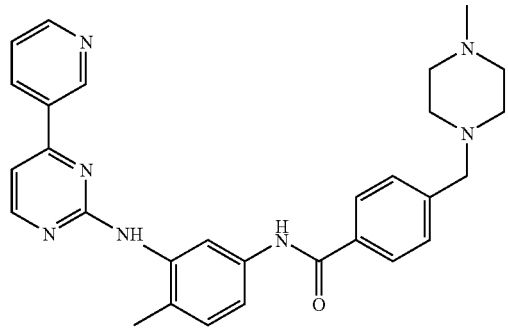

Gleevec (imatinib) - STI 571
inhibitor of the Abelson kinase;
approved for chronic myelogenous leukemia

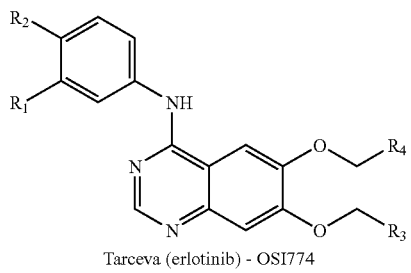

Tarceva (erlotinib) - OSI774
R1 = CCH; R2 = H; R3 = R4 = CH$_2$OCH$_3$

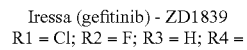

Iressa (gefitinib) - ZD1839
R1 = Cl; R2 = F; R3 = H; R4 =

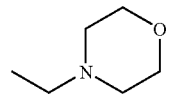

inhibitors of epidermal growth factor receptor (EGFR); approved for lung cancer

Modulation of protein activity by kinase-mediated phosphorylation or phosphatase-mediated dephosphorylation of a serine, threonine or tyrosine residue is at the center of most signal transduction mechanisms. (T. Hunter, *Cell*, 100:113 (2000)). Small molecule inhibitors such as 6-dimethylaminopurine and staurosporine were instrumental in elucidating the importance of such phosphorylation mechanisms and shed light on the biological function of kinases. Kinases bind to ATP with a K$_m$ of 0.1-10 µM, and transfer the γ-phosphate group selectively to a specific residue of a given protein. The core domain of kinases, consisting of the ATP-binding site with the residues involved in phosphotransfer reaction, are highly conserved throughout the kinome. (G. Manning et al., *Science*, 298:1912 (2002)). This led to the speculation that inhibitors targeting this highly conserved ATP-binding pocket would not only have to compete with ATP present at high concentration (mM) but would necessarily lack selectivity. The discovery that modified purines such as (R)-roscovitine were potent and fairly selective inhibitors (L. Meijer and E. Raymond, *Acc. Chem. Res.*, 36:417 (2003)) refuted that notion and inspired the synthesis of combinatorial libraries around the purine scaffold (Y. T. Chang et al., *Chem. Biol.*, 6:361 (1999); S. Ding et al., *J. Am. Chem. Soc.*, 124:1594 (2002)), yielding important leads. (N. S. Gray et al., *Science*, 281:533 (1998); M. Knockaert et al., *Chem. Biol.*, 7:411 (2000)).

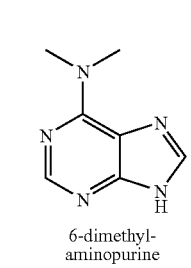

6-dimethyl-
aminopurine

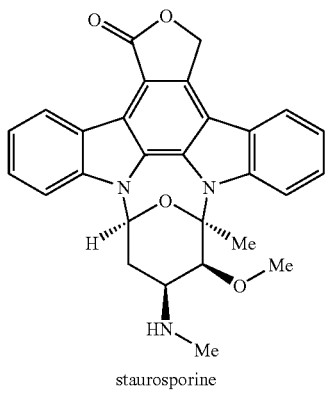

staurosporine

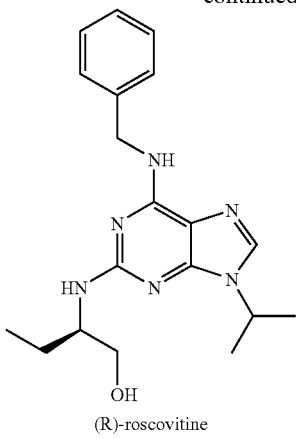

(R)-roscovitine

Macrocyclic resorcylic acid lactones have also been investigated in this respect. The archetypes of this class of compounds are radicicol and the related pochonins, which are a structurally related group of secondary metabolites isolated from cultures of the clavicipitaceous hyphomycete *Pochonia* genus, such as *Pochonia chlamydosporia* var. *catenulate* strain P0297. See, e.g., V. Hellwig et al., *J. Natural Prod.*, 66(6):829-837 (2003). Halohydrin and oxime derivatives of radicicol were prepared and evaluated for their v-src tyrosine kinase inhibitory, antiproliferative, and antitumor in vitro activity (T. Agatsuma et al., *Bioorg. & Med. Chem.*, 10(11): 3445-3454 (2002).

Like kinases, heat shock proteins (HSPs) interact with ATP and are important targets for controlling disease, however they have a different mechanistic effect. Immediately after exposure to a stress such as heat, hypoxia or acidosis, cells in most tissues rapidly escalate production rate of the HSPs. It is now believed that heat HSPs are molecular chaperones, i.e., they prevent improper associations and assist in the correct folding of other cellular proteins collectively termed clients and substrates. HSP's are also found in association with tumors and other pathophysiological conditions. In fact, chaperone proteins facilitate the survival of tumor cells in stressful environments by facilitating tolerance of alterations inside the cell. HSPs are ubiquitous, highly conserved among the species, and usually classified by molecular weight to the following major families: HSP100, HSP90, HSP70, HSP60 and small HSPs. These families have structural and functional differences, but work cooperatively at different stages of protein folding. HSP90 has attracted particular attention due to its association with many types of signaling molecules such as v-Src and Raf that play a critical role in malignant transformation and metastasis development. Thus, HSP90 inhibitors are desired for designing chemotherapies, and also for elucidating the interplay in complex signaling networks.

Heat Shock Protein 90's (Hsp90s) are ubiquitous chaperone proteins that maintain the proper conformation of many "client" proteins (see Kamal et. al. *Trends Mol. Med.* 2004, 10, 283-290; Dymock et. al. *Expert Opin. Ther. Patents* 2004, 14, 837-847; Isaacs et. al. *Cancer Cell*, 2003, 3, 213; Maloney et. al. *Expert Opin. Biol. Ther.* 2002, 2, 3-24 and Richter et. al. *J. Cell. Physiol.* 2001, 188, 281-290), and are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner, *TIBS*, 1999, 24, 136-141; Stepanova et. al., *Genes Dev.* 1996, 10, 1491-502; Dai et. al., *J. Biol. Chem.* 1996, 271, 22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see for example Caplan, *Trends in Cell Biol.*, 1999, 9, 262-268). Inhibition of Hsp90 causes these client proteins to adopt aberrant conformations, and these abnormally folded proteins are rapidly eliminated by the cell via ubiquitinylation and proteasome degradation. Interestingly, the list of Hsp90 client proteins includes a series of notorious oncogenes. Four of them are clinically validated cancer targets: HER-2/neu (Herceptin® (trastuzumab)), Bcr-Abl (Gleevec® (imatinib mesylate)), the estrogen receptor (tamoxifen), and the androgen receptor (Casodex® (bicalutamide)), while the others play a critical role in the development of cancer. Some of the most sensitive Hsp90 clients are involved in growth signalling (Raf-1, Akt, cdk4, Src, Bcr-Abl, etc). In contrast, few tumor suppressor genes, if any, seem to be clients of Hsp90 (for lists of client proteins see Pratt et. al. *Exp. Biol. Med.* 2003, 228, 111-133; Workman et. al. *Cancer Lett.* 2004, 206, 149-157 and Zhang et. al. *J. Mol. Med.* 2004, 82, 488-499.), and consequently, inhibition of Hsp90 has an overall anti-proliferative effect. In addition, some client proteins are involved in other fundamental processes of tumorigenesis, namely apoptosis evasion (e.g. Apaf-1, RIP, Akt), immortality (e.g. hTert), angiogenesis (e.g. VEGFR, Flt-3, FAK, HIF-1), and metastasis (c-Met).

However medicinal HSP inhibitors must be selective because HSPs also play a constructive role. Under nonstressed conditions, HSP90 is one of the most abundant proteins present in the eukaryotic cells, representing between 1-2% of the total cellular protein content and increasing only about two-fold when cells are stressed. Upon binding with the native client HSP90 is an essential housekeeper, e.g., for folding of nascent polypeptides, transporting proteins across membranes, and for normal protein turnover. Moreover, HSP90 plays a crucial role in post-translational regulation of signaling molecules, leading to their activation. HSP90 rarely functions alone but instead works with chaperone HSP70, with co-chaperones (HSP40, CDC37/p50, AHAL, p23), and with accessory proteins.

The numerous client proteins of HSP90 play a crucial role in growth control, cell survival and development processes, and those clients are known to include receptor tyrosine kinases, serine/threonine kinases, steroid hormone receptors, transcription factors and telomerase. Oncogenic mutants of clients are also clients themselves but have higher requirements for HSP90 function, for instance the mutant v-SRC tyrosine kinase requires more protein-folding capability from HSP90's cooperative assembly of proteins (Y. Xu et al., *Proc. Natl. Acad. Sci. U.S.A.*, 96:109 (1999); H. Oppermann et al., Ibid., 78:1067 (1981); L. Whitesell et al., Ibid., 91:8324 (1994). Likewise, mutations of the tumor-suppressor protein p53 lead to the most common molecular genetic defect found in human cancers, and most p53 mutants show extended interactions with HSP90 (probably because of aberrant conformations), preventing their usual ubiquitylation and subsequent degradation by the proteasome (M. V. Blagoskionny et al., Ibid., 93:8379 (1996). However despite its ubiquitous participation, HSP90's clients are mostly pro-growth signaling proteins, and its chaperoning function is subverted during oncogenesis, leading to development of malignant transformation and the maintenance of transformed phenotypes.

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating ischemia, and agents useful in treating neurodegenerative diseases and in promoting nerve regeneration (see M. Waza et al, *Nature Med.* 11:1088 (2005); Rosen et al., WO 02/09696; PCT/US01/23640; Degranco et al., WO 99/51223; PCT/US99/07242; Gold, U.S. Pat. No. 6,210,974 B1). There are reports in the literature that fibrogenetic disorders including but not limited to scleroderma, polymyositis, systemic lupus, rheumatoid arthritis, liver cirrhosis, keloid formation, interstitial nephritis, and pulmonary fibrosis may be treatable. (Strehlow, WO 02/02123; PCT/US01/20578).

Ansamycins and other HSP90 inhibitors thus hold great promise for the treatment and/or prevention of many types of disorders. However, many of the natural-product derived Hsp90 inhibitors exhibit pharmaceutical deficiencies; their relative insolubility makes them difficult to formulate and administer, and they are not easily synthesized and currently must, at least in part, be generated through fermentation. Further, the dose limiting toxicity of ansamyins is hepatic. For example, the semi-synthetic inhibitor 17-allylamino,17-desmethoxy-geldanamycin (17-AAG), currently in phase II clinical trials, is expensive to manufacture, difficult to formulate (the NCI clinical protocol consists of injecting a DMSO solution of 17-AAG) and at present administered only parenterally. Although the 17-dimethylaminoethylamino analog (17-DMAG) is more soluble, it exhibits all of the side effects of 17-AAG as well as gastrointestinal hemorrhaging in preclinical toxicity studies (Glaze et. al. *Proc. Am. Assoc. Cancer. Res.* 2003, 44, 162-162 and Eiseman et. al. *Cancer Chemother. Pharmacol.* 2005, 55, 21-32). Radicicol (RC), another natural product Hsp90 inhibitor, is poorly water-soluble and is inactive in tumor xenograft models. Semi-synthetic oxime derivatives of radicicol provide better solubility and substantially improved the pharmacological profile in murine models, but are still limited to intravenous administration (Ikuina et. al. *J. Med. Chem.* 2003, 46, 2534-2541. Furthermore, radicicol and its oximes contain an oxirane ring which has been viewed as a liability for stability and toxicity, prompting the synthesis of cyclopoparadicicol: Yang et. al. *J. Am. Chem. Soc.* 2004, 126, 7881 and 2003, 125, 9602-9603.) Despite the potential of ansamycins, alternative HSP90 inhibitors are therefore needed.

Fully synthetic, orally active inhibitors of Hsp90 have been sought in order to provide more flexible dosing schedule options, and to possibly avoid the side-effects of the natural product inhibitors. Chiosis et al. described the design and synthesis of purine analogs that mimic geldanamycin and other ansamycins in their ability to bind the ATP binding pocket of, and thus inhibit, HSP90. See International Patent Application PCT/US01/46303 (WO 02/36075; Chemistry & Biology 8:289-299 (2001). The specific compounds that Chiosis et al. described included a trimethoxybenzyl entity substituted at positions 3, 4, and 5. Using gel-binding assays, these were shown to bind HSP90 approximately 20-fold less avidly than 17-AAG.

More recently, other novel non-natural product Hsp90 inhibitors have been reported (e.g. PU3 and CCT018159; see Chiosis et. al. *Bioorg. Med. Chem. Lett.* 2002, 10, 3555-3564; Vilenchik et. al. *Chem. Biol.* 2004, 11, 787-797; Chiosis et. al. WO 0236075, 2002; Drysdale et. al. WO 03/055860 A1, 2003; Wright et. al. *Chem. Biol.* 2004, 11, 775-785; Dymock et. al. *Bioorg. Med. Chem. Lett.* 2004, 14, 325-328; Dymock et. al. *J. Med. Chem.* 2005, 48, 4212-4215. Structure of Hsp90 in complex with PU3 pdb code 1UY6, and with PU24FCl: pdb code 1UYF and Clevenger et. al. *Org. Lett.* 2004, 6, 4459-4462). The structures of these inhibitors were designed using the crystal structures of Hsp90 in complex with ATP, geldanamycin, or radicicol. The 8-benzyladenines such as PU3 were designed to adopt the same C-shaped conformation as geldanamycin (Chiosis et. al. *Current Cancer Drug Targets,* 2003, 3, 371-376) with the adenine ring pointing to the adenine-binding site (hinge region), and the trimethoxybenzene ring emulating the H-bond accepting nature of the quinone ring of geldanamycin. (The benzene ring of PU3 was not designed to have exactly the same orientation as the quinone ring of geldanamycin. Rather, the trimethoxybenzene moiety was designed to point in the same general direction and form a hydrogen bond with Lys112, an amino acid which forms a hydrogen bond with the quinone ring of geldanamycin.) The recently obtained crystal structure of Hsp90 in complex with PU3 confirmed that the purine ring occupies the position normally occupied by ADP/ATP, but the benzene ring points in a direction opposite to the predicted one, to form a r-stacking interaction with Phe138. Nevertheless, PU3 inhibits Hsp90 (HER-2 degradation assay, HER-2 $IC_{50}$=40 µM) and afforded a valuable starting point for further optimization. Structure-activity studies based on PU3 led to the more active PU24FCl (HER-2 $IC_{50}$=1.7 µM) which was subsequently also co-crystallized with Hsp90. When PU24FCl was formulated in DMSO/EtOH/phosphate-buffered saline 1:1:1 and administered intraperitoneally to mice bearing MCF-7 xenograft tumors, it induced at 100-300 mg/kg down-regulation of HER-2 and Raf-1, a pharmacodynamic response consistent with Hsp90 inhibition, and at 200 mg/kg it significantly repressed tumor growth. Very high doses (500-1000 mg/kg) of PU24FCl were required to observe a similar pharmacodynamic response upon oral administration, and no 8-benzyladenine has been reported to inhibit tumor growth by the oral route. In our hands, PU24FCl proved to be too insoluble to be effectively formulated and delivered orally. So far, despite extensive SAR studies to improve potency and pharmaceutics properties, Hsp90 inhibitors have not demonstrated activity in animal models of human cancer (xenografts) when administered orally.

The discovery of the 8-benzyladenines led to the design of 8-sulfanyladenines (Kasibhatla et. al. WO 3037860, 2003 and Llauger et. al. *J. Med. Chem.* 2005, 48, 2892-2905), exemplified by 8-(2-iodo-5-methoxy-phenylsulfanyl)-9-pent-4-ynyl-9H-purin-6-ylamine, which exhibited excellent potency in several cell-based assays, but was poorly soluble in water and did not have sufficient oral bioavailability in clinically acceptable formulations.

When HSP90 is inhibited, its clients are degraded, i.e., the unfolded protein is ubiquitinated, followed by proteasome-mediated hydrolysis. Most of the inhibitors reported so far bind to the N-terminal domain (vide infra), but some are reported to interact with the C-terminal domain; HSP90 has binding sites for ATP in both locations. The function of HSP90's C terminus is not entirely clear, but compounds interacting in this domain clearly impair HSP90 function and have anti-cancer effects. Some resorcylic acid lactones have been found to inhibit HSP90, thus natural products radicicol and geldanamycin (P. Delmotte and J. Delmotte-Plaquee, *Nature (London),* 171:344 (1953); and C. DeBoer et al., *J Antibiot (Tokyo),* 23:442 (1970), respectively) were shown to suppress the transformed phenotype of cell expressing activated Src (H. J. Kwon et al., *Cancer Research,* 52:6926 (1992); Y. Uehara et al., *Virology,* 164:294 (1988)). Related compounds such as herbimycin have been reported to have similar effects (S. Omura et al., *J Antibiot (Tokyo),* 32:255 (1979).

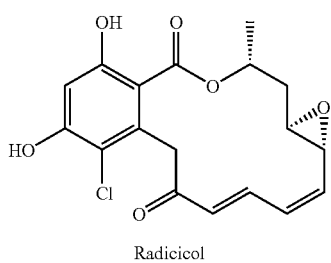
Radicicol

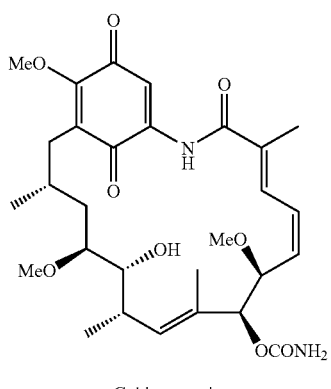
Geldanamycin

Other resorcylic acid lactones (RALs) studied in this respect include 17-allylamino-17-demethoxygeldanamycin (17AAG) (D. B. Solit et al., *Clin. Cancer Res.*, 8:986 (2002); L. R. Kelland et al., *J. Natl. Cancer Inst.*, 91:1940 (1999)); 17DMAG (J. L. Eiseman et al., *Cancer Chemother. Pharmacol.*, 55:21-32 (2005)); IPI-504 (J. Ge et al., *J. Med. Chem.*, 49:4606 (2006); oxime derivatives such as KF25706 (S. Soga, et al., *Cancer Res.*, 59:2931 (1999)) and KF55823 (S. Soga et al., *Cancer Chemotherapy and Pharmacology*, 48:435 (2001)); and Danishefsky et al.'s cycloproparadicicol (A. Rivkin et al., Ibid., 44:2838 (2005)). Structurally related variants include chimeric inhibitors having radicicol's carboxyresorcinol and the geldanamycin's benzoquinone (R. C. Clevenger and B. S. Blagg, *Org. Lett.*, 6:4459 (2004); G. Shen and B. S. Blagg, Ibid., 7:2157 (2004); G. Shen et al., *J. Org. Chem.*, 71:7618 (2006)).

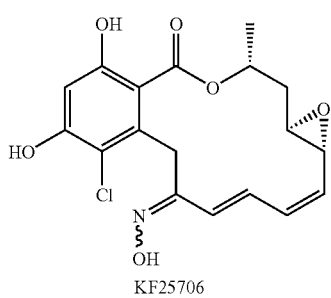
KF25706

1-26

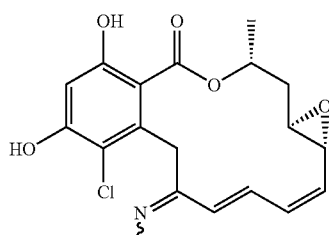
KF55823

1-27

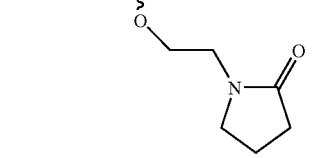
Cycloproparadicicol 1-28

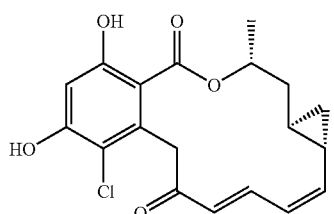

Radicicol-Based HSP90 Inhibitors 1-29

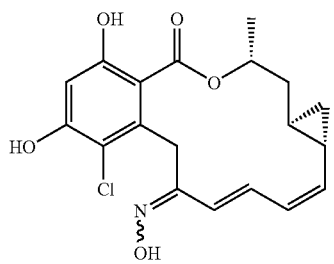
Radamide

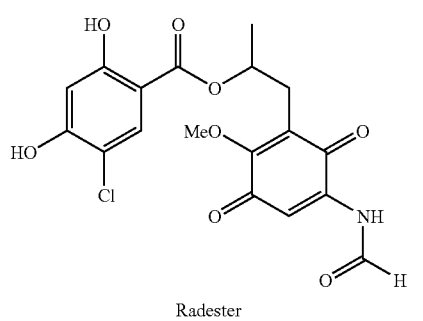
Radester

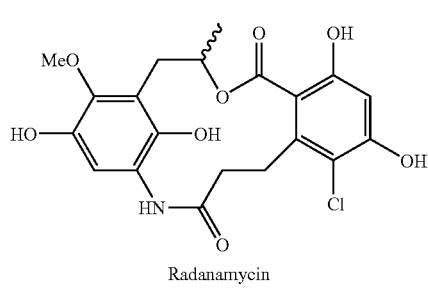
Radanamycin

Chimeric Inhibitors of HSP90

Purines such as PU3 have been studied in an effort to design small molecules that fit HSP90's ATP binding site (G. Chiosis, et al., *Chem Biol* 8, 289-299 (2001); G. Chiosis, et al., *Bioorg. Med. Chem.*, 10:3555 (2002); L. LLauger, et al., *J. Med. Chem.* 48:2892 (2005); H. He et al., Ibid., 49:381 (2006); M. A. Biamonte et al., Ibid., 49:817 (2006)).

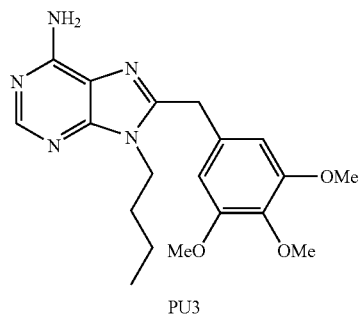
PU3

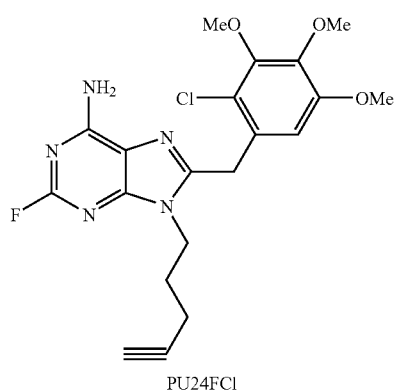
PU24FCl

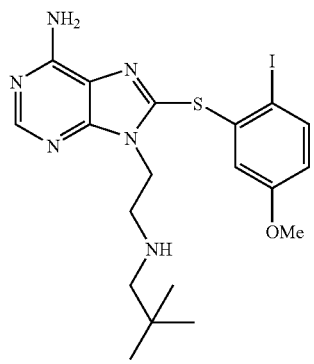

Purine-Based Designed HSP90 Inhibitors

Pyrazoles (1-35) (M. G. Rowlands et al., *Anal. Biochem.*, 327:176 (2004); B. W. Dymock et al., *J. Med. Chem.*, 48:4212 (2005)) and benzothiazolothio-purines (1-36) (L. Zhang. et al., *J. Med. Chem.*, 49:5352 (2006) have been reported recently also as small-molecule inhibitors of these enzymes.

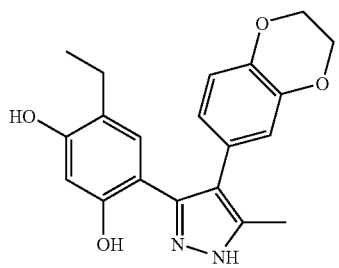

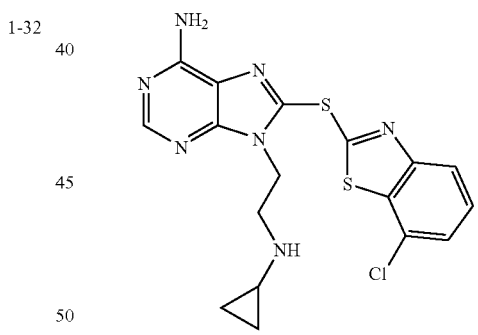

Other Classes of HSP90 Inhibitors

Radicicol has been of particular interest. A 14-member macrolide, and also known as monorden, radicicol is a potent, highly competitive and highly selective ligand for HSP90's ATP-binding pocket. HSP90 is an ATPase rather than a kinase, and its ATP-binding pocket has a Bergerat fold (A. Bergerat et al., *Nature*, 386:414 (1997); R. Dutta and M. Inouye, *Trends Biochem. Sci.*, 25:24 (2000)) which is distinct from kinases' ATP-binding pockets. (S. M. Roe et al., *J. Med. Chem.*, 42:260 (1999)). Considerable interest in radicicol's medicinal applications have followed the initial findings. (See U.S. Pat. No. 6,946,456; and U.S. Patent Application Publication Nos. 2003-0211469, 2004-0102458, 2005-

0074457, 2005-0261263, 2005-0267087, 2006-0073151, 2006-0251574, 2006-0269618, 2007-0004674, and 2007-0010432).

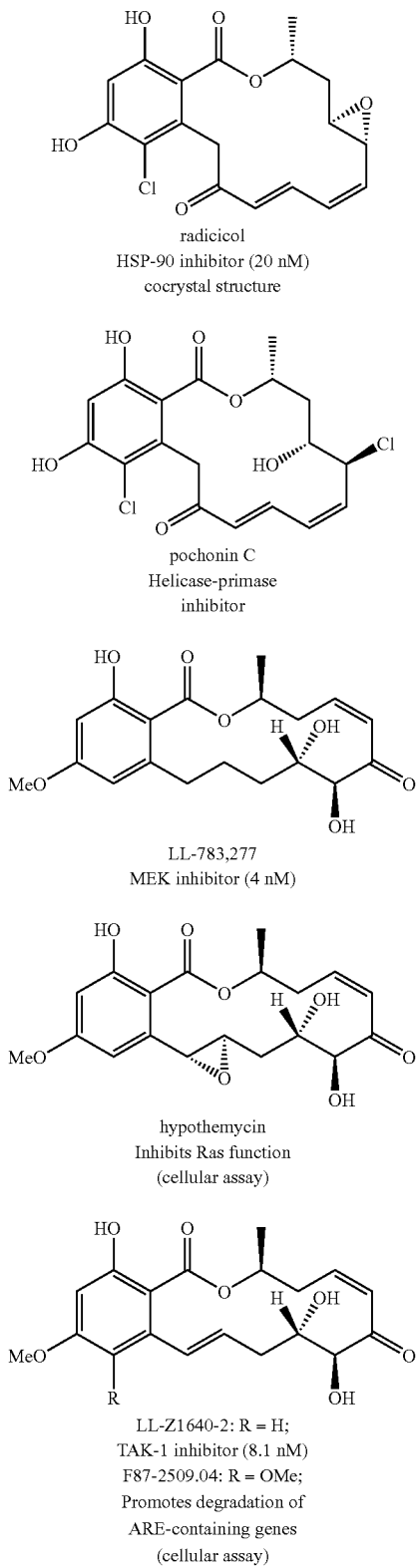

radicicol
HSP-90 inhibitor (20 nM)
cocrystal structure pochonin C
Helicase-primase
inhibitor LL-783,277
MEK inhibitor (4 nM)

hypothemycin
Inhibits Ras function
(cellular assay)

LL-Z1640-2: R = H;
TAK-1 inhibitor (8.1 nM)
F87-2509.04: R = OMe;
Promotes degradation of
ARE-containing genes
(cellular assay)

-continued

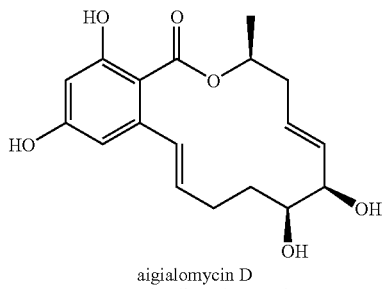

aigialomycin D
CDK1/cyclin B (5.7 mM)
CDK5/p25 (5.8 mM)

Strikingly, some resorcylic macrolides that are close analogs of radicicol are known to inhibit kinases but not HSP90. Indeed, LL-Z1640-2 was found to be a potent and selective inhibitor of TAK1 kinase for which radicicol and other resorcylides were not active. (J. Ninomiya-Tsuji et al., *J. Biol. Chem.*, 278:18485 (2003); P. Rawlins et al., *Int. J. Immunopharma.*, 21:799 (1999); K. Takehana et al., *Biochem. Biophys. Res. Comm.*, 257:19 (1999); A. Zhao et al., *J. Antibiotics*, 52:1086 (1999)). Closely related LL-783,227, where one of the olefins has been reduced, is a potent inhibitor of MEK kinase. (A. Zhao et al., *J. Antibiotics* 52:1086 (1999)). Compound F87-2509.04 was found to induce degradation of mRNA containing AU-rich elements (ARE) (T. Kastelic et al., *Cytokine*, 8:751 (1996)) and hypothemycin was found to inhibit the Ras-mediated cellular signaling. (H. Tanaka et al., *Jap. J. Cancer Res.*, 90:1139 (1999)). We have recently shown that aigialomycin D is a CDK inhibitor. (S. Barluenga et al., *Angew. Chem., Int. Ed.*, 46(24):3951 (2006)).

Other close analogs of radicicol do inhibit HSP90. Pochonin D is a potent inhibitor of HSP90. (E. Moulin et al., *J. Am. Chem. Soc.*, 127(19):6999 (2005)). And pochonin A has been reported to be a 90 nM inhibitor of HSP90. Pochonin C was found to be an inhibitor of herpes' helicase-primase, which is an ATPase rather than a kinase. (V. Hellwig et al., *J. Nat. Prod.*, 66:829 (2003)). Although radicicol and pochonin C are structurally very similar, they have very different conformations in solution, and different biological activities. (S. Barluenga et al., *Chem. Eur. J.*, 11:4935 (2005). Thus it appears the "floppiness" of the macrocyclic may play an essential role in inhibitory differences among resorcylic acid macrolides, and in any case makes those effects difficult to predict by theoretical methods.

Some resorcylic acid macrolides had been known as kinase or phosphatase inhibitors (U.S. Pat. Nos. 5,674,892; 5,728, 726; 5,731,343; and 5,795,910), or to inhibit other enzymes (U.S. Pat. No. 5,710,174 inhibiting FXIIIa catalysis of fibrin cross-linking). Resorcylic acid macrolides were also employed for other medical indications (U.S. Pat. Nos. 3,453, 367; 3,965,275; 4,035,504; 4,670,249; 4,778,821; 4,902,711; and 6,635,671).

Radicicol and the pochonins are natural products; intermediates for synthesizing some of their analogues of them may be obtained by fermentation, however relying only upon those natural products or their fermentation derivatives severely limits the range of compounds. Thus a number of novel resorcylic acid macrolides have been synthesized. Many of these are zearalane and related compounds in which the macrocyclic ring contains no carbon-carbon double bond other than between carbons of the phenyl ring. (U.S. Pat. Nos. 3,373,038; 3,586,701; 3,621,036; 3,631,179; 3,687,982; 3,704,249; 3,751,431; 3,764,614; 3,810,918; 3,836,544;

3,852,307; 3,860,616; 3,901,921; 3,901,922; 3,903,115; 3,957,825; 4,042,602; 4,751,239; 4,849,447; and 2005-0256183). Syntheses have also been reported for resorcylic acid macrolides characterized by one double bond between ring carbons outside the phenyl ring. (U.S. Pat. Nos. 3,196,019; 3,551,454; 3,758,511; 3,887,583; 3,925,423; 3,954,805; and 4,088,658). Most of those are 14-member macrocycles, but syntheses have also been reported for the 12-member macrocycle analogs. (U.S. Pat. Nos. 5,710,174; 6,617,348; and 2004-0063778. and PCT publication no. WO 02/48135)

Syntheses have also been reported for radicicol-related compounds having two non-aromatic double bonds and either a halide or a 1,2-oxo group (i.e., an epoxide) on the macrocyclic ring. (U.S. Pat. Nos. 4,228,079; 5,597,846; 5,650,430; 5,977,165; 7,115,651; and Japanese patent document nos. JP 6-279279A, JP 6-298764A, JP 9-202781A, JP 10-265381A2; and JP 2000-236984). Syntheses of oximes of radicicol-related compounds are disclosed in U.S. Pat. Nos. 5,977,165; 6,239,168; 6,316,491; 6,635,662; 2001-0027208; 2004-0053990; Japanese patent document no. JP 2003-113183A2; and PCT publication no. WO 99/55689 Synthesis of cyclopropa-analogs of radicicol is disclosed in U.S. Pat. No. 7,115,651 and PCT Publication No. WO 05/061481. Syntheses of some other resorcylic acid macrolide analogs are disclosed in U.S. patent publication no. 2006-0247448 and in PCT publication no. WO 02/48135. Radicicol as well as Pochonins A and C have also been synthesized. (S. Barluenga et al., *Angew. Chemie*, 43(26):3467-3470 (2004); S. Barluenga et al., *Chemistry—A European Journal*, 11(17): 4935-4952 (Aug. 19, 2005); E. Moulin et al., et al., *Organic Letters*, 7(25):5637-5639 (Dec. 8, 2005).

Despite the progress described above, chemical biologists continue to suffer from a limited ability to knock out specific kinase activity in order to deconvolute the role of specific kinases within complex signaling networks. Small molecules that can permeate cells have promise for solving this problem. And it has become increasingly apparent that the biological function of kinases is often regulated by their conformation, which is in turn dictated by their phosphorylation level and by intra- and inter-molecular associations. Small molecule inhibitors also have the potential to discriminate between different conformations of a given kinase, thus small molecules offer a means to dissect the respective functions of those conformation. Unfortunately the portfolio of known kinase inhibitors cannot yet support the full range of work to be done in parsing the roles of the various members of the kinome. This is not a merely academic pursuit, because the rationality of drug design will continue to suffer until kinase mechanisms and their selectivity is understood.

Thus there is an ongoing need for kinase inhibitors and HSP90 inhibitors that have improved potency and selectivity. Moreover, the design and synthesis of such inhibitors and of targeted libraries of inhibitors remains challenging, thus there is an ongoing need for improved synthetic methods.

SUMMARY OF THE INVENTION

Novel analogs of the pochonin macrolides of formulae I, II, III, IV and V, tautomers thereof, pharmaceutically acceptable salts, solvates, esters or prodrugs thereof, and pharmaceutical compositions comprising the compounds for the treatment of kinase-mediated or HSP90-mediated disorders are provided. Also presented are methods for the treatment of kinase-mediated or HSP90-mediated disorders using the compounds of formulae I, II, III, IV and V. The compounds of the invention are active as kinase inhibitors and inhibitors of HSP90. In addition, improved processes for the preparation of the compounds that are amenable to automated synthesis techniques are provided.

In a first principal embodiment of the invention, a compound of formula I, a tautomer thereof, or a pharmaceutically acceptable salt, solvate, ester or prodrug thereof, is provided:

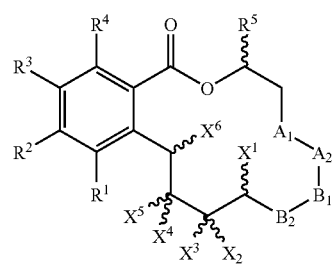

wherein:
$R^1$, $R^2$, $R^3$, $R^4$ and $R^5$ are independently hydrogen, halogen, nitro, cyano, alkyl, substituted alkyl, lower alkyl, alkenyl, alkynyl, alkylaryl, aralkyl, aryl, heteroalkyl, alkylheteroaryl, heterocyclyl, heteroaryl, OH, OR, $NH_2$, $N(R)_2$, SR, S(O)R, $S(O)_2R$, —$SO_2N(R)_2$, —N(R)$SO_2R$, —N(CO)R, —N(CO)N(R)$_2$, —N(CO)OR, —O(CO)R, —(CO)R, —(CO)OR, —(CO)N(R)$_2$, —O(CO)OR, or —O(CO)N(R)$_2$, wherein each R can be the same or different;

$A_1$ and $A_2$ together are —$CH_2$—$CH_2$—, —CH=CH—, —CH(OH)—CH(OH)—, —CH(OH)—CH(halogen)-, —CH(halogen)-CH(OH)—, 1,2-cyclopropadiyl, or 1,2-oxirane;

$B_1$ and $B_2$ together are —$CH_2$—$CH_2$— or $B_1$ and $B_2$ together represent a covalent bond, wherein each R can be the same or different;

$X^1$ is hydrogen, halogen, OH, OR, $NH_2$, $N(R)_2$, NH—OR, SR, S(O)R, $S(O)_2R$, —NH—O—(CH$_2$)$_n$—CO$_2$—R, —NH—O—(CH$_2$)$_n$—CON(R)$_2$; or $X_1$ together with $X_2$ or $X_3$ represents a covalent bond, wherein each R can be the same or different;

$X^4$ and $X^5$ together are =O, =S, =N—OR, =N—O—(CH$_2$)$_n$COOR, =N—O—(CH$_2$)$_n$CON(R)$_2$, =N—N(R)$_2$, =N—N—SOR or =N—N—$SO_2R$, wherein the groups —OR, —O—(CH$_2$)$_n$COOR, —O—(CH$_2$)$_n$CON(R)$_2$, —N(R)$_2$, —N—SOR or —N—$SO_2R$ bound to the nitrogen may be in Z- or E-configuration; or one of $X_4$ and $X_5$ is hydrogen and the other is OH, OR, O(CO)R, O(CO)OR, O(CO)N(R)$_2$, —(CH$_2$)$_n$C(O)OR, or —(CH$_2$)$_n$C(O)N(R)$_2$, and n is 0, 1, 2, or 3; or one of $X^4$ and $X^5$ together with $X^6$ represents a covalent bond and the other of $X^4$ and $X^5$ is OH, OR, O(CO)R, O(CO)OR, —N(R)$_2$ or O(CO)N(R)$_2$, wherein each R can be the same or different;

$X^6$ is hydrogen or $X^6$ together with one of $X^4$ and $X^5$ represents a covalent bond; and R is hydrogen, alkyl, substituted alkyl, lower alkyl, acyl, aryl, alkaryl, arylalkyl including benzyl, heteroalkyl, heteroaryl, heterocyclyl, a protecting group; or two R on the same nitrogen are taken together with the nitrogen to form a 5-8 membered heterocyclic or heteroaryl ring; and n is 0, 1, 2 or 3.

In a second embodiment of the invention, a compound of formula II, a tautomer thereof, or a pharmaceutically acceptable salt, solvate, ester or prodrug thereof, is provided:

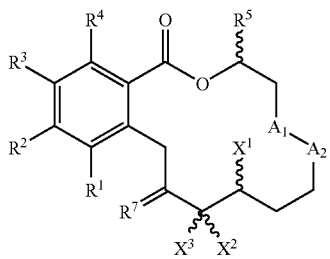

wherein, R, $R^1$, $R^2$, $R^3$, $R^4$, $R^5$, $A_1$, $A_2$, $X^1$, $X^2$ and $X^3$ are as defined for formula I above; and $R^7$ is =O, =S, =N—OR, =N—O—$(CH_2)_n$COOR, =N—O—$(CH_2)_n$CON$(R)_2$, =N—N$(R)_2$, =N—N—SOR or =N—N—$SO_2$R, wherein the groups —OR, —O—$(CH_2)_n$COOR, —O—$(CH_2)_n$CON$(R)_2$, —N$(R)_2$, —N—SOR or —N—$SO_2$R bound to the nitrogen may be in Z- or E-configuration; and wherein R can be the same or different.

In one subembodiment of formula II, $A_1$ and $A_2$ together are —CH=CH—.

In another subembodiment of formula II, $A_1$ and $A_2$ together are —CH(OH)—CH(OH)—, —CH(OH)—CH(halogen)- or —CH(halogen)-CH(OH)—.

In still another subembodiment of formula II, $A_1$ and $A_2$ together are 1,2-oxirane.

In third embodiment of the invention, a compound of formula III, a tautomer thereof, or a pharmaceutically acceptable salt, solvate, ester or prodrug thereof, is provided:

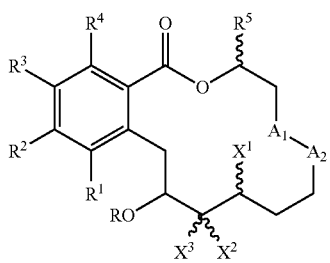

wherein, $R^1$, $R^2$, $R^3$, $R^4$, $R^5$, $A_1$, $A_2$, $X^1$, $X^2$ and $X^3$ are as defined for formula I above;

and R is hydrogen, alkyl, arylalkyl, acyl or a protecting group.

In one subembodiment of formula III, $A_1$ and $A_2$ together are —CH=CH—.

In another subembodiment of formula III, $A_1$ and $A_2$ together are —CH(OH)—CH(OH)—, —CH(OH)—CH(halogen)- or —CH(halogen)-CH(OH)—.

In still another subembodiment of formula III, $A_1$ and $A_2$ together are 1,2-oxirane.

In a fourth embodiment of the present invention, a compound of formula IV, a tautomer thereof, or a pharmaceutically acceptable salt, solvate, ester or prodrug thereof, is provided:

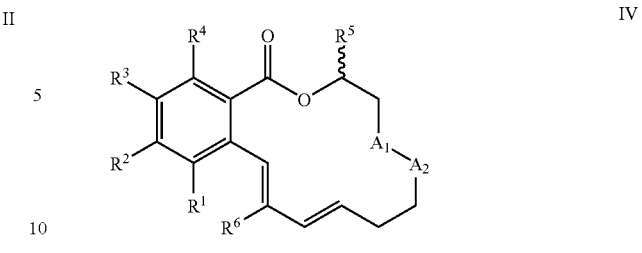

wherein, R, $R^1$, $R^2$, $R^3$, $R^4$, $R^5$, $A_1$ and $A_2$ are as defined for formula I above; and $R^6$ is hydrogen, OR, or N$(R)_2$.

In one subembodiment of formula IV, $A_1$ and $A_2$ together are —CH=CH—.

In another subembodiment of formula IV, $A_1$ and $A_2$ together are —CH(OH)—CH(OH)—, —CH(OH)—CH(halogen)- or —CH(halogen)-CH(OH)—.

In a further subembodiment of formula IV, $A_1$ and $A_2$ together are 1,2-oxirane.

In a fifth embodiment of the invention, a compound of formula V, a tautomer thereof, or a pharmaceutically acceptable salt, solvate, ester or prodrug thereof, is provided:

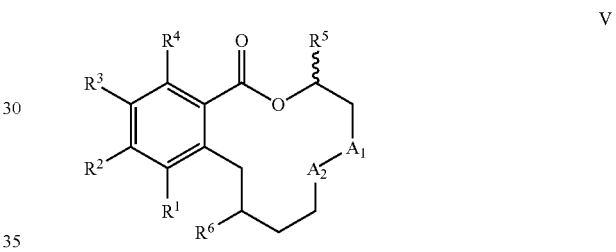

wherein, R, $R^1$, $R^2$, $R^3$, $R^4$, $R^5$, $A_1$ and $A_2$, are as defined for formula I above;

$R^6$ is $(CH_2)_n$C(O)OR, or —$(CH_2)_n$C(O)N$(R)_2$; and n is 0, 1, 2 or 3.

In one subembodiment of formula V, $A_1$ and $A_2$ together are —CH=CH—.

In another subembodiment of formula V, $A_1$ and $A_2$ together are —CH(OH)—CH(OH)—, —CH(OH)—CH(halogen)- or —CH(halogen)-CH(OH)—.

In a third subembodiment of formula V, $A_1$ and $A_2$ together are 1,2-oxirane.

In another embodiment, a pharmaceutical composition comprising an effective kinase-inhibiting amount of a compound of formula I, II, III, IV or V in combination with a pharmaceutically acceptable carrier is provided.

In another embodiment, a pharmaceutical composition comprising an effective HSP 90-inhibiting amount of a compound of formula I, II, III, IV or V in combination with a pharmaceutically acceptable carrier is provided. In some embodiments, the carrier is suitable for oral, parenteral, inhalation, topical or intradermal administration.

In still other embodiments, the pharmaceutical compositions comprising the compounds of formula I, II, III, IV or V comprises particles that are less than about 2 microns average particle size. In still other embodiments, the composition is incorporated into a biodegradable or non-biodegradable polymer.

In one embodiment, the composition comprises an additive selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

In another embodiment, the invention provides a method of treating a patient with a disease comprising administering to the patient with the disease an effective amount of a compound of formula I, II, III, IV or V, wherein the disease is an autoimmune disease, an inflammatory disease, a neurological or neurodegenerative disease, cancer, a cardiovascular disease, allergy, asthma, or a hormone-related disease.

In one embodiment, a method of treating a patient with cancer is provided comprising administering to the patient having the cancer an effective cancer-treating amount of a compound of formula I, II, III, IV or V, wherein the cancer may be a solid tumor, a blood borne tumor, breast cancer, cancer of the ovary, cancer of the cervix, prostate cancer, cancer of the testis, cancer of the urinary tract, cancer of the esophagus, cancer of the larynx, glioblastoma, stomach cancer, skin cancer, keratoacanthoma, lung cancer, epidermoid carcinoma, large cell carcinoma, small cell carcinoma, lung adenocarcinoma, bone cancer, colon cancer, adenoma, cancer of the pancreas, adenocarcinoma, thyroid cancer, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity cancer, pharynx cancer, lip cancer, tongue cancer, mouth cancer, cancer of the pharynx, cancer of the small intestine, colon-rectum cancer, cancer of the large intestine, cancer of the rectum, brain cancer and cancer of the central nervous system, or leukemia.

In another embodiment, the invention provides a method of treating a patient with a disease associated with undesirable neovascularization comprising administering to the patient with the undersirable neovascularization an effective amount of a compound of formula I, II, III, IV or V.

The disease associated with undesirable neovasculariation comprises ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, or corneal graph rejection, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, or post-laser complications.

In still another embodiment, a method of treating a patient with an inflammatory disease is provided comprising administering to the patient with the inflammatory disease an effective amount of a compound of formula I, II, III, IV or V.

The inflammatory disease may be excessive or abnormal stimulation of endothelial cells, atherosclerosis, vascular malfunctions, abnormal wound healing, inflammatory and immune disorders, Bechet's disease, gout or gouty arthritis, abnormal angiogenesis accompanying rheumatoid arthritis, skin diseases, psoriasis, diabetic retinopathy, retinopathy of prematurity, retrolental fibroplasia, macular degeneration, corneal graft rejection, neovascular glaucoma or Osler Weber syndrome.

DETAILED DESCRIPTION OF THE INVENTION

Figure 1:
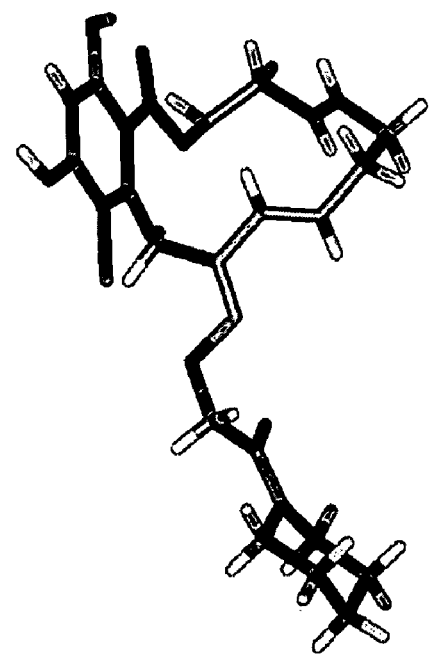
FIG. 1 shows a crystal structure of oxime a2-1 (E-isomer).

Provided are novel compounds based on the resorcylic acid lactones that are useful as inhibitors of kinases and HSP90. Also provided are compositions comprising the compounds and processes for the preparation of the compounds. Use of the compounds for the inhibition of kinases and HSP-90, and a method for the treatment of kinase-mediated or HSP90-mediated diseases comprising administering an effective kinase-inhibiting amount or an effective HSP90-inhibiting amount of a compound of formula I, II, III, IV or V to a patient with a kinase-mediated or HSP90-mediated disease, are provided.

Compounds

In a first embodiment of the invention, a compound of formula I, a tautomer thereof, or a pharmaceutically acceptable salt, solvate, ester or prodrug thereof, is provided:

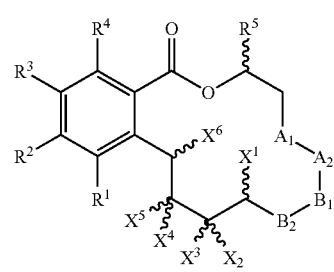

wherein:
$R^1$, $R^2$, $R^3$, $R^4$ and $R^5$ are independently hydrogen, halogen, nitro, cyano, alkyl, substituted alkyl, lower alkyl, alkenyl, alkynyl, alkylaryl, aralkyl, aryl, heteroalkyl, alkylheteroaryl, heterocyclyl, heteroaryl, OH, OR, $NH_2$, $N(R)_2$, SR, S(O)R, $S(O)_2R$, —$SO_2N(R)_2$, —N(R)$SO_2R$, —N(CO)R, —N(CO)N(R)$_2$, —N(CO)OR, —O(CO)R, —(CO)R, —(CO)OR, —(CO)N(R)$_2$, —O(CO)OR, or —O(CO)N(R)$_2$, wherein each R can be the same or different;

$A_1$ and $A_2$ together are —$CH_2$—$CH_2$—, —CH=CH—, —CH(OH)—CH(OH)—, —CH(OH)—CH(halogen)-, —CH(halogen)-CH(OH)—, 1,2-cyclopropadiyl, or 1,2-oxirane;

$B_1$ and $B_2$ together are —$CH_2$—$CH_2$— or $B_1$ and $B_2$ together represent a covalent bond, wherein each R can be the same or different;

$X^1$ is hydrogen, halogen, OH, OR, $NH_2$, $N(R)_2$, NH—OR, SR, S(O)R, $S(O)_2R$, —NH—O—$(CH_2)_n$—$CO_2$—R, —NH—O—$(CH_2)_n$—CON(R)$_2$; or $X_1$ together with $X_2$ or $X_3$ represents a covalent bond, wherein each R can be the same or different;

$X^2$ and $X^3$ are both hydrogen, or one of $X_2$ and $X_3$ is hydrogen and the other together with $X_1$ represents a covalent bond;

$X^4$ and $X^5$ together are =O, =S, =N—OR, =N—O—$(CH_2)_n$COOR, =N—O—$(CH_2)_n$CON$(R)_2$, =N—N$(R)_2$, =N—N—SOR or =N—N—$SO_2$R, wherein the groups —OR, —O—$(CH_2)_n$COOR, —O—$(CH_2)_n$CON$(R)_2$, —N$(R)_2$, —N—SOR or —N—$SO_2$R bound to the nitrogen may be in Z- or E-configuration; or one of $X_4$ and $X_5$ is hydrogen and the other is OH, OR, O(CO)R, O(CO)OR, O(CO)N$(R)_2$, —$(CH_2)_n$C(O)OR, or —$(CH_2)_n$C(O)N$(R)_2$, and n is 0, 1, 2, or 3; or one of $X_4$ and $X_5$ together with $X^6$ represents a covalent bond and the other of $X^4$ and $X^5$ is OH, OR, O(CO)R, O(CO)OR, —N$(R)_2$ or O(CO)N$(R)_2$, wherein each R can be the same or different;

$X^6$ is hydrogen or $X^6$ together with one of $X^4$ and $X^5$ represents a covalent bond; and R is hydrogen, alkyl, lower alkyl, acyl, aryl, alkaryl, arylalkyl including benzyl, heteroalkyl, heteroaryl, heterocyclyl, a protecting group; or two R on the same nitrogen are taken together with the nitrogen to form a 5-8 membered heterocyclic or heteroaryl ring; and n is 0, 1, 2 or 3.

In one subembodiment of compound I, $R^1$ is H, halogen or heterocyclyl.

In another subembodiment of compound I, $R^5$ is hydrogen, alkyl, lower alkyl, aryl, heteroaryl or arylalkyl.

In another subembodiment of compound I, $A_1$ and $A_2$ together are —$CH_2$—$CH_2$— or —CH=CH—.

In still another subembodiment of compound I, $A_1$ and $A_2$ together are —CH(OH)—CH(OH)—, —CH(OH)—CH(halogen)- or CH(halogen)-CH(OH)—.

In a further subembodiment of compound I, $A_1$ and $A_2$ together are 1,2-cyclopropadiyl, or 1,2-oxirane.

In second embodiment of the invention, a compound of formula II, a tautomer thereof, or a pharmaceutically acceptable salt, solvate, ester or prodrug thereof, is provided:

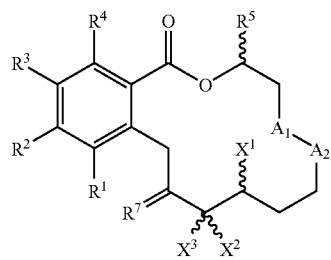

II wherein:

R, $R^1$, $R^2$, $R^3$, $R^4$, $R^5$, $X^1$, $X^2$, $X^3$, $A_1$ and $A_2$ are as defined above for formula I; and $R^7$ is =O, =S, =N—OR, =N—O—$(CH_2)_n$COOR, =N—O—$(CH_2)_n$CON$(R)_2$, =N—N$(R)_2$, =N—N—SOR or =N—N—$SO_2$R, wherein the groups —OR, —O—$(CH_2)_n$COOR, —O—$(CH_2)_n$CON$(R)_2$, —N$(R)_2$, —N—SOR or —N—$SO_2$R bound to the nitrogen may be in a Z- or E-configuration; and wherein R can be the same or different.

In one subembodiment of compound II, $R^1$ is H, halogen or heterocyclyl.

In another subembodiment of compound II, $R^5$ is hydrogen, alkyl, lower alkyl, aryl, heteroaryl or arylalkyl.

In another subembodiment of compound II, $A_1$ and $A_2$ together are —$CH_2$—$CH_2$— or —CH=CH—.

In still another subembodiment of compound II, $A_1$ and $A_2$ together are —CH(OH)—CH(OH)—, —CH(OH)—CH(halogen)- or —CH(halogen)-CH(OH)—.

In a further subembodiment of compound II, $A_1$ and $A_2$ together are 1,2-cyclopropadiyl, or 1,2-oxirane.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH—;
$X^1$ together with $X^2$ represent a covalent bond; and
$R^7$ is =O.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH—;
$X^1$ together with $X^2$ represent a covalent bond; and
$R^7$ is =N—OR, =N—O—$(CH_2)_n$COOR, =N—O—$(CH_2)_n$CON$(R)_2$, =N—N$(R)_2$, or =N—N—SOR, wherein the groups —OR, —O—$(CH_2)_n$COOR, —O—$(CH_2)_n$CON$(R)_2$, —N$(R)_2$, —N—SOR or —N—$SO_2$R bound to the nitrogen may be in Z- or E-configuration.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH— or —C(OH)—C(OH)—;
$X^1$ is hydrogen, halogen or NH—OR; and
$R^7$ is =O.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH— or —C(OH)—C(OH)—;
$X^1$ is hydrogen, halogen or NH—OR; and
$R^7$ is =N—OR, =N—O—$(CH_2)_n$COOR, =N—O—$(CH_2)_n$CON$(R)_2$, =N—N$(R)_2$ or =N—N—SOR.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH(OH)—CH(OH)—, —CH(OH)—CH(halogen)- or —CH(halogen)-CH(OH)—;
$X^1$ together with $X^2$ represent a covalent bond; and
$R^7$ is =O.

In another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH(OH)—CH(OH)—, —CH(OH)—CH(halogen)- or —CH(halogen)-CH(OH)—;
$X^1$ together with $X^2$ represent a covalent bond; and
$R^7$ is =N—OR, =N—O—$(CH_2)_n$COOR, =N—O—$(CH_2)_n$CON$(R)_2$, =N—N$(R)_2$, =N—N—SOR, =N—N—$SO_2$R.

In another subembodiment of compound II:
$R^1$ is H, Cl or heterocyclyl;
$R^2$ and $R^4$ are independently OH or OR;
$R^5$ is hydrogen, alkyl or aryl;
$A_1$ and $A_2$ together are —CH(OH)—CH(OH)—, —CH(OH)—CH(halogen)- or —CH(halogen)-CH(OH)—;
$X^1$ is hydrogen, halogen, NH—O—$(CH_2)_n$COOR, or NH—O—$(CH_2)_n$CON$(R)_2$ NH—OR; and $R^7$ is =O, =N—OR, =N—O—$(CH_2)_n$COOR, =N—O—$(CH_2)_n$CON$(R)_2$, =N—N$(R)_2$, =N—N—SOR, or =N—N—$SO_2$R.

In still another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are 1,2-oxirane or 1,2-cyclopropadiyl;
$X^1$ together with $X^2$ represent a covalent bond; and
$R^7$ is =O, =N—OR, =N—O—$(CH_2)_n$COOR, =N—O—$(CH_2)_n$CON$(R)_2$, =N—N$(R)_2$, =N—N—SOR, or =N—N—$SO_2$R.

In still another subembodiment of compound II:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are 1,2-oxirane or 1,2-cyclopropadiyl;
$X^1$ is hydrogen, halogen, NH—OR, NH—O—$(CH_2)_n$COOR, or NH—O—$(CH_2)_n$CON$(R)_2$; and
$R^7$ is =O, =N—OR, =N—O—$(CH_2)_n$COOR, =N—O—$(CH_2)_n$CON$(R)_2$, =N—N$(R)_2$, =N—N—SOR, or =N—N—$SO_2$R.

In still a further subembodiment of compound II:
$R^1$ is H or Cl;
$R^2$ and $R^4$ are independently OH or OR;
$R^5$ is hydrogen;
$A_1$ and $A_2$ together —CH=CH—;
$X^1$ together with $X^2$ represent a covalent bond; and
$R^7$ is =O.

In still a further subembodiment of compound II:
$R^1$ is H or Cl;
$R^2$ and $R^4$ are independently OH or OR;
$R^5$ is hydrogen;
$A_1$ and $A_2$ together —CH=CH—;
$X^1$ together with $X^2$ represent a covalent bond; and
$R^7$ is =N—OR, =N—O—$(CH_2)_n$COOR, or =N—O—$(CH_2)_n$CON$(R)_2$.

In yet another subembodiment of compound II:
$R^1$ is H or Cl;
$R^2$ and $R^4$ are independently OH or OR;
$R^5$ is hydrogen;
$A_1$ and $A_2$ together are 1,2-oxirane;
$X^1$ together with $X^2$ represent a covalent bond; and
$R^7$ is =O.

In yet another subembodiment of compound II:
$R^1$ is H or Cl;
$R^2$ and $R^4$ are independently OH or OR;
$R^5$ is hydrogen;
$A_1$ and $A_2$ together are 1,2-oxirane;
$X^1$ together with $X^2$ represent a covalent bond; and
$R^7$ is =N—OR, =N—O—$(CH_2)_n$COOR, =N—O—$(CH_2)_n$CON$(R)_2$.

In a further subembodiment of formula II:
$R^1$ is H or Cl;
$R^2$ and $R^4$ are OH;
$R^5$ is hydrogen;
$A_1$ and $A_2$ together are —CH=CH—;
$X^1$ together with $X^2$ represent a covalent bond;
$R^7$ is =N—O—$CH_2$COOR or =N—O—$CH_2$CON$(R)_2$; and
R is H, lower alkyl, or two R together on the same nitrogen form a six-membered heterocyclyl ring.

In another embodiment of the invention, a compound of formula III, a tautomer thereof, or a pharmaceutically acceptable salt, solvate, ester or prodrug thereof is provided:

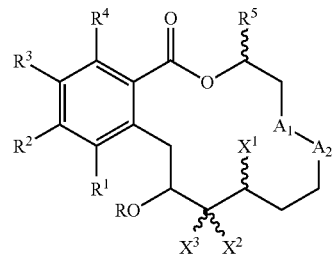

wherein:
R, $R^1$, $R^2$, $R^3$, $R^4$, $R^5$, $X^1$, $X^2$, $X^3$, $A_1$ and $A_2$ are as defined above for formula I.

In one subembodiment of compound III, $X^1$ and $X^2$ together form a double bond.

In one subembodiment of compound III, R is hydrogen or acyl.

In one subembodiment of compound III, $R^1$ is H, halogen or heterocyclyl.

In another subembodiment of compound III, $R_5$ is hydrogen, alkyl, lower alkyl, aryl, heteroaryl or arylalkyl.

In another subembodiment of compound III, $A_1$ and $A_2$ together are —$CH_2$—$CH_2$— or —CH=CH—.

In still another subembodiment of compound III, $A_1$ and $A_2$ together are —CH(OH)—CH(OH)—, —CH(OH)—CH(halogen)- or CH(halogen)-CH(OH)—.

In a further subembodiment of compound III, $A_1$ and $A_2$ together are 1,2-cyclopropadiyl, or 1,2-oxirane.

In one subembodiment of formula III, a compound is provided wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH—; and
$X^1$ together with $X^2$ represent a covalent bond.

In another subembodiment of formula III, a compound is provided wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH—; and
$X^1$ is hydrogen, halogen, NH—OR, NH—O—$(CH_2)_n$COOR, or NH—O—$(CH_2)_n$CON$(R)_2$.

In yet another subembodiment of formula III, a compound is provided wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH(OH)—CH(OH)—, —CH(OH)—CH(halogen)- or —CH(halogen)-CH(OH)—; and
$X^1$ together with $X^2$ represent a covalent bond.

In a further subembodiment of formula III, a compound is provided wherein:
$R^1$ is H, Cl or heterocyclyl;
$R^2$ and $R^4$ are independently OH or OR;
$R^5$ is hydrogen, alkyl or aryl;
$A_1$ and $A_2$ together are —CH(OH)—CH(OH)—, —CH(OH)—CH(halogen)- or —CH(halogen)-CH(OH)—; and
$X^1$ is hydrogen, halogen, NH—OR, NH—O—$(CH_2)_n$COOR, or NH—O—$(CH_2)_n$CON$(R)_2$.

In still another subembodiment of formula III, a compound is provided wherein:

$R^1$ is H, Cl or heterocyclyl;
$R^2$ and $R^4$ are independently OH or OR;
$R^5$ is hydrogen, alkyl or aryl;
$A_1$ and $A_2$ together are 1,2-oxirane or 1,2-cyclopropadiyl; and
$X^1$ together with $X^2$ represent a covalent bond.

In another subembodiment of formula III, a compound is provided wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are 1,2-oxirane or 1,2-cyclopropadiyl; and
$X^1$ is hydrogen, halogen, NH—OR, NH—O—$(CH_2)_n$COOR, NH—O—$(CH_2)_n$CON(R)$_2$.

In a fourth principal embodiment of the invention, a compound of formula IV, a tautomer thereof, or a pharmaceutically acceptable salt, solvate, ester or prodrug thereof, is provided:

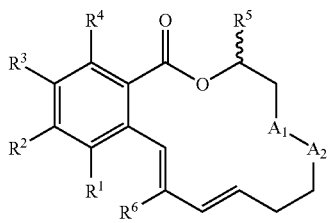

IV wherein:
R, $R^1$, $R^2$, $R^3$, $R^4$, $R^5$, $A_1$ and $A_2$ are as defined above for formula I; and
$R^6$ is hydrogen, OR or N(R)$_2$; and wherein R can be the same or different.

In one subembodiment of compound IV, $R^6$ is hydrogen.
In another subembodiment of compound IV, $R^6$ is O-acetyl or O-trifluoroacetyl.
In another subembodiment of compound IV, $R^1$ is H, halogen or heterocyclyl.
In still another subembodiment of compound IV, $R^5$ is hydrogen, alkyl, lower alkyl, aryl, heteroaryl or arylalkyl.
In another subembodiment of compound IV, $A_1$ and $A_2$ together are —CH$_2$—CH$_2$— or —CH=CH—.
In still another subembodiment of compound IV, $A_1$ and $A_2$ together are —CH(OH)—CH(OH)—, —CH(OH)—CH(halogen)- or —CH(halogen)-CH(OH)—.
In a further subembodiment of compound IV, $A_1$ and $A_2$ together are 1,2-cyclopropadiyl, or 1,2-oxirane.
In one subembodiment of formula IV, a compound is provided wherein:
$R^1$ is H, Cl or heterocyclyl;
$R^2$ and $R^4$ are independently OH or OR;
$R^5$ is hydrogen, alkyl, aryl or aralkyl;
$R^6$ is hydrogen or OR; and
$A_1$ and $A_2$ together are —CH=CH—.
In another subembodiment of compound IV:
$R^1$ is H, Cl or heterocyclyl;
$R^2$ and $R^4$ are independently OH or OR;
$R^5$ is hydrogen, alkyl, aryl or aralkyl;
$R^6$ is hydrogen or OR; and
$A_1$ and $A_2$ together are —CH(OH)—CH(OH)—, —CH(OH)—CH(halogen)- or —CH(halogen)-CH(OH)—.
In still another subembodiment of formula IV, a compound is provided wherein:

$R^1$ is H, Cl or heterocyclyl;
$R^2$ and $R^4$ are independently OH or OR;
$R^5$ is $R^5$ is hydrogen, alkyl, aryl or aralkyl;
$R^6$ is hydrogen or OR; and
$A_1$ and $A_2$ together are 1,2-oxirane or 1,2-cyclopropadiyl.

In a fifth principal embodiment of the invention, a compound of formula V, a tautomer thereof, or a pharmaceutically acceptable salt, solvate, ester or prodrug thereof, is provided:

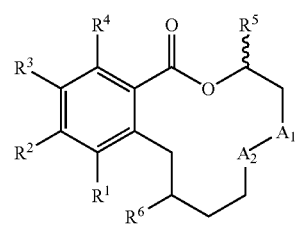

V wherein R, $R^1$, $R^2$, $R^4$, $R^3$, $R^5$, $A_1$ and $A_2$ are as defined above for formula I; and
$R^6$ is $(CH_2)_n$C(O)OR, —$(CH_2)_n$C(O)N(R)$_2$, or —$(CH_2)_n$C(O)N(R)—OR; where n is 0, 1, 2 or 3; and wherein each R can be the same or different.

In one subembodiment of compound V, $R^6$ is —CH$_2$C(O)N(Me)OMe.
In one subembodiment of compound V, $R^1$ is H, halogen or heterocyclyl.
In another subembodiment of compound V, $R^5$ is hydrogen, alkyl, lower alkyl, aryl, heteroaryl or arylalkyl.
In another subembodiment of compound V, $A_1$ and $A_2$ together are —CH=CH—.
In still another subembodiment of compound IV, $A_1$ and $A_2$ together are —CH(OH)—CH(OH)—, —CH(OH)—CH(halogen)- or CH(halogen)-CH(OH)—.
In a further subembodiment of compound V, $A_1$ and $A_2$ together are 1,2-cyclopropadiyl, or 1,2-oxirane.
In one subembodiment of formula V, a compound is provided wherein:
$R^1$ is H, Cl or heterocyclyl;
$R^2$ and $R^4$ are independently OH or OR;
$R^5$ is hydrogen, alkyl, aryl or aralkyl; and
$A_1$ and $A_2$ together are —CH=CH— or —CH$_2$—CH$_2$—.
In another subembodiment of formula V, a compound is provided wherein:
$R^1$ is H, Cl or heterocyclyl;
$R^2$ and $R^4$ are independently OH or OR;
$R^5$ is hydrogen, alkyl or aryl; and
$A_1$ and $A_2$ together are —CH(OH)—CH(OH)—, —CH(OH)—CH(halogen)- or —CH(halogen)-CH(OH)—.
In still another subembodiment of formula V, a compound is provided wherein:
$R^1$ is H, Cl or heterocyclyl;
$R^2$ and $R^4$ are independently OH or OR;
$R^5$ is hydrogen, alkyl, aryl or aralkyl; and
$A_1$ and $A_2$ together are 1,2-oxirane or 1,2-cyclopropadiyl.

In specific embodiments of the present invention, the compounds presented in Table 1, tautomers thereof, or pharmaceutically acceptable salts, solvates, esters or prodrugs thereof, are provided:

TABLE 1

| Compound Designation | Structure |
|---|---|
| (R)-2-85e (Ex. 134-I) | 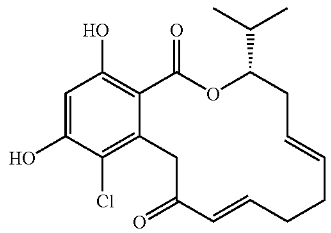 |
| (R)-2-85f | 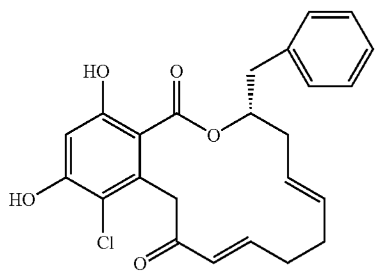 |
| (S)-2-85 (Ex. 134-F) | 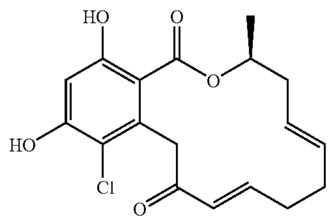 |
| (R)-2-85a (Ex. 134-G) | 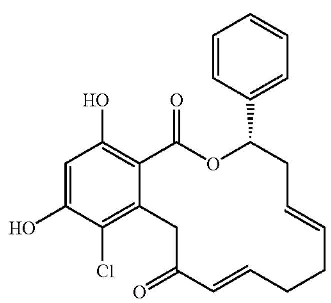 |
| (S)-2-85a (Ex. 134-H) | 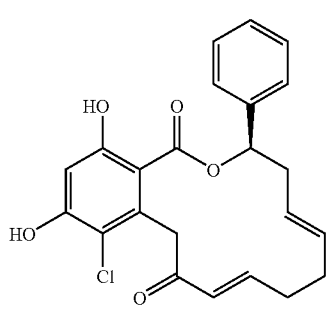 |

TABLE 1-continued

| Compound Designation | Structure |
|---|---|
| (S)-145a | 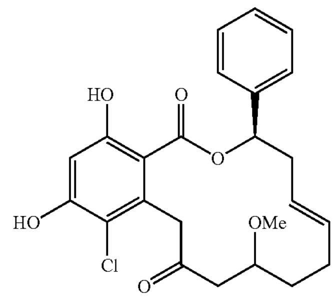 |
| (R)-2-103d (Ex. 134-N) | 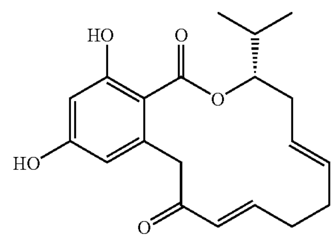 |
| (R)-2-103a (Ex. 134-L) | 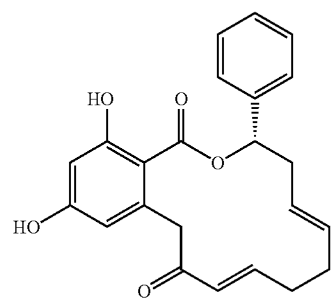 |
| (S)-2-103a (Ex. 134 M) | 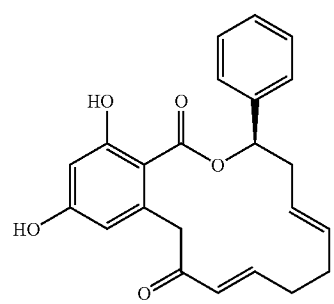 |
| (R)-2-103e (Ex. 134-O) | 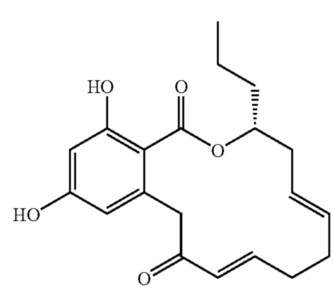 |

TABLE 1-continued

| Compound Designation | Structure |
|---|---|
| (S)-2-103 | 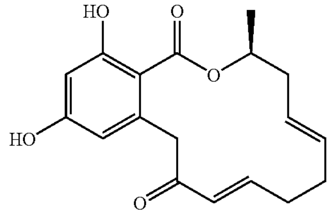 |
| (R)-2-103f | 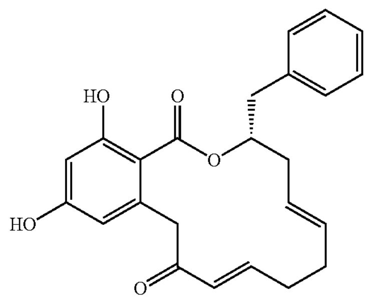 |
| 2-121g | 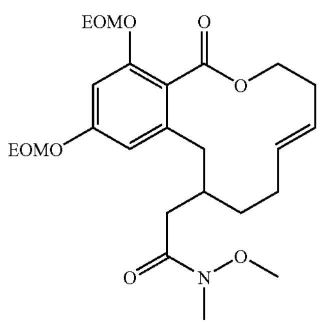 |
| d-2-121g | 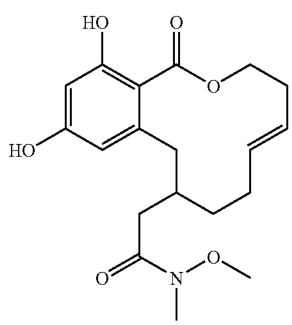 |
| (S)-d-2-121 (Ex. 134-A) | 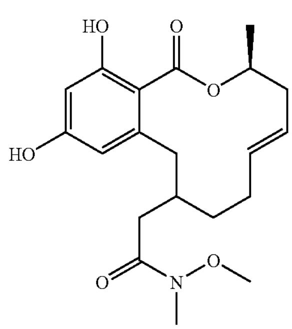 |
| (R)-d-2-121d (Ex. 134-D) | |
| (R)-d-2-121a (Ex. 134-B) | |
| (R)-2-152a | |
| (S)-2-152a | |

TABLE 1-continued

| Compound Designation | Structure |
|---|---|
| (S)-2-152a-1<br>X = Cl | |
| (S)-d-2-121a<br>(Ex. 134C) | |
| (S)-2-145a<br>X = Cl | |
| (R)-2-149-1<br>X = Cl | |
| (R)-2-151 | |
| (R)-2-151-1<br>X = Cl | 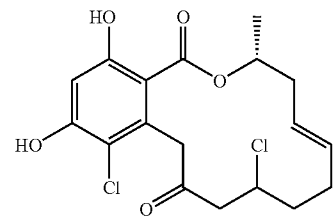 |
| (R)-2-151a-1<br>X = Cl | 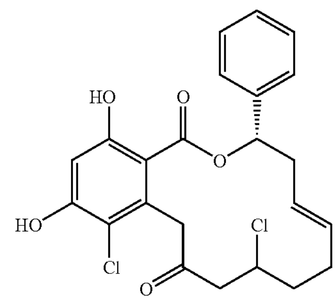 |
| (R)-2-142-1<br>X = Cl<br>(Ex. 136-A) | 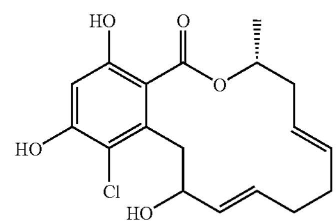 |
| (R)-2-144-1<br>X = Cl | 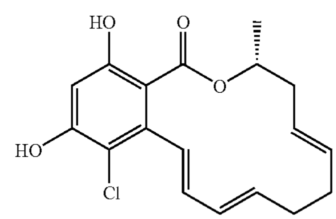 |
| (R)-2-146-1<br>X = Cl | 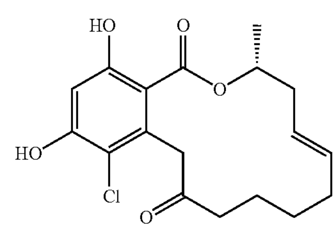 |
| (R)-2-147-1<br>X = Cl | 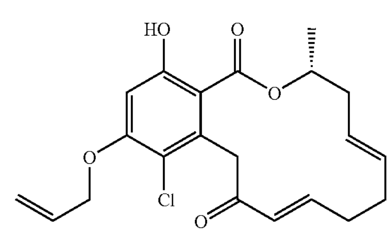 |

TABLE 1-continued

| Compound Designation | Structure |
|---|---|
| (R)-trans-2-150-1 (Ex. 125) | [structure] |
| (R)-2-150c-1 X = Cl | [structure] |
| (R)-2-150e | [structure] |
| Z-(R)-2-155-1 | [structure] Z-isomer |
| E-(R)-2-155-1 | [structure] E-isomer |
| (R)-2-147-4 X = Cl | [structure] |
| (R)-2-153 | [structure] |
| (S)-2-150-1 X = Cl | [structure] |
| (S)-cis-2-150 | [structure] |
| (R)-2-150f | [structure] |
| (R)-cis-2-150e | [structure] |
| (S)-trans-2-150 | [structure] |

TABLE 1-continued
| Compound Designation | Structure |
|---|---|
| (S)-2-150a-1<br>X = Cl | 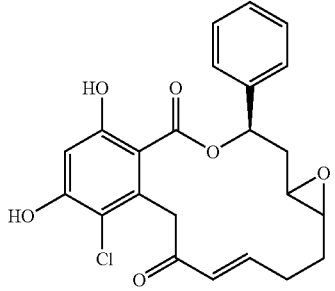 |
| (S)-2-150a | 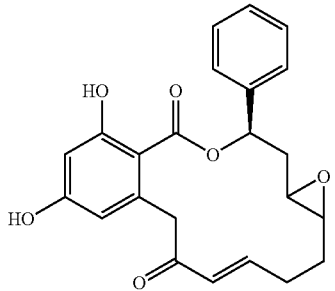 |
| (R)-2-150a | 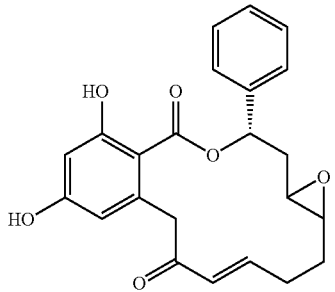 |
| (R)-trans-2-150e | 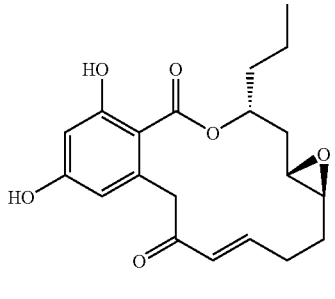 |
| E-(R)-2-155-1 | 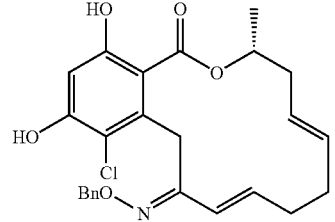 |
| 2-147-3 | 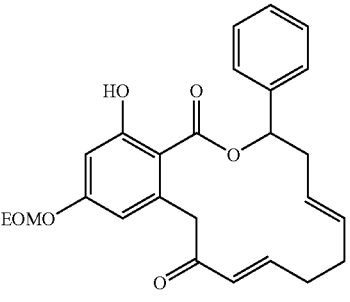 |
| (R)-2-147-3<br>X = Cl | 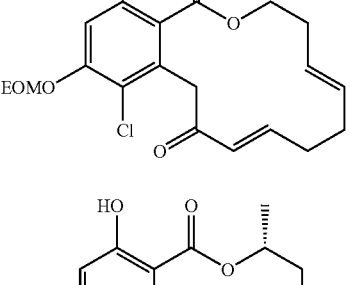 |
| (R)-2-147-2 | 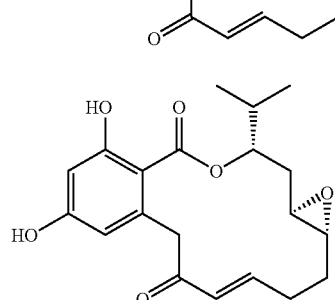 |
| (R)-cis-2-150d | 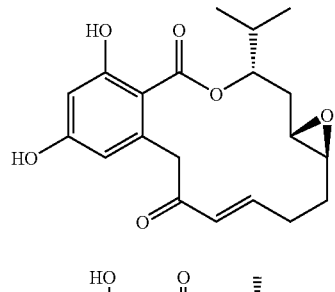 |
| (R)-trans-2-150d | 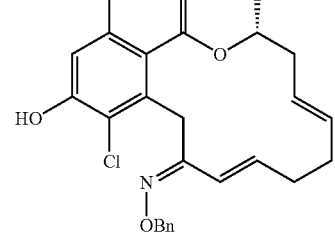 |
| Z-(R)-2-158-1<br>X = Cl | 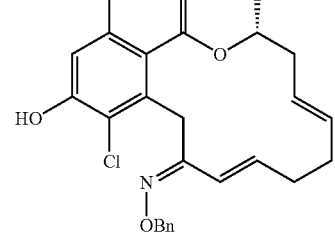 |

TABLE 1-continued

| Compound Designation | Structure |
|---|---|
| (R)-2-112d (Ex. 133-D) | 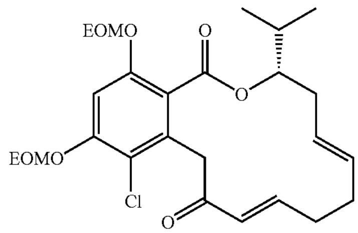 |
| (S)-2-112 | 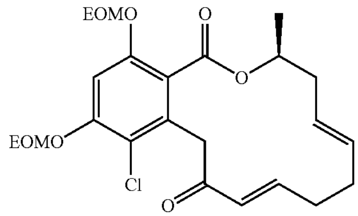 |
| (R)-2-112a (Ex. 3) | 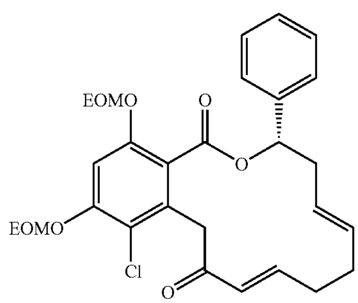 |
| (S)-2-112a (Ex. 133-C) | 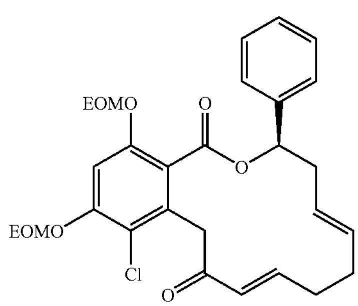 |
| (R)-2-120d (Ex. 133-I) | 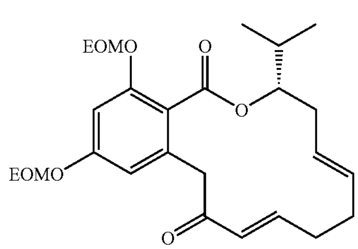 |
| (R)-2-120a (Ex. 133-G) | 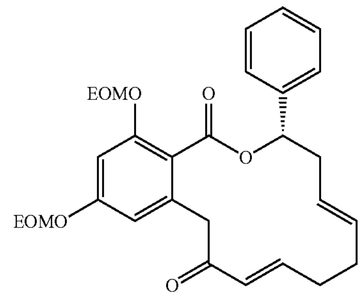 |
| 2-185g | 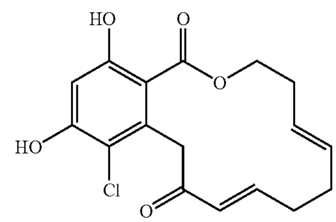 |
| 2-103g | 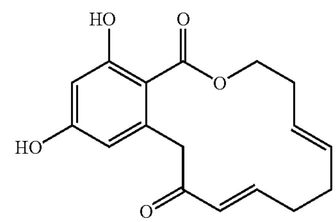 |
| (R)-2-112 (Ex. 105) | 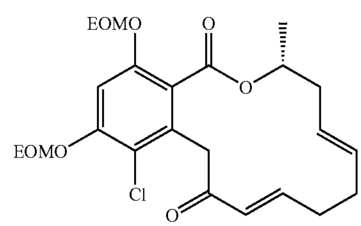 |
| (S)-2-120aa (Ex. 133-H) | 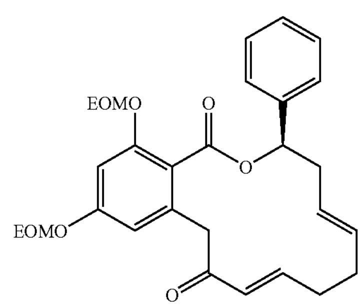 |
| (R)-2-112e (Ex. 133-J) | 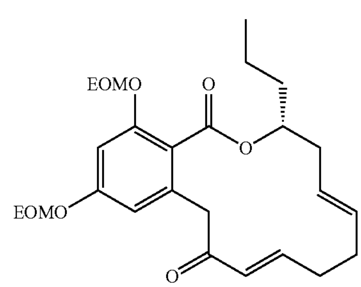 |

TABLE 1-continued

| Compound Designation | Structure |
|---|---|
| (R)-2-112f  X = Cl | *(structure)* |
| (R)-2-128 | *(structure)* |
| Z-(R)-2-157-1 | *(structure, Z-isomer)* |
| E-(R)-2-157-1 | *(structure, E-isomer)* |
| (R)-2-154-1 | *(structure)* |
| (R)-2-112 | *(structure)* |
| (S)-2-120  (Ex. 133-F) | *(structure)* |
| (R)-2-141-2  X = Cl | *(structure)* |
| (R)-2-141  X = Cl | *(structure)* |
| (R)-2-143  X = Cl | *(structure)* |
| 2-154-2 bis  $R^1$ = Cl | *(structure)* |

TABLE 1-continued

| Compound Designation | Structure |
|---|---|
| 2-158-2 bis R¹ = Cl | |
| 7-1 R¹ = H R⁴X = O | |
| 2-156-2 | |
| 2-156-3 | |
| (R) 2-147-5 | 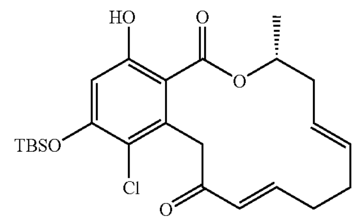 |
| 2-154-4 | 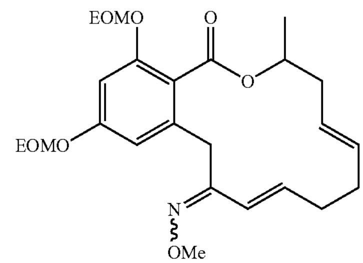 |
| 2-154-6 | 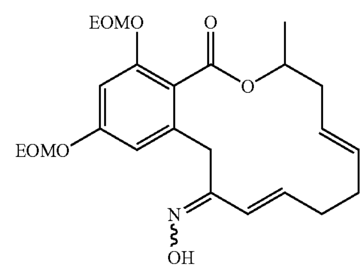 |
| 2-154-5 | 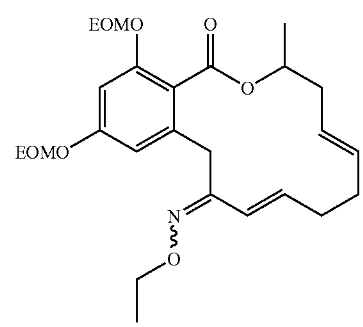 |
| 2-154-7 | 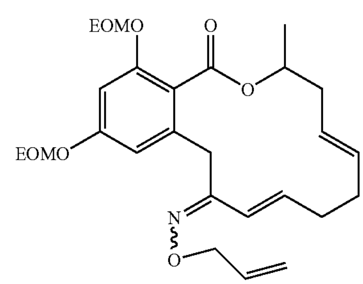 |

TABLE 1-continued
| Compound Designation | Structure |
|---|---|
| 2-154-8 | 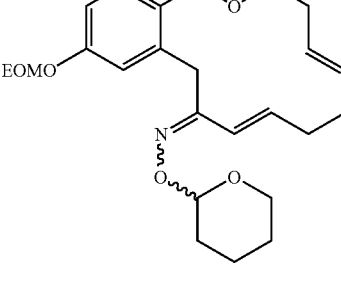 |
| 2-154-3 | 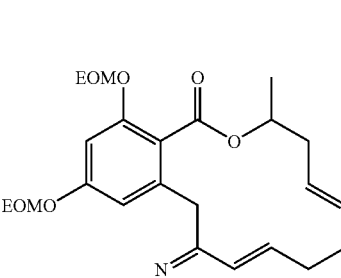 |
| 2-154-9 | 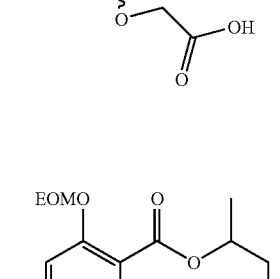 |
| 2-170 | 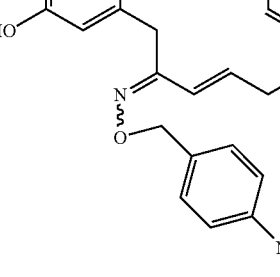 |
| 2-171 | 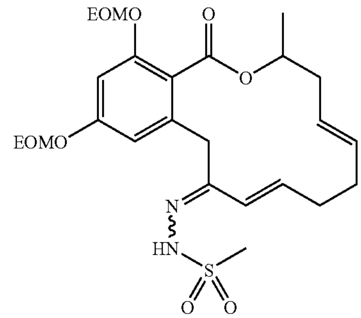 |
| 2-172-1 X = H | 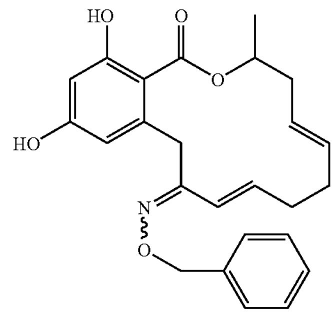 |
| 2-172-4 | 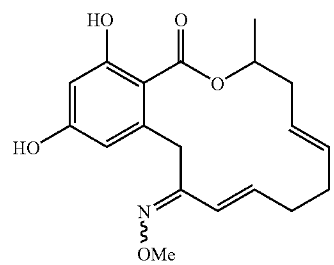 |
| 2-172-6 | 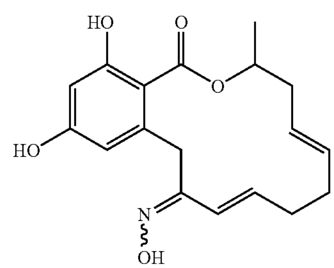 |
| 2-172-7 | 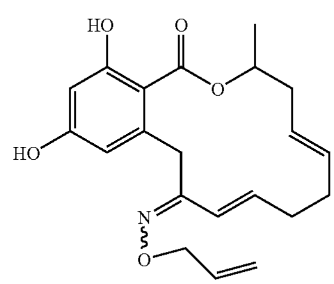 |

TABLE 1-continued

| Compound Designation | Structure |
|---|---|
| 2-172-2, | (structure) |
| 2-172-9 | (structure) |
| (R)-2-154d-1 | (structure) |
| (R)-2-154d-5 | (structure) |
| (R)-2-154d-3 | (structure) |
| (R)-2-154a-1 | (structure) |
| (R)-2-154a-5 | (structure) |
| (R)-2-154a-3 | (structure) |

TABLE 1-continued

| Compound Designation | Structure |
|---|---|
| (S)-2-154a-1 | 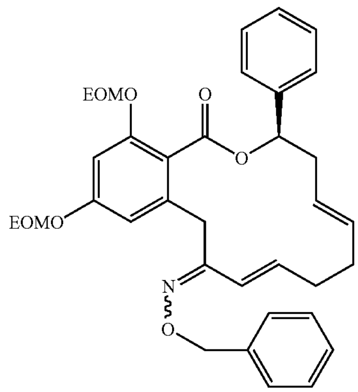 |
| (R)-2-154a-5 | 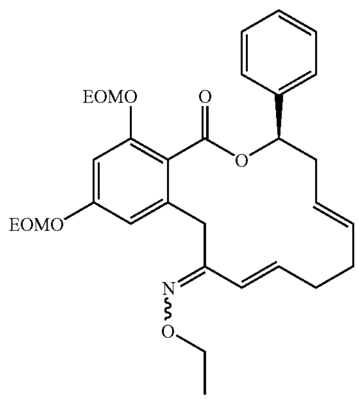 |
| (S)-2-154a-3 | 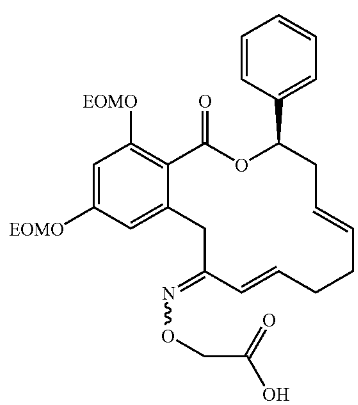 |
| (R)-2-154d-5 | 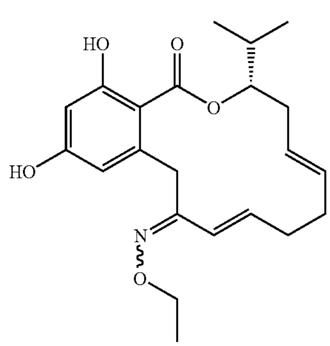 |
| (R)-2-154d-3 | |
| (R)-2-172a-1 | |
| (R)-2-172d-1 | |
| (R)-2-172a-5 | |

TABLE 1-continued

| Compound Designation | Structure |
|---|---|
| (R)-2-172a-2 | |
| (S)-2-172a-1 | |
| (S)-2-173a-5 | |
| (S)-2-172a-2 | |
| 2-155-4 | 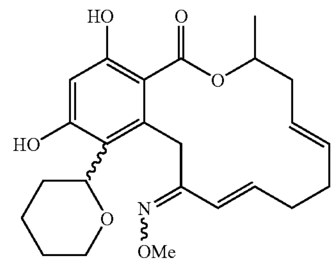 |
| 2-155-7 | 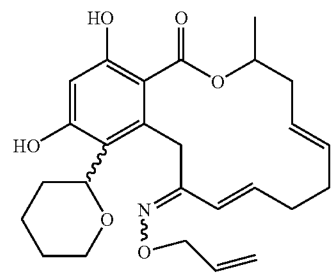 |
| 2-144 | 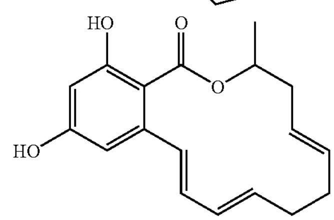 |
| (R)-2-144a | 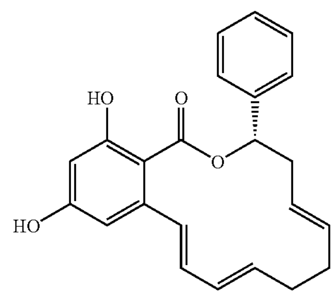 |
| 2-141d | 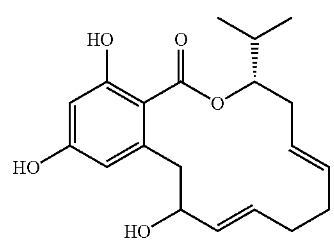 |
| 2-174d | 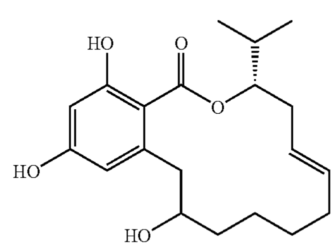 |

TABLE 1-continued
| Compound Designation | Structure |
|---|---|
| 2-174 | 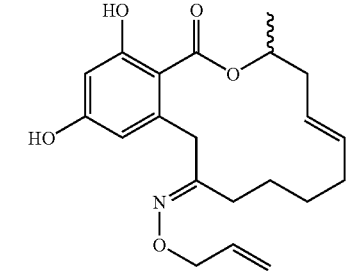 |
| (S)-2-142-1  X = Cl | 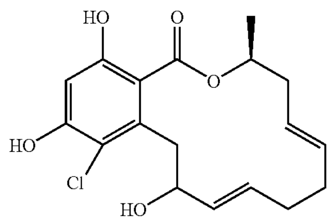 |
| (S)-2-142 | 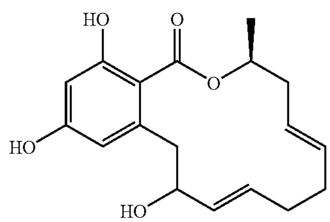 |
| 2-172-4 | 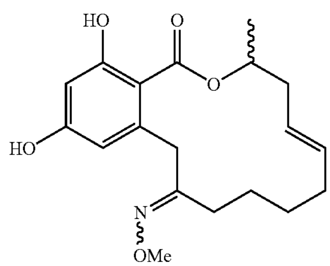 |
| 2-172-1 | 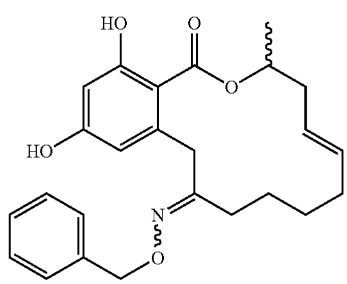 |
| (R)-2-120f | 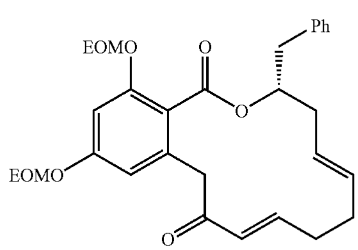 |
| 2-172-7 | 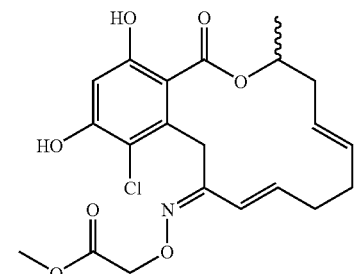 |
| 2-172-2 | |
| (R)-2-120 | |
| (S)-2-174 | |
| (R)-2-154d-3 | |

TABLE 1-continued

| Compound Designation | Structure |
|---|---|
| (R)-172-2 | 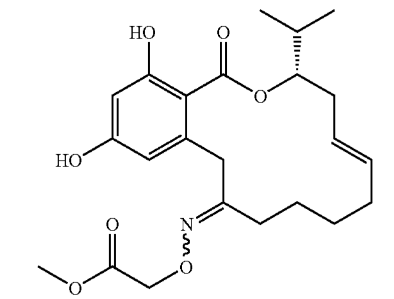 |
| 2-43b | 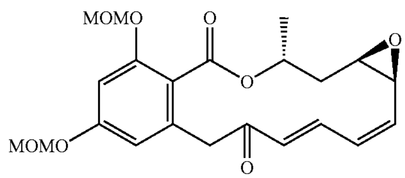 |
| Z-2-a1 | Z-isomer |
| E-2a1 | E-izomer |
| Z-2-a1-1 | Z-isomer |
| E-2-a1 | E-isomer |
| 2a-19 | |
| (R)-p-2-150 | |

TABLE 1-continued

| Compound Designation | Structure |
|---|---|
| (R)-2-175 | *(chemical structure)* |
| 2-163 | *(chemical structure)* |
| 2-164 | *(chemical structure)* |
| 2-165 | *(chemical structure)* |
| 2-166 | *(chemical structure)* |
| 2-167 | *(chemical structure)* |
| 2-168 | *(chemical structure)* |
| 2-169 | *(chemical structure)* |
| 2-a2 | *(chemical structure)* |
| 2-a3 | *(chemical structure)* |

TABLE 1-continued

| Compound Designation | Structure |
|---|---|
| 2-a4 | 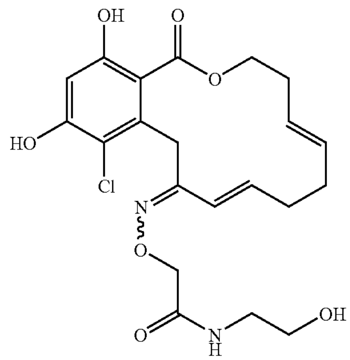 |
| 2-a5 | 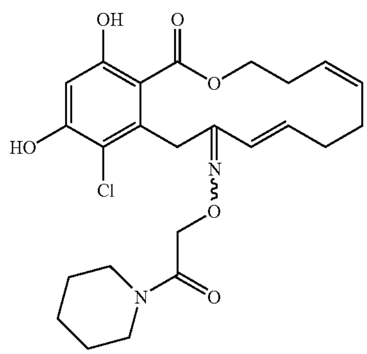 |
| 2-a6 | 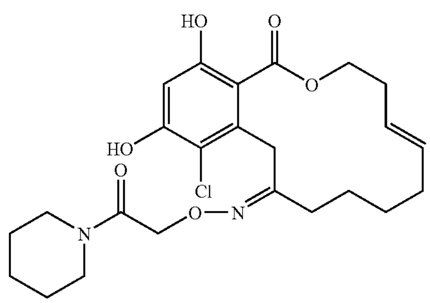 |
| 2-a7 | 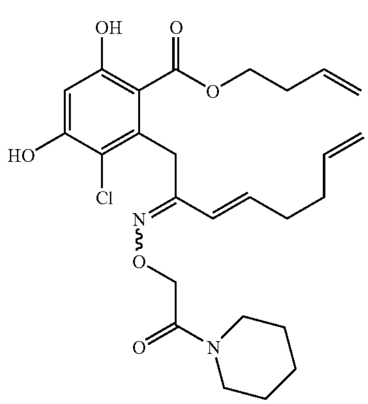 |
| 2-a8 | |
| 2-a9 | |
| 2-a10 | |
| 2-a11 | |

TABLE 1-continued

| Compound Designation | Structure |
|---|---|
| 2-a12 | (structure) |
| 2-a12 | (structure) |
| 2-a13 | (structure) E isomer |
| 2-a15 | (structure) |
| 2-a16 | (structure) |
| 2-a17 | (structure) |
| 2-a18 | (structure) |

Pharmaceutically Acceptable Salts and Prodrugs

The terms "pharmaceutically acceptable salt" and "prodrug" are used throughout the specification to describe any pharmaceutically acceptable form (such as a salt, an ester, a phosphate ester, salt of an ester or a related group) of a compound which, upon administration to a patient, provides the compound described in the specification. In cases where compounds are sufficiently basic or acidic to form stable nontoxic acid or base salts, administration of the compounds as salts may be appropriate. The term pharmaceutically acceptable salts or complexes refers to salts or complexes that retain the desired biological activity of the compounds of the present invention and exhibit minimal undesired toxicological effects.

Nonlimiting examples of such salts are (a) acid addition salts formed with inorganic acids such as sulfate, nitrate, bicarbonate, and carbonate salts (for example, hydrochloric acid, hydrobromic acid, sulfuric acid, phosphoric acid, nitric acid, and the like), and salts formed with organic acids including tosylate, methanesulfonate, acetate, citrate, malonate, tartarate, succinate, benzoate, ascorbate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable salts may be obtained using standard procedures well known in the art, for example by reacting a sufficiently basic compound such as an amine with a suitable acid affording a physiologically acceptable anion.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. For example, a suitable prodrug may be an ester or an amide of a carboxylic acid that is hydrolyzed to form the acid. Non-limiting examples of prodrugs include but are not limited to alkyl or aralkyl esters or amides, including methyl, ethyl, propyl, benzyl and substituted benzyl esters or amides. Prodrugs also comprise phosphate esters of the compounds.

Stereoisomerism and Polymorphism

Compounds of the present invention having a chiral center may exist in and be isolated in optically active and racemic forms. The present invention encompasses any racemic, optically-active, diastereomeric, polymorphic, or stereoisomeric form, or mixtures thereof, of a compound of the invention, which possess the useful properties described herein.

In one embodiment, the compounds are prepared in optically active form by asymmetric synthesis using the processes described herein or synthetic transformations known to those skilled in the art.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; or xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

DEFINITIONS

Whenever a term in the specification is identified as a range (i.e. $C_{1-4}$ alkyl), the range independently refers to each element of the range. As a non-limiting example, $C_{1-4}$ alkyl means, independently, $C_1, C_2, C_3$ or $C_4$ alkyl. Similarly, when one or more substituents are referred to as being "independently selected from" a group, this means that each substituent can be any element of that group, and any combination of these groups can be separated from the group. For example, if $R^1$ and $R^2$ can be independently selected from X, Y and Z, this separately includes the groups $R^1$ is X and $R^2$ is X; $R^1$ is X and $R^2$ is Y; $R^1$ is X and $R^2$ is Z; $R^1$ is Y and $R^2$ is X; $R^1$ is Y and $R^2$ is Y; $R^1$ is Y and $R^2$ is Z; $R^1$ is Z and $R^2$ is X; $R^1$ is Z and $R^2$ is Y; and $R^1$ is Z and $R^2$ is Z.

The term "alkyl" as used herein, unless otherwise specified, refers to a saturated straight, branched, or cyclic, primary, secondary, or tertiary hydrocarbon, including but not limited to groups with $C_1$ to $C_{10}$.

The term "lower alkyl" refers to a saturated straight, branched, or cyclic, primary, secondary, or tertiary hydrocarbon, including groups with $C_1$ to $C_4$, and if appropriate a cyclic alkyl group (for example cyclopropyl).

Illustrative examples of alkyl groups are methyl, ethyl, propyl, isopropyl, cyclopropyl, butyl, secbutyl, isobutyl, tertbutyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The term "halo" or "halogen", as used herein, includes chloro, bromo, iodo, and fluoro.

The term "chiral" as used herein includes a compound that has the property that it is not superimposable on its mirror image.

The term "tautomer" as used herein refers to alternate structures which are recognized in the art to be in equilibrium with the depicted structure. For example, the enol structure below is a tautomer of the ketone structure and recognized to be in equilibrium with the ketone structure.

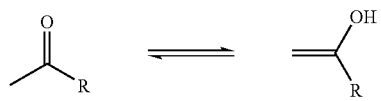

As used herein, the term "solvate" or "pharmaceutically acceptable solvate," is a solvate formed from the association of one or more solvent molecules to one or more molecules of a compound of any one of formulas I, II, III, IV or V or the compounds depicted in Table 1. The term solvate includes hydrates (e.g., hemi-hydrate, mono-hydrate, dihydrate, trihydrate, tetrahydrate, and the like).

The term "alkylthio" refers to a straight or branched chain alkylsulfide of the number of carbons specified, such as for example, $C_{1-4}$ alkylthio, ethylthio, —S-alkyl, —S-alkenyl, —S-alkynyl, etc.

The terms "alkylamino" or "arylamino" refer to an amino group that has one or two alkyl or aryl substituents, respectively. Unless otherwise specifically stated in this application, when alkyl is a suitable moiety, then it is a lower alkyl, whether substituted or unsubstituted.

The term "alkylsulfonyl" means a straight or branched alkylsulfone of the number of carbon atoms specified, as for example, $C_{1-6}$ alkylsulfonyl or methylsulfonyl.

The term "alkoxycarbonyl" refers to a straight or branched chain ester of a carboxylic acid derivative of the number of carbon atoms specified, such as for example, a methoxycarbonyl, MeOCO—.

As used herein, the term "nitro" means —$NO_2$; the term "sulfhydryl" means —SH; and the term "sulfonyl" means —$SO_2$.

The terms "alkenyl" and "alkynyl" refer to alkyl moieties, including both substituted and unsubstituted forms wherein at least one saturated C—C bond is replaced by a double or triple bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $C_{2-6}$ alkynyl may be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" includes a saturated, straight chain, divalent alkyl radical of the formula —$(CH_2)_n$—, wherein "n" may be any whole integer from 1 to 10.

"Alkyl", "alkoxy", "alkenyl", "alkynyl", etc., includes both straight chain and branched groups. However, reference to an individual radical such as "propyl" embraces only that straight-chain radical, whereas a branched chain isomer such as "isopropyl" is specifically termed such.

The term "aryl" as used herein and unless otherwise specified refers to any stable monocyclic, bicyclic, or tricyclic carbon ring of up to 8 members in each ring, wherein at least one ring is aromatic as defined by the Huckel 4n+2 rule, and especially phenyl, biphenyl, or naphthyl. The term includes both substituted and unsubstituted moieties. The aryl group can be substituted with any described moiety, including but not limited to one or more moieties selected from the group consisting of halogen (fluoro, chloro, bromo or iodo), hydroxyl, amino, azido, alkylamino, arylamino, alkoxy, aryloxy, nitro, cyano, sulfonic acid, sulfate, phosphonic acid, phosphate, or phosphonate, either protected or unprotected as necessary, as known to those skilled in the art, for example, as taught in Greene et al., *Protective Groups in Organic Synthesis*, John Wiley & Sons, $3^{rd}$ Ed., 1999.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "cycloalkyl" includes a ring of $C_{3-8}$, including but not limited to cyclopropyl, cyclobutyl, cyclopentyl, cyclohexyl, cycloheptyl and cyclooctyl.

The term "alkoxy" means a straight or branched chain alkyl group having an attached oxygen radical, the alkyl group having the number of carbons specified or any number within this range. For example, a "—O-alkyl", $C_{1-4}$ alkoxy, methoxy, etc.

The term "acyl" includes a group of the formula C(O)R', wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups optimally comprise a phenyl group. In nonlimiting embodiments, acyl groups include acetyl, trifluoroacetyl, methylacetyl, cyclopropylacetyl, cyclopropyl-carboxy, propionyl, butyryl, isobutyryl, hexanoyl, heptanoyloctanoyl, neo-heptanoyl, phenylacetyl, 2-acetoxy-2-phenylacetyl, diphenylacetyl, α-methoxy-α-trifluoromethyl-phenylacetyl, bromoacetyl, 2-nitro-benzeneacetyl, 4-chloro-benzeneacetyl, 2-chloro-2, 2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoro-heptanoyl, 7H-dodecafluoro-heptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6-dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl.

The term "acylamino" includes a group having a structure of "—N(R')—C(=O)—R'", wherein each R' is independently as defined above.

The term "ester" includes a group of the structure "—C(=O)—O—R'" or "—O—C(=O)—R'", wherein R' is an straight, branched, or cyclic alkyl (including lower alkyl), carboxylate residue of an amino acid, aryl including phenyl, heteroaryl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups optimally comprise a phenyl group.

The term "heteratom" includes an atom other than carbon or hydrogen in the structure of a heterocyclic compound, nonlimiting examples of which are nitrogen, oxygen, sulfur, phosphorus or boron.

The term "carbonyl" or "includes a group of the structure "—C(=O)—X—R'" or "X—C(=O)—R'", where X is O, S, or a bond, and each R is independently as defined above for "ester".

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

The term "amino" as used herein unless otherwise specified, includes a moiety represented by the structure "—N(R)$_2$", and includes primary, secondary and tertiary amines optionally substituted by alkyl, aryl, heterocyclyl, and/or sulfonyl groups. Thus (R)$_2$ may represent two hydrogen atoms, two alkyl moieties, or one hydrogen and one alkyl moiety.

The term "amido" as used herein includes an amino-substituted carbonyl, while the term "amidino" means a group having the structure "—C(=NH)—NH$_2$".

The term "quaternary amine" as used herein includes quaternary ammonium salts that have a positively charged nitrogen. They are formed by the reaction between a basic nitrogen in the compound of interest and an appropriate quaternizing agent such as, for example, methyliodide or benzyliodide. Appropriate counterions accompanying a quaternary amine include acetate, trifluoroacetate, chloro, bromo and iodo ions.

The term "substituted" includes multiple degrees of substitution by one or more named substituents such as, for example, halo, hydroxyl, thio, alkyl, alkenyl, alkynyl, nitro, cyano, azido, amino, carboxamido, etc. Where multiple substituent possibilities exist, the compound can be substituted by one or more of the disclosed or claimed substituent groups, independently from one another, and taken singly or plurally.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "protecting group" as used herein refers to a group that may be attached to a reactive group, including heteroatoms such as oxygen or nitrogen, to prevent the reactive group from participating in a reaction. Any protecting groups taught in Greene, et al., *Protective Groups in Organic Synthesis*, John Wiley and Sons, Second Edition, 1991 may be used. Examples of suitable protecting groups include but are not limited to alkoxyalkyl groups such as ethoxymethyl and methoxymethyl; silyl protecting groups, such tert-butyldimethyl silyl (TBS), phenyldimethylsilyl, trimethylsilyl (TMS), 2-trimethylsilylethoxymethyl (SEM) and 2-trimethylsilylethyl; and benzyl and substituted benzyl.

It should be understood that the various possible stereoisomers of the groups mentioned above and herein are within the meaning of the individual terms and examples, unless otherwise specified. As an illustrative example, "1-methyl-butyl" exists in both (R) and the (S) form, thus, both (R)-1-methyl-butyl and (S)-1-methyl-butyl is covered by the term "1-methyl-butyl", unless otherwise specified.

The term "patient" includes human and veterinary subjects.

An "effective amount" is the quantity of compound in which a beneficial outcome is achieved when the compound is administered to a patient or alternatively, the quantity of compound that possesses a desired activity in vivo or in vitro. In the case of proliferative disorders, a beneficial clinical outcome includes reduction in the extent or severity of the symptoms associated with the disease or disorder and/or an increase in the longevity and/or quality of life of the patient compared with the absence of the treatment. For example, for a subject with cancer, a "beneficial clinical outcome" includes a reduction in tumor mass, a reduction in the rate of tumor growth, a reduction in metastasis, a reduction in the severity of the symptoms associated with the cancer and/or an increase in the longevity of the subject compared with the absence of the treatment. The precise amount of compound administered to a subject will depend on the type and severity of the disease or condition and on the characteristics of the patient, such as general health, age, sex, body weight and tolerance to drugs. It will also depend on the degree, severity and type of proliferative disorder. The skilled artisan will be able to determine appropriate dosages depending on these and other factors.

The term "kinase-inhibiting amount" as used herein, refers to an amount of the compound that inhibits a kinase enzyme compared to a control as tested by the methods described herein.

The term "HSP 90-inhibiting amount" as used herein, refers to an amount of the compound that inhibits HSP90 compared to a control as tested by the methods described herein.

The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

The term "cancer" includes, but is not limited to, solid tumors and blood borne tumors and include, but is not limited to, the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia. The term "cancer" includes primary cancer, cancers secondary to treatment, and metastatic cancers.

The term "pharmaceutically acceptable carrier" refers to a non-toxic carrier, adjuvant, or vehicle that may be administered to a patient, together with a compound of this invention, and which does not destroy the pharmacological activity thereof.

The terms "GSK-3-mediated disease, or "GSK-3-mediated condition", as used herein, mean any disease or other deleterious condition or state in which GSK-3 is known to play a role. Such diseases or conditions include, without limitation, diabetes, Alzheimer's disease, Huntington's Disease, Parkinson's Disease, AIDS-associated dementia, amyotrophic lateral sclerosis (AML), multiple sclerosis (MS), schizophrenia, cardiomycete hypertrophy, reperfusion/ischemia, and baldness.

The terms "CDK-2-mediated disease" or CDK-2-mediated condition", as used herein, mean any disease or other deleterious condition in which CDK-2 is known to play a role. The terms "CDK-2-mediated disease" or "CDK-2-mediated condition" also mean those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis, such as are described for example in Fischer, P. M. and Lane, D. P., Current Medicinal Chemistry, 7, 1213-1245 (2000); Mani, S., Wang, C., Wu, K., Francis, R. and Pestell, R., Exp. Opin. Invest. Drugs, 9, 1849 (2000); Fry, D. W. and Garrett, M. D., Current Opinion in Oncologic, Endocrine & Metabolic Investigational Drugs, 2, 40-59 (2000).

The terms "ERK-mediated disease" or "ERK-mediated condition", as used herein mean any disease or other deleterious condition in which ERK may play a role. The terms "ERK-2-mediated disease" or "ERK-2-mediated condition" also mean those diseases or conditions that are alleviated by treatment with a ERK-2 inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. ERK-2 protein kinase and its implication in various diseases has been described for example in Bokemeyer et al. 1996, Kidney Int. 49, 1187; Anderson et al., 1990, Nature 343, 651; Crews et al., 1992, Science 258, 478; Bjorbaek et al., 1995, J. Biol. Chem. 270, 18848; Rouse et al., 1994, Cell 78, 1027; Raingeaud et al., 1996, Mol. Cell. Biol. 16, 1247; Raingeaud et al. 1996; Chen et al., 1993 Proc. Natl. Acad. Sci. USA 90, 10952; Oliver et al., 1995, Proc. Soc. Exp. Biol. Med. 210, 162; Moodie et al., 1993, Science 260, 1658; Frey and Mulder, 1997, Cancer Res. 57, 628; Sivaraman et al., 1997, J. Clin. Invest. 99, 1478; Whelchel et al., 1997, Am. J. Respir. Cell Mol. Biol. 16, 589.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described for example in Khwaja, A., Nature, pp. 33-34, 1990; Zang, Q. Y., et al, Oncogene, 19 2000; Kazuhiko, N., et al, The Journal of Neuroscience, 20 2000.

The terms "Src-mediated disease" or "Src-mediated condition", as used herein mean any disease or other deleterious condition in which Src is known to play a role. The terms "Src-mediated disease" or "Src-mediated condition" also mean those diseases or conditions that are alleviated by treatment with a Src inhibitor. Such conditions include, without limitation, hypercalcemia, osteoporosis, osteoarthritis, cancer, symptomatic treatment of bone metastasis, and Paget's disease. Src protein kinase and its implication in various diseases has been described for example in Soriano, Cell, 69, 551 (1992); Soriano et al., Cell, 64, 693 (1991); Takayanagi, J. Clin. Invest., 104, 137 (1999); Boschelli, Drugs of the Future 2000, 25(7), 717, (2000); Talamonti, J. Clin. Invest., 91, 53 (1993); Lutz, Biochem. Biophys. Res. 243, 503 (1998); Rosen, J. Biol. Chem., 261, 13754 (1986); Bolen, Proc. Natl. Acad. Sci. USA, 84, 2251 (1987); Masaki, Hepatology, 27, 1257 (1998); Biscardi, Adv. Cancer Res., 76, 61 (1999); Lynch, Leukemia, 7, 1416 (1993); Wiener, Clin. Cancer Res., 5, 2164 (1999); Staley, Cell Growth Diff., 8, 269 (1997).

The terms "Lck-mediated disease" or "Lck-mediated condition", as used herein, mean any disease state or other deleterious condition in which Lck is known to play a role. The terms "Lck-mediated disease" or "Lck-mediated condition" also mean those diseases or conditions that are alleviated by treatment with an Lck inhibitor. Lck-mediated diseases or conditions include, but are not limited to, autoimmune diseases such as transplant rejection, allergies, rheumatoid arthritis, and leukemia. The association of Lck with various diseases has been described for example in Molina et al., Nature, 357, 161 (1992).

The terms "Abl-mediated disease" or "Abl-mediated condition", as used herein, mean any disease state or other deleterious condition in which Abl is known to play a role. The terms "Abl-mediated disease" or "Abl-mediated condition" also mean those diseases or conditions that are alleviated by treatment with an Abl inhibitor. Abl-mediated diseases or conditions include, but are not limited to, leukemias, particularly chronic myeloid leukemia. The association of Abl with various diseases has been described for example in Druker, et al., N. Engl. J. Med. 2001, 344, 1038-1042.

The terms "cKit-mediated disease" or "cKit-mediated condition", as used herein, mean any disease state or other deleterious condition in which cKit is known to play a role. The terms "cKit-mediated disease" or "cKit-mediated condition" also mean those diseases or conditions that are alleviated by treatment with an cKit inhibitor. cKit-mediated diseases or conditions include, but are not limited to, mastocytosis/mast cell leukemia, gastrointestinal stromal tumor, sinonasal natural killer/T-cell lymphoma, seminoma/dysgerminoma, throid carcinoma, samll-cell lung carcinoma, malignant melanoma, adenoid cystic carcinoma, ovarian carcinoma, acute myelogenious leukemia, anaplastic large-cell lymphoma, angiosarcoma, endometrial carcinom, pediatric T-cell ALL/lymphoma, breast carcinoma and prostate carcinoma. The association of cKit with various diseases has been described for example in Heinrich, et al., J. Clinical Oncology 2002, 20, 1692-1703.

The terms "Flt3-mediated disease" or "Flt3-mediated condition", as used herein, mean any disease state or other deleterious condition in which Flt3 is known to play a role. The terms "Flt3-mediated disease" or "Flt3-mediated condition" also mean those diseases or conditions that are alleviated by treatment with an Flt3 inhibitor. Flt3-mediated diseases or conditions include, but are not limited to, acute myelogenous leukemia, mixed lineage leukemia and acute lymphocytic leukemia. The association of Flt3 with various diseases has been described for example in Sternberg and Licht, Curr. Opin Hematol. 2004, 12, 7-13.

The terms "KDR-mediated disease" or "KDR-mediated condition", as used herein, mean any disease state or other deleterious condition in which KDR is known to play a role. The terms "KDR-mediated disease" or "KDR-mediated condition" also mean those diseases or conditions that are alleviated by treatment with an KDR inhibitor. KDR-mediated diseases or conditions include, but are not limited to, carcinoma of the lung, breast, gastrointestinal tract, kidney, bladder, ovary and endometrium, intracranial tumors including glioblatoma multiforme, sporadic capillary hemangioblastoma, hematological malignancies, including T cell lymphoma, acute lymphoblastic leukemia, Burkitt's lymphoma and promyelocytic leukemia, age-related macular degeneration, herpetic ocular disease, rheumatoid arthritis, cerebral ischemia and endometriosis. The association of KDR with various diseases has been described for example in Ferrara, Endocrine Reviews 2004, 25, 581-611.

The term "HSP90-mediated disease" or "HSP90-mediated condition" refers to a condition in which HSP90 is known to pay a role. The conditions include but are not limited to inflammatory disorders, abnormal cellular proliferation, autoimmune disorders, ischemia, fibrogenetic disorders including but not limited to scleroderma, polymyositis, systemic lupus, rheumatoid arthritis, liver cirrhosis, keloid formation, interstitial nephritis, and pulmonary fibrosis. (Strehlow, WO 02/02123; PCT/US01/20578).

Method of Treatment

The compounds described herein, are particularly useful for the treatment or prevention of a disorder mediated by kinases or mediated by HSP90. In one embodiment, the compounds described herein, are useful for the treatment or prevention of a proliferative disorder, including cancer metastasis. In another embodiment, the compounds described herein, are useful for the treatment or prevention of an inflammatory disorder associated by kinases or HSP90.

An aspect of the invention relates to compounds and compositions that are useful for treating cancer.

Another aspect of the invention relates to the treatment of the following cancers: breast, ovary, cervix, prostate, testis, genitourinary tract, esophagus, larynx, glioblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another aspect of the invention is a method for treating cancer comprising administering an effective amount of a compound of formula I, II, III, IV or V described herein to a patient with cancer.

Angiogenesis is characterized by the proliferation of endothelial cells to form new blood vessels (often called neovascularization). Inhibition of mitosis of endothelial cells results in inhibition of angiogenesis. Another aspect of this invention therefore relates to inhibition of undesirable mitosis, including undesirable angiogenesis. A mammalian disease characterized by undesirable cell mitosis, as defined herein, includes, but is not limited to, excessive or abnormal stimulation of endothelial cells (e.g., atherosclerosis), solid tumors and tumor metastasis, benign tumors, for example, hemangiomas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease).

Other undesired angiogenesis involves normal processes including ovulation and implantation of a blastula. The compositions described above can be used as a birth control agent by reducing or preventing uterine vascularization required for embryo implantation. Accordingly, the compositions described above can be used to block ovulation and implantation of a blastula or to block menstruation (induce amenorrhea).

Diseases associated with undesirable mitosis including neovascularization can be treated according to the present invention. Such diseases include, but are not limited to, ocular neovascular disease, diabetic retinopathy, retinopathy of prematurity, corneal graft rejection, neovascular glaucoma and retrolental fibroplasias, epidemic keratoconjunctivitis, Vitamin A deficiency, contact lens overwear, atopic keratitis, superior limbic keratitis, pterygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, marginal keratolysis, trauma, rheumatoid arthritis, systemic lupus, polyarteritis, Wegener's sarcoidosis, Scleritis, Steven-Johnson disease, pemphigoid, radial keratotomy, and corneal graph rejection.

Other diseases associated with undesirable mitosis including neovascularization can be treated according to the present invention. Such diseases include, but are not limited to, sickle cell anemia, sarcoid, pseudoxanthoma elasticum, Paget's disease, vein occlusion, artery occlusion, carotid obstructive disease, chronic uveitis/vitritis, Lyme's disease, systemic lupus erythematosis, Eales' disease, Bechet's disease, infections causing a retinitis or choroiditis, presumed ocular histoplasmosis, Best's disease, myopia, optic pits, Stargart's disease, pars planitis, chronic retinal detachment, hyperviscosity syndromes, toxoplasmosis, and post-laser complications. Other diseases include, but are not limited to, diseases associated with rubeosis (neovascularization of the iris and the angle) and diseases caused by the abnormal proliferation of fibrovascular or fibrous tissue including all forms of proliferative vitreoretinopathy, whether or not associated with diabetes.

Another aspect of the invention relates to the treatment of inflammatory diseases including, but no limited to, excessive or abnormal stimulation of endothelial cells (e.g., atherosclerosis), solid tumors and tumor metastasis, benign tumors, for example, hemangiomas, acoustic neuromas, trachomas, and pyogenic granulomas, vascular malfunctions, abnormal wound healing, inflammatory and immune disorders, Bechet's disease, gout or gouty arthritis, abnormal angiogenesis accompanying rheumatoid arthritis, skin diseases, such as psoriasis, diabetic retinopathy and other ocular angiogenic diseases such as retinopathy of prematurity (retrolental fibroplasic), macular degeneration, corneal graft rejection, neovascular glaucoma and Osler Weber syndrome (Osler-Weber-Rendu disease). Other undesired angiogenesis involves normal processes including ovulation and implantation of a blastula. Accordingly, the compositions described above can be used to block ovulation and implantation of a blastula or to block menstruation (induce amenorrhea).

Another aspect of this invention relates to a method of inhibiting HSP90 activity in a patient, comprising administering to a patient an effective amount of a compound of formula I, II, III, IV or V or a pharmaceutically acceptable salt or prodrug thereof. The invention also provides a method for treating a disease that is mediated by HSP90.

Another aspect of this invention relates to a method of inhibiting Aurora A activity in a patient, comprising administering to a patient an effective amount of a compound of formula I, II, III, IV or V or a pharmaceutically acceptable salt or prodrug thereof.

Another aspect of this invention relates to a method of treating or preventing a GSK-3-mediated disease with a GSK-3 inhibitor, comprising administering to a patient an effective amount of a compound of formula I, II, III, IV or V or a pharmaceutically acceptable salt or prodrug thereof.

One aspect of this invention relates to a method of enhancing glycogen synthesis and/or lowering blood levels of glucose in a patient in need thereof, which method comprises administering to the patient a therapeutically effective amount of a compound of formula I, U, III, IV or V or a pharmaceutical composition thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of .beta.-catenin, which is useful for treating schizophrenia.

Another aspect of the invention relates to inhibiting GSK-3 activity in a biological sample, which method comprises contacting the biological sample with a GSK-3 inhibitor of formula I, II, III, IV or V.

Another aspect of this invention relates to a method of inhibiting GSK-3 activity in a patient comprising administering to the patient a compound of formula I, II, III, IV or V or a composition comprising said compound.

Another aspect of this invention relates to a method of treating or preventing a CDK-2-mediated disease comprising administering to a patient in need of such a treatment a therapeutically effective amount of a compound of formula I, II, III, IV or V or a pharmaceutical composition thereof.

Another aspect of the invention relates to inhibiting CDK-2 activity in a biological sample or a patient, which method comprises administering to the patient a compound of formula I, II, III, IV or V, or a composition comprising said compound.

Another aspect of this invention relates to a method of treating or preventing an ERK-2-mediated diseases comprising administering to a patient in need of such a treatment a therapeutically effective amount of a compound of formula I, II, III, IV or V or a pharmaceutical composition thereof.

Another aspect of the invention relates to inhibiting ERK-2 activity in a biological sample or a patient, which method comprises administering to the patient a compound of formula I, II, III, IV or V, or a composition comprising said compound.

Another aspect of this invention relates to a method of treating or preventing an AKT-mediated diseases comprising administering to a patient in need of such a treatment a therapeutically effective amount of a compound of formula I, II, III, IV or V or a pharmaceutical composition thereof.

Another aspect of the invention relates to inhibiting AKT activity in a biological sample or a patient, which method comprises administering to the patient a compound of formula I, II, III, IV or V, or a composition comprising said compound.

Another aspect of this invention relates to a method of treating or preventing a Src-mediated disease comprising administering to a patient in need of such a treatment a therapeutically effective amount of a compound of formula I, II, III, IV or V or a pharmaceutical composition thereof.

Another aspect of the invention relates to inhibiting Src activity in a biological sample or a patient, which method comprises administering to the patient a compound of formula I, II, III, IV or V, or a composition comprising said compound.

Another aspect of this invention relates to a method of treating or preventing an Lck-mediated disease with an Lck inhibitor, which method comprises administering to a patient in need of such a treatment a therapeutically effective amount of a compound of formula I, II, III, IV or V, or a pharmaceutical composition thereof.

Another aspect of the invention relates to inhibiting Lck activity in a biological sample or a patient, which method comprises administering to the patient a compound of formula I, II, III, IV or V, or a composition comprising said compound.

Another aspect of this invention relates to a method of treating or preventing an Abl-mediated disease with an Abl inhibitor, which method comprises administering to a patient in need of such a treatment a therapeutically effective amount of a compound of formula I, II, III, IV or V, or a pharmaceutical composition thereof.

Another aspect of the invention relates to inhibiting Abl activity in a biological sample or a patient, which method comprises administering to the patient a compound of formula I, II, III, IV or V, or a composition comprising said compound.

Another aspect of this invention relates to a method of treating or preventing a cKit-mediated disease comprising administering to a patient in need of such a treatment a therapeutically effective amount of a compound of formula I, II, I, IV or V, or a pharmaceutical composition thereof.

Another aspect of the invention relates to inhibiting cKit activity in a biological sample or a patient, which method comprises administering to the patient a compound of formula I, II, III, IV or V, or a composition comprising said compound.

Another aspect of this invention relates to a method of treating or preventing a Flt3-mediated disease comprising administering to a patient in need of such a treatment a therapeutically effective amount of a compound of formula I, II, III, IV or V, or a pharmaceutical composition thereof.

Another aspect of the invention relates to inhibiting Flt3 activity in a biological sample or a patient, which method comprises administering to the patient a compound of formula I, II, I, IV or V, or a composition comprising said compound.

Another aspect of this invention relates to a method of treating or preventing a KDR-mediated disease comprising administering to a patient in need of such a treatment a therapeutically effective amount of a compound of formula I, II, III, IV or V, or a pharmaceutical composition thereof.

Another aspect of the invention relates to inhibiting KDR activity in a biological sample or a patient, which method comprises administering to the patient a compound of formula I, II, III, IV or V, or a composition comprising said compound.

An amount effective to inhibit protein kinase, is an amount that causes measurable inhibition of the kinase activity when compared to the activity of the enzyme in the absence of an inhibitor. Any method may be used to determine inhibition, such as, for example, the Biological Testing Examples described below.

Pharmaceutical Compositions

Mammals, and specifically humans, suffering from a respiratory disorder can be treated by the inhalation, systemic, oral, topical, or transdermal administration of a composition comprising an effective amount of the compounds described herein or a pharmaceutically acceptable salt, ester or prodrug thereof, optionally in a pharmaceutically acceptable carrier or diluent.

The compounds or compositions are typically administered by oral or inhalation administration. Alternatively, compounds can be administered subcutaneously, intravenously, intraperitoneally, intramuscularly, parenterally, orally, submucosally, by inhalation, transdermally via a slow release patch, or topically, in an effective dosage range to treat the target condition.

An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication.

In a separate embodiment, the compounds of the invention are in the form of an inhaled dosage. In this embodiment, the compounds may be in the form of an aerosol suspension, a dry powder or liquid particle form. The compounds may be prepared for delivery as a nasal spray or in an inhaler, such as a metered dose inhaler. Pressurized metered-dose inhalers ("MDI") generally deliver aerosolized particles suspended in chlorofluorocarbon propellants such as CFC-11, CFC-12, or the non-chlorofluorocarbons or alternate propellants such as the fluorocarbons, HFC-134A or HFC-227 with or without surfactants and suitable bridging agents. Dry-powder inhalers can also be used, either breath activated or delivered by air or gas pressure such as the dry-powder inhaler disclosed in the Schering Corporation International Patent Application No. PCT/US92/05225, published 7 Jan. 1993 as well as the Turbuhaler™ (available from Astra Pharmaceutical Products, Inc.) or the Rotahaler™ (available from Allen & Hanburys) which may be used to deliver the aerosolized particles as a finely milled powder in large aggregates either alone or in combination with some pharmaceutically acceptable carrier e.g. lactose; and nebulizers.

The compounds of the invention may be also administered in specific, measured amounts in the form of an aqueous suspension by use of a pump spray bottle. The aqueous suspension compositions of the present invention may be prepared by admixing the compounds with water and other pharmaceutically acceptable excipients. The aqueous suspension compositions according to the present invention may contain, inter alia, water, auxiliaries and/or one or more of the excipients, such as: suspending agents, e.g., microcrystalline cellulose, sodium carboxymethylcellulose, hydroxypropyl-methyl cellulose; humectants, e.g. glycerin and propylene glycol; acids, bases or buffer substances for adjusting the pH, e.g., citric acid, sodium citrate, phosphoric acid, sodium phosphate as well as mixtures of citrate and phosphate buffers; surfactants, e.g. Polysorbate 80; and antimicrobial preservatives, e.g., benzalkonium chloride, phenylethyl alcohol and potassium sorbate.

Typical systemic dosages for all of the herein described conditions are those ranging from 0.01 mg/kg to 1500 mg/kg of body weight per day as a single daily dose or divided daily doses. Preferred dosages for the described conditions range from 0.5-1500 mg per day. A more particularly preferred dosage for the desired conditions ranges from 5-750 mg per day. Typical dosages can also range from 0.01 to 1500, 0.02 to 1000, 0.2 to 500, 0.02 to 200, 0.05 to 100, 0.05 to 50, 0.075 to 50, 0.1 to 50, 0.5 to 50, 1 to 50, 2 to 50, 5 to 50, 10 to 50, 25 to 50, 25 to 75, 25 to 100, 100 to 150, or 150 or more mg/kg/day, as a single daily dose or divided daily doses. In one embodiment, the compounds are given in doses of between about 1 to about 5, about 5 to about 10, about 10 to about 25 or about 25 to about 50 mg/kg. Typical dosages for topical application are those ranging from 0.001 to 100% by weight of the active compound.

The compounds are conveniently administered in units of any suitable dosage form, including but not limited to one containing from about 7 to 3000 mg, from about 70 to 1400 mg, or from about 25 to 1000 mg of active ingredient per unit dosage form. For example, an oral dosage of from about 50 to 1000 mg is usually convenient, including in one or multiple dosage forms of 50, 100, 200, 250, 300, 400, 500, 600, 700, 800, 900 or 1000 mgs. Lower dosages may be preferable, for example, from about 10-100 or 1-50 mgs. Also contemplated are doses of 0.1-50 mg, 0.1-20 mgs., or 0.1-10 mgs. Furthermore, lower doses may be utilized in the case of administration by a non-oral route, as for example, by injection or inhalation.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects. Pharmaceutically acceptable carriers that may be used in these pharmaceutical compositions are generally known in the art. They include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, solvents, salts or electrolytes, such as protamine sulfate, disodium hydrogen phosphate, potassium hydrogen phosphate, sodium chloride, zinc salts, silicates, colloidal silica, magnesium trisilicate, polyvinyl pyrrolidone, cellulose-based substances, polyethylene glycol, sodium carboxymethylcellulose, polyacrylates, waxes, oils, polyethylene-polyoxypropylene-block polymers, polyethylene glycol and wool fat. Pharmaceutically accepted vehicles can contain mixtures of more than one excipient in which the components and the ratios can be selected to optimize desired characteristics of the formulation including but not limited to shelf-life, stability, drug load, site of delivery, dissolution rate, self-emulsification, control of release rate and site of release, and metabolism.

Formulations can be prepared by a variety of techniques known in the art. Examples of formulation techniques can be found in literature publications and in texts such as "Water-insoluble drug formulation", edited by Rong Liu, 2000, Interpharm Press.

If administered intravenously, carriers can be physiological saline, bacteriostatic water, Cremophor EL™ (BASF, Parsippany, N.J.) or phosphate buffered saline (PBS). Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other surface-active emulsifying agents or bioavailability enhancers which are commonly used in the manufacture of pharmaceutically acceptable solid, liquid, or other dosage forms may also be used for the purposes of formulation.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

One mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Combination Treatment

The compound can also be mixed with other active materials which do not impair the desired action, or with materials that supplement the desired action. The active compounds can be administered in conjunction, i.e. combination or alternation, with other medications used in the treatment of disorders that are mediated by kinases or HSP90.

The compounds can be administered in combination or alternation with drugs typically useful for treatment or prevention of asthma, such as certain anti-inflammatory drugs and bronchodilators. Corticosteroids (inhaled and oral), mast cell stabilizers, and the leukotriene modifier drugs are typically a useful anti-inflammatory medication for people suffering from asthma. These drugs reduce swelling and mucus production in the airways. Bronchodilators typically relieve the symptoms of asthma by relaxing the muscle bands that tighten around the airways. This action rapidly opens the airways, letting more air come in and out of the lungs. Bronchodilators also help clear mucus from the lungs.

Typically used compounds include Inhaled corticosteroids, which prevent rather than relieve symptoms. Inhaled corticosteroids include: Advair (a combination medication that includes a corticosteroid (fluticasone) plus a long acting bronchodilator drug (in this case a β-2 adrenergic receptor agonist, salmeterol)), aerobid (flunisolide), azmacort (triamcinolone), flovent (fluticasone), methylprednisolone, prednisone, pulmicort or serevent diskus (salmeterol powder), theophylline, qvar, and xopenex (levalbuterol), Inhaled corticosteroids come in three forms: the metered dose inhaler (MDI), dry powder inhaler (DPI) and nebulizer solutions. Systemic steroids include: methylprednisolone (Medrol, Methylpred, Solu-Medrol), prednisone (Deltasone) and prednisolone (Prelone, Pediapred, Orapred). Mast Cell Stabilizers include Intal and Tilade, which work by preventing the release of irritating and inflammatory substances from mast cells. Leukotriene modifiers include accolate and singular and accolate (zafirlukast), singulair (montelukast) and zyflo (zileuton).

The compounds can be administered in combination with nonsteroidal antiinflammatories such as ibuprofen, indomethacin, fenoprofen, mefenamic acid, flufenamic acid, sulindac. The compound can also be administered with corticosteriods. Any of the compounds described herein for combination or alternation therapy can be administered as any prodrug that upon administration to the recipient, is capable of providing directly or indirectly, the parent compound. Nonlimiting examples are the pharmaceutically acceptable salts (alternatively referred to as "physiologically acceptable salts"), and a compound which has been alkylated or acylated at an appropriate position. The modifications can affect the biological activity of the compound, in some cases increasing the activity over the parent compound.

Processes for the Preparation of the Compounds

Modular synthetic processes directed to the synthesis of pochonin D and pochonin A were adapted to the synthesis of a library of resorcylic acid lactones that extend beyond the natural resorcylides. The syntheses developed utilize resin-assisted or solid phase synthesis to minimize and facilitate the isolation of intermediate and final products. First, a description of the synthetic protocols directed to the natural resorsylic acid lactones is presented followed by the synthesis of the library of compounds.

The following abbreviations are used herein.

| | |
|---|---|
| Ac | Acetyl (CH3C=O) |
| ADP | Adenosine diphosphate |
| AIBN | Azobis(isobutyronitrile) |
| All | Allyl |
| ATP | Adenosine triphosphate |
| BER | Borohydride exchange resin |
| BBN | Borabicyclononane |
| Bn | Benzyl |
| Bz | Benzoyl |
| CAN | Ceric ammonium nitrate |
| CSA | Camphorsulfonic acid |
| δ | Chemical shift (NMR) |
| dba | Dibenzylideneacetone |
| DBU | 1,8-Diazabicyclo[5.4.0]undec-7-ene |
| DDQ | 2,3-Dichloro-5,6-dicyano-1,4-benzoquinone |
| DEAD | Diethyl azodicarboxylate |
| DIAD | Diisopropyl azodicarboxylate |

| | |
|---|---|
| d.e. | Diastereoisomeric excess |
| DET | Diethyl tartrate |
| DHP | Dihydropyran |
| DIBAL or Dibal-H | Diisobutylaluminum hydride |
| DIC | N,N'-diisopropylcarbodiimide |
| DMAP | 4-Dimethylaminopyridine |
| DMDO | Dimethyldioxirane |
| DMF | Dimethylformamide |
| DMPI | Dess-Martin periodinane |
| DMSO | Dimethylsulfoxide |
| DNA | Desoxyribo nucleic acid |
| dppe | 1,2-Bis(diphenylphosphino)ethane |
| $EC_{50}$ | Plasma concentration required for obtaining 50% of maximum effect in vivo |
| EDC | 1-Ethyl-3-[3-dimethylaminopropyl]carbodiimide hydrochloride |
| EDTA | Ethylenediaminetetraacetic acid |
| e.e. | Enantiomeric excess |
| EOM | Ethoxymethyl ($CH_3CH_2OCH_2$—) |
| FDA | Food and Drug Administration |
| Fmoc | 9-Fluorenylmethoxycarbonyl |
| $GI_{50}$ | Concentration required for 50% inhibition of cell growth |
| Grubbs' II | Grubbs' second generation catalyst: (ruthenium[1,3-bis(2,4,6-trimethylphenyl)-2-imidazolinylidene)dichloro(phenyl-methylene)(tricyclohexylphosphane) |

Grubbs' II

| | |
|---|---|
| HFIP | Hexafluoroisopropanol |
| HMDS | Hexamethyldisilazide |
| HMPA | Hexamethylphosphorictriamide |
| HOBT | N-Hydroxybenzotriazole |
| RCM | Ring-closing metathesis |
| RedAl | Sodium bis(methoxyethoxy) aluminum hydride |
| $R_f$ | Retention factor |
| RNA | Ribonucleic acid |
| RT | Room temperature |
| SAE | Sharpless asymmetric epoxidation |
| SAR | Structure-activity relationship |
| SEM | 2-Trimethylsilylethoxymethoxy |
| TBAF | Tetra-n-butylammonium fluoride |
| TBAI | Tetra-n-butylammonium iodide |
| TBDPS | t-Butyldiphenylsilyl |
| TBHP | t-Butylhydroperoxide |
| TBS | t-Butyldimethylsilyl |
| Teoc | 2-(Trimethylsilyl)ethoxycarbonyl |
| Tf | Triflate ($CF_3SO_3$) |
| TFA | Trifluoroacetic acid |
| TFAA | Trifluoroacetic acetic anhydride |
| THF | Tetrahydrofuran |
| THP | Tetrahydropyran |
| TLC | Thin layer chromatography |
| TMS | Trimethylsilyl |
| Ts | Tosyl (p-$CH_3C_6H_4SO_2$) |
| p-TSOH | para-Toluenesulfonic acid |

I. Synthesis of Pochonin D

Preliminary Studies

Retrosynthetic disconnections for pochonin D (2-85) depicting the synthetic strategy are shown below. A Mitsunobu esterification, an acylation and a ring-closing metathesis are shown as the main disconnections using three building blocks: acid 2-87, alcohol (S)-2-27 and Weinreb amide 2-88.

| | |
|---|---|
| HPLC | High performance chromatography |
| HRMS | High resolution mass spectrometry |
| HSP90 | Heat shock protein 90 |
| Hunig's Base | Diisopropylethylamine |
| $IC_{50}$ | Concentration of a drug that is required for 50% inhibition in vitro |
| imid. | Imidazole |
| $Ipc_2BH$ | Bis-isopinocamphorylborane |
| J | Coupling constant |
| KHMDS | Potassium hexamethyldisilylamide |
| L.C. | Liquid chromatography |
| LDA | Lithium diisopropylamide |
| LiHMDS | Lithium hexamethyldisilazide ($LiN(SiMe_3)_2$) |
| µM | Micromolar concentration (µmol · l$^{-1}$) |
| MAP | Mitogen-activated protein |
| mCPBA | meta-Chloroperoxybenzoic acid |
| MOM | Methoxymethyl ($CH_3OCH_2$—) |
| mRNA | Messenger ribonucleic acid |
| M.S. | Mass spectrum |
| NaHMDS | Sodium hexamethyldisilazide |
| NMR | Nuclear magnetic resonance |
| NMM | N-Methylmorpholine |
| NMO | N-Methylmorpholine-N-oxide |
| NOE(SY) | Nuclear overhauser effect |
| PCC | Pyridinium chlorochromate |
| PDC | Pyridinium dichromate |
| PG | Protecting Group |
| PMB | para-Methoxybenzyl |
| PNA | Peptide nucleic acid |
| Piv | Pivaloyl |
| PS- | Polymer supported |
| PS-TBD | (1,5,7)-Triaza-bicyclo[4.4.0]dodeca-5-ene-7-methyl polystyrene |
| Pyr or Py | Pyridine |
| rac | Racemic |
| RAL | Resorcylic acid lactone |

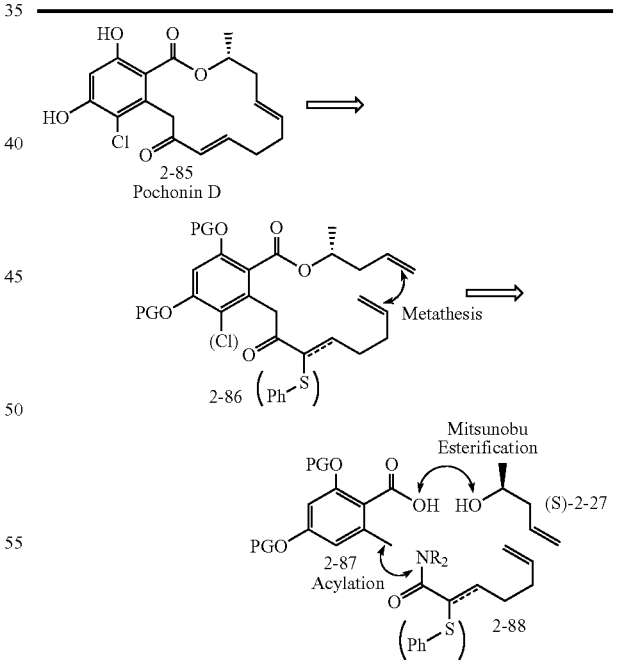

Retrosynthetic analysis for pochonin D based on radicol and pochonin C syntheses The Weinreb amide moiety 2-88 was synthesized as shown in Scheme 1. Thus, alkylation of intermediate 2-7 with 5-iodo-1-pentene yielded Weinreb amide 2-88 in two steps from thiophenol.

Scheme 1: First generation of Weinreb amide synthesis

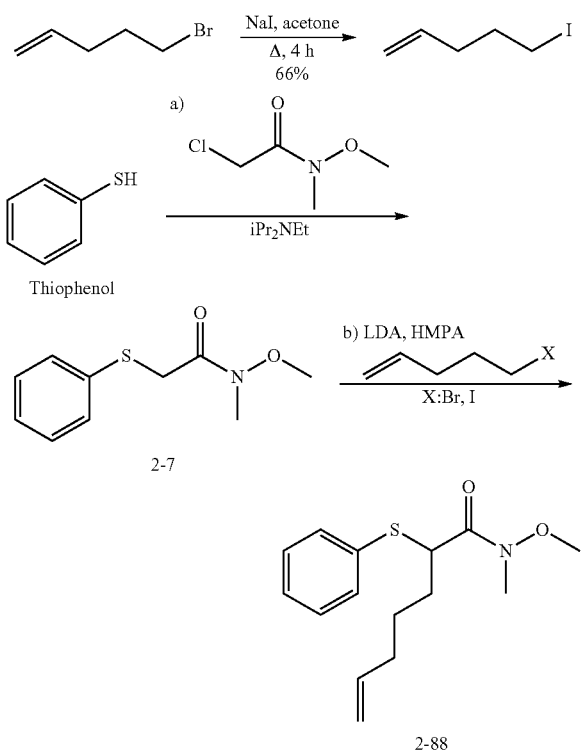

2-88

Best conditions: X = I, LDA 30 min at -78° C., HMPA 30 min at -78° C., on R.T.

a) thiophenol (1.0 equiv.), K$_2$CO$_3$ (1.0 equiv.) DMF, 23° C.; 2-chloro-N-methoxy-N-methylacetamide (1.0 equiv.), 23° C., 4 h, 95%; b) LDA (2.0 equiv.), HMPA (2.0 equiv.), 5-iodo-1-pentene (2.0 equiv.), -78 → 23° C., 13 h, 30%.

In parallel, an alternative synthetic pathway was developed, starting with commercially available cis-6-nonen-1-ol (Scheme 2).

Following a classical oxidation procedure (PDC in DMF), acid 2-89 was then α-chlorinated by formation of the enolate using LDA and subsequent chlorine addition using carbon tetrachloride (Snider, B. B. & Kulkarni, Y. S., *J Org Chem* 1987, 52, 307-310). After work-up, compound 2-90 was obtained as a black oil although as a pure compound by $^1$H NMR. Efforts to purify this acid proved disappointed and it was used directly in the following step. Further amide formation using N,O-dimethylhydroxylamine and EDC and displacement of the chlorine atom with thiophenol afforded compound 2-92 in 74% overall yield from cis-6-nonen-1-ol. Via the oxidation/elimination reaction, the thioether Weinreb amide 2-92 could be converted in its closely related derivative 2-93.

Due to the high cost of commercially available 2,4-dihydroxy-6-methylbenzoic acid, a protocol was developed that allows the synthesis of 2,4-dihydroxy-6-methylbenzaldehyde which can further be derivatized in the corresponding acid using various protecting groups (Scheme 3). Starting from orcinol and following a Vilsmeier-Haack procedure, aldehyde 2-94a was obtained in 45% yield (72% based on recovered S.M.). As described in the experimental section, this aldehyde precipitates at pH=7 and is recovered with good purity (>95% as judged by $^1$H NMR).

Scheme 3: Resorcylic acid synthesis from orcinol

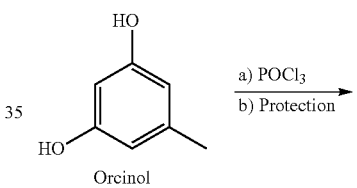

Orcinol

Scheme 2: Second generation of Weinreb amide synthesis

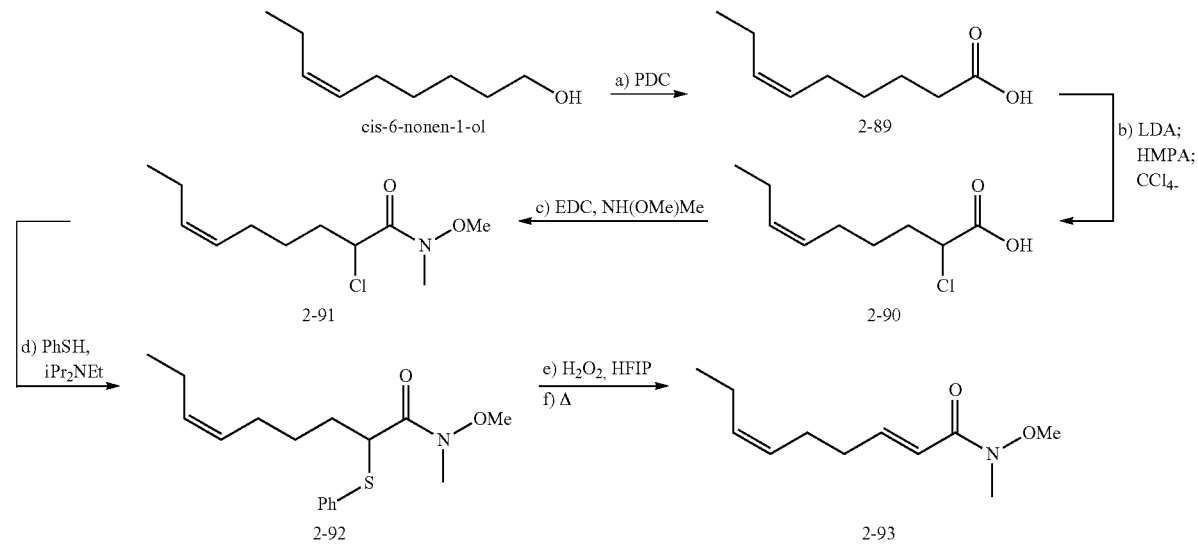

a) PDC (2.0 equiv.), DMF, 23° C., 12 h, quant.; b) iPr$_2$NH (2.6 equiv.), nBuLi (2.2 equiv.), HMPA, CCl$_4$ (5.0 equiv.), THF, -78 → 0° C., 3 h,
c) N,O-dimethylhydroxylamine hydrochloride (2.0 equiv.) DMAP (cat.), EDC (2.0 equiv.), CH$_2$Cl$_2$, 23° C., 4 h, 88% (2 steps); d) iPr$_2$NEt
(0.9 equiv.), thiophenol (0.9 equiv.), DMF, 80° C., 12 h, 84%; e) H$_2$O$_2$ (2.0 equiv.), HFIP, 23° C., 3 h; f) toluene, 80° C., 8 h, 75% over 2 steps.

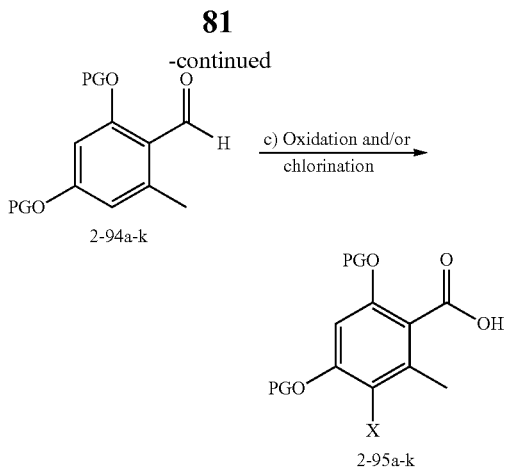

PG = H (a, b), Me (c, d), SEM (h), EOM (e, f, g), TBDPS (i, j, k)
X = H, Cl
a) POCl₃ (4.0 equiv.), DMF, 0 → 23 → 80° C., 3 h, 45%; b) General procedure: PGCl, iPrNEt, CH₂Cl₂, 23° C., 1 h, see experimental sections for each PG; c) See the following table.

Compound 2-94a was then protected with different groups to generate aldehydes 2-94c-k which were subsequently oxidized to afford the corresponding acids 2-95a-k in good yields (Scheme 3, Table 2). By varying the oxidation conditions, it was found possible to chlorinate the ring in a one pot sequence (oxidation/chlorination) in the required position for the synthesis of pochonin D.

Depending on the protecting group, two different acidic buffers ($NH_2SO_3H$ or $NaH_2PO_4$) and various solvent systems were used (Table 2). To avoid any chlorination reaction, a small percentage of DMSO as a mixture in THF/$H_2O$ along with sulfamic acid ((a) Lindgren, B. O. & Nilsson, *Acta Chem. Scand.* 27, 888-890 (1973), (b) Colombo, L et al., *J. Chem. Soc., Perkin Trans.* 1, 136-140 (1980)). proved to be essential and very effective to quench HOCl (entries a, c, j), (Dalcanale, E. & Montanari, F. Selective oxidation of aldehydes to carboxylic acids with sodium chlorite-hydrogen peroxide. *J Org Chem* 51, 567-569 (1986)). The one pot oxidation/chlorination sequence was done in absence of DMSO and required longer time to reach completion (entries b, d, f, h). Due to the acidic liability of the EOM protecting groups, $NaH_2PO_4$ was used as instead of sulfamic acid and the oxidation was carried out in pure DMSO. The bis-protected compound was selectively deprotected to afford the chlorinated analog of compound 2-95g in 77% yield over the two steps (vide infra). In the first sequence used for the synthesis of this pochonin, the mono-MOM protected acid 2-96 was used. Mitsunobu esterification under standard conditions (DIAD, PPh₃) between this acid 2-96 and racemic alcohol 2-27 afforded the desired ester 2-97 which was further converted to the bis-protected ester 2-98 (Scheme 4).

TABLE 2

Oxidation conditions to yield various protected resorcylic acid

| 2-95 | PG₁ | PG₂ | X | Acid | NaClO₂ | Solvent sytem[a] | Time[b] | Yield [%] |
|------|------|------|----|---------------------|-----------|---|---------|----|
| a | H | H | H | NH₂SO₃H | 3.25 equiv. | A | 1 h | 86 |
| b | H | H | Cl | NH₂SO₃H[c] | 2.0 equiv. | B | 12 h | 90 |
| c | Me | Me | H | NH₂SO₃H | 3.25 equiv. | A | 1 h | 82 |
| d | Me | Me | Cl | NH₂SO₃H | 3.25 equiv. | B | 12 h | 89 |
| e | EOM | EOM | H | NaH₂PO₄ | 5.0 equiv. | C | 12 h | 68 |
| f | EOM | EOM | Cl | NaH₂PO₄ | 5.0 equiv. | B | 12 h | 89 |
| g[d] | EOM | H | H | NaH₂PO₄ | 5.0 equiv. | C | 12 h | 87 |
| h | SEM | H | Cl | NH₂SO₃H | 3.25 equiv. | B | 12 h | 70 |
| i | TBDPS | H | Cl | NH₂SO₃H | 3.25 equiv. | B | 30 min | 93 |
| j | TBDPS | TBDPS | H | NH₂SO₃H | 3.25 equiv. | A | 30 min | 92 |
| k | TBDPS | TBDPS | Cl | NH₂SO₃H | 3.25 equiv. | B | 30 min | 95 |

[a]A: H₂O/THF/DMSO (20:10:1) or B: H₂O/THF (2:1) or C: DMSO,
[b]When run for more than 1 h, the reaction was heated up slowly to room temperature,
[c]In this case, only 2 equiv. of acid were used to avoid over-chlorination,
[d]This compound was previously assigned as compound 2-66.

Scheme 4: Synthesis of MOM protected Monocillin II (2-102)

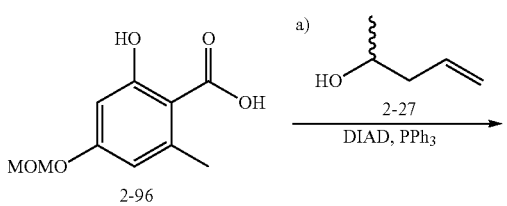

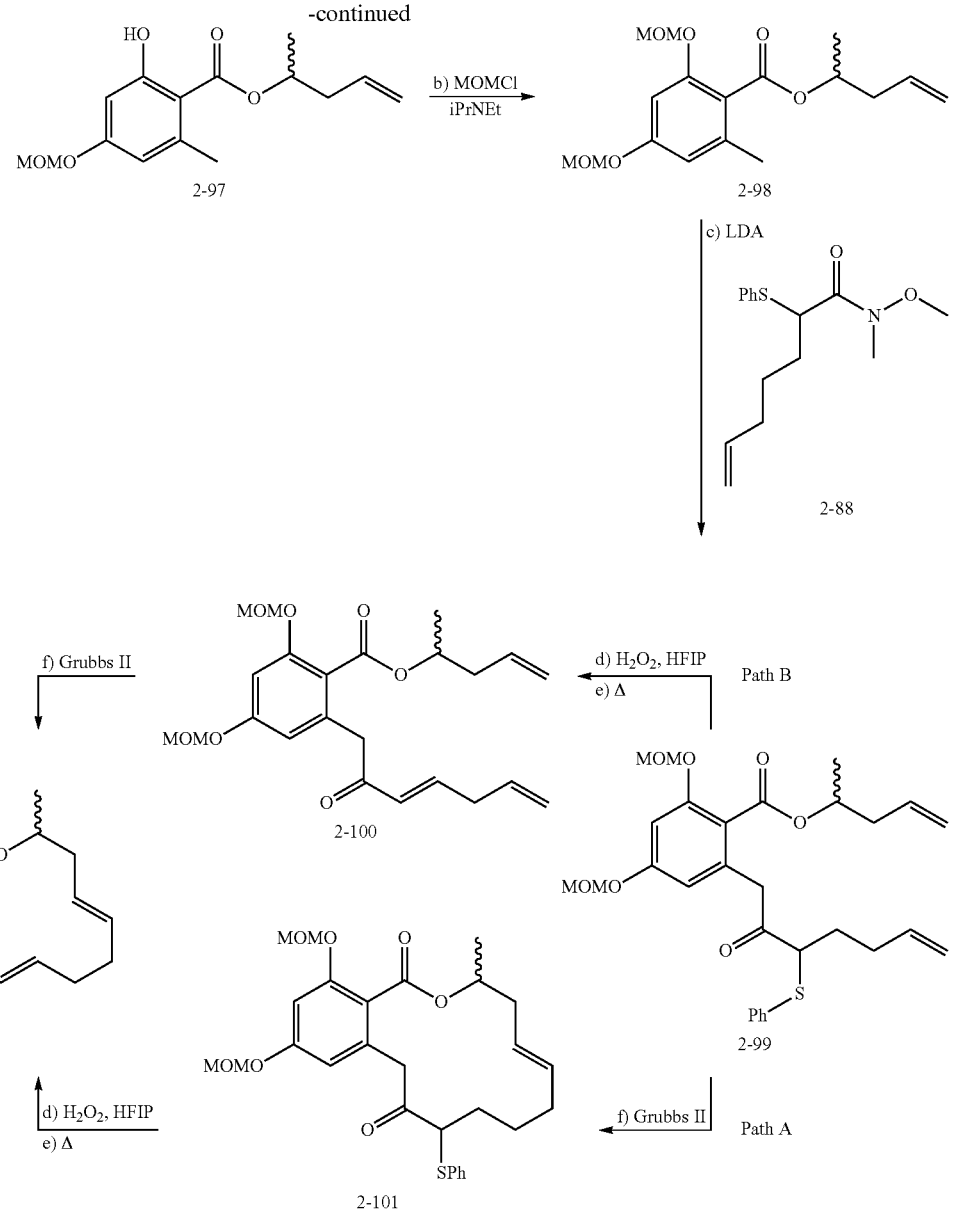

a) 2-27 (1.0 equiv.), P(mClPh)₃ (2.0 equiv.), DIAD (2.0 equiv.), toluene, 23° C., 3 h, 59%; b) MOMCl (4.0 equiv.), EtiPr₂N (4.0 equiv.), TBAI (cat.), DMF, 80° C., 3 h, 78%; c) LDA (2.0 equiv.), THF,. -78° C.; 2-88 (1.0 equiv.), 10 min, 50%; d) H₂O₂ (2.0 equiv.), HFIP, 23° C., 3 h; e) toluene, 80° C., 4 h, 68% two steps (Path A), 48% two steps (Path B); f: Grubbs' II (5% mol), toluene (2mM), reflux, 15 min, 63% (path A, trans/cis 4:1), quant. (path B, trans/cis 7:1).

Acylation using previously optimised conditions (2 equiv. of LDA at −78° C.) allowed the formation of the acyclic precursor 2-99 along with some unreacted starting material. Two different sequences (oxidation/elimination followed by ring-closing metathesis (path A) or vice-versa (path B)) to yield compound 2-102 were envisioned. Both pathways proved similar (same overall yield) albeit with a higher selectivity in the metathesis reaction when following path B (cis/trans ratio 7:1 vs. 4:1 for path A). Having compound 2-102, MOM deprotection and chlorination of the aromatic ring, was planned for the formation of pochonin D (2-85, Scheme 5).

Scheme 5: Synthesis of racemic Monocillin II (2-103)

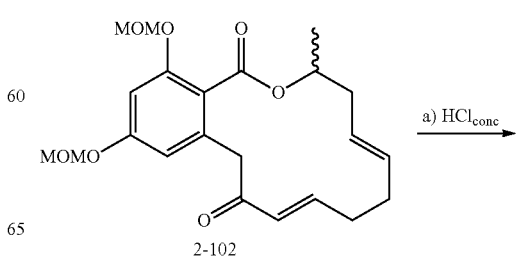

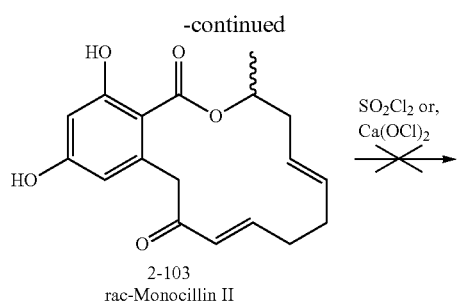

2-103
rac-Monocillin II

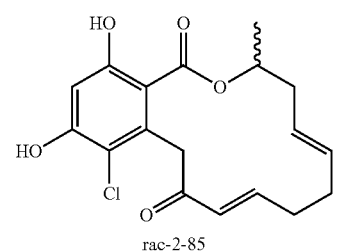

rac-2-85 a) HCl$_{conc}$ (2.5% in dioxane), 0 → 23° C., 1 h, 79%; b) SO$_2$Cl$_2$, Et$_2$O or CH$_2$Cl$_2$, 0° C., or Ca(OCl)$_2$, Acetone, H$_2$O/AcOH, 0° C.

Deprotection of the MOM groups following a well-known procedure allowed easily the generation of racemic monocillin II (2-103) but the chlorination to form pochonin D proved problematic.

As an alternative, starting with the chlorinated analog of acid 2-96 and following the two steps sequence developed for MOM-protected Monocillin II (Scheme 4), compound 2-104 was obtained in good quantities (Scheme 6). Although acylation reaction using Weinreb amide 2-7 led to the isolation of compound 2-103 in 37% yield, no reaction was observed when using Weinreb amide 2-88. As an alternate, the α,β-conjugated analog 2-93 was used directly.

Scheme 6: Acylation trials with various Weinreb amide

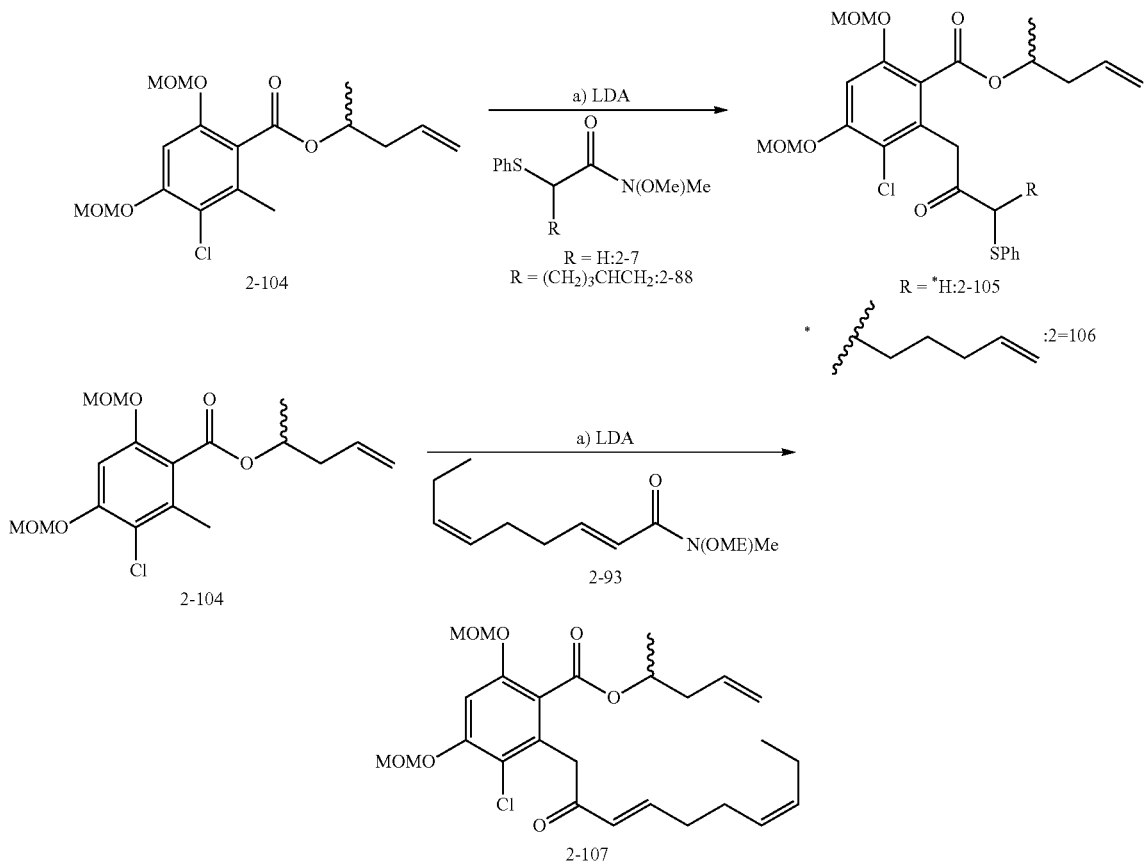

a) LDA (2.0 equiv.), THF, -78° C.; 2-7 or 2-88 or 2-93 (1.0 equiv.), 10 min, 37% (2-105), 40% (2-107).

Indeed, acylation reaction between the toluic anion of ester 2-104 and Weinreb amide 2-93 led to the isolation of acyclic compound 2-107 in 40% yield along with some unreacted starting material. The possibility of achieving the acylation reaction on the chlorinated toluic ester opened the door for the completion of pochonin D synthesis.

Total Synthesis of Pochonin D

EOM protecting groups were chosen for phenolic protection. Using the chemistry described above to synthesize toluic acids, mono-EOM chlorinated acid 2-108 was synthesized in three steps from formylated orcinol 2-94a (Scheme 7). The selective deprotection of the ortho-phenol was achieved using a specific concentration of TFA in a THF/MeOH mixture (THF/TFA/MeOH 7:1.5:1 (vol.)) without any bis-deprotection. Further Mitsunobu esterification using standard protocol (DIAD, PPh$_3$, toluene) and reprotection of the ortho-phenol allowed the formation of compound 2-110 in 51% yield from acid 2-108.

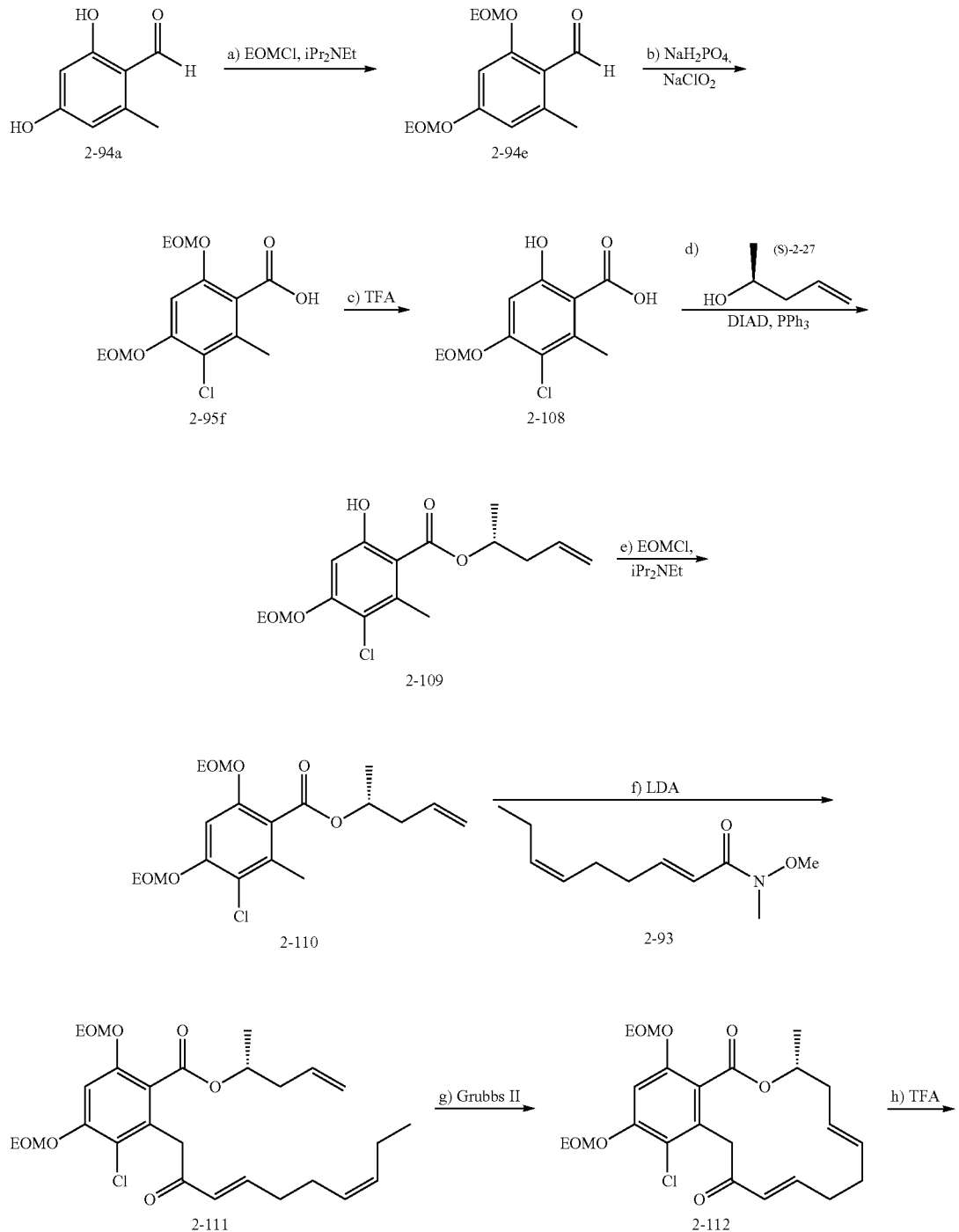

Scheme 7: First total synthesis of pochonin D

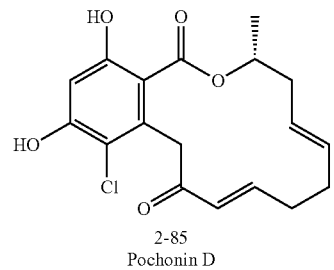

2-85
Pochonin D a) EOMCl (4.0 equiv.), iPr$_2$NEt (4.0 equiv.), CH$_2$Cl$_2$, 23° C., 1 h, 81%; b) NaH$_2$PO$_4$ (5.0 equiv.), NaClO$_2$ (5.0 equiv.), H$_2$O/THF 2:1, 0 → 23° C., 12 h, 89%; c) THF/TFA/MeOH 7:1.5:1, 23° C., 45 min, 80%; d) (S)-2-27 (1.0 equiv.), PPh$_3$ (2.0 equiv.), DIAD (2.0 equiv.), toluene, 23° C., 3 h, 72%; e) EOMCl (2.0 equiv.), Et/Pr$_2$N (2.0 equiv.), TBAI (cat.), DMF, 80° C., 3 h, 70%; f) LDA (2.0 equiv.), THF, -78° C.; 2-93 (1.0 equiv.), 10 min, 52%; g) Grubbs' II (10% mol), toluene (2 mM), 80° C., 12 h, 94%; h) TFA (20%), CH$_2$Cl$_2$, 23° C., 2 h, 72%.

Deprotonation of the toluic ester 2-110 followed by addition of Weinreb amide 2-93 afforded the desired metathesis precursor 2-111 in 52% yield along with some unreacted starting material. Treatment of triene 2-111 with the Grubbs' second generation catalyst ((a) Chatterjee, A. K., Morgan, J. P., Scholl, M. & Grubbs, R. H., *J Am Chem Soc* 122, 3783-3784 (2000), (b) Scholl, M., Ding, S., Lee, C. W. & Grubbs, R. H., *Org Lett* 1, 953-956 (1999)). at 120° C. for 15 min afforded the desired cyclization product 2-112 in an excellent yield albeit as an unseparable mixture of cis/trans olefins 1:4. Metathesis reaction under thermodynamic control at 80° C. overnight (Lee, C. W. & Grubbs, R. H. Stereoselectivity of Macrocyclic Ring-Closing Olefin Metathesis. *Org Lett* 2, 2145-2147 (2000)) shifted the equilibrium to the trans intermediate 2-112 with >95% selectivity (as judged by $^1$H NMR) and 94% yield. It should be noted that this reaction could be performed at millimolar concentration without any detectable amount of dimerization or oligomerization. Importantly, the 10-membered ring macrocycle was not observed. Further EOM deprotection using TFA in dichloromethane allowed the first total synthesis of pochonin D which was found to have an identical NMR spectrum to the natural product.

For the purpose of diversity-oriented synthesis and as the presence of a thioether linkage was not possible having the chlorine atom on the aromatic ring, a more concise synthesis of pochonin D with polymer-supported reagents was developed ((a) Ley, S. V. & Baxendale, I. R., *Nat Rev Drug Discov* 1, 573-86 (2002), (b) Ley, S. V. et al., *J. Chem. Soc., Perkin Trans.* 1 23, 3815-4195 (2000)). The Mitsunobu reaction using directly 2,4-dihydroxy-6-methylbenzoic acid was envisaged leading to an even more concise pathway to pochonin D. As (S)-4-penten-2-ol ((S)-2-27) is commercially available, improvements to the sequence leading to the aliphatic Weinreb amide 2-93 were undertaken. A protocol using solid-support was developed to minimize the need to purification of intermediates and final product. Commercially available 2-chloro-N-methoxy-N-methylacetamide (Scheme 8) was selectively S-alkylated with 3-mercaptophenol using one equivalent of base, and then loaded onto Merrifield resin in the same pot reaction by the successive addition of a second equivalent of K$_2$CO$_3$, the resin, and raising the temperature to 50° C.

Scheme 8: Solid-phase synthesis of Weinreb amide 2-114

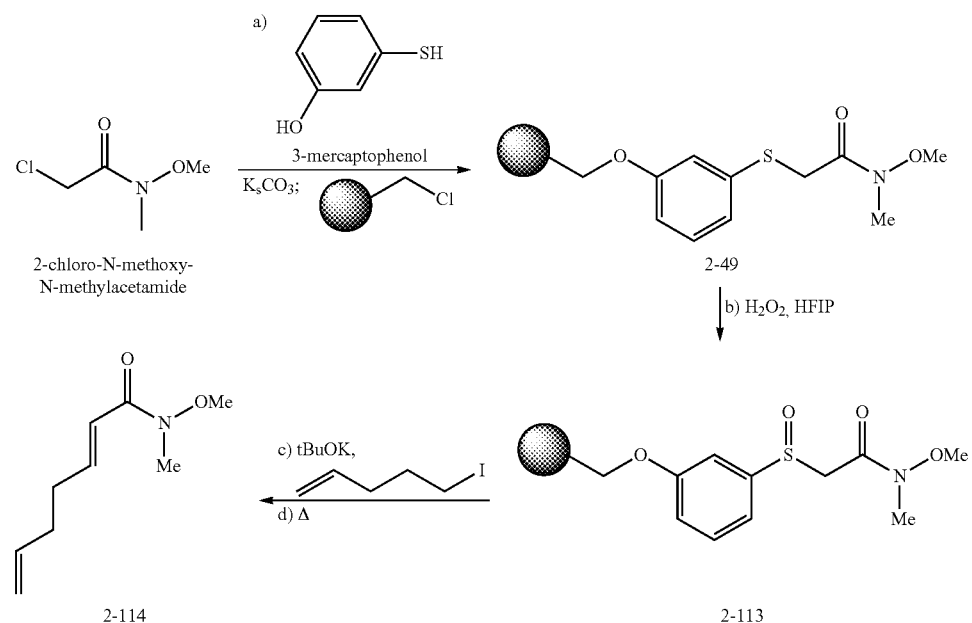

a) 3-mercaptophenol (1.0) equiv.), K$_2$CO$_3$ (1.0 equiv.), DMF, 23° C., after 8 hours, K$_2$CO$_3$ (1.7 equiv.), Merrifield resin, TBAI (cat.), 12 h, 50° C., 98%; b) H$_2$O$_2$ (2.0 equiv.), HFIP/CH$_2$Cl$_2$ 1:1, 12 h; c) tBuOK (1.0 equiv.), 5-iodo-1-pentene (1.0 equiv.), DMSO, 23° C., 3 h; d) toluene, 80° C., 8 h, 77%.

This method afforded the polymer-bound Weinreb amide 2-49 in one step. Oxidation of the thioether 2-49 to the corresponding sulfoxide 2-113 was carried out using the aforementioned procedure involving $H_2O_2$ in $HFIP/CH_2Cl_2$ (Ravikumar, K. S., Begue, J.-P. & Bonnet-Delpon, D. A selective conversion of sulfide to sulfoxide in hexafluoro-2-propanol. *Tetrahedron Letters* 39, 3141-3144 (1998)). This oxidation procedure was found practical and reliable with no over-oxidation to the sulfone and easy recycling of the fluorinated solvent as the reaction was carried out on solid phase. The amidosulfoxide 99 was then deprotonated with tBuOK, and the resulting enolate was quenched with 5-iodo-1-pentene. Use of DMSO avoided sulfoxide elimination, and the reaction could be heated up to 60° C. Resuspension of the resin in toluene and heating up to 80° C. released, after elimination, the desired fragment 2-114 with 77% yield and 95% purity (judged by $^1H$ NMR). This methodology on solid support was found very practical in terms of yield and purity of the building block 2-114 as no column chromatography was needed.

Based on the chemistry developed in solution (Scheme 7), a selective Mitsunobu esterification of 2,4-dihydroxy-6-methylbenzoic acid (2-95a) with (S)-4-penten-2-ol ((S)-2-27) using polymer-bound DEAD afforded ester 2-116 (Scheme 9). The use of $(mClPh)_3P$ was found essential to suppress any competing ether formation with the para-phenol. Protection of both phenols with EOM groups afforded non-chlorinated ester 2-117, which could be used in the subsequent alkylation without further purification.

Scheme 9: Synthesis of intermediate 2-110 and 2-117 using polymer-bound reagents

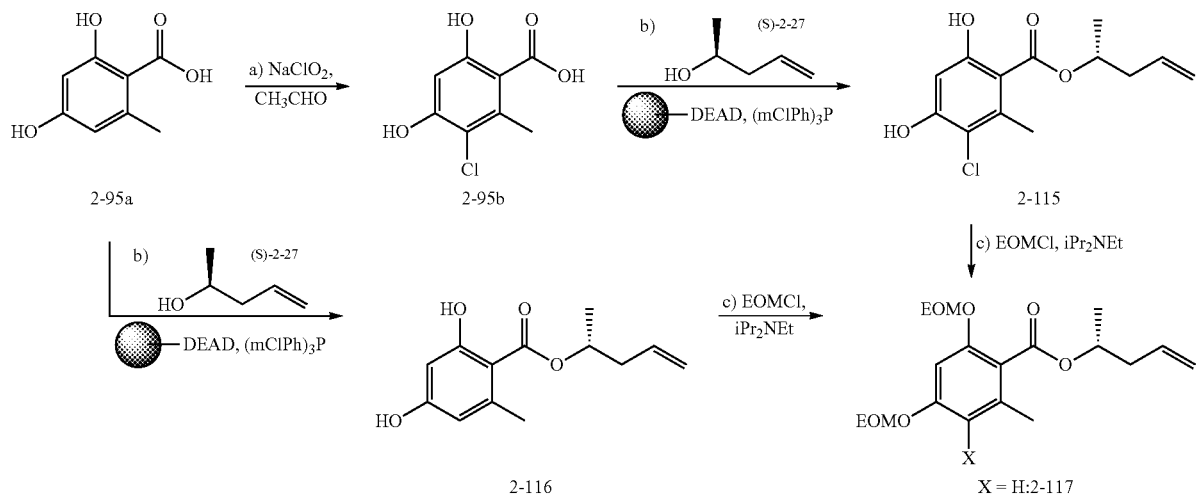

a) $NaClO_2$ (5.0 equiv.), $NH_2SO_3H$ (5.0 equiv.), $CH_3CHO$ (1.0 equiv.), $THF/H_2O$ 5:1, 0° C., 0.5 h, 92%; b) PS-DEAD (2.5 equiv., 1.3 mmol.g-1), (S)-4-penten-2-ol (1.0 equiv.), $P(mClPh)_3$ (2.0 equiv.), $CH_2Cl_2$, 23° C., 0.5 h, 68% for 2-117 and 65% for 2-110; c) iPrEtN (4.0 equiv.), EOMCl (4.0 equiv.), TBAI (cat.), DMF, 80° C., 5 h, 95%.

The chlorine was introduced prior to esterification using HClO generated in situ by the oxidation of acetaldehyde with $NaClO_2$/sulfamic acid. Acid 2-95b was obtained from its non-chlorinated parent 2-95a in 92% yield without seeing any over-chlorination. Esterification of this product under the same conditions as for 2-95a afforded compound 2-115. Further bis-protection with EOM groups led to ester 2-110 which could also be used in subsequent reactions without any purification. Deprotonation of the toluic esters 2-110 and 2-117 followed by addition of Weinreb amide 2-114 afforded the desired metathesis precursors 2-118 and 2-119 which could be used directly in the following step (Scheme 10). When the acylation reaction was performed on the non-chlorinated ester 2-117, 20% of product stemming from a 1,4-conjugated addition on the Weinreb amide was obtained.

Scheme 10: Synthesis of pochonin D (2-85) and monocillin II (2-103) using supported reagents

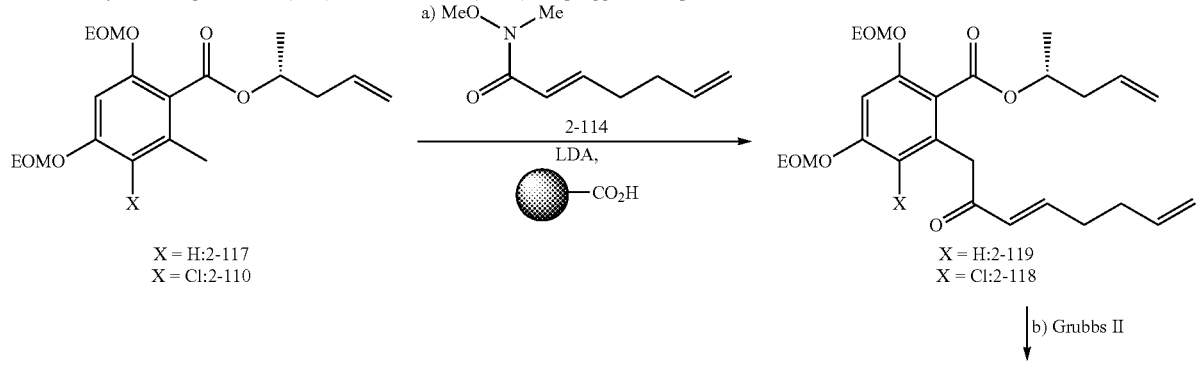

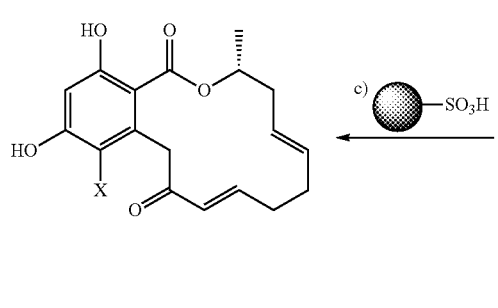
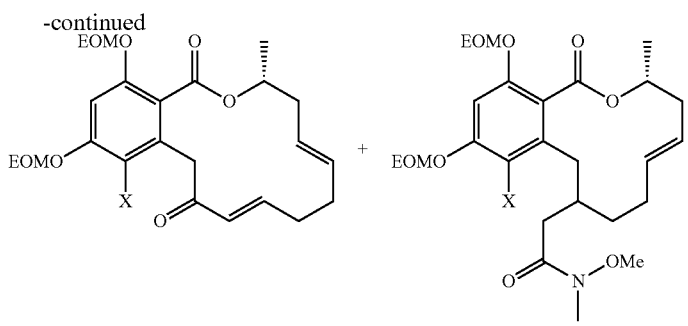

X = H:2-103 (Monocillin II)  
X = Cl:2-85 (Pochonin D)

X = H:2-120  
X = Cl:2-112

2-121 a) LDA (2.0 equiv.), THF, -78° C.; 2-114 (1.0 equiv.), 10 min, Amberlite IRC-50 (20.0 eq. 10.0 mmol.g$^{-1}$); b) Grubbs' II (10% mol.) toluene (2mM), 80° C., 12 h, 40% for 2-120 and 44% for 2-112 after two steps; c) PS-TsOH (10 equiv., 3.2 mmol.g$^{-1}$), MeOH, 40° C., 4 h, 90% for 2-85 and 92% for 2-103.

Treatment of crude trienes 2-118 and 2-119 with the Grubbs' second generation catalyst under thermodynamic control at 80° C. overnight led exclusively (more than 95% selectivity) to the trans macrocycles 2-112 and 2-120. A simple filtration through a path of silica was then used to remove all of the catalyst and its by-products, affording compound 2-112 in 44% yield over two steps. While the metathesis reaction carried out on purified triene 2-118 was nearly quantitative, it was found more practical to carry out the whole synthetic sequence from compound 2-95a without any purification, thus affording the protected pochonin D 2-112 in 25% yield over five steps. Purification with column chromatography isolated 2-120 from the 12-membered macrocycle 2-121. Removal of EOM groups from both macrocycles 2-112 and 2-120 using sulfonic acid resin in MeOH allowed the synthesis of both pochonin D (2-85) and monocillin II (2-103) in 90% and 92% yield, respectively. As shown for the acylation reaction, the presence or absence of the chlorine atom on the aromatic ring seems to influence the reactivity of the conjugated olefin. Indeed, deprotection of compound 2-120 with HCl (2.5% in dioxane) led to the conjugated addition of the chlorine ion, whereas compound 2-112 could be deprotected with HCl to obtain pochonin D (2-85). This synthesis using polymer-supported reagents allowed the achievement of pochonin D and monocillin II in six (23% yield) and five (24% yield) steps respectively. Starting from commercially available building blocks, only one chromatographic purification of the final compound is required for all the synthetic pathway and this methodology could be used for the synthesis of libraries. Evaluation for HSP90 affinity in a competition assay with geldanamycin revealed that pochonin D is a good ligand for HSP90 with an IC$_{50}$ of 80 nM as compared to 20 nM for radicicol (vide infra).

II Synthesis of Pochonin A

Having access to pochonin D (2-85), pochonin A (2-122) was then prepared not only to confirm its structure but also to compare its biological activity to pochonin D and radicicol.

-continued

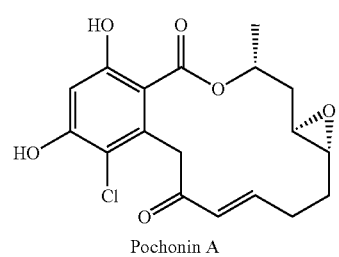

Pochonin A 2-122

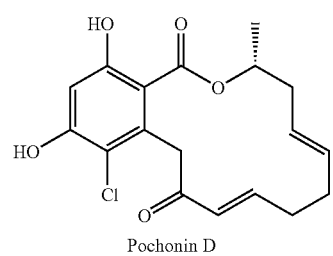

Pochonin D 2-85

Epoxidation of pochonin D using DMDO allowed the formation of pochonin A as a 1:1 mixture of diastereoisomers that could be separated by column chromatography. An alternate route is depicted in Scheme 11. Epoxidation of bis-EOM protected pochonin D (2-112) also gave the epoxide as a mixture of diastereomers.

Scheme 11: Direct conversion of bis-EOM pochonin D (2-112)

2-1

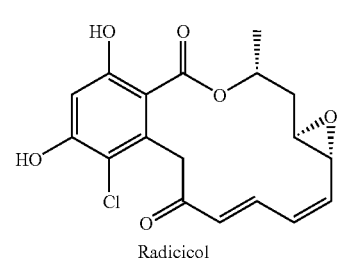

Radicicol

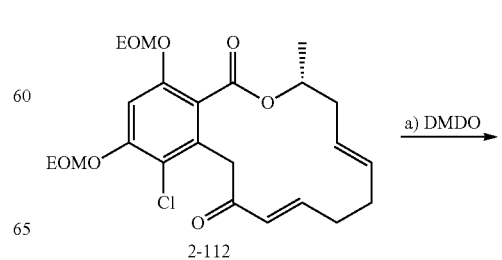

2-112

95
-continued

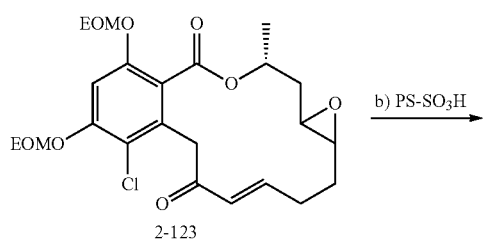

2-123

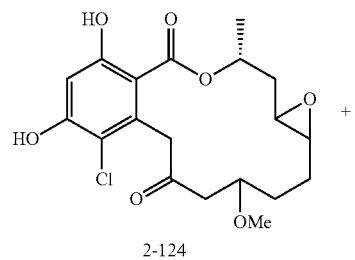

2-124

96
-continued

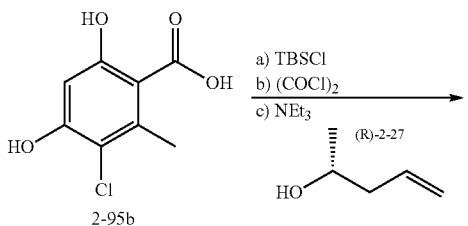

2-125 a) DMDO (1.0 equiv.), CH₃CN, 0° C. → 23° C., 1.5 h, 79%; b) PS-TsOH (10.0 equiv., 3.2 mmol.g⁻¹), MeOH, 40°C., 1 h.

The suitability of silyl based protecting groups to access this type of molecules was investigated. Thus, persilylation of benzoic acid 81b (Scheme 12), followed by "acid-free" conversion of the silyl ester to the corresponding acyl chloride yielded key intermediate 112 upon esterification with alcohol (R)-27 (Wisnner, A. & Grudzinskas, C. V., *J Org Chem* 43, 3972-3974 (1978)).

Scheme 12: Pochonin A synthesis using TBS-protecting groups

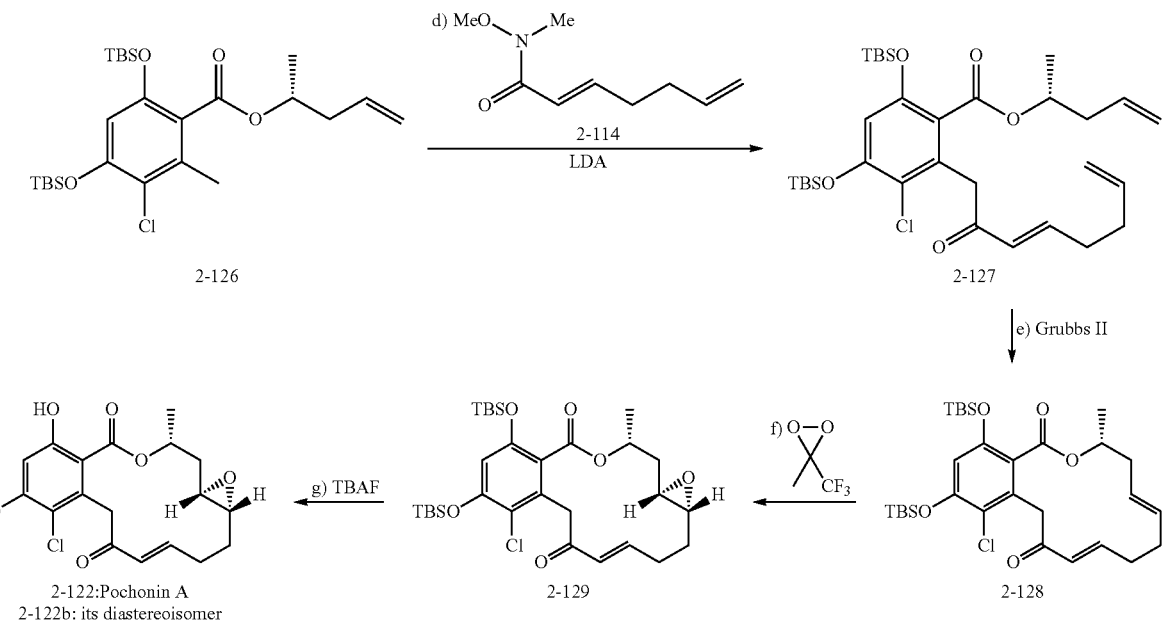

a) iPr₂EtN (6.0 equiv.), TBSCl (3.0 equiv.), CH₂Cl₂, 23° C., 3 h; b) Oxalyl chloride (1.0 equiv.), DMF (cat.), CH₂Cl₂, 0 → 23° C., 1 h; c) Et₃N (2.26 equiv.), R-(-)-penten-2-ol (3.0 equiv.), DMAP 0 → 23° C., 12 h, 29% over 3 steps; d) LDA (2.0 equiv.), THF, -78° C., Weinreib amide 100 (1.0 equiv.), 10 min 35%; e) Grubbs' II (10% mol), toluene (2 mM), 80° C., 12 h, 79%; f) CF₃COCH₃, NaHCO₃ (7.0 equiv.), Oxone (4.7 equiv.), Na₂•EDTA (4 x 10⁻⁴M), CH₃CN/Dimethoxymethane, 0° C., 2 h, 83%; g) TBAF (2.2 equiv.), THF, 23° C., 20 min, 80%, 3:1 mixture of diastereoisomers.

Deprotonation of the toluic ester 2-126 followed by reaction with Weinreb amide 2-114 afforded metathesis precursor 2-127. Ring-closing metathesis using Grubbs' second generation catalyst under aforementioned thermodynamic conditions (80° C., overnight) afforded macrocycle 2-128 in good yield and excellent cis/trans ratio (<5% cis). Epoxidation of the non-conjugated olefin was optimal when carried out at 0° C. with methyl(trifluoromethyl)-dioxirane generated in situ (Yang, D., et al. *J. Org. Chem.,* 60, 3887-3889 (1995) affording TBS-protected pochonin A (2-129) in excellent yield as an inseparable 3:1 diastereoisomeric mixture. Deprotection of compound 2-129 using classical silyl deprotection conditions (TBAF in THF) afforded a separable diastereomeric mixture and confirmed that the major product was indeed the desired pochonin A (2-122).

Alternative protecting groups were evaluated to improve the yield of the esterification and acylation reactions. Based on their stability toward basic conditions but also on their liability towards TBAF, SEM protecting groups were considered. Following the procedure described for the polymer-assisted synthesis of pochonin D, selective Mitsunobu reaction between benzoic acid 2-95b and chiral alcohol (S)-2-27 using polymer-bound DEAD and subsequent protection with SEM-Cl afforded ester 2-130 in 72% yield (Scheme 13).

Acylation of toluate ester 2-130 using Weinreb amide 2-114 led to the isolation of the acyclic precursor 2-131 in 60% yield. Treatment of the triene 2-131 with the Grubbs' second generation catalyst under thermodynamic conditions (80° C., overnight) afforded the corresponding macrocycle 2-132 in 87% yield (<5% cis olefin), which was epoxidized under the same conditions as for the TBS-protected compound 2-128 [methyl(trifluoromethyl)-dioxirane], yielding compound 2-133 in 83% yield albeit in a 1:1 diastereomeric ratio (inseparable). Deprotection of 2-133 was achieved with 8.0 equiv. of MgBr$_2$.Et$_2$O affording the desired pochonin A (2-122) along with its diastereoisomer (2-122b) as a separable mixture. Pochonin A was found to be a good ligand of HSP90 with an IC$_{50}$ of 90 nM (vide infra).

III. Diversity Oriented Synthesis of Pochonin Analogues

With the objective to extend the diversity of the compounds in the hope of finding new ATPase and kinase inhibitors, a library of pochonin analogues was prepared and evaluated for biological activity. This library was envisioned to stem from five points of diversity around the resorcylic macrolide scaffold: modifications of the para-phenol ($R^1$, a number of natural resorcylides bearing a methyl group at this position), the group on C17 ($R^2$, both stereochemistry are present in natural resorcylides; however, only with a methyl substituent), Scheme 13: Pochonin A synthesis using SEM-protecting groups

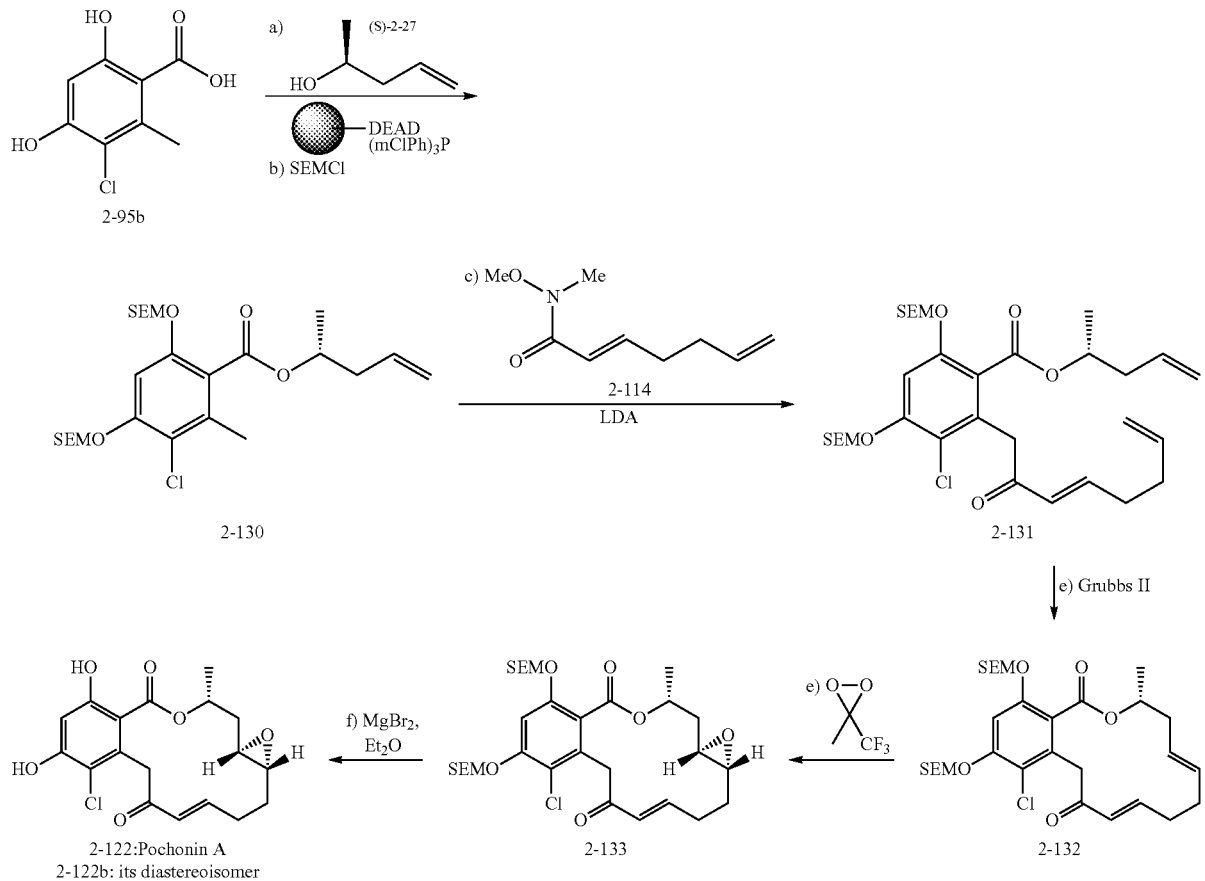

a) PS-DEAD (2.5 equiv., 1.3 mmol.g$^{-1}$), S-(-)-4-penten-2-ol (2.0 equiv.), P(mClPh)$_3$ (2.0 equiv.), toluene, 23° C., 10 min; b) NaH 60% (4.0 equiv.), SEMCl (4.0 equiv.), THF, 0° C., 2 h, 72% over 2 steps; c) LDA (2.0 equiv.), THF, -78° C., Weinreib amide 2-114 (1.0 equiv.), 10 min, 60%; d) Grubbs' II (10% mol), toluene (2 mM), 80° C., 12 h, 87%; e) DMDO (1.0 equiv.), CH$_3$CN, 0 → 23° C., 1.5 h, 83%, 1:1 mixture of diastereoisomers; f) MgBr$_2$•Et$_2$O (8.0 equiv.), CH$_2$Cl$_2$, 23° C, 1 h, 70%.

General structure and retrosynthetic analysis of the library

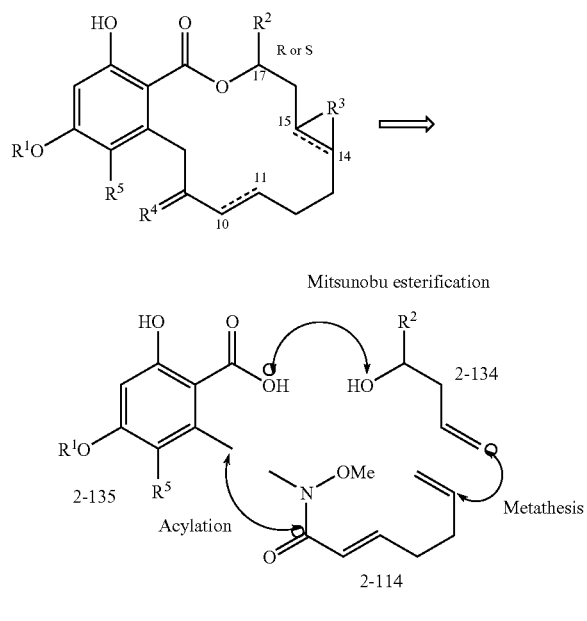

the C14-C15 olefin ($R^3$), the C9 carbonyl ($R^4$), the olefin C10-C11, and the meta position on the aryl ring ($R^5$, a number of natural resorcylides bear a chlorine at this position). To minimize traditional chromatography, the synthesis was conducted with polymer-bound reagents. The assembly of the macrocycle relied on the chemistry developed for the synthesis of pochonin D using polymer-bound reagents (Schemes 9 and 10).

A variety of homoallylic alcohols 2-134 bearing various substituent at $R^2$ was prepared. Homoallylic alcohols 2-134 that are not commercially available may be obtained in by any suitable method. In one embodiment, the homoallylic alcohols 2-134 were obtained in their highest enantiomeric form either by enzymatic resolution of the racemic alcohol (H. E. Master et al., Tet. Lett., 37:9253 (1996); S. Singh et al., Tet. Asymm., 13:2679 (2002) or via Brown allylation of the corresponding aldehyde (H. C. Brown and P. K. Jadhav J. Am. Chem. Soc., 105:2092 (1983). The phenyl (2-134a), the pyridinyl (2-134b) and the furyl (2-134c) alcohols were prepared by enzymatic resolution (Scheme 14). Racemic alcohols 2-134a-c were obtained after Grignard addition of commercially available allylmagnesium bromide on their corresponding aldehyde 2-134a-c.

Scheme 14: Synthesis of chiral alcohols 2-134a-c using enymatic resolution

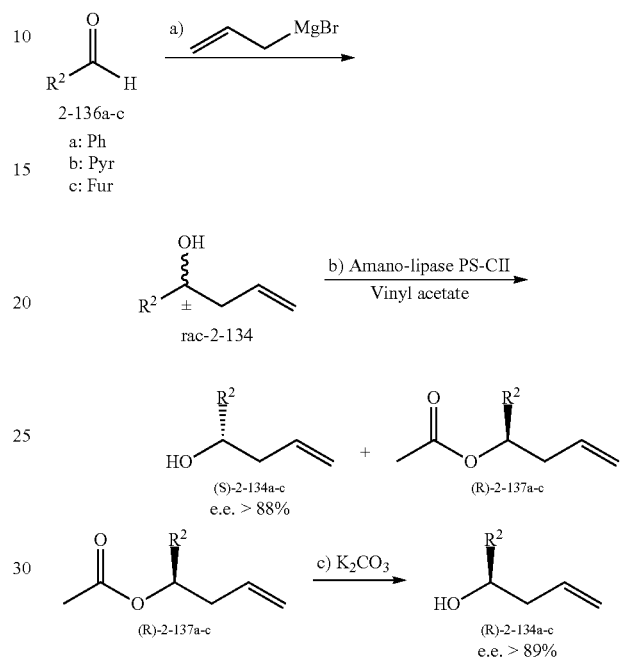

a) AllyMgBr (1.5 equiv.), THF, 0.5 h, 0° C., 71% (2-134a), 41% (2-134b), 74% (2-134c); b) $R^2$ = Ph: vinyl acetate (32.5 equiv.), Amano Lipase PS-C II (50 mg/mmol of 2-134), 23° C., 30 h (monitored by $^1$H NMR), $R^2$ = Pyr, Fur: vinyl acetate (10.0 equiv.), Amano Lipase PS-C II (50 mg/mmol of 2-134), THF, 23° C., 5-30 h (monitored by $^1$H NMR); c) $K_2CO_3$ (0.8 equiv.), MeOH, 23° C., 98% ((R)-2-134a), 92% ((R)-2-134b), 84% ((R-2-134c).

Kinetic enzymatic resolution of racemic alcohols 2-134a-c was realized using the highly efficient Amano lipase (an immobilized version of *Pseudomonas cepacia*). This enzyme catalyzed a selective transesterification of alcohols (R)-2-134a-c with vinyl acetate as an acyl donor, the (S) alcohols 2-134a-c being isolated in excellent yields and good enantiomeric excesses (Table 3).

TABLE 3

Enantioselective acylation of alcohols rac-2-134a-c by transesterification with lipase

| Entry | Substrate | Time (h) | Conv. Ratio (%) (OH/OAc) | Yield (%) (S)-2-134 | e.e. (%) (S)-2-134 | Yield (%) (R)-2-134 | e.e. (%) (R)-2-134 |
|---|---|---|---|---|---|---|---|
| 1 | rac-2-134a | 30 | 50:50 | 45 | 98 | 49 | 93 |
| 2 | rac-2-134b | 30 | 52:48 | 50 | 89 | 39 | 94 |
| 3 | rac-2-134c | 5 | 49:51 | 44 | 88 | 49 | 89 |

Enantiomeric excess obtained with this methodology are all above 88%. Acetylated alcohols (R)-2-137 were then hydrolysed to the corresponding alcohols (R)-2-134a-c in excellent yields. In addition, a second process based on Brown allylation was developed for the synthesis of the isopropyl (2-134d), the propyl (2-134e) and the benzyl (2-134f) alcohols (Scheme 15).

Scheme 15: Synthesis of chiral alcohols 120d-f using Brown allylation

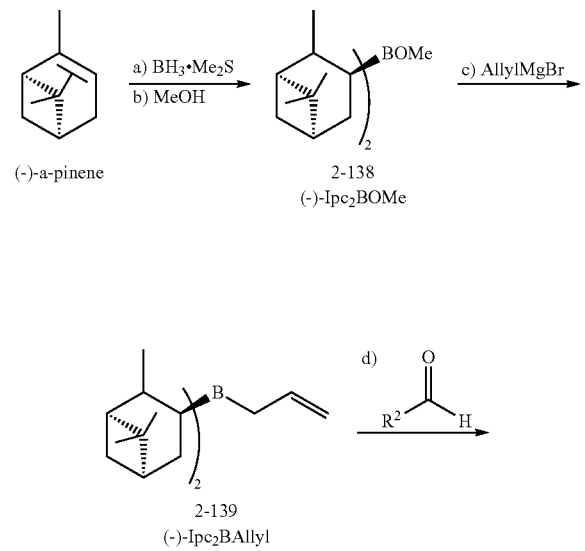

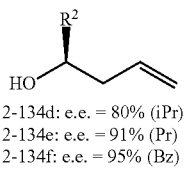

2-134d: e.e. = 80% (iPr)
2-134e: e.e. = 91% (Pr)
2-134f: e.e. = 95% (Bz)

a) (−)-α-pinene (2.4 equiv.), BH$_3$·Me$_2$S (1.0 equiv.), THF, 23° C. for 1 h and then 4° C. for 12 h, 76%; b) MeOH (1.2 equiv.), Et$_2$O, 0° C., 2 h, 94%; c) AllylMgBr (0.95 equiv.), Et$_2$O 0 → 23° C., 1 h, 92%; d) 122d-f (1.05 equiv.), Et$_2$O, -100° C., 0.5 h; 3N NaOH, H$_2$O$_2$ 35%, reflux, 3 h, 77-93%. Enantiomeric excesses of alcohols were determined by chiral HPLC analysis after acylation with 3,5-dinitrobenzoyl chloride.

(−)-B-Allyldiisopinocampheylborane (2-139, (−)-Ipc$_2$BAllyl) was synthesized in a three steps sequence from (−)-α-pinene involving an hydroboration, the formation of the corresponding MeO-borinic ester 2-138 and its treatment with a Grignard reagent. Further condensation on aldehydes 2-134d-f followed by oxidation of the resulting borinates with alkaline hydrogen peroxide allowed the formation of the chiral homoallylic alcohols 2-134d-f in good enantiomeric excess.

The macrocycle assembly was modeled after the synthesis of pochonin D. (E. Moulin, V. Zoete, S. Barluenga, M. Karplus, N. Winssinger, *J. Am. Chem. Soc.*, 127:6999 (2005)). Thus as shown in Scheme 16, commercially available benzoic acid 2-95a and its chlorinated analog 2-95b (the chlorine atom was introduced on acid 2-95a prior to esterification using HClO generated in situ by the oxidation of acetaldehyde with NaClO$_2$/sulfamic acid were esterified with a variety of homoallylic alcohols using polymer-supported DEAD to yield esters 2-115a-g and 2-116a-g in excellent purity. (E. Moulin et al., *J. Am. Chem. Soc.*, 127:6999 (2005)). The products 2-115a-g and 2-116a-g were then protected with ethoxymethylene chloride (EOM-Cl) in the presence of Hunig's base to obtain the corresponding protected toluic esters 2-110a-g and 2-117a-g which could be used in the subsequent carbon-acylation reaction without further purification.

Scheme 16: Synthesis of macrocyclic precursors 2-112a-g, 2-120a-g and 2-121a-g

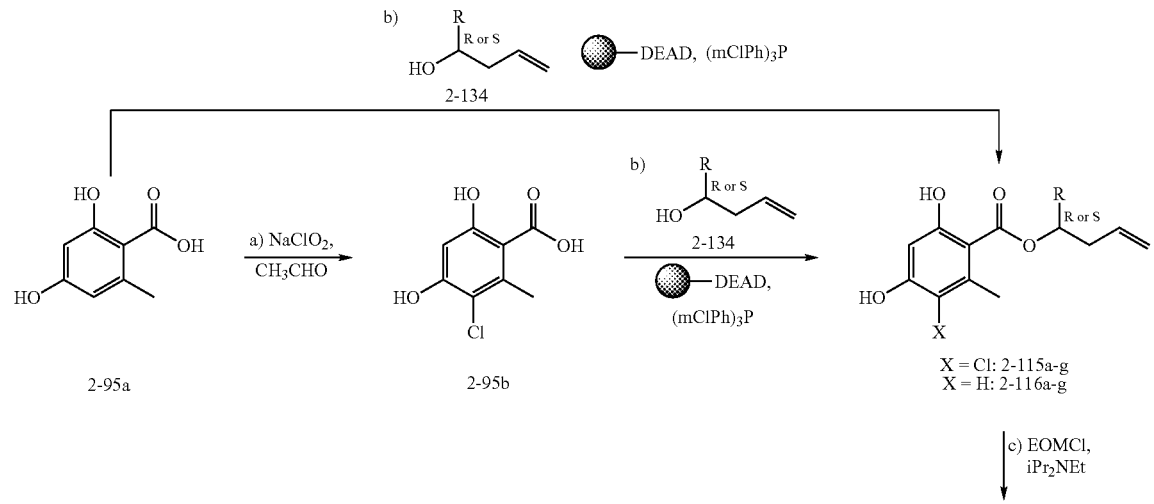

-continued

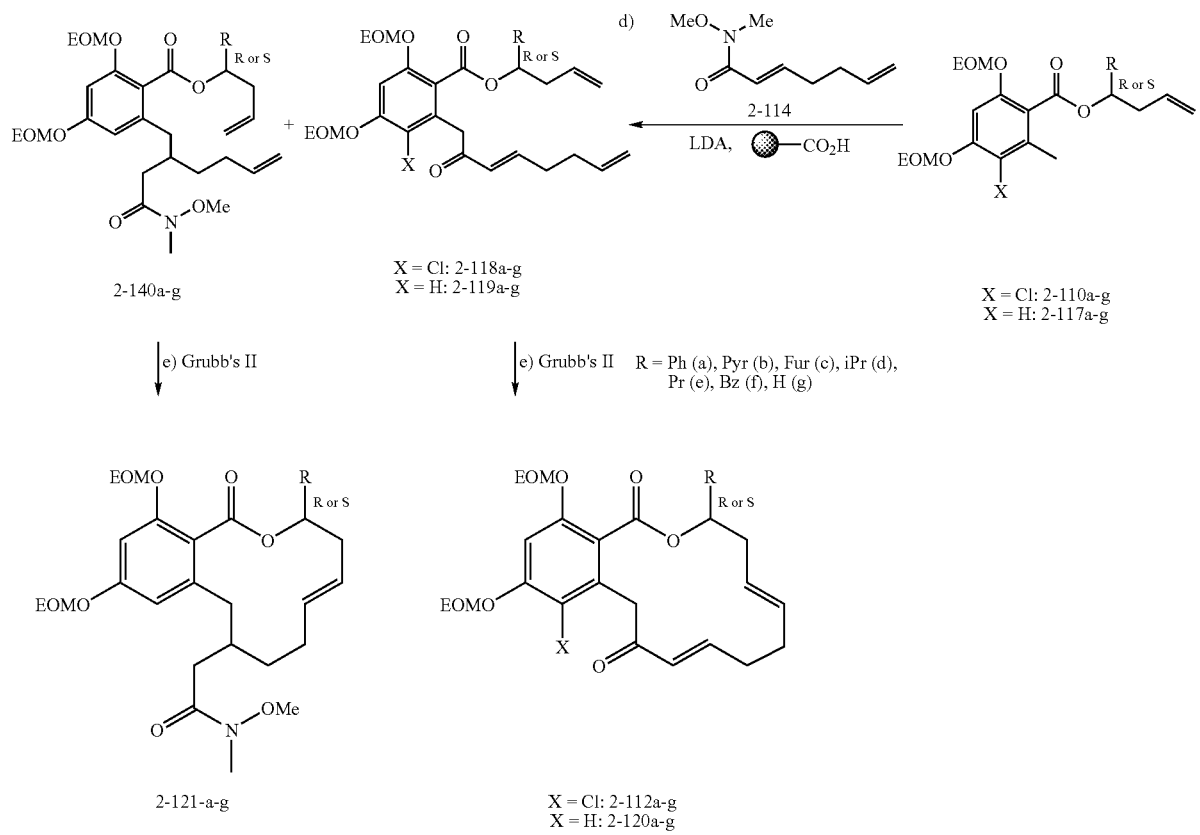

a) NaClO$_2$ (5.0 equiv.), NH$_2$SO$_3$H (5.0 equiv.), CH$_3$CHO (1.0 equiv.), THF/H$_2$O 5:1, 0° C., 0.5 h, 92%; b) PS-DEAD (2.5 equiv., 1.3 mmol.g$^{-1}$), (R)- 2-134a-g or (S)- 2-134a-g (1.0 equiv.), P(mClPh)$_3$ (2.0 equiv.), CH$_2$Cl$_2$, 23° C., 0.5 h, 60-80%; c) iPr$_2$EtN (4.0 equiv.), EOMCl (4.0 equiv.), TBAI (cat.), DMF, 80° C., 5 h, 80-90%; d) LDA (2.0 equiv.), THF, -78° C., 2-114 (1.0 equiv.), 10 min, Amberlite IRC-50 (20.0 eq, 10.0 mmol.g$^{-1}$); e) Grubbs' II (10% mol), toluene (2 mM), 80° C., 12 h, 38-70% after two steps.

Deprotonation of the toluic esters 2-110a-g and 2-117a-g using two equivalents of LDA, followed by addition of the α,β-unsaturated Weinreb amide prepared via solid phase chemistry (E. Moulin et al., *J. Am. Chem. Soc.*, 127:6999 (2005)) afforded acylation products 2-118a-g and 2-119a-g. The reaction was quenched with a polymer bound acid which also sequestered all the diisopropyl amine. This reaction can lead to some level of 1,4-conjugate addition product (S. Barluenga et al., *Chem. Eur. J.*, 11:4935 (2005)). While the bulky chlorine present in pochonin D suppresses this reaction, compounds lacking the aryl chloride afforded 20% of the conjugate addition products 2-140a-g. Nevertheless, the crude mixtures of these reactions were used in the subsequent cyclization step. The trienes were then subjected to ring closing metathesis using Grubbs' second generation catalyst (A. K. Chatterjee et al., *J. Am. Chem. Soc.*, 122:3783 (2000); M. Scholl et al., *Org. Lett.*, 1:953 (1999)) under thermodynamic conditions (C. W. Lee, and R. H. Grubbs, *Org. Lett.*, 2:2145 (2000)), affording the desired 14-membered macrocycles. In the cases where metathesis reactions were carried out with a mixture of 2-118a-g, 2-119a-g and 2-140a-g, the corresponding 12-membered ring products 2-121a-g were obtained in addition to 2-112a-g and 2-120a-g as a separable mixture. All successful reaction sequences were purified by standard chromatography yielding the macrocycle 2-112a-g and 2-120a-g and 2-121a-g in 30-60% and 8-10% overall yield respectively from 2-95.

Macrocycles 2-112a-g and 2-120a-g were then used as the starting point for further diversifications. Deprotection of the EOM groups of 2-112a-g and 2-120a-g using sulfonic acid resin afforded compounds 2-103a-g and 2-85a-g in pure form and excellent yields after simple filtration of the resin and evaporation of the solvents (Scheme 17). The 12-membered ring products 2-121a-g were deprotected just as smoothly (not shown). Treatment of 2-112a-g and 2-120a-g with reducing agents led to either carbonyl reduction using Dibal or mixtures of carbonyl and 1,4-reduction with NaBH$_4$. It is known that using non-coordinating counter ion for borohydride can favor the carbonyl reduction (H. W. Gibson and F. C. Baily, *J. Chem. Soc. Chem. Commun.*, 1977:815; A. Kirschning, *J. Prakt. Chem.*, 2000:342). This was most conveniently achieved using a polymer supported quaternary ammonium borohydride known as borohydride exchange resin (BER). Thus, ketones 2-112a-g and 2-120a-g could be reduced using BER-resin to obtain both diastereoisomers of 2-141a-g in ~60% yield. Deprotection of the EOMs with sulfonic acid resin under regular conditions afforded compounds 2-142a-g. Acetylation of the reduced intermediates 2-141a-g using PS-NMM/Ac$_2$O yielded compounds 2-143a-g which led to elimination upon deprotection to afford trienes 2-144 as a mixture of olefin geometries.

Scheme 17: Deprotection and Synthesis of the Reduced Ketone Analogues.

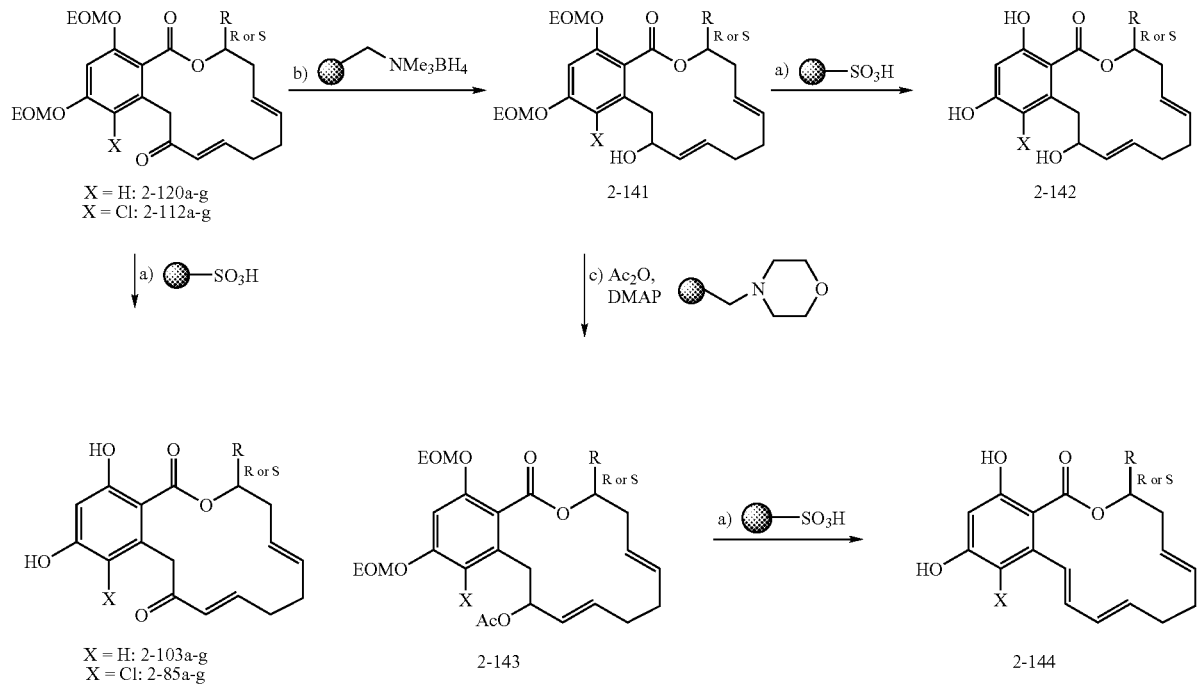

a) PS-TsOH (10.0 equiv., 3.2 mmol.g$^{-1}$), MeOH, 40° C., 4 h, >90%; b) BER resin (1.0 equiv., 2.5 mmol.g$^{-1}$), MeOH, 0° C., 12 h, ~60%; c) Ac$_2$O (1.2 equiv.), PS-NMM (1.2 equiv., 3.20 mmol.g$^{-1}$), DMAP (0.05 equiv.), DMF, 23° C., 0.5 h, ~80%. BER resin = borohydride exchange resin, PS-TsOH = sulfonic acid resin MP, DIBAL = diisobutylaluminum hydride, DMAP = dimethylaminopyridine, DMF = dimethylformamide, PS-NMM = morpholinomethyl polystyrene.

Prolonged exposure of resorcylides 2-112a-g and 2-120a-g to methanol in the presence of sulfonic acid resin was found to lead to conjugate addition; this observation was exploited to drive the reaction to completion cleanly. Thus phenol 2-85a-g was quantitatively converted to product 2-145a-g in 15 h (Scheme 18). This product could obviously be obtained directly from 2-120a-g under the same conditions.

Scheme 18: Synthesis of Analogues 2-145 by Conjugate Addition.

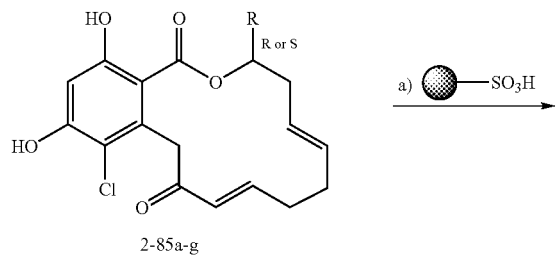

-continued

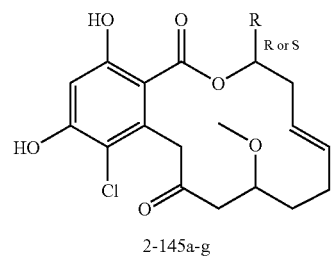

2-145a-g a) PS-TsOH (10.0 equiv., 3.2 mmol.g$^{-1}$), MeOH, 40° C., 15 h, 80%.

Compounds 2-103a-g and 2-85a-g were also used as the starting points for further diversifications (Scheme 19). Thus, treatment of 2-103a-g and 2-85a-g with polymer-bound cyanoborohydride afforded the 1,4-reduction products 2-146 in moderate yields. The more acidic para-hydroxyl groups of 2-103a-g and 2-85a-g were substituted via either Mitsunobu reaction using polymer bound DEAD or alkylation using a polymer-bound base to afford compounds with general structure 2-147 and 2-148 respectively. Oxidation with OsO$_4$ afforded the dihydroxylation products 2-149 as a mixture of isomers as well as the products corresponding to the dihydroxylation of the conjugate olefin (product not shown). Treatment of 2-103a-g and 2-85a-g with freshly prepared dimethyldioxirane led to the selective epoxidation of the non-conjugated olefin as a mixture of distereoisomers of pochonin A analogues 2-150. Although higher diastereoselectivity may be obtained for pochonin A if the phenols are protected with TBS (E. Moulin et al., *Org. Lett.*, 7:5637 (2005)), protection was not needed here.

Scheme 19: Derivatization of Compounds 2-85a-g and 2-103a-g.

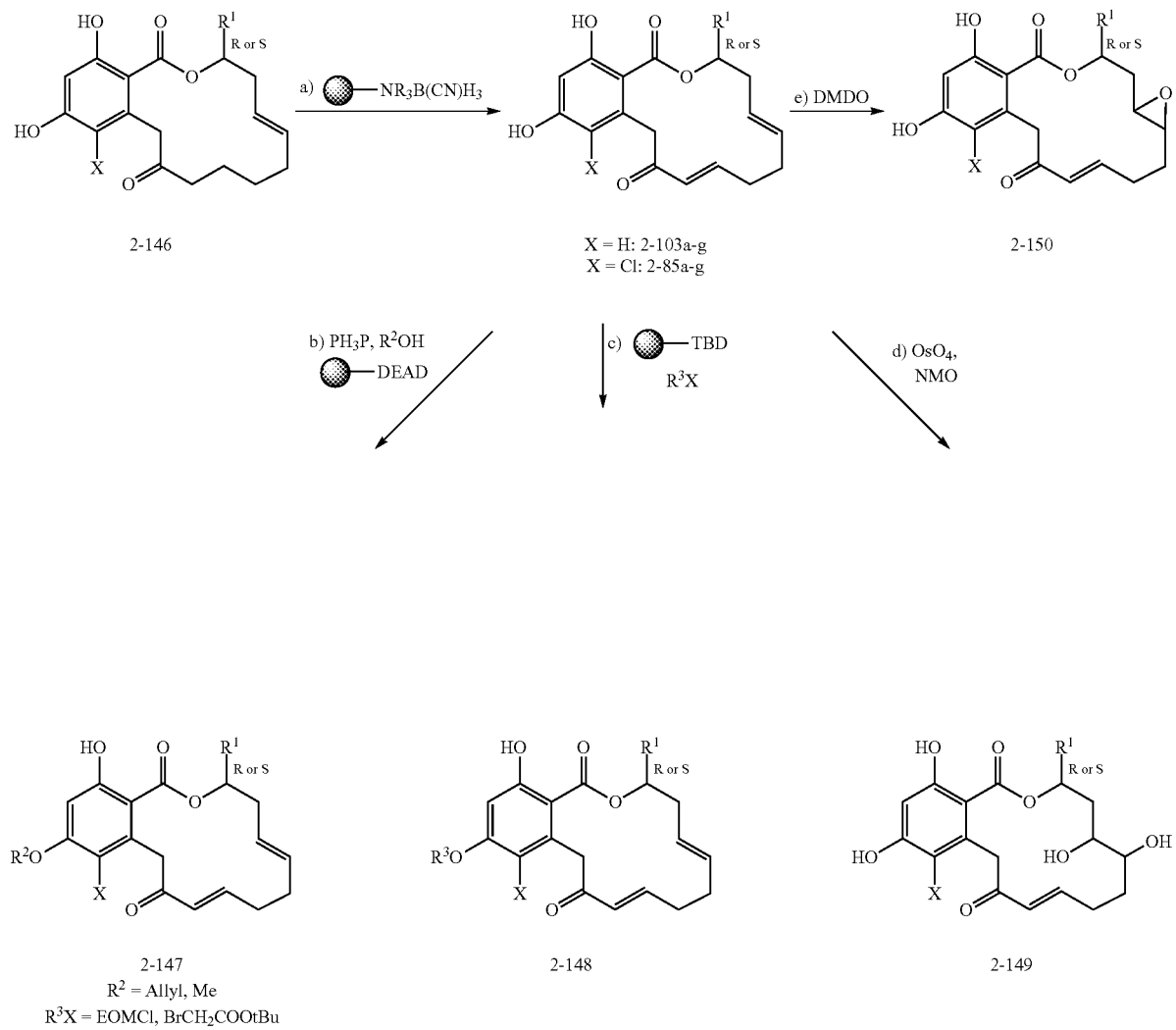

a) PS-TMABH₃CN (2.0 equiv., 3.5 mmol.g⁻¹), CH₂Cl₂/AcOH 10:1, 23° C., 4 h, ~50%; b) PPh₃ (2.0 equiv.), R²OH (2.0 equiv.), PS-DEAD (2.0 equiv., 1.3 mmol.g⁻¹), CH₂Cl₂, 23° C., 8 h ~60%; c) R³X (0.9 equiv.), PS-TBD (2.0 equiv., 2.9 mmol.g⁻¹), CH₂Cl₂, 23° C., 3 h, ~90%; d) OsO₄ (0.1 equiv.), NMO (1.0 equiv.), Acetone/H₂O 10:1, 23° C., 1 h, > 70%; e) DMDO (1.2 equiv., 0.04 M in acetone), CH₃CN, 0° C., 30 min, > 90%. AllOH = Allylalcohol, DMDO = dimethyldioxirane, NMO = 4-methylmorpholine N-oxide, PS-DEAD = ethoxycarbonylazocarboxymethyl polystyrene, PS-TBD = TBD-methyl polystyrene, PS-TMABH₃CN = (polystirylmethyl)trimethylammonium cyanoborohydride.

It is interesting to note that the conjugated olefin proved to have different reactivity depending on the presence or absence of the chlorine atom on the aryl ring. Whereas EOM deprotection of compound 2-120 where X=Cl and R=Me could be carried out with HCl in dioxane, treatment of the corresponding compound 2-112 where X=H and R=Me by the same conditions led to the conjugate addition of the chlorine ion during the deprotection, affording compound 2-151 (Scheme 20). The β-chlorine could be cleanly eliminated in the presence of polymer-bound base to recover the conjugate compound 2-103a-g.

Scheme 20: Derivatization of Macrocycles 2-120 and 2-120a-g.

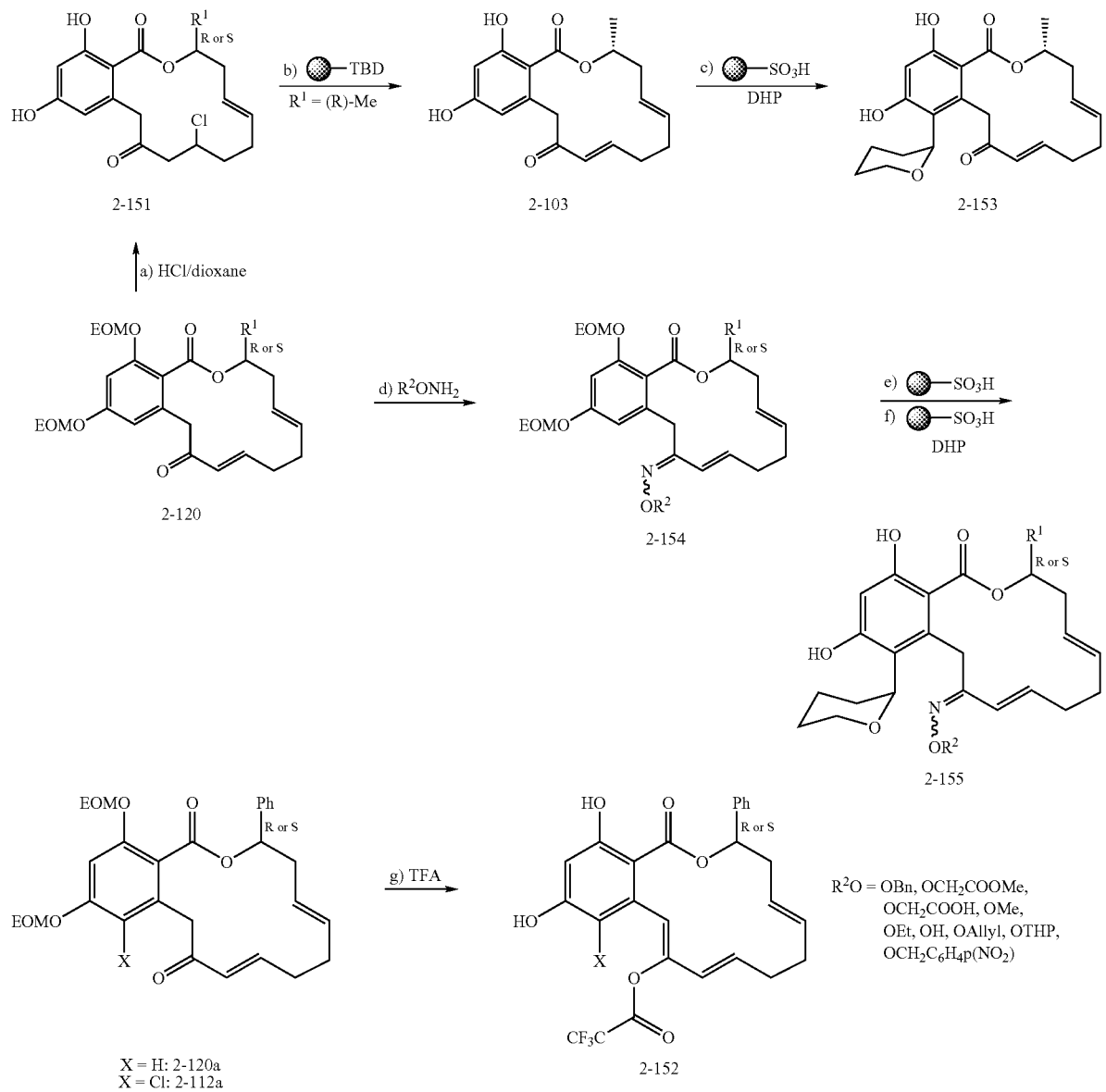

a) HCl (2.5% in dioxane), 23° C., 3 h, >75%; b) PS-TBD (0.5 equiv., 2.6 mmol.g$^{-1}$), CH$_2$Cl$_2$, 23° C., 8 h, ~90%; c) PS-TsOH (1.0 equiv., 3.2 mmol.g$^{-1}$), DHP (1.0 equiv.), CH$_2$Cl$_2$, 23° C, 5 h, ~80%; d) R$^2$ONH$_2$•HCl (5.0 equiv.), Pyr/AcOH 5:1, 40° C., 12 h, ~90%; e) PS-TsOH (10.0 equiv., 3.2 mmol.g$^{-1}$), MeOH, 40° C., 4 h, ~80% f) PS-TsOH (cat., 3.2 mmol.g$^{-1}$), DHP (1.0 equiv.), CH$_2$Cl$_2$ 23° C., 5 h, ~70%; g) TFA (20%), CH$_2$Cl$_2$, 23° C., 2 h. DHP = dihydropyran, PS-TBD = TBD-methyl polystyrene, PS-TsOH = sulfonic acid resin.

While evaluating protecting groups for the phenols, it was noticed that dihydropyran, in the presence of a strong acid such as sulfonic acid, led to electrophilic aromatic substitution rather than phenol protection. (see also T. Kometani et al., Synthesis, 1988:1005). Applying these conditions to compounds 2-103 (Scheme 20) afforded 2-153 as a separable mixture of diastereoisomers.

Compounds 2-120 (X=H, Scheme 20) protected with EOM groups underwent smooth oxime formation with nine different hydroxylamines to obtain compounds 2-154 as E/Z mixtures with variable ratios. EOM deprotection of 2-154 with sulfonic acid resin in methanol followed by treatment with sulfonic acid resin in DCM in the presence of dihydropyran afforded oximes 2-155 bearing a pyran substitution on the aromatic ring as a mixture of diastereoisomers. In the case where the side chain contains an acid (R$^2$X=OCH$_2$COOH), the deprotection of the EOM with the sulfonic acid resin in methanol was accompanied by esterification of the carboxylate. Treatment of compounds 2-120a and 2-112a with trifluoroacetic acid led to the formation of trifluoroacetate 2-152. Oxime formation in the chlorinated analogues with or without EOM protecting groups generated mostly the corresponding 1,4-addition of the hydroxylamines (Scheme 21). Surprisingly, when pochonin D was protected with TBS groups, (2-128a-g, Scheme 21) the formation of the desired oxime 2-157a-g was the only product observed under the same reaction conditions. Deprotection of the TBS groups was than achieved using TBAF to obtain oximes 2-158a-g. Treatment of pochonin D with hydroxylamines led to the formation of the 1,4-addition product 2-156.

Scheme 21: Oxime Formation with Compounds 2-85.

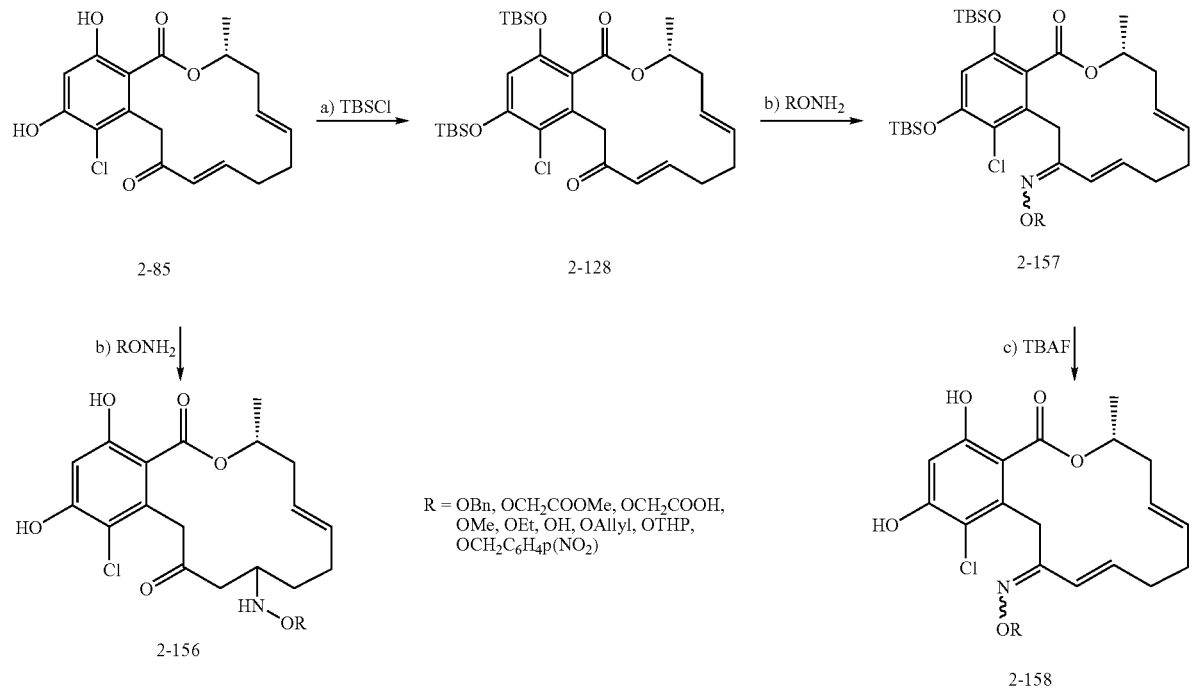

a) TBSCl (5.0 equiv.), imid. (5.0 equiv.), DMF, 23° C., 3 h, ~90%; b) RONH₂•HCl (5.0 equiv.), Pyr/AcOH 5:1, 40° C., 12 h, ~ 90%; c) TBAF (2.5 equiv.), THF, 23° C., 2 h, ~80%. DMF = dimethylformamide, Imid. = imidazole, TBAF = tetrabutylammonium fluoride, TBS-Cl = tert-butyldimethylsilyl chloride.

In another embodiment, the bis-methylated compounds 2-164 were prepared (Scheme 22). Acid 2-108 was used in a standard Mitsunobu esterification with alcohol 2-159. Compound 2-160 was protected as the ortho-phenol followed by acylation reaction with Weinreb amide 2-114 to yield the acyclic precursor 2-162. Ring-closing metathesis followed by removal of the EOM protecting groups on compound 2-163 using sulfonic acid resin furnished the bis-methylated analog 2-164.

Scheme 22: Synthesis of bis-methyl substituted analog (2-164) of pochonin D

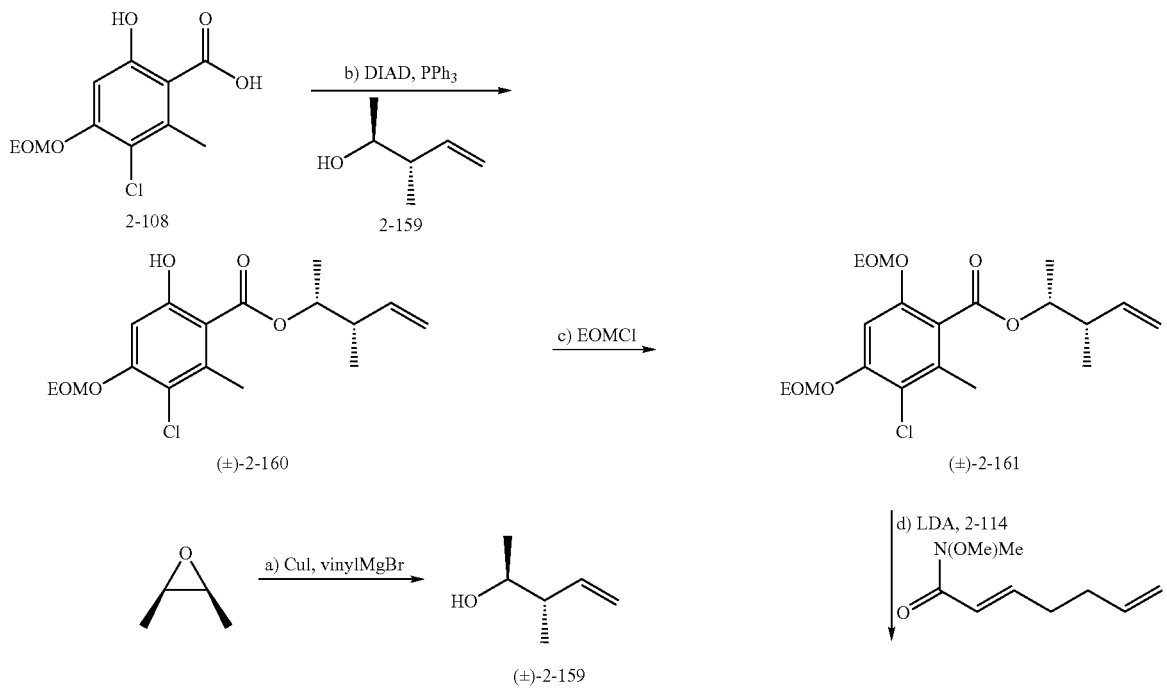

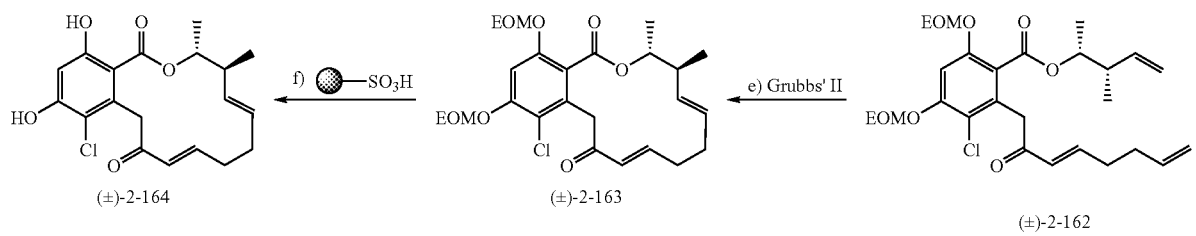

a) VinylMgBr (2.0 equiv.), CuI (0.3 equiv.), Et$_2$O, -30 → 23° C., 12 h, 65%; b) 2-159 (1.0 equiv.), PPh$_3$ (2.0 equiv.), DIAD (2.0 equiv.), toluene, 23° C., 3 h, 23%; c) EOMCl (2.0 equiv.), NaH 60% (2.0 equiv.), THF, 0° C., 2 h, 66%; d) LDA (2.0 equiv.), THF -78°C.; 2-114 (1.0 equiv.), 10 min, 57%; e) Grubbs' II (10% mol), toluene (2 mM), 80° C., 12 h, 57%; f) PS-TsOH (10 equiv., 3.2 mmol.g$^{-1}$), MeOH, 40° C., 2.5 h, 40%.

Additionally, oxime derivatives 2-165 and 2-167 were synthesized from macrocycle 2-163 as a separable mixture with the 1,4-addition product (Scheme 23). The carboxylic acid moiety of oxime 2-167 was then esterified to form the corresponding piperidine amide oxime 2-168. Removal of the EOM groups using sulfonic acid resin allowed the isolation of both oximes 2-166 and 2-167 from 2-165 and 2-168 respectively.

Scheme 23: Synthesis of oxime derivatives of compound 2-164

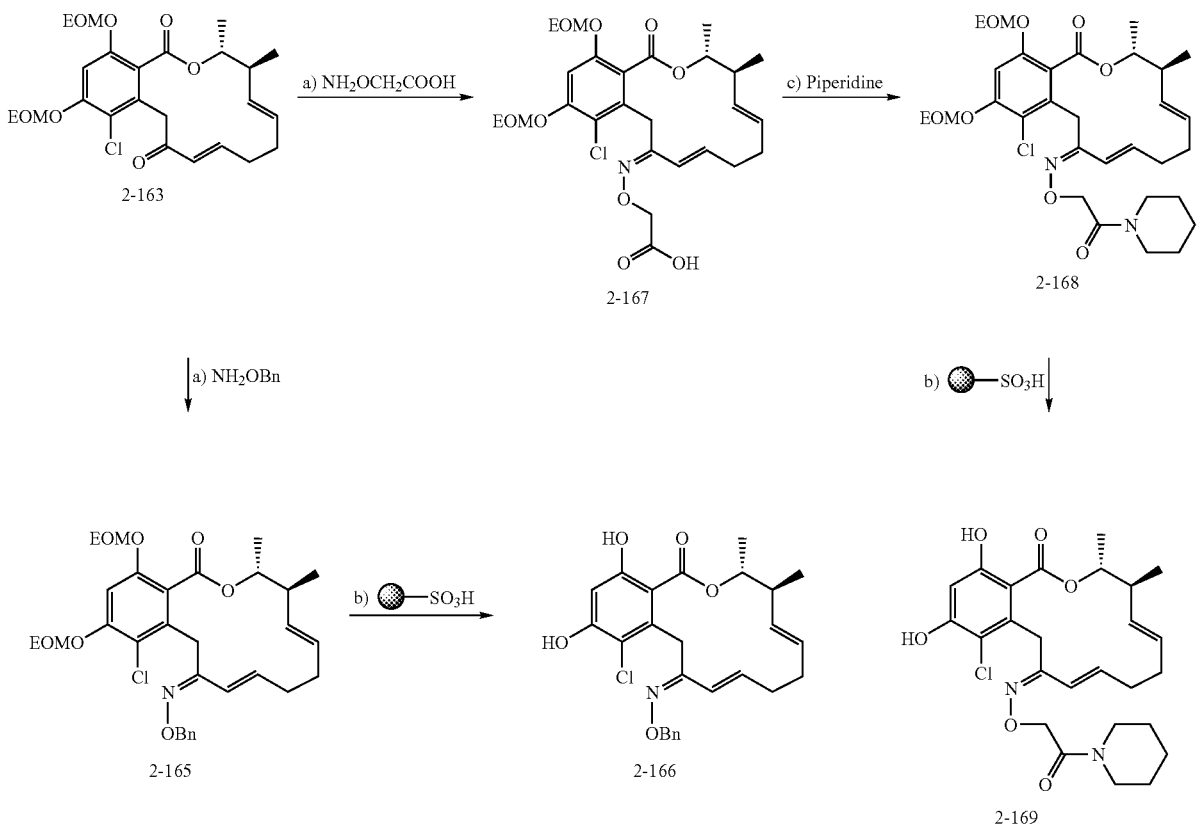

a) BnONH$_2$·HCl or NH$_2$OCH$_2$CO$_2$H (5.0 equiv.), Pyr/AcOH 5:1, 40° C., 24 h, 20-35%; b) PS-TsOH (10.0 equiv., 3.2 mmol.g$^{-1}$), MeOH, 40° C., 2.5 h, 77-80%; c) Piperidine (1.1 equiv.), EDC (1.1 equiv.), HOBt (1.1 equiv.), DMF, 23° C., 2 h, 75-80%.

In another embodiment, the pochonin oximes were prepared from cyclization of the pre-formed oximes as shown in Scheme 24. For example protected pre-formed oxime 1 was bound to Wang resin using N,N'-diisopropylcarbodiimide and dimethylaminopyridine. The allyl protecting group was removed and the phenol was functionalized under Mitsunobu conditions. This was followed by deprotection of the carboxylic acid and esterification with R³OH. Ring-closing was effected with the use of Grubbs II catalyst as described before to provide resin-bound oxime 5. Deprotection and removal from the resin was achieved with trifluoroacetic acid to provide oxime 6. The carboxylic acid can be reacted with a variety of groups R⁴XH to provide the oximes 7, wherein X is oxygen, sulfur, amino or substituted amino. The oximes 7 were generally obtained as a 1:1 mixture of E:Z isomers which could be separated by chromatography.

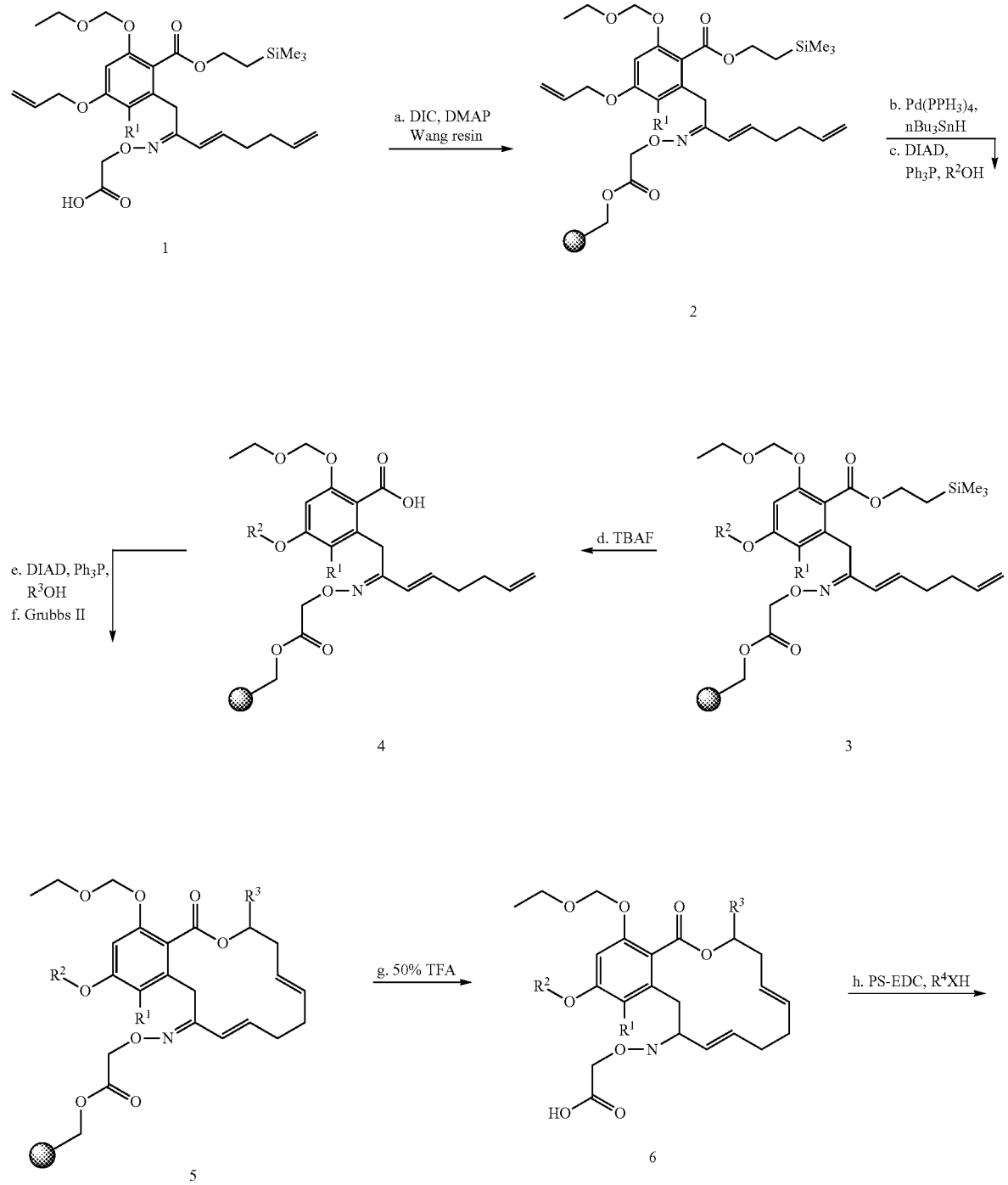

Scheme 24

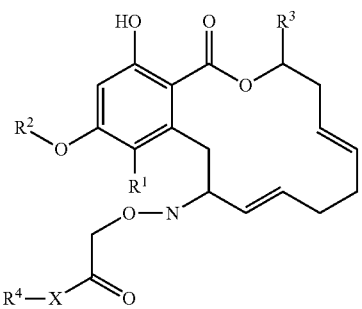

In another embodiment, the pochonin oximes were prepared by an alternate process which utilized a Mitsunobu esterification to construct the macrocylic ring. Scheme 25 shows a non-limiting example for the formation of the macrocycle 2-a1 via a Mitsunobu esterification. Orcinol (compound 8) is oxidized with phosphoryl chloride in DMF to provide aldehyde 9, which is protected as the bis-ethoxymethyl ether and subjected to oxidative chlorination with NaClO$_2$ to produce carboxylic acid 10. The carboxylic acid is protected as a trimethylsilylethyl ester and treated with LDA and Weinreb amide 12 (Scheme 26) to provide the α,β-unsaturated ketone 13. Ketone 13 is reacted with carboxymethoxylamine hemihydrochloride in pyridine at 40° C. to produce the corresponding oximes as a mixture of E and Z isomers. The oximes were converted to the desired amides 14 as a mixture of E and Z isomers by treatment with EDC and piperidine. Macrocyclization of precursor 14 to protected compound 15 was performed under Mitsunobu conditions by slow addition of DIAD to a solution of compound 14 and PhP$_3$ in toluene. The phenol groups were deprotected by treatment with sulfonic acid resin at 40° C. to produce 2a-1 as a mixture of E and Z isomers. The mixture of E- and Z-isomers was separated to obtain the pure E and Z isomers 2a-1.

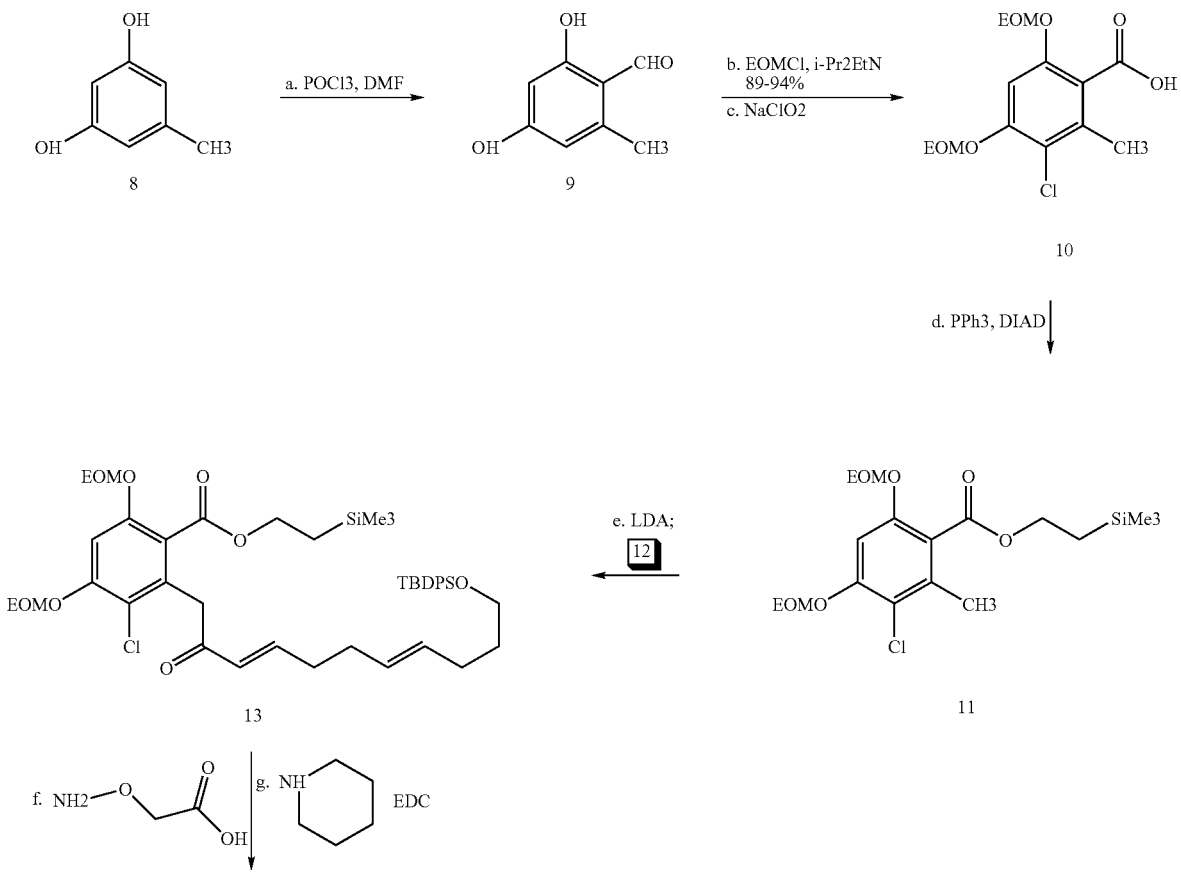

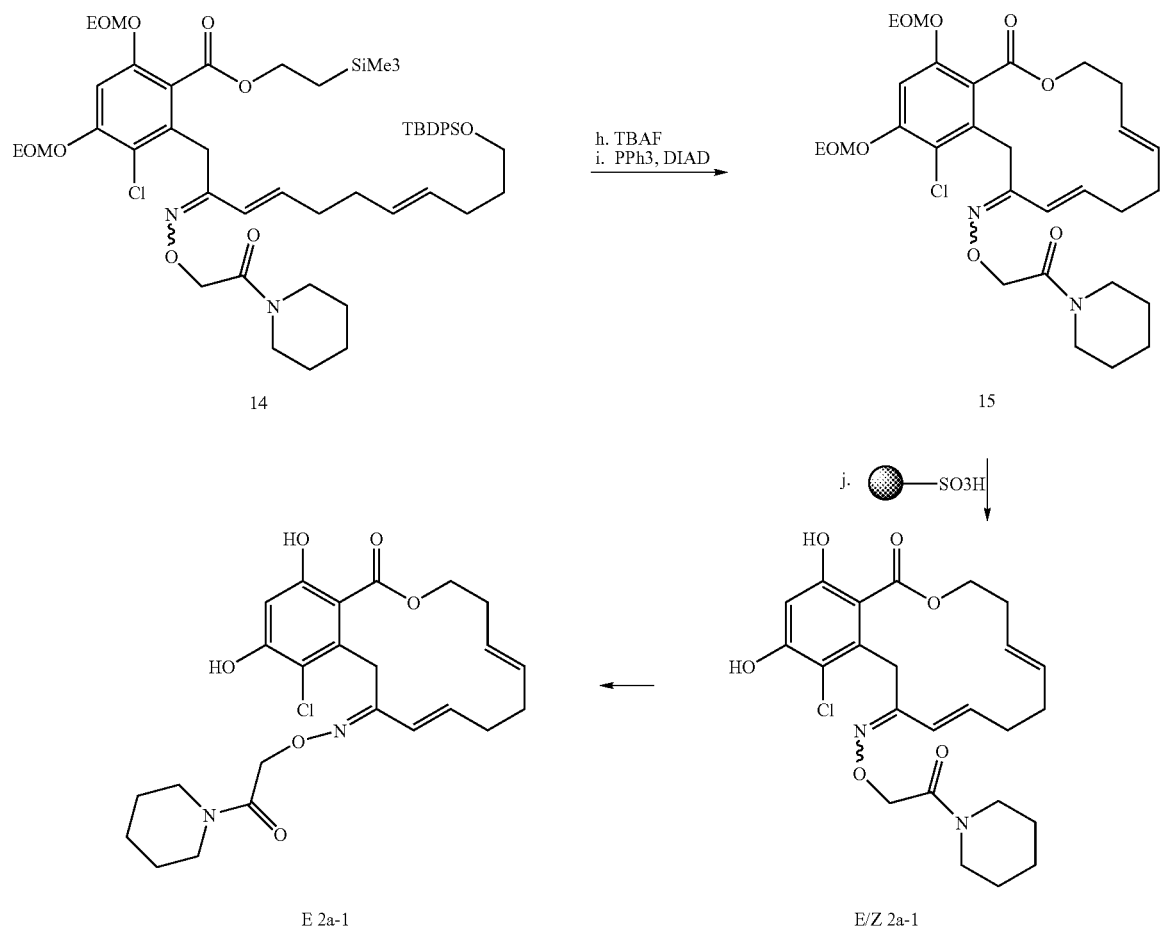

The diene Weireb amide 12 was prepared according to the process shown in Scheme 26. Trans-3-hexenedioic acid dimethyl ester 16 was reduced to the corresponding diol with lithium aluminum hydride. The diol was mono-protected as the tert-butyldiphenylsilyl ether 17, and the free alcohol was converted to aldehyde 20 in three steps via the nitrile 19. Aldehyde 20 was then treated with Weireb amide ylide 21 to produce the diene Weireb amide 12, which was used to prepare compound 13 (Scheme 24).

Figure 2:
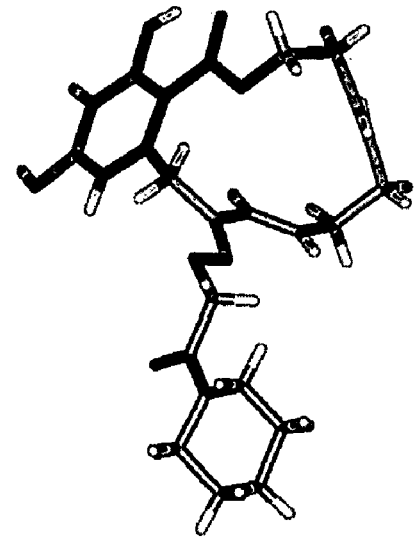
FIG. 2 shows a crystal structure of oxime a2-13 (E-isomer).

Crystal structures of the E-izomer 2a-1 and the related E-oxime 2a-13, which lacks the chloro substituent on the aromatic ring, were obtained. The crystal structures are shown in FIGS. 1 and 2.

The solubility of compounds 2a-1 and 2a-13 was determined. Both compounds were determined to be highly soluble in DMSO and DMA (>5 g/mL). The good solubility of the compounds in DMSO and DMA enable formulations for intravenous or intraperitoneal administration. In one non- Scheme 26

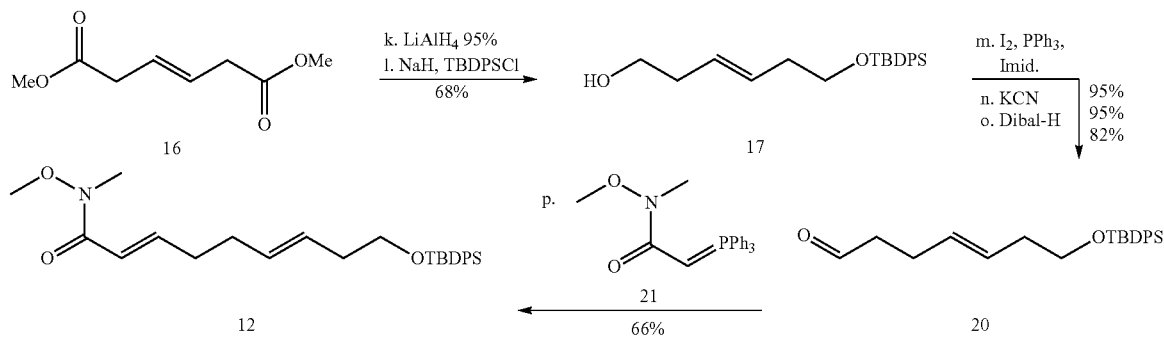

limiting example, a formulation of the oximes in DMSO/ Tween 20/0.9% NaCl (Oct. 5, 1985) was prepared.

Biological Activity

A representative subset of the pochonin analogue library (84 compounds) was tested for its inhibition in a panel of 24 kinase (AKT1, ARK5, Aurora-A, Aurora-B, B-RAF-VE, CDK2/CycA, CDK4/CycD1, CK2-α1, FAK, EPHB4, ERB2, EGF-R, IGF1-R, SRC, VEGF-R2, VEGF-R3, FLT3, INS-R, MET, PDGFR-β, PLK1, SAK, TIE2, COT) at 10 μM. A description of the assay method and results is presented in Example 24.

Significantly, twelve compounds showed more than 50% inhibition, which represents a >14% hit rate for a kinase. Surprisingly, pochonin D, pochonin A and radicicol, though they had been shown to be powerful inhibitors of HSP90, showed no significant activity against this panel of kinases. Nine compounds were selected to calculate $IC_{50}$ against each of the 24 kinases (table 4). In this more detailed analysis, radicicol showed only very mild activity against VGFR-R2 with no inhibition for the twenty-three other kinases. Several pochonin analogues showed a well-defined pattern of activity against therapeutically relevant enzymes such as Src (8 μM for A2), Aurora A (12 μM for A3), IGF1-R (11 μM for A5). Importantly, the compounds that proved to be kinase inhibitors were not inhibitors of HSP90 and are not indiscriminate ATP-surrogates.

Another subset of the library was tested for HSP90 inhibition by measuring direct interaction in a competitive assay and measuring depletion of HSP90 client proteins in a cellular assay. HSP90's ATPase pocket has a specific fold that is present in a superfamily which includes functionally diverse proteins such as DNA topoisomerase II, helicase, MutL and histidine kinases (Bergerat fold). (A. Bergerat et al., *Nature*, 386:414 (1997); R. Dutta and M. Inouye, *Trends Biochem. Sci.*, 25:24 (2000)). In fact, it has been shown that radicicol does inhibit other members of this family albeit with lower affinity. (D. Gadelle et al., *Nucleic Acids Res.*, 33:2310 (2005); P. G. Besant et al., *Mol. Pharmacol.*, 62:289 (2002). Yet remarkably, the best HSP90 inhibitors of the invention were selective for HSP90 with respect to the panel of kinases. Sixteen compounds were found to have an IC50<1 μM.

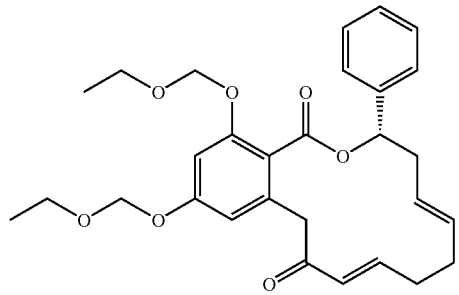

(R)-2-112a

A-1

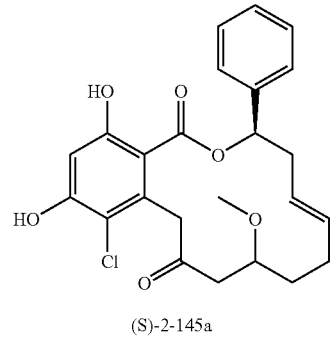

(S)-2-145a

A-2

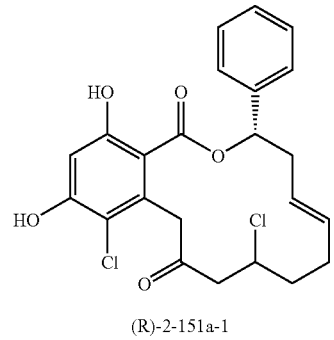

(R)-2-151a-1

A-3

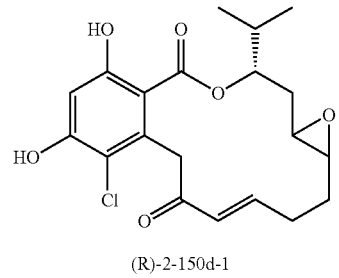

(R)-2-150d-1

A-4

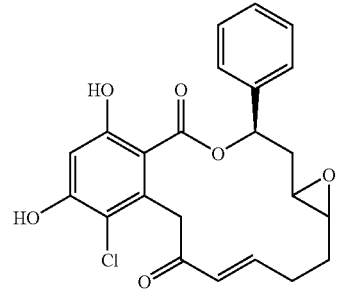

(S)-2-150a

A-5

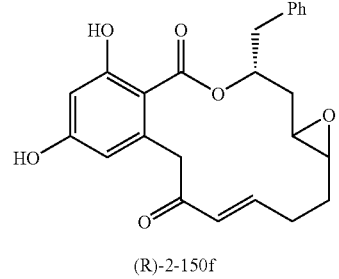

(R)-2-150f

A-6

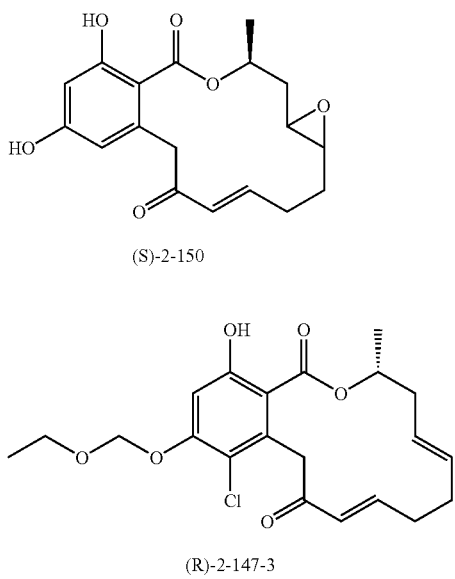

(S)-2-150

(R)-2-147-3

Pochonin Analogs Selected for IC$_{50}$ Determination pochonin library described above will certainly contain some compounds that are good inhibitors of enzymes bearing a Bergerat fold, we wished to evaluate whether modification around the pochonin scaffold could retune the selectivity of these compounds from HSP90 inhibitors to kinase inhibitors. The fact that more than fourteen percent of the compounds showed a kinase inhibition of greater than 50% at 10 mM clearly supports the hypothesis that RAL is a good scaffold for kinase inhibition.

Screening of the library for HSP90 affinity in the competition assay led to the following general trends regarding structure activity relationships (numbering and nomenclature based on formula A): While large substituents at $R_1$ are well tolerated for kinase activity, methyl or hydrogen were generally found to be better for HSP90 affinity; substitution at $R_2$ generally led to a decrease of HSP90 affinity; alkene at C14-15 (AB) were generally comparable in activity to the corresponding epoxide for HSP90 affinity however the corresponding diols were generally less active and trans alkenes were better than a cis alkenes; the presence of an alkene at C10-11 (CD) was generally found to be superior to the corresponding alkane or the products of substitution at C11 for HSP90 affinity; reduction of the C9 carbonyl generally led to lower HSP90 affinity while some substitution with hydroxyl amines increase affinity for HSP90; substitution at $R_4$ with small groups such as chlorine was generally found to improve

TABLE 4

Inhibitory activity (IC$_{50}$: μM) of selected pochonin analogs in a panel of 24 kinase assays (a blank represents an IC$_{50}$ >50 μM).

| Kinase | Radicicol | Resorcylic Acid Species |       |       |       |       |       |       |       |
|--------|-----------|-------|-------|-------|-------|-------|-------|-------|-------|
|        |           | A-1   | A-2   | A-3   | A-4   | A-5   | A-6   | A-7   | A-8   |
| AKT1   |           |       |       |       |       |       |       |       |       |
| ARK5   |           |       |       |       |       |       |       |       |       |
| Aurora-A |         |       | 14    | 12    | 30    | 47    |       |       |       |
| Aurora-B |         |       | 16    | 14    | 36    |       | 16    |       |       |
| B-RAF-VE |         |       |       |       |       | 50    |       |       |       |
| CDK2/CycA |        |       |       |       |       |       |       |       |       |
| CDK4/CycD1 |       |       | 50    | 30    | 48    | 45    | 37    |       |       |
| CK2-α1 |           |       |       |       |       |       |       |       |       |
| FAK    |           |       | 14    | 9     | 37    | 38    | 34    |       |       |
| EPHB4  |           |       | 16    | 40    |       | 49    | 40    |       |       |
| ERBB2  |           |       | 16    | 24    |       |       |       |       |       |
| EGF-R  |           | 33    | 10    | 14    | 22    | 16    | 32    |       |       |
| IGF1-R |           | 23    | 16    | 19    | 13    | 11    | 21    |       |       |
| SRC    |           | 11    | 8     | 14    | 12    | 12    | 20    |       |       |
| VEGF-R2 | 49       |       | 19    | 20    | 30    | 19    | 25    |       |       |
| VEGF-R3 |          |       | 40    | 19    | 31    | 31    | 34    |       |       |
| FLT3   |           |       | 23    | 23    | 45    |       | 44    |       |       |
| INS-R  |           |       | 36    | 44    |       |       |       |       |       |
| MET    |           |       | 32    | 29    |       |       | 36    |       |       |
| PDGFR-β |          |       |       |       |       |       |       |       |       |
| PLK1   |           |       |       |       |       |       |       |       |       |
| SAK    |           |       | 17    | 25    | 19    | 20    | 17    |       |       |
| TIE2   | 72        |       | 16    | 15    |       |       | 25    |       |       |
| COT    |           |       |       |       |       |       |       |       |       |

The ATP-binding pocket of HSP90 targeted by radicicol and pochonin D has a specific fold that is present in a superfamily which includes functionally diverse proteins, such as DNA topoisomerase II, helicase, MutL, and histidine kinases (R. Dutta and M. Inouye, *Trends Biochem. Sci.*, 24:24 (2000)). In fact, it has been shown that radicicol does inhibit other members of this family albeit with lower affinity (D. Gadelle et al., *Nucleic Acids Res.*, 33:2310 (2005); P. G. Besant et al., *Mol. Pharmacol.*, 62:289 (2002)). While the HSP90 activity except in some permutations of substitutions at $R_1$ and $R_3$ where a hydrogen is superior to a chlorine; substitutions of the phenols are tolerated of increase affinity for kinases but generally decrease affinity for HSP90.

It is important to note that generally, the compounds that showed potent affinity for HSP90 were not good inhibitors of kinases strongly suggesting that this scaffold is not an indiscriminate purine agonist.

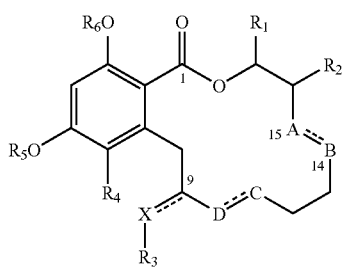

Formula A

Antitumor Activity

The compounds of the invention were evaluated for antitumor activity in mice. Tumors were induced intraperitoneally in healthy CB17/SCID mice by injecting HCC1954 cells into the right flank of 70 mice. Once the induced tumors were an average size of 80 mm, the mice were treated with compound a2-1 at 25 mg/kg, 50 mg/kg and 100 mg/kg. Controls of vehicle alone and Herceptin® at 10 mg/kg were utilized. A dose-dependent reduction in tumor size was observed for the mice which were treated with compound 2a-1. The results were superior to those obtained in mice treated with Herceptin®, even at the 25 mg/kg dose for three weeks. Importantly, the re-growth of tumor after the last treatment did not occur for three to seven days, indicating that a administration schedule of one to three times per week should be effective.

Example 26 shows the antitumor activity of selected pochonin analogs agains HCC1954 and SK-BR-3 tumor cells. Compounds showing significant cytotoxixty were further examined for their ability to induce degradation of known HSP90 client proteins such as ErbB2 in SK-BR3. Thus, after 18 hrs treatment with the compounds, the whole cell protein lysates were obtained, protein concentrations were normalized and the concentration of ErbB2 was quantified by Western blotting (C. Chavany et al *J. Biol. Chem.* 271:4974-4977 (1996)). In this assay compound 2a-1 had an $EC_{50}$ of 26 nM and compound 2a-13 had an $EC_{50}$ of 12 nM whereas radicicol had an $IC_{50}$ of 289 nM. It is noteworthy that one oxime isomer was systematically more active than the other. For 2a-11 and 2a-13, the E-isomer was 5 to 10 times more active than the Z-isomer.

Maximum Tolerated Dose

Three healthy CB17/SCID mice were treated with compound 2a-1 at 25 mg/kg, 50 mg/kg and 100 mg/kg once daily for five consecutive days. Mice treated at the 25 mg/kg concentration did not show any weight loss. Mice treated at the 50 mg/kg and 100 mg/kg dose levels show a slight, but acceptable body weight loss.

EXAMPLES

General Techniques. All reactions were carried out under a nitrogen atmosphere with dry (anhydrous) solvents under anhydrous conditions, unless otherwise noted. Anhydrous solvents were obtained by passing them through commercially available alumina column (Innovative Technology, Inc.,® VA). All substituted polystyrene resins (100-200 mesh, 1% DVB) were purchased from Novabiochem® or Aldrich®. The Grubbs' II catalyst was purchased from Materia Inc.® Solid phase reactions were carried on a Quest® 210 or round bottom flasks and filtered in fritted funnels. Reactions were monitored by thin layer chromatography (TLC) carried out on 0.25 mm E. Merck® silica gel plates (60F-254) using UV light as visualizing agent and 10% ethanolic phosphomolybdic acid or vanillin solution and heat as developing agents. E. Merck® silica gel (60, particle size 0.040-0.063 mm) was used for flash column chromatography. PTLC (preparative thin layer chromatography) were carried out on 0.25 mm E. Merck® silica gel plates. NMR spectra were recorded on a Bruker Advance-400® instrument and calibrated by using residual undeuterated solvent as an internal reference. The following abbreviations were used to explain the multiplicities: s=singlet, d=doublet, t=triplet, q=quartet, m=multiplet, b=broad. IR spectra were recorded on a Perkin-Elmer 1600 series FT-IR spectrometer. LC-MS were recorded using an Agilent 1100® HPLC with a Bruker® micro-TOF instrument (ESI). Unless otherwise stated, a Supelco® C8 (5 cm×4.6 mm, 5 µm particles) column was used with a linear elution gradient from 100% $H_2O$ (0.5% $HCO_2H$) to 100% MeCN in 13 min at a flow rate of 0.5 ml/min. Unless otherwise stated, LDA was prepared at a concentration of 0.566 M by treating a solution of diisopropylamine (1.0 equiv.) in THF at −78° C. with n-butyllithium (1.0 equiv.) and stirred for 30 min at this temperature before use.

Example 1

General Procedure for the Synthesis of Compounds 2-110

As depicted in Scheme 16, a solution of acid 2-95A or 2-95b (1.0 equiv), homoallylic alcohol (1.0 equiv) and tris-(3-chlorophenyl)phosphine (2.0 equiv) in anhydrous toluene (0.05 M) was treated at room temperature with PS-DEAD (2.5 equiv, 1.3 mmol $g^{-1}$). After stirring for 10 min, the reaction mixture was filtered on silica and washed with hexane/EtOAc (10/1, 100 ml) and hexane/EtOAc (3/1, 100 ml). The 3/1 mixture was concentrated under reduced pressure to yield compound 2-115 (60-80%). Without further purification, compound 2-115 (1.0 equiv) and tetrabutylammonium iodide (catalytic amount) were dissolved in DMF (0.15 M) and treated with diisopropylethylamine (4.0 equiv) and (chloromethyl)ethyl ether (4.0 equiv). After stirring overnight at 80° C., the reaction mixture was diluted with EtOAc and washed several times with a saturated $NH_4Cl$ solution. The organic phase was dried over $MgSO_4$ and concentrated under reduce pressure to yield compounds 2-110 (80-90%). Using this method, a variety of compounds 2-110 were prepared.

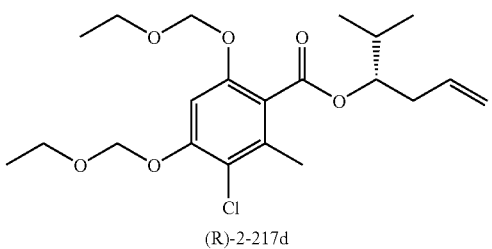

(R)-2-217d $^1$H NMR (CDCl$_3$, 400 MHz, 25° C.) δ 7.04 (s, 1H), 5.89 (ddt, J=17.0, 10.5, 7.0 Hz, 1H), 5.31 (s, 2H), 5.21 (s, 2H), 5.22-5.06 (m, 3H), 3.79 (q, J=7.0 Hz, 2H), 3.72 (q, J=7.0 Hz, 2H), 2.48-2.44 (m, 2H), 2.36 (s, 3H), 2.01 (qd, J=12.4, 7.0 Hz, 1H), 1.25 (t, J=7.0 Hz, 3H), 1.23 (t, J=7.0 Hz, 3H), 1.02 (d, J=6.4 Hz, 3H), 1.01 (d, J=7.0 Hz, 3H); $^{13}$C NMR (CDCl$_3$, 100 MHz, 25° C.) δ 167.3, 154.0, 152.9, 134.8, 134.1, 120.4, 117.5, 117.1, 101.5, 93.9, 93.4, 79.0, 64.6, 64.3, 35.6, 30.8, 18.4, 17.6, 17.5, 15.0 (×2); HRMS (ESI-TOF) m/z 437.1574 ([M+Na$^+$], $C_{21}H_{31}O_6ClNa$ requires 437.1701).
The following non-limiting examples of compounds 2-217 were prepared.
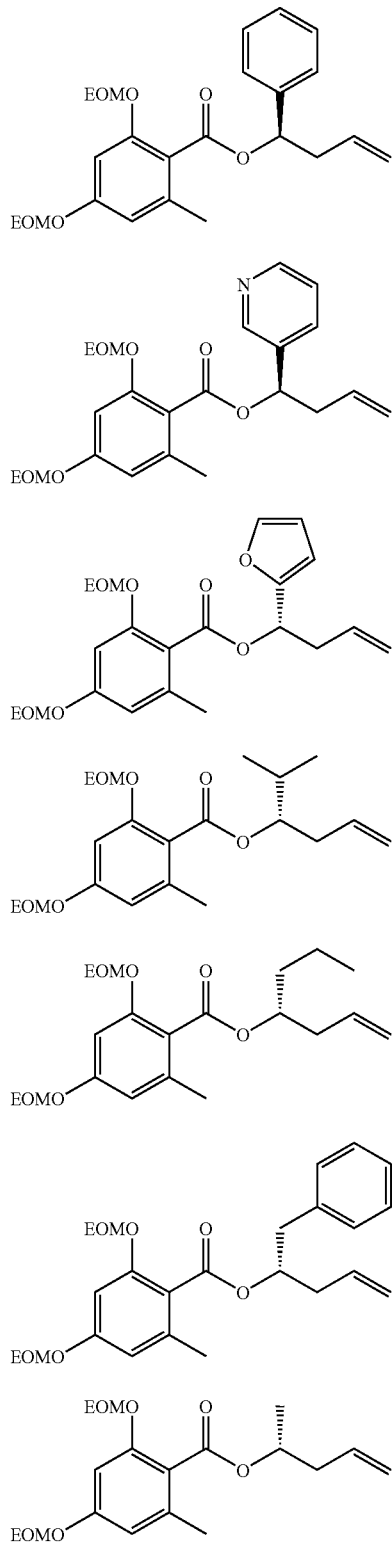
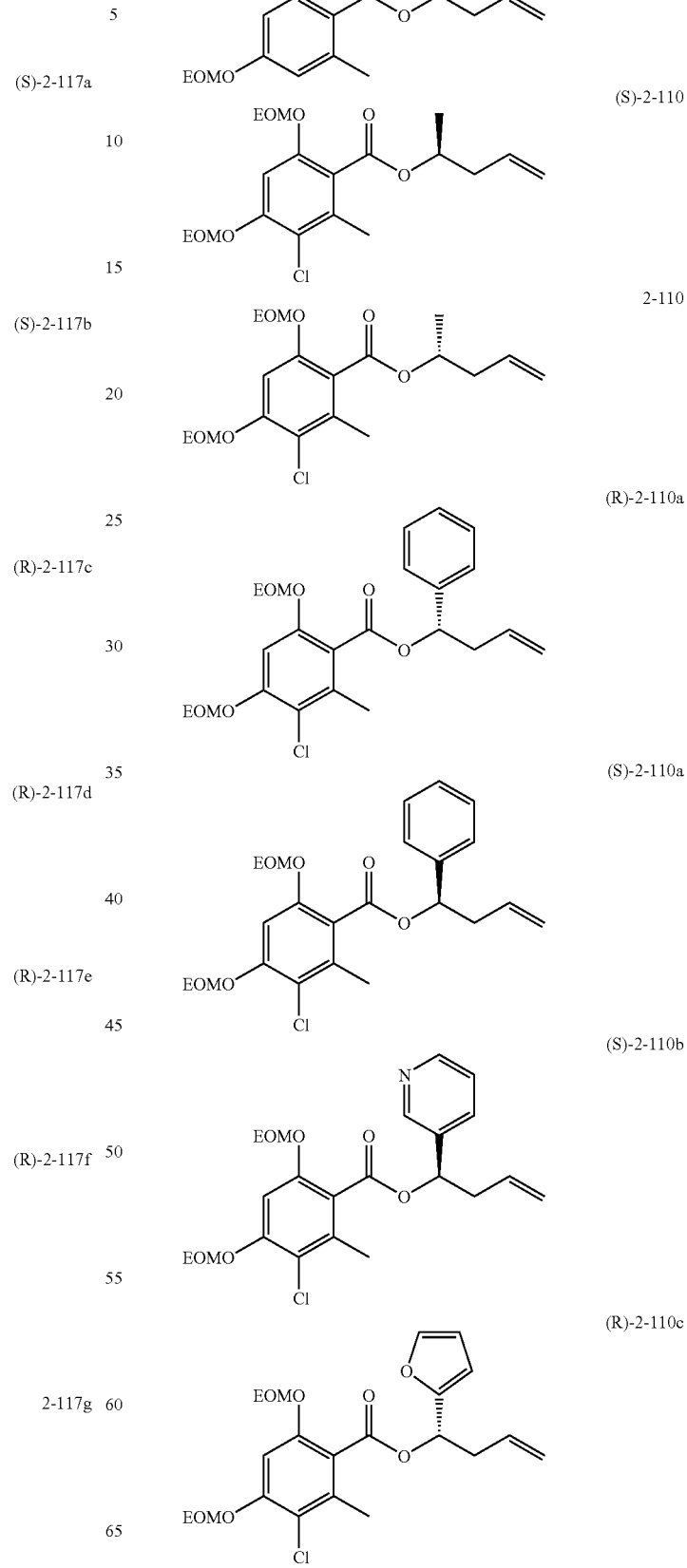

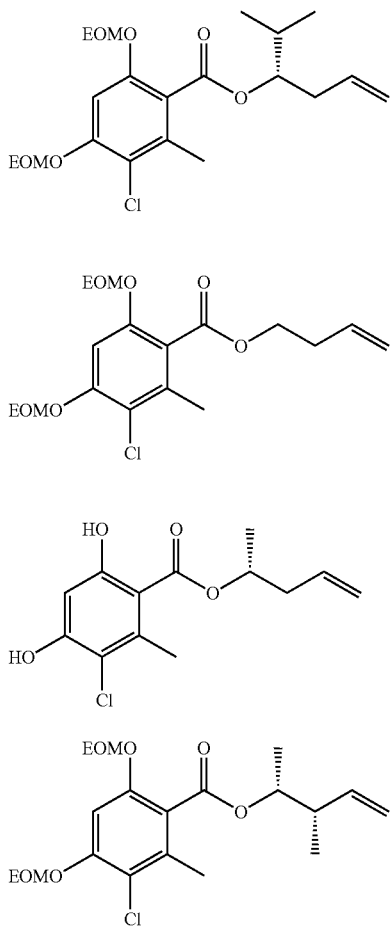

(R)-2-110d 2-110g 2-115

(±)-2-161

Example 2

General Procedure for the Synthesis of Compounds 2-118, 2-119 and 2-140

As depicted in Scheme 16, a solution of compound 2-110 or 2-117 (1.0 equiv) in anhydrous THF (0.2 M) was treated at −78° C. with freshly made LDA (2.0 equiv). Immediately after, the α,β-unsaturated Weinreb amide (S. V. Ley and I. R. Baxendale, *Nat. Rev. Drug Discov.*, 1:573 (2002)) was added to the cooled solution (1.0 equiv). The resulting mixture was then stirred for 10 min at −78° C. and quenched by addition of Amberlite® resin (20 equiv). Upon warming up to room temperature, the reaction was filtered on a pad of silica and washed with EtOAc. Concentration under reduced pressure afforded the desired compound 2-118 or 2-119. This compound was used directly in the metathesis reaction without any further purification. When X=H, 20% of the corresponding 1,4-addition compound was observed and a fraction of the mixture was purified for characterization of compounds 2-118/2-119 and 2-140 (SiO$_2$, 0-20% EtOAc/cyclohexane gradient). Illustrative examples of compounds 2-118/2-119 and 2-140 follow; their characterization follows respectively in the text below each figure.

Illustrative Compound 2-119:

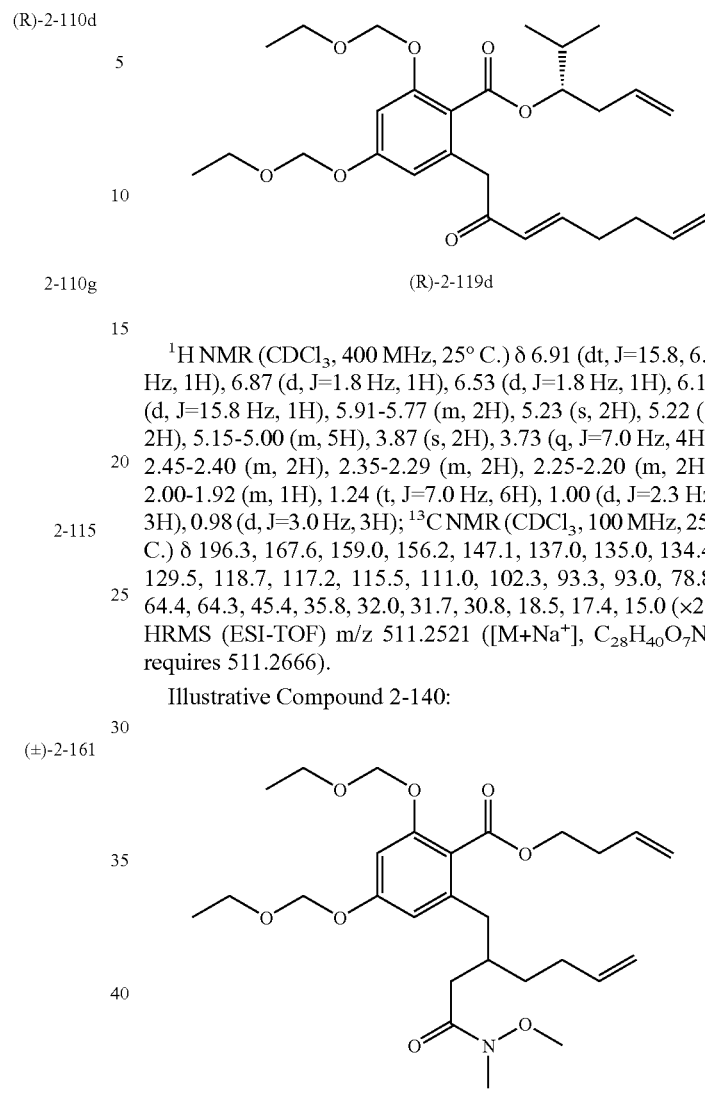

(R)-2-119d $^1$H NMR (CDCl$_3$, 400 MHz, 25° C.) δ 6.91 (dt, J=15.8, 6.7 Hz, 1H), 6.87 (d, J=1.8 Hz, 1H), 6.53 (d, J=1.8 Hz, 1H), 6.19 (d, J=15.8 Hz, 1H), 5.91-5.77 (m, 2H), 5.23 (s, 2H), 5.22 (s, 2H), 5.15-5.00 (m, 5H), 3.87 (s, 2H), 3.73 (q, J=7.0 Hz, 4H), 2.45-2.40 (m, 2H), 2.35-2.29 (m, 2H), 2.25-2.20 (m, 2H), 2.00-1.92 (m, 1H), 1.24 (t, J=7.0 Hz, 6H), 1.00 (d, J=2.3 Hz, 3H), 0.98 (d, J=3.0 Hz, 3H); $^{13}$C NMR (CDCl$_3$, 100 MHz, 25° C.) δ 196.3, 167.6, 159.0, 156.2, 147.1, 137.0, 135.0, 134.4, 129.5, 118.7, 117.2, 115.5, 111.0, 102.3, 93.3, 93.0, 78.8, 64.4, 64.3, 45.4, 35.8, 32.0, 31.7, 30.8, 18.5, 17.4, 15.0 (×2); HRMS (ESI-TOF) m/z 511.2521 ([M+Na$^+$], C$_{28}$H$_{40}$O$_7$Na requires 511.2666).

Illustrative Compound 2-140:

$^1$H NMR (CDCl$_3$, 400 MHz, 25° C.) δ 6.72 (s, 1H), 6.57 (s, 1H), 5.89-5.71 (m, 2H), 5.20-5.16 (m, 4H), 5.12-4.90 (m, 4H), 4.33 (t, J=6.8 Hz, 2H), 3.69 (2×q, J=7.0 Hz, 4H), 3.57 (s, 3H), 3.13 (s, 3H), 2.69-2.64 (m, 1H), 2.53-2.45 (m, 4H), 2.32 (m, 2H), 2.08-2.03 (m, 2H), 1.19 (t, J=6.8 Hz, 6H), 1.01 (t, J=6.5 Hz, 2H); HRMS (ESI-TOF) m/z 508.2873 ([M+H$^+$], C$_{27}$H$_{42}$O$_8$N requires 508.2905).

Using the procedure above, the following non-limiting examples of compounds 2-118/2-119 shown below were prepared.

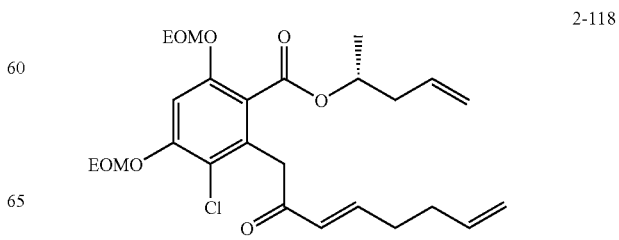

2-118

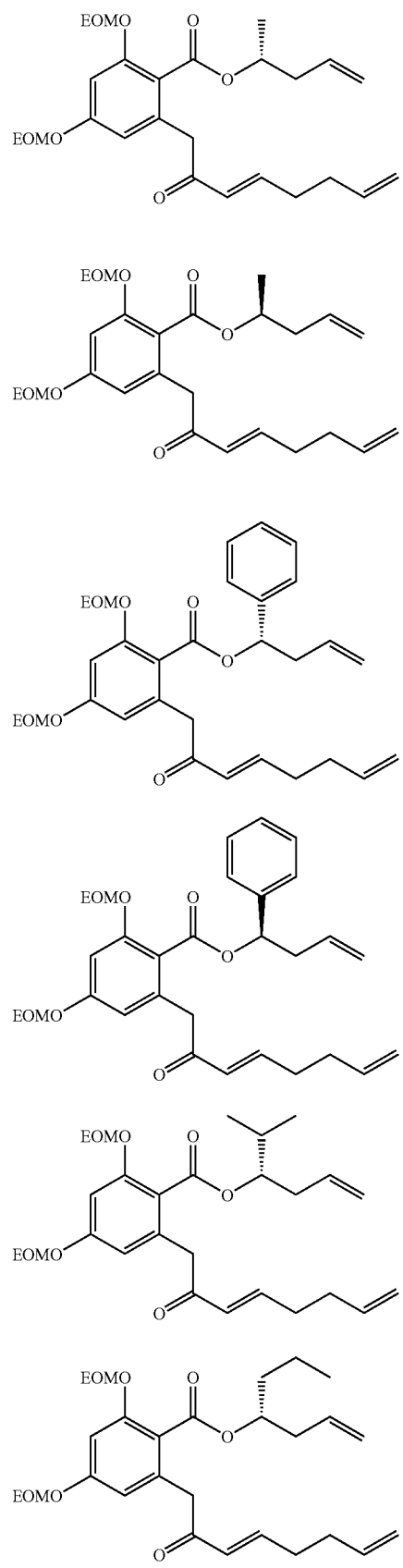
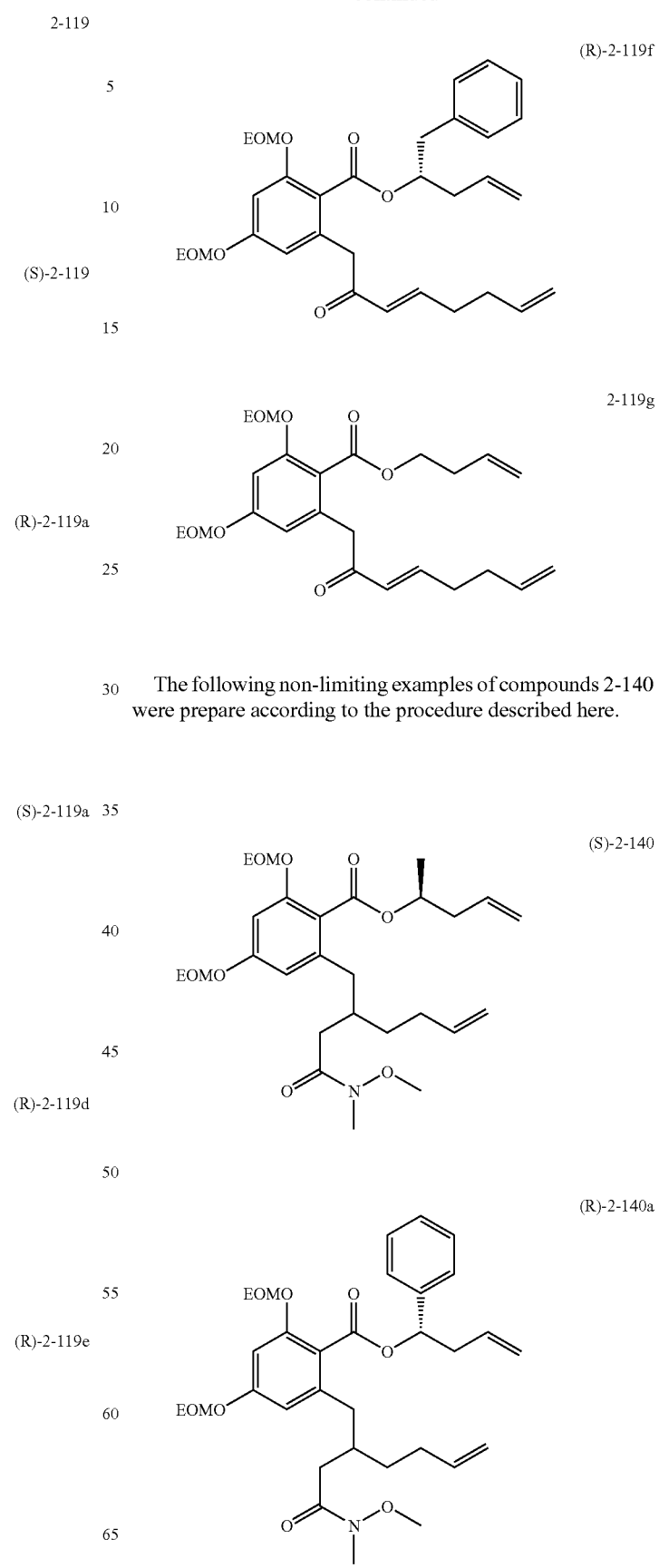
The following non-limiting examples of compounds 2-140 were prepare according to the procedure described here.

Illustrative Compounds 2-112/2-120:

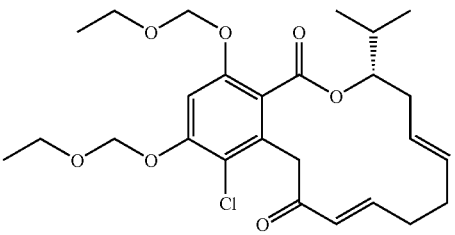

$^1$H NMR (CDCl$_3$, 400 MHz, 25° C.) δ 7.14 (s, 1H), 6.72-6.66 (m, 1H), 5.88 (d, J=15.2 Hz, 1H), 5.33-5.17 (m, 6H), 4.92-4.88 (m, 1H), 4.21 (d, J=17.0 Hz, 1H), 3.92 (d, J=17.0 Hz, 1H), 3.79-3.67 (m, 4H), 2.33-2.17 (m, 5H), 2.07-1.96 (m, 2H), 1.23 (t, J=7.0 Hz, 3H), 1.21 (t, J=7.0 Hz, 3H), 1.00 (d, J=5.8 Hz, 6H); $^{13}$C NMR (CDCl$_3$, 100 MHz, 25° C.) δ 195.7, 167.1, 154.7, 154.4, 147.4, 133.7, 131.2, 128.8, 128.4, 119.7, 118.0, 102.7, 93.9, 93.5, 80.0, 64.8, 64.5, 44.1, 32.3, 31.2, 30.7, 30.6, 18.3, 17.2, 15.0, 14.9; HRMS (ESI) m/z 517.1844 ([M+Na$^+$], C$_{26}$H$_{35}$O$_7$ClNa requires 517.1964); [α]$^{25}_D$ +21.3 (c 1.00, CHCl$_3$).

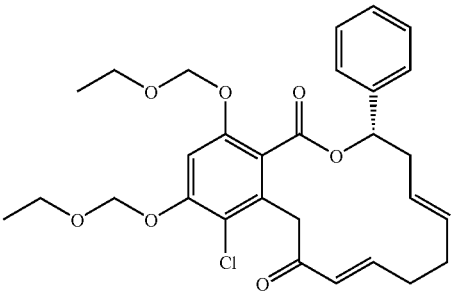

$^1$H NMR (CDCl$_3$, 400 MHz, 25° C.) δ 7.49-7.47 (m, 2H), 7.40-7.29 (m, 3H), 7.10 (s, 1H), 6.84-6.77 (m, 1H), 5.98 (d, J=15.2 Hz, 1H), 5.78 (d, J=8.8 Hz, 1H), 5.44-5.30 (m, 4H), 5.15 (d, J=7.0 Hz, 1H), 5.05 (d, J=6.8 Hz, 1H), 4.07 (d, J=17.0 Hz, 1H), 3.90 (d, J=17.0 Hz, 1H), 3.80 (d, J=7.0 Hz, 2H), 3.60-3.51 (m, 2H), 2.68-2.62 (m, 1H), 2.50-2.47 (m, 1H), 2.38-2.29 (m, 2H), 2.14-2.02 (m, 2H), 1.25 (t, J=7.0 Hz, 3H), 1.17 (t, J=7.0 Hz, 3H); $^{13}$C NMR (CDCl$_3$, 100 MHz, 25° C.) δ 195.7, 166.7, 154.8, 154.2, 147.3, 140.7, 133.3, 132.1, 128.5, 128.3 (×2), 128.2, 127.9, 127.7, 126.7 (×2), 120.1, 118.1, 102.9, 93.9, 93.4, 77.4, 64.8, 64.4, 44.5, 40.5, 30.7, 15.0, 14.9; HRMS (ESI) m/z 551.1807 ([M+Na$^+$], C$_{29}$H$_{33}$O$_7$ClNa requires 551.1680); [α]$^{25}_D$ −40.4 (c 0.79, CHCl$_3$).

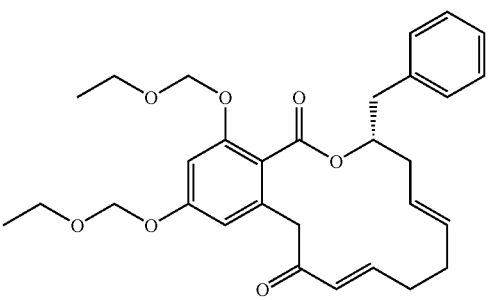

$^1$H NMR (CDCl$_3$, 400 MHz, 25° C.) δ 7.39-7.33 (m, 4H), 7.31-7.27 (m, 1H), 6.82 (s, 1H), 6.82-6.75 (m, 1H), 6.63 (s,

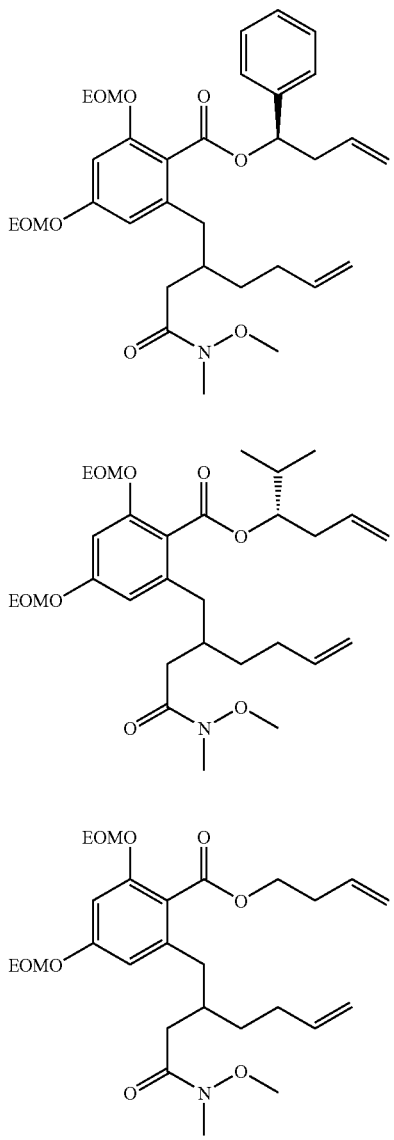

Example 3

General Procedure for the Metathesis Reaction

As depicted in Scheme 16, a solution of crude 2-118 or 2-119 (or mixture 2-118/2-119 and 2-140 when X=Cl), in anhydrous toluene (2 mM) was treated with Grubbs' second generation catalyst (0.10 equiv) and heated at 80° C. for 12 h. The reaction was cooled down to room temperature and the mixture was filtered through a pad of SiO$_2$, washed with CH$_2$Cl$_2$ followed by a mixture EtOAc/cyclohexane 1/1 and concentrated under reduced pressure. Purification by flash chromatography (SiO$_2$, 0-25% EtOAc/cyclohexane gradient) afforded compounds 2-112 or 2-120 or 2-140 (60-85% over two steps). Illustrative examples of compounds 2-112 or 2-120 and 2-140 follow; their characterization follows respectively in the text below each figure.

1H), 6.02 (d, J=16.4 Hz, 1H), 5.35-5.29 (m, 2H), 5.27-5.20 (m, 5H), 4.16 (d, J=14.6 Hz, 1H), 3.79-3.70 (m, 4H), 3.52 (d, J=14.6 Hz, 1H), 3.37 (dd, J=13.4, 4.1 Hz, 1H), 2.78 (dd, J=13.5, 9.4 Hz, 1H), 2.37-2.12 (m, 5H), 2.06-2.02 (m, 1H), 1.26 (t, J=7.0 Hz, 3H), 1.24 (t, J=7.0 Hz, 3H); $^{13}$C NMR (CDCl$_3$, 100 MHz, 25° C.) δ 197.6, 167.8, 159.2, 156.5, 149.0, 137.3, 135.5, 131.8, 129.9, 129.5 (×2), 128.6 (×2), 128.4, 126.7, 118.1, 109.9, 102.3, 93.5, 93.1, 75.8, 64.6, 64.4, 44.4, 41.0, 36.2, 31.0, 30.6, 15.0 (×2); HRMS (ESI) m/z 531.2350 ([M+Na$^+$], C$_{30}$H$_{36}$O$_7$Na requires 531.2359); [α]$^{25}$$_D$ −24.1 (c 0.33, CHCl$_3$).

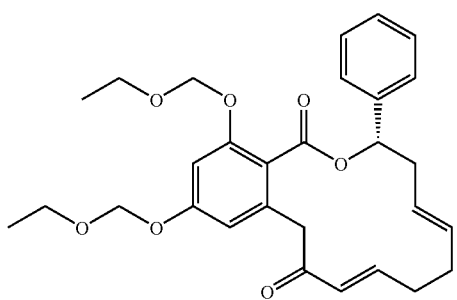

$^1$H NMR (CDCl$_3$, 400 MHz, 25° C.) δ 7.56-7.54 (m, 2H), 7.41-7.29 (m, 3H), 6.89-6.82 (m, 1H), 6.78 (d, J=2.3 Hz, 1H), 6.61 (d, J=1.8 Hz, 1H), 6.06 (d, J=16.4 Hz, 1H), 5.98 (dd, J=11.7, 2.4 Hz, 1H), 5.53-5.51 (m, 2H), 5.20 (d, J=7.0 Hz, 1H), 5.17 (d, J=6.4 Hz, 1H), 5.07 (d, J=7.0 Hz, 1H), 4.96 (d, J=7.0 Hz, 1H), 4.20 (d, J=14.6 Hz, 1H), 3.73-3.68 (m, 2H), 3.54-3.45 (m, 3H), 2.71-2.66 (m, 1H), 2.55-2.51 (m, 1H), 2.38-2.32 (m, 2H), 2.23-2.06 (m, 2H), 1.22 (t, J=7.0 Hz, 3H), 1.14 (t, J=7.0 Hz, 3H); $^{13}$C NMR (CDCl$_3$, 100 MHz, 25° C.) δ 197.6, 167.4, 159.3, 156.6, 149.0, 140.8, 135.6, 132.2, 129.9, 128.5, 128.2 (×2), 127.9, 126.9 (×2), 117.9, 109.9, 102.3, 93.2, 93.0, 76.6, 64.4, 64.3, 44.4, 40.5, 31.0, 30.6, 15.0, 14.9; HRMS (ESI) m/z 517.2062 ([M+Na], C$_{29}$H$_{34}$O$_7$Na requires 517.2197). [α]$^{25}$$_D$ −108.3 (c 1.00, CHCl$_3$).

Illustrative Compounds 2-121:

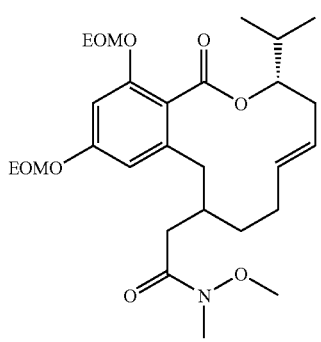

Mixture of 4 diastereoisomers: $^1$H NMR (CDCl$_3$, 400 MHz, 25° C.) δ 6.77 (s, 1H), 6.52 (s, 0.5H), 6.46 (s, 0.5H), 5.59-5.37 (m, 2H), 5.21-5.18 (m, 4H), 5.09-4.92 (m, 1H), 3.75-3.70 (m, 4H), 3.53-3.48 (m, 3H), 3.38-3.34 (m, 1H), 3.19-3.10 (m, 3H), 2.65-2.47 (m, 3H), 2.29-2.04 (m, 6H), 1.89-1.72 (m, 2H), 1.31-1.20 (m, 6H), 1.06-0.96 (m, 6H); HRMS (ESI-TOF) m/z 544.2907 ([M+Na$^+$], C$_{28}$H$_{43}$O$_8$NNa requires 544.2881).

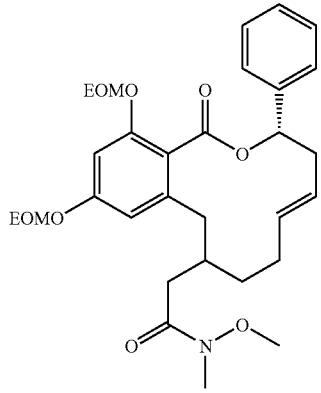

Mixture of 4 diastereoisomers: $^1$H NMR (CDCl$_3$, 400 MHz, 25° C.) δ 7.51-7.42 (m, 2H), 7.38-7.31 (m, 3H), 6.73-6.70 (m, 1H), 6.60-6.49 (m, 1H), 6.45-6.31 (m, 1H), 5.73-5.39 (m, 2H), 5.23-5.00 (m, 4H), 3.75-3.69 (m, 2H), 3.56-3.34 (m, 6H), 3.19-3.09 (m, 3H), 2.66-2.08 (m, 8H), 1.31-1.19 (m, 5H), 1.10-1.04 (m, 3H); HRMS (ESI-TOF) m/z 578.2715 ([M+Na$^+$], C$_{31}$H$_{41}$O$_8$NNa requires 578.2724).

Example 4

General Procedure for the EOM Deprotection to Generate Compounds Deprotected-2-121 and 2-85

As depicted in Scheme 17 for compounds 2-103/2-85, to a solution of the corresponding compound 2-120/2-112 or 2-121 (1.0 equiv) in MeOH (0.03 M) was added PS-TsOH (10.0 equiv, 3.2 mmol/g) and the suspension was shaken at 40° C. for 1 to 4 h. The reaction mixture was filtered and the methanolic solution concentrated under reduced pressure. Purification by flash chromatography (SiO$_2$, 0-20% EtOAc/cyclohexane gradient) afforded the corresponding compound deprotected-2-121 or compound 2-103/2-85. (>90%). Illustrative examples of compounds deprotected-2-121 and of 2-103/2-85 follow; their characterization follows respectively in the text below each figure.

Illustrative Compound Deprotected-2-121:

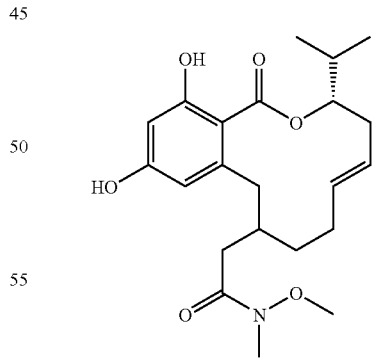

Mixture of 4 diastereoisomers: $^1$H NMR (CDCl$_3$, 400 MHz, 25° C.) δ 11.54 (s, 1H), 6.33 (d, J=2.3 Hz, 1H), 6.25 (s, 1H), 5.53-5.51 (m, 1H), 5.44-5.41 (m, 1H), 5.11-5.08 (m, 1H), 4.01 (d, J=11.7 Hz, 2H), 3.45 (s, 3H), 3.11 (s, 3H), 2.83-2.73 (m, 1H), 2.68-2.59 (m, 1H), 2.27-2.20 (m, 1H), 2.10-1.87 (m, 6H), 1.82-1.72 (m, 1H), 1.01-0.94 (m, 6H); HRMS (ESI-TOF) m/z 428.2109 ([M+Na$^+$], C$_{22}$H$_{31}$O$_6$NNa requires 428.2044).

Illustrative Compounds 2-103/2-85:

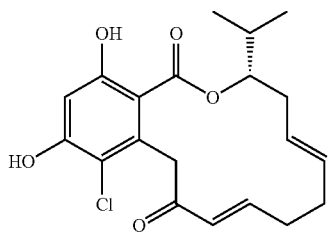

¹H NMR (C₆D₆, 400 MHz, 25° C.) δ 12.31 (s, 1H), 6.83 (s, 1H), 6.74-6.67 (m, 1H), 5.84 (bs, 1H), 5.82 (d, J=15.8 Hz, 1H), 5.03-4.95 (m, 1H), 4.88-4.86 (m, 1H), 4.76-4.70 (m, 1H), 4.40 (d, J=17.6 Hz, 1H), 4.15 (d, J=17.5 Hz, 1H), 2.40-2.34 (m, 1H), 2.22-2.18 (m, 1H), 1.87-1.65 (m, 4H), 1.53-1.48 (m, 1H), 0.92 (d, J=6.4 Hz, 3H), 0.66 (d, J=7.0 Hz, 3H); ¹³C NMR (C₆D₆, 100 MHz, 25° C.) δ 193.7, 164.2, 156.8, 145.8, 137.2, 131.8, 129.3, 126.3, 115.3, 107.9, 103.6, 82.1, 46.4, 33.3, 30.9, 30.7, 28.8, 20.1, 18.5, 18.3; HRMS (ESI-TOF) m/z 401.1170 ([M+Na⁺], C₂₀H₂₃ClO₅Na requires 401.1126); [α]²⁵_D −35.6 (c 0.52, CHCl₃).

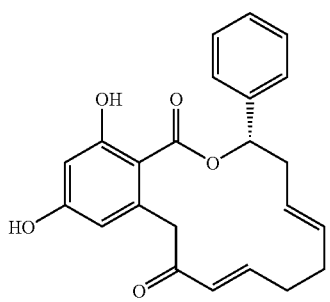

¹H NMR (C₆D₆, 400 MHz, 25° C.) δ 12.0 (bs, 1H), 7.32-7.29 (m, 3H), 7.19-7.15 (m, 2H), 6.86-6.79 (m, 1H), 6.51 (d, J=2.4 Hz, 1H), 6.27-6.25 (m, 1H), 6.11 (d, J=2.4 Hz, 1H), 6.02 (d, J=15.8 Hz, 1H), 5.49 (s, 1H), 5.17-5.10 (m, 1H), 4.97-4.90 (m, 1H), 4.40 (d, J=16.4 Hz, 1H), 3.97 (d, J=17.2 Hz, 1H), 2.83-2.76 (m, 1H), 2.45-2.38 (m, 1H), 1.89-1.78 (m, 2H), 1.67-1.58 (m, 2H); ¹³C NMR (C₆D₆, 100 MHz, 25° C.) δ 196.5, 169.6, 166.1, 161.3, 146.0, 140.5, 138.8, 132.1, 130.0, 128.6 (×2), 127.3, 126.6 (×2), 126.3, 112.2, 105.9, 103.0, 77.1, 48.6, 38.4, 30.9, 30.3; HRMS (ESI) m/z 401.1271 ([M+Na⁺], C₂₃H₂₂O₅Na requires 401.1359); [α]²⁵_D −10.3 (c 0.25, CHCl₃).

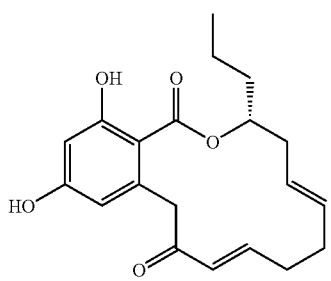

¹H NMR (CDCl₃, 400 MHz, 25° C.) δ 12.43 (s, 1H), 6.74 (d, J=1.7 Hz, 1H), 6.73-6.65 (m, 1H), 6.48 (d, J=1.7 Hz, 1H), 5.92 (d, J=15.8 Hz, 1H), 5.12-5.00 (m, 2H), 4.91-4.80 (m, 1H), 4.19 (d, J=17.0 Hz, 1H), 3.84 (d, J=16.4 Hz, 1H), 2.77 (m, 1H), 2.64-2.57 (m, 1H), 2.01-1.97 (m, 1H), 1.89-1.70 (m, 3H), 1.61-1.56 (m, 2H), 1.30-1.21 (m, 2H), 0.90 (t, J=6.7 Hz, 3H); ¹³C NMR (CDCl₃, 100 MHz, 25° C.) δ 197.5, 169.9, 165.6, 160.6, 147.5, 140.2, 131.9, 129.5, 127.0, 112.8, 106.1, 102.9, 76.2, 48.7, 35.7, 34.3, 31.1, 29.7, 19.4, 13.8; HRMS (ESI-TOF) m/z 367.1330 ([M+Na⁺], C₂₀H₂₄O₅Na requires 367.1521); [α]²⁵_D +21.6 (c 0.36, CHCl₃).

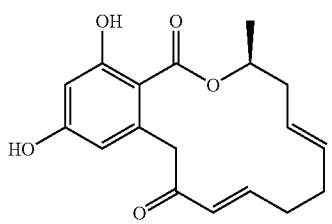

¹H NMR (CD₃OD, 400 MHz, 25° C.) δ 6.78-6.71 (m, 1H), 6.29 (d, J=2.4 Hz, 1H), 6.22 (d, J=2.0 Hz, 1H), 5.87 (d, J=15.5 Hz, 1H), 5.37-5.23 (m, 3H), 4.01 (d, J=17.2 Hz, 1H), 3.92 (d, J=17.0 Hz, 1H), 2.67-2.61 (m, 1H), 2.29-2.15 (m, 5H), 1.31 (d, J=6.4 Hz, 3H); ¹³C NMR (CD₃OD, 100 MHz, 25° C.) δ 198.5, 169.8, 164.2, 162.3, 148.4, 139.1, 131.6, 129.6, 127.3, 111.7, 101.7, 72.0, 47.7, 36.8, 30.8, 30.7, 17.4, (1 quarternary carbon is not visible); HRMS (ESI) m/z 339.1141 ([M+Na], C₁₈H₂₀O₅Na requires 339.1203). [α]²⁵_D −45.1 (c 0.27, CHCl₃).

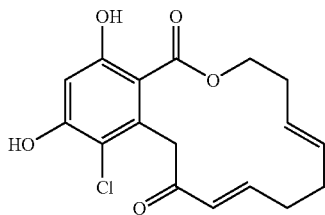

¹H NMR (CD₃OD, 400 MHz, 25° C.) δ 6.74-6.68 (m, 1H), 6.48 (s, 1H), 5.86 (d, J=15.2 Hz, 1H), 5.31-5.25 (m, 2H), 4.39 (t, J=5.3 Hz, 2H), 4.27 (s, 2H), 2.43-2.40 (m, 2H), 2.25 (m, 4H); ¹³C NMR (CD₃OD, 100 MHz, 25° C.) δ 196.9, 170.1, 161.9, 158.1, 147.8, 135.9, 130.9, 130.2, 129.9, 115.2, 107.3, 102.4, 65.9, 46.2, 31.3, 30.9, 30.5; HRMS (ESI) m/z 337.0797 ([M+H⁺], C₁₇H₁₈O₅Cl requires 337.0837).

Example 5

General Procedure for the Synthesis of Compounds 2-141

As depicted in Scheme 17, to a solution of corresponding compound 2-120/2-112 (1.0 equiv) in MeOH (0.03 M) at 0° C. was added BER-resin (Borohydride on Amberlite®, 1.0 equiv, 2.5 mmol g⁻¹) and the reaction was stirred over 12 h. The reaction was then filtered and concentrated under reduced pressure. Purification by flash chromatography (SiO₂, 0-20% EtOAc/cyclohexane gradient) afforded 2-141 (~60%) as a mixture of two diastereoisomers (1:1). An illustrative example of compound 2-141 follows; its characterization data are in the text below the figure.

Illustrative Compound 2-141:

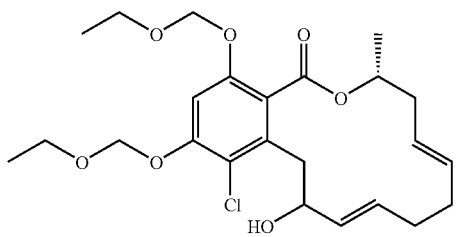

$^1$H NMR (CD$_3$Cl, 400 MHz) δ 7.05 (s, 1H), 6.99 (s, 1H), 5.64-5.57 (m, 2H), 5.54-5.53 (m, 2H), 5.49-5.35 (m, 6H), 5.31-5.28 (m, 4H), 5.24-5.16 (m, 4H), 5.13-5.08 (m, 1H, 35'), 4.68 (m, 1H, 35'), 4.56 (m, 1H, 35), 3.81-3.69 (m, 8H), 3.25 (dd, J=13.9, 8.0 Hz, 1H, 35), 3.19 (dd, J=13.7, 4.8 Hz, 1H, 35'), 3.11 (dd, J=13.5, 10.1 Hz, 1H, 35'), 2.90 (dd, J=13.9, 5.12 Hz, 1H, 35), 2.35 (m, 9H), 2.09-1.95 (m, 1H), 1.80-1.70 (m, 2H), 1.39 (d, J=2.9 Hz, 3H, 35), 1.37 (d, J=3.2 Hz, 3H, 35'), 1.24 (2×q, J=6.9 and 5.0 Hz, 12H, 35+35'); HRMS (ESI) m/z 491.1729 ([M+Na$^+$], C$_{24}$H$_{33}$ClO$_7$Na requires 491.1807).

Example 6

General Procedure for the Synthesis of Compounds 2-142

As depicted in Scheme 17, to a solution of the corresponding compound 2-141 (1.0 equiv) in MeOH (0.02 M) was added PS-TsOH (10.0 equiv, 3.2 mmol g$^{-1}$) and the suspension was shaken at 40° C. for 4 h. The reaction mixture was then filtered and the methanolic solution concentrated under reduced pressure. Purification by preparative TLC (SiO$_2$, 25% EtOAc/cyclohexane) afforded 2-142 (~90%) as a mixture of two diastereoisomers (1:1). An illustrative example of compound 2-142 follows; its characterization data are in the text below the figure.

Illustrative Compound 2-142:

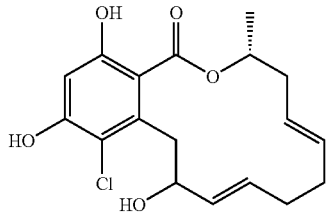

$^1$H NMR ((CD$_3$)$_2$CO, 400 MHz) δ 12.30 (s, 2H), 11.43 (s, 2H), 6.75 (s, 2H), 6.00 (bdd, J=6.4, 6.2 Hz, 1H), 5.97 (bdd, J=6.4, 6.2 Hz, 1H), 5.97 (bd, J=6.7 Hz, 1H), 5.77 (bd, J=6.7 Hz, 1H), 5.57-5.48 (m, 4H), 5.18-5.14 (m, 2H), 3.38-3.28 (m, 3H), 3.02 (dd, J=16.1, 10.5 Hz, 1H), 2.41-2.09 (m, 12H), 1.11 (d, J=6.2 Hz, 6H); HRMS (ESI) m/z 375.1029 ([M+Na$^+$], C$_{18}$H$_{21}$ClO$_5$Na requires 375.0970).

Example 7

General Procedure for the Synthesis of Compounds 2-143

As depicted in Scheme 17, to a solution of the corresponding compound 2-141 (1.0 equiv) in DMF (0.02 M) were added Ac$_2$O (1.2 equiv), morpholinomethyl polystyrene (1.2 equiv, 3.2 mmol g$^{-1}$) and DMAP (0.05 equiv) at 23° C. and the mixture was stirred for 30 min, followed by TLC until consumption of the starting material. Then, the resin was filtered and the organic phase was concentrated under reduced pressure. Purification by PTLC (SiO$_2$, 20% EtOAc/cyclohexane) afforded corresponding 2-143 (~80%) as a mixture of two diastereoisomers 1:1: An illustrative example of compound 2-143 follows; its characterization data are in the text below the figure.

Illustrative Compound 2-143:

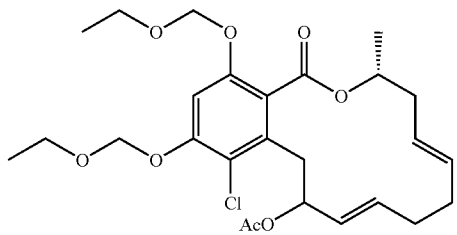

$^1$H NMR (CD$_3$Cl, 400 MHz) δ 7.04 (s, 1H), 7.01 (s, 1H), 5.86 (dd, J=15.0, 6.9 Hz, 1H), 5.67 (dd, J=12.4, 6.2 Hz, 1H), 5.60-5.54 (m, 4H), 5.48 (dd, J=7.2, 7.2 Hz, 1H), 5.41-5.34 (m, 3H), 5.32-5.30 (m, 4H), 5.28-5.23 (m, 2H), 5.21 (dd, J=11.0, 6.7 Hz, 2H), 5.17 (dd, J=11.8, 6.9 Hz, 2H), 3.81-3.69 (m, 8H), 3.43 (dd, J=14.2, 7.5 Hz, 1H), 3.23-3.15 (m, 2H), 2.85 (dd, J=13.9, 5.4 Hz, 1H), 2.30-2.17 (m, 8H), 2.12 (s, 3H), 2.06 (s, 3H), 1.95-2.00 (m, 4H), 1.39 (2×d, J=5.6 Hz, 6H), 1.24 (m, 12H); HRMS (ESI) m/z 533.1864 ([M+Na$^+$], C$_{26}$H$_{35}$ClO$_8$Na requires 533.1913).

Example 8

General Procedure for the Synthesis of Compounds 2-144

As depicted in Scheme 17, to a solution of corresponding compound 2-143 (1.0 equiv) in MeOH (0.02 M) was added PS-TsOH (10.0 equiv, 3.2 mmol/g) and the suspension was shaken at 40° C. for 4 h. The reaction mixture was filtered and the methanolic solution concentrated under reduced pressure. Purification by PTLC (SiO$_2$, 20% EtOAc/cyclohexane) afforded compounds 2-144 (~60% yield). An illustrative example of compound 2-144 follows; its characterization data are in the text below the figure.

Illustrative Compound 2-144:

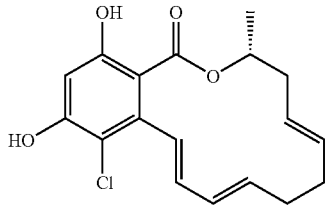

Mixture of diastereoisomers 2:1: $^1$H NMR (CD$_3$Cl, 400 MHz) δ 12.6 (s, 1H), 12.12 (s, 0.5H), 6.93 (d, J=8.7 Hz, 0.5H), 6.66 (s, 1H), 6.64 (s, 0.5H), 6.62-6.60 (m, 1H), 6.10-6.05 (m, 3H), 5.47-5.33 (m, 4.5H), 2.60-2.53 (m, 1.5H), 2.26-2.02 (m, 7.5H), 1.44 (d, J=6.2 Hz, 1.5H), 1.43 (d, J=6.4 Hz, 3H); HRMS (ESI) m/z 357.0898 ([M+Na$^+$], C$_{18}$H$_{19}$ClO$_4$Na requires 357.0864).

Example 9

General Procedure for the Synthesis of Compounds 2-145

As depicted in Scheme 18, to a solution of corresponding compound 2-85 (1.0 equiv) in methanol (0.03 M) was added sulfamic acid resin (10.0 equiv) and the suspension was stirred for 15 h at 40° C. with. The reaction was then filtered, the resin washed several times with $CH_2Cl_2$. Concentration under reduced pressure followed by purification on PTLC (Hexane/EtOAc: 1/1) afforded desired compounds 2-145 as a mixture diastereoisomers (2:1). An illustrative example of compound 2-145 follows; its characterization data are in the text below the figure.

Illustrative Compound 2-145:

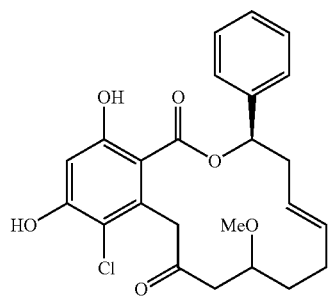

$^1$H NMR ($C_6D_6$, 400 MHz, 25° C.) δ 12.28 (s, 0.4H), 11.91 (s, 0.6H), 7.21-7.11 (m, 5H), 6.62 (s, 1H), 6.03-6.01 (m, 1H), 5.58 (bs, 1H), 5.38-5.33 (m, 1H), 5.27-5.20 (m, 1H), 4.76 (d, J=17.5 Hz, 0.6H), 4.02 (d, J=17.0 Hz, 0.4H), 4.18 (d, J=18.1 Hz, 0.6H), 4.09 (d, J=17.0 Hz, 0.4H), 3.87 (bs, 0.4H), 3.81 (bs, 0.6H), 3.15 (s, 1.8H), 3.12 (s, 1.2H), 2.83-2.78 (m, 1H), 2.45-2.30 (m, 2H), 2.18-2.16 (m, 1H), 2.02-1.97 (m, 2H), 1.79-1.72 (m, 2H); HRMS (ESI-TOF) m/z 467.1366 ([M+Na$^+$], $C_{24}H_{25}O_6ClNa$ requires 467.1232).

Example 10

General Procedure for the Synthesis of Compounds 2-146

As depicted in Scheme 19, to a solution of corresponding compound 2-103/2-85 (1.0 equiv) in $CH_2Cl_2$/AcOH 10/1 (0.08 M) (polystyrylmethyl)trimethylammonium cyanoborohydride (2.0 equiv, 3.5 mmol g$^{-1}$) was added at 23° C. and the reaction was monitored by TLC until the starting material had been consumed (4 h). Then, the resin was filtered and the organic phase was concentrated under reduced pressure. Purification by PTLC (SiO$_2$, 30% EtOAc/cyclohexane) afforded compounds 2-146 (50-60%). An illustrative example of compound 2-146 follows; its characterization data are in the text below the figure.

Illustrative Compound 15:

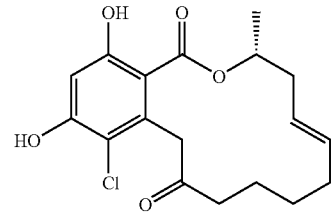

$^1$H NMR (CD$_3$Cl, 400 MHz) δ 11.75 (s, 1H), 6.65 (s, 1H), 5.48 (m, 2H), 5.49 (ddt, J=6.1, 3.5, 2.9 Hz, 1H), 4.53 (d, J=17.5 Hz, 1H), 4.04 (d, J=17.7 Hz, 1H), 2.61-2.54 (m, 2H), 2.48-2.28 (m, 3H), 2.19-2.14 (m, 1H), 2.08-1.99 (m, 1H), 1.72-1.61 (m, 3H), 1.41 (d, J=6.4 Hz, 3H); HRMS (ESI) m/z 375.1050 ([M+Na$^+$], $C_{18}H_{21}ClO_5Na$ requires 375.0970).

Example 11

General Procedure for the Synthesis of Compounds 2-147

As depicted in Scheme 19, to a solution of corresponding compound 2-103/2-85 (1.0 equiv), in THF (0.05 M) were added in a sequential manner the corresponding alcohol (2.0 equiv), triphenylphosphine (2.0 equiv) and ethoxycarbonylazocarboxymethyl polystyrene (2.0 equiv, 1.3 mmol g$^{-1}$). The reaction mixture was shaken at room temperature for 8 hours, and then, the resin was filtered and the filtrates were directly purified by PTLC (SiO$_2$, 10% EtOAc/cyclohexane) to afford a mixture of compound 2-147 along with the bis-allylated product (78%). An illustrative example of compound 2-147 follows; its characterization data are in the text below the figure.

Illustrative Compound 2-147:

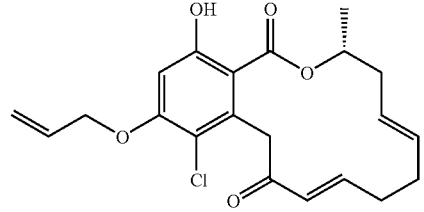

Mixture with the corresponding bis-allylated compound (1:1): $^1$H NMR (CD$_3$Cl, 400 MHz) δ 11.83 (s, 1H), 6.82 (ddd, J=15.7, 8.2, 4.6 Hz, 1H), 6.72-6.65 (m, 1H), 6.46 (s, 1H), 6.41 (s, 1H), 6.09-5.98 (m, 3H), 5.82 (d, J=15.7 Hz, 1H), 5.46-5.16 (m, 8H), 4.57-4.54 (m, 3H), 4.51-4.49 (m, 3H), 4.19 (d, J=17.5 Hz, 1H), 4.11 (d, J=14.6 Hz, 1H), 3.78 (d, J=17.0 Hz, 1H), 3.51 (d, J=14.2 Hz, 1H), 2.76-2.69 (m, 1H), 2.38-2.05 (m, 11H), 1.42 (d, J=6.2 Hz, 3H), 1.35 (d, J=6.3 Hz, 3H); mono-allylated compound HRMS (ESI) m/z 413.1103 ([M+Na$^+$], $C_{21}H_{23}ClO_5Na$ requires 413.1132); bis-allylated compound HRMS (ESI) m/z 453.1422 ([M+Na$^+$], $C_{24}H_{27}ClO_5Na$ requires 453.1449).

Example 12

General Procedure for the Synthesis of Compounds 2-148

As depicted in Scheme 19, to a solution of the corresponding compound 2-103/2-85 (1.0 equiv) in CH$_2$Cl$_2$ (0.05 M)

was added TBD-methyl polystyrene (2.0 equiv, 2.9 mmol g$^{-1}$) and the corresponding alkyl bromide or chloride (BrCH$_2$COO$^t$Bu, EOMCl) (0.9 equiv) at 23° C. and the mixture was shaken for 3 h. The resin was then filtered and the filtrates were concentrated under reduced pressure. Purification by PTLC (SiO$_2$, 30% EtOAc/cyclohexane) afforded corresponding compound 2-148 (>90%). Illustrative examples of compound 2-148 follows; their characterization data are presented respectively in the text below each figure.

Illustrative Compounds 2-148:

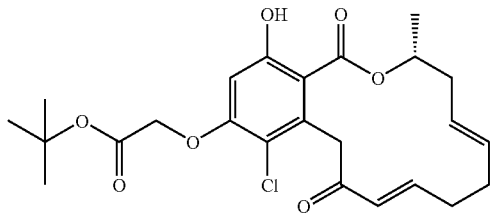

$^1$H NMR (CD$_3$Cl, 400 MHz) δ 11.84 (s, 1H), 6.69 (m, 1H), 6.41 (s, 1H), 5.76 (d, J=15.0 Hz, 1H), 5.43 (m, 1H), 5.26 (ddd, J=15.0, 9.1, 4.8 Hz, 1H), 5.18-5.11 (m, 1H), 4.65 (s, 2H), 4.33 (d, J=17.7 Hz, 1H), 4.16 (d, J=17.5 Hz, 1H), 2.65-2.58 (m, 1H), 2.37-2.34 (m, 2H), 2.25-2.21 (m, 1H), 2.12-2.01 (m, 2H), 1.53 (s, 9H), 1.34 (d, J=6.5 Hz, 3H); HRMS (ESI) m/z 487.1498 ([M+Na$^+$], C$_{24}$H$_{29}$ClO$_7$Na requires 487.1494).

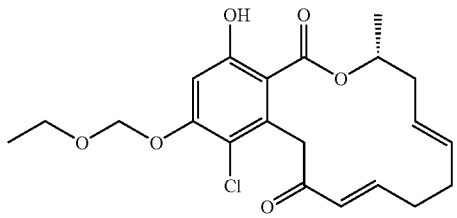

$^1$H NMR (C$_6$D$_6$, 400 MHz, 25° C.) δ 11.76 (s, 1H), 6.86 (s, 1H), 6.70 (dt, J=14.9, 7.3 Hz, 1H), 5.77 (d, J=15.8 Hz, 1H), 5.46-5.42 (m, 1H), 5.37 (s, 2H), 5.30-5.19 (m, 2H), 4.34 (d, J=17.6 Hz, 1H), 4.16 (d, J=18.1 Hz, 1H), 3.80 (q, J=7.0 Hz, 2H), 2.66-2.59 (m, 1H), 2.37-2.34 (m, 2H), 2.26-2.21 (m, 1H), 2.13-2.06 (m, 2H), 1.34 (d, J=6.4 Hz, 3H), 1.27 (t, J=7.0 Hz, 3H); HRMS (ESI) m/z ([M+Na], C$_{21}$H$_{25}$O$_6$ClNa requires 431.1237).

Example 13

General Procedure for the Synthesis of Compounds 2-149

As depicted in Scheme 19, to a solution of compound 2-103/2-85 (1.0 equiv) in acetone/H$_2$O 10/1 (0.05 M) was added OsO$_4$ (0.1 equiv) followed by NMO (1.0 equiv) at 23° C. and the mixture was stirred for 1 h. The crude mixture was filtered through a plug of silica, concentrated and purified by PTLC (SiO$_2$, 30% EtOAc/cyclohexane) to afford 2-149 (>70%) as a mixture of two diastereoisomers. An illustrative example of compound 2-149 follows; its characterization data are in the text below the figure.

Illustrative Compound 2-149:

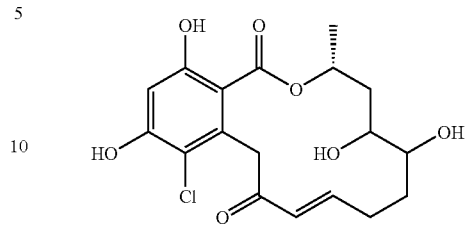

$^1$H NMR (CD$_3$OD, 400 MHz) δ 7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 2H), 2.39-2.30 (m, 2H), 2.27-2.18 (m, 2H), 2.08-2.98 (m, 2H), 2.00-1.85 (m, 4H), 1.44 (d, J=6.4 Hz, 6H); HRMS (ESI) m/z 407.1031 ([M+Na$^+$], C$_{18}$H$_{21}$ClO$_7$Na requires 407.0868).

Example 14

General Procedure for the Synthesis of Compounds 2-150

As depicted in Scheme 19, to a solution of compound 2-103/2-85 (1.0 equiv) in CH$_3$CN (0.03 M) at 0° C. was added freshly made DMDO (1.2 equiv, 0.04 M in acetone) and the mixture was stirred for 30 min. After evaporation of the solvents under reduced pressure, purification by PTLC (SiO$_2$, 30% EtOAc/cyclohexane) afforded epoxides 2-150 (>90%) as a mixture of two diastereoisomers. Illustrative examples of compound 2-150 follow; their characterization data are presented respectively in the text below each figure.

Illustrative Compounds 2-150:

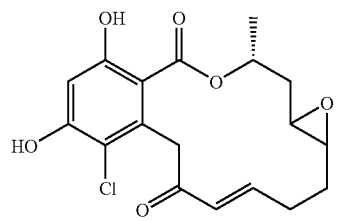

$^1$H NMR (CDCl$_3$, 400 MHz) δ 11.84 (s, 2H), 6.94-6.82 (m, 2H), 6.69 (s, 1H), 6.66 (s, 1H), 6.23 (d, J=17.1 Hz, 1H), 6.11 (dd, J=13.2, 1.6 Hz, 1H), 5.39 (tdd, J=7.5, 3.2, 2.7 Hz, 1H), 5.32 (m, 1H), 4.53 (d, J=17.7 Hz, 2H), 4.27 (d, J=17.7 Hz, 2H), 2.79-2.76 (m, 1H), 2.74-2.69 (m, 1H), 2.58 (m, 1H), 2.56 (m, 1H), 2.47-2.24 (m, 8H), 2.13-2.08 (m, 1H), 2.05-2.03 (m, 1H), 1.91 (dd, J=4.3, 4.3 Hz, 1H), 1.87 (dd, J=4.3, 4.3 Hz, 1H), 1.51 (d, J=6.4 Hz, 3H), 1.35 (d, J=6.4 Hz, 3H); HRMS (ESI) m/z 389.0724 ([M+Na$^+$], C$_{18}$H$_{19}$ClO$_6$Na requires 389.0762).

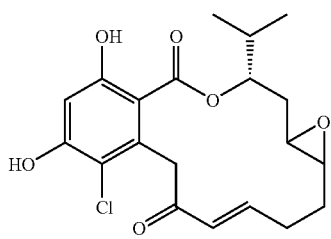

¹H NMR (C₆D₆, 400 MHz, 25° C.) δ 11.56 (2×s, 2H), 6.92-6.82 (m, 2H), 6.71 (s, 1H), 6.67 (s, 1H), 6.20 (m, 3H), 6.06 (d, J=15.8 Hz, 1H), 5.11 (bs, 1H), 5.94 (m, 1H), 4.46 (2×d, J=18.1 Hz, 2H), 4.20 (2×d, J=18.1 Hz, 2H), 2.72-2.70 (m, 2H), 2.53-2.48 (m, 4H), 2.38-2.35 (m, 3H), 2.25-2.13 (m, 5H), 1.84-1.77 (m, 2H), 1.05-1.01 (m, 6H), 0.91-0.88 (m, 3H), 0.86-0.84 (m, 3H); HRMS (ESI) m/z 417.1128 ([M+Na⁺], $C_{20}H_{23}O_6ClNa$ requires 417.1075).

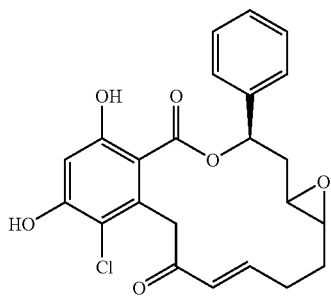

¹H NMR (C₆D₆, 400 MHz, 25° C.) δ 11.80 (2×s, 2H), 7.43-7.18 (m, 10H), 7.03-6.95 (m, 2H), 6.69 (s, 1H), 6.61 (s, 1H), 6.30 (d, J=16.4 Hz, 1H), 6.21 (d, J=15.8 Hz, 1H), 6.15-6.10 (m, 1H), 6.03 (d, J=11.1 Hz, 1H), 4.84 (2×d, J=18.1 Hz, 2H), 4.41 (2×d, J=17.6 Hz, 2H), 2.68-2.60 (m, 4H), 2.41-2.27 (m, 8H), 1.83-1.76 (m, 4H); HRMS (ESI) m/z 451.1028 ([M+Na], $C_{23}H_{21}O_6ClNa$ requires 451.0919).

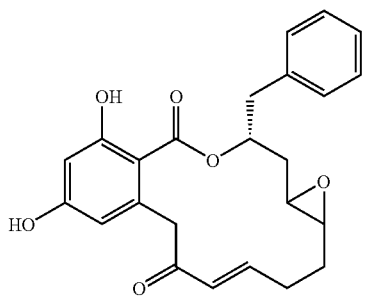

Major isomer: ¹H NMR (C₆D₆, 400 MHz, 25° C.) δ 11.94 (s, 1H), 7.36-7.28 (m, 5H), 6.95-6.88 (m, 1H), 6.42 (s, 1H), 6.22 (s, 1H), 6.11 (d, J=15.8 Hz, 1H), 5.47 (m, 1H), 5.41 (bs, 1H), 4.43 (d, J=17.5 Hz, 1H), 3.56 (d, J=17.6 Hz, 1H), 3.19 (dd, J=13.7, 6.0 Hz, 1H), 3.03 (dd, J=13.7, 7.9 Hz, 1H), 2.87 (bs, 1H), 2.70-2.28 (m, 4H), 2.03-1.93 (m, 2H); HRMS (ESI) m/z 431.1578 ([M+Na], $C_{24}H_{24}O_6Na$ requires 431.1465).

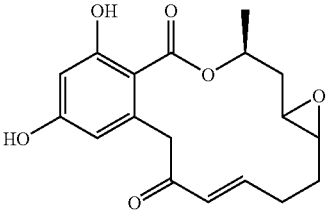

¹H NMR (C₆D₆, 400 MHz, 25° C.) δ 11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (m, 2H), 2.57-2.52 (m, 2H), 2.46-2.27 (m, 2H), 2.14-2.10 (m, 1H), 1.93-1.88 (m, 1H), 1.48 (d, J=6.4 Hz, 3H); other isomer: ¹H NMR (C₆D₆, 400 MHz, 25° C.) δ 11.67 (s, 1H), 6.89-6.83 (m, 1H), 6.40 (d, J=2.4 Hz, 1H), 6.24 (d, J=2.9 Hz, 1H), 6.21 (d, J=16.4 Hz, 1H), 5.37 (bs, 1H), 5.22 (m, 1H), 4.20 (d, J=17.0 Hz, 1H), 4.06 (d, J=17.0 Hz, 1H), 2.74 (m, 2H), 2.57-2.20 (m, 4H), 1.80-1.76 (m, 1H), 1.68-1.60 (m, 1H), 1.37 (d, J=6.4 Hz, 3H); HRMS (ESI) m/z 355.1249 ([M+Na], $C_{18}H_{20}O_6Na$ requires 355.1152).

Example 15

General Procedure for the Synthesis of Compounds 2-151

As depicted in Scheme 20, to a solution of compound 2-120 (1.0 equiv) in dioxane (0.05 M) at 23° C. was added HCl$_{conc.}$ (20 equiv), and the mixture was stirred for 3 h. After that time the reaction was filtered through a plug of silica gel, the solvents were evaporated under reduced pressure, and purified by PTLC (SiO₂, 30% EtOAc/cyclohexane) to afford compound 2-151 (>75%) as a mixture of two diastereoisomers. Illustrative examples of compound 2-151 follow; their characterization data are presented respectively in the text below each figure.

Illustrative Compounds 2-151:

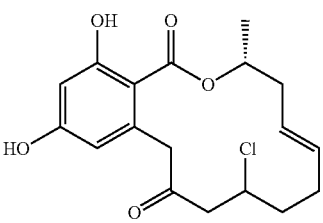

¹H NMR (CDCl₃, 400 MHz) δ 12.11 (s, 1H), 11.78 (s, 1H), 6.51 (s, 1H), 6.43 (s, 1H), 6.41 (d, J=2.4 Hz, 1H), 6.37 (d, J=2.7 Hz, 1H), 6.21 (d, J=2.4 Hz, 1H), 6.11 (d, J=2.4 Hz, 1H), 5.59-5.51 (m, 3H), 5.40-5.32 (m, 3H), 4.54 (d, J=17.2 Hz, 1H), 4.42 (d, J=17.2 Hz, 1H), 3.60 (d, J=17.2 Hz, 1H), 3.45 (d, J=17.0 Hz, 1H), 3.28 (dd, J=18.5, 9.4 Hz, 1H), 3.11 (dd, J=13.7, 6.2 Hz, 1H), 3.07 (dd, J=13.4, 4.6 Hz, 1H), 2.76 (dd, J=19.0, 6.2 Hz, 1H), 2.62 (ddd, J=15.5, 8.8, 4.0 Hz, 1H), 2.54 (ddd, J=15.3, 6.2, 3.2 Hz, 1H), 2.40-2.26 (m, 4H), 2.25-2.13 (m, 4H), 2.03-1.91 (m, 2H), 1.42 (d, J=6.4 Hz, 3H), 1.40 (d, J=6.4 Hz, 3H); HRMS (ESI) m/z 375.0928 ([M+Na⁺], $C_{18}H_{21}ClO_5Na$ requires 375.0970).

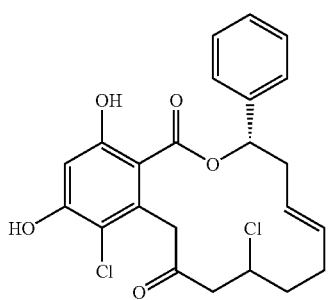

¹H NMR (C₆D₆, 400 MHz, 25° C.) δ 11.76 (s, 0.5H), 11.36 (s, 0.5H), 7.40-7.29 (m, 5H), 6.65 (s, 0.5H), 6.62 (s, 0.5H), 6.18 (t, J=5.8 Hz, 1H), 6.14 (s, 0.5H), 6.12 (s, 0.5H), 5.67-5.62 (m, 1H), 5.55-5.49 (m, 1H), 4.93 (d, J=18.1 Hz, 0.5H), 4.80 (d, J=17.1 Hz, 0.5H), 4.58-4.56 (m, 1H), 4.38 (d, J=18.1 Hz, 0.5H), 4.18 (d, J=17.1 Hz, 0.5H), 3.33-3.27 (m, 1H), 3.10 (dd, J=18.4, 3.8 Hz, 0.5H), 2.84-2.68 (m, 2.5H), 2.42-2.32 (m, 2H), 2.23-2.17 (m, 1H), 2.13-2.04 (m, 1H); HRMS (ESI-TOF) m/z 471.0754 ([M+Na⁺], $C_{23}H_{22}O_5Cl_2Na$ requires 471.0737).

Example 16

General Procedure for the Elimination of β-Cl from Compounds 2-151

As depicted in Scheme 20, to a solution of compound 2-151 (95 mg, 270 mmol) in CH₂Cl₂ (5 ml) at 23° C. PS-TBD (51 mg, 2.6 mmol/g) was added, and the mixture was stirred for 8 hours. After that time the reaction was filtered, the solvents were evaporated under reduced pressure, and purification by flash chromatography (SiO₂, 0-30% EtOAc/cyclohexane gradient) afforded 2-103 (X=Cl, R=Me) (84 mg, 98%).

Example 17

General Procedure for the Synthesis of Compounds 2-153

As depicted in Scheme 20, to a solution of compound 2-103 (X=Cl, R=Me) (12.9 mg, 40.8 mmol) in CH₂Cl₂ (1 ml) at 23° C. DHP (3.7 μL, 40.8 μmol) and PS-TsOH (12.7 mg, 40.8 μmol, 3.2 mmol/g) were added, and the mixture was stirred for 5 hours. After that time the reaction was filtered and the solvents were evaporated under reduced pressure. Purification by PTLC (SiO₂, 30% EtOAc/cyclohexane) afforded 2-153 (13.8 mg, 85%) as a mixture of two diastereoisomers. An illustrative example of compounds 2-153 follows; its characterization data are in the text below the figure.

Illustrative Compound 2-153:

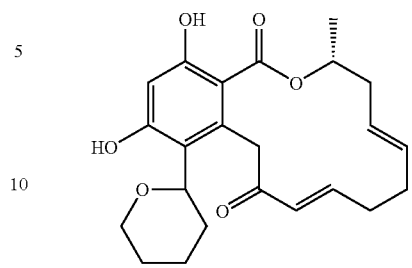

¹H NMR (CDCl₃, 400 MHz) δ 12.33 (s, 1H), 12.11 (s, 1H), 9.45 (s, 1H), 9.40 (s, 1H), 6.67, (m, 2H), 6.28 (2×s, 2H), 5.83 (d, J=13.2 Hz, 1H), 5.79 (d, J=12.9 Hz, 1H), 5.35-5.30 (m, 3H), 5.27-5.22 (m, 3H), 5.06 (bd, J=8.2 Hz, 2H), 4.10 (d, J=17.5 Hz, 2H), 3.90-3.85 (m, 1H), 3.80-3.76 (m, 1H), 3.65 (d, J=17.7 Hz, 2H), 3.57-3.52 (m, 2H), 3.46-3.41 (m, 2H), 2.77-2.71 (m, 3H), 2.53-2.49 (m, 3H), 2.36-2.29 (m, 4H), 2.24-1.56 (m, 12H), 1.31 (d, J=6.4 Hz, 3H), 1.28 (d, J=6.4 Hz, 3H); HRMS (ESI) m/z 423.1778 ([M+Na⁺], $C_{23}H_{28}O_6Na$ requires 423.1778.

Example 18

General Procedure for the Synthesis of Compounds 2-154

As depicted in Scheme 20, to a solution of corresponding compound 2-120 (1.0 equiv) in pyridine/AcOH (5/1, 0.03 M) was added the corresponding hydroxylamine (5.0 equiv) and the mixture was heated up to 40° C. After stirring overnight the solvents were evaporated under reduced pressure with SiO₂. Elution of the compound over a short path of SiO₂ with a mixture of 30% EtOAc/cyclohexane afforded after evaporation 2-154 (~99%) as a mixture of two diastereoisomers cis/trans). An illustrative example of compound 2-154 follows; its characterization data are in the text below the figure.

Illustrative Compound 2-154:

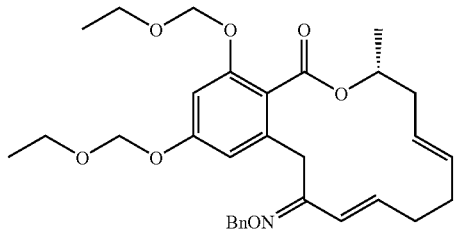

¹H NMR (CDCl₃, 400 MHz) δ 7.50-7.25 (m, 10H), 6.82 (s, 1H), 6.75 (s, 1H), 6.66 (s, 1H), 6.48 (s, 1H), 6.24-6.11 (m, 2H), 6.11-6.05 (m, 2H), 5.45-5.38 (m, 4H), 5.34-5.31 (m, 14H), 4.50 (d, J=17.2 Hz, 1H), 3.38-3.65 (m, 8H), 3.60 (d, J=17.1 Hz, 1H), 3.54 (d, J=17.1 Hz, 1H), 3.24 (d, J=17.2 Hz, 1H), 2.48-2.36 (m, 4H), 2.17-2.21 (m, 2H), 2.04-2.11 (m, 2H), 1.95-1.83 (m, 2H), 1.62-1.51 (m, 2H), 1.49 (d, J=6.4 Hz, 6H), 1.20-1.32 (m, 12H); ¹³C NMR (CDCl₃, 100 MHz) δ 168.02, 167.85, 159.08, 158.83, 157.23, 155.55, 155.36, 154.19, 140.75, 138.23, 138.19, 137.75, 136.93, 136.74, 132.32, 132.28, 128.34 (×2), 128.31 (×2), 128.18, 128.09 (×2), 127.99 (×2), 127.71, 127.63, 125.50, 118.82, 118.56, 118.34, 108.84, 108.50, 101.72, 101.68, 93.49, 93.44, 93.12 (×2), 77.21, 76.02, 75.88, 71.18, 70.99, 64.47, 64.45, 64.33, 64.31, 39.99, 39.96, 34.87, 32.42, 32.31, 31.63, 31.09, 28.86, 20.25, 20.19, 15.04 (×2), 14.98 (×2); HRMS (ESI) m/z 560.2627 ([M+Na$^+$], C$_{31}$H$_{39}$NO$_7$Na requires 560.2619.

Example 19

General Procedure for the Synthesis of Compounds 2-155

As depicted in Scheme 20, to a solution of compound 2-154 (1.0 equiv) in MeOH (0.02 M) was added PS-TsOH (10.0 equiv, 3.2 mmol/g) and the suspension was shaken at 40° C. for 4 h. The reaction mixture was filtered and the methanolic solution concentrated under reduced pressure. The crude product obtained was submitted without further purification to the next step. Thus to a solution in CH$_2$Cl$_2$ (0.02 M) of this crude at 23° C. were added DHP (1.0 equiv) and PS-TsOH (cat, 3.2 mmol/g) and the mixture was stirred for 5 hours. After that time the mixture was filtered, the solvents were evaporated under reduced pressure, and purification by PTLC (SiO$_2$, 30% EtOAc/cyclohexane) afforded two different diastereoisomers 1:1 of 2-155 (~65%). An illustrative example of compound 2-155 follows; its characterization data are in the text below the figure.

Illustrative Compound 2-155:

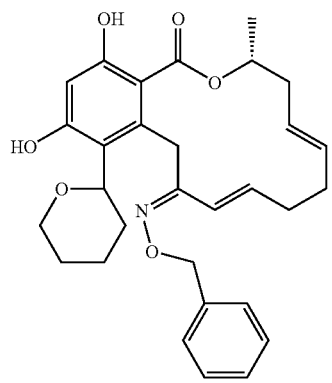

Less polar diastereoisomers: $^1$H NMR (CDCl$_3$, 400 MHz, 25° C.) δ 9.25 (s, 1H), 9.24 (s, 1H), 7.46-7.33 (m, 10H), 6.29 (s, 1H), 6.26 (s, 1H), 6.07-6.02 (m, 2H), 5.75 (d, J=15.8 Hz, 1H), 5.69 (d, J=15.8 Hz, 1H), 5.44-5.38 (m, 6H), 5.23 (s, 4H), 5.03 (d, J=8.8 Hz, 2H), 4.34-4.13 (m, 6H), 3.69-3.63 (m, 2H), 2.70-2.67 (m, 2H), 2.30-2.16 (m, 6H), 2.08-1.94 (m, 8H), 1.73-1.65 (m, 8H), 1.42 (t, J=6.4 Hz, 3H), 1.39 (t, J=7.0 Hz, 3H); HRMS (ESI) m/z 528.2562 ([M+Na$^+$], C$_{30}$H$_{35}$NO$_6$Na requires 528.2357.

More polar diastereoisomers: $^1$H NMR (CDCl$_3$, 400 MHz, 25° C.) δ 11.61 (s, 1H), 9.27 (s, 1H), 7.41-7.33 (m, 5H), 6.62 (d, J=16.4 Hz, 1H), 6.47 (s, 1H), 6.15-6.07 (m, 1H), 5.50-5.38 (m, 3H), 5.16 (s, 2H), 5.04 (d, J=10.5 Hz, 1H), 4.30 (d, J=15.2 Hz, 1H), 4.24 (d, J=10.5 Hz, 1H), 3.84 (d, J=15.2 Hz, 1H), 3.66 (t, J=11.4 Hz, 1H), 2.71-2.65 (m, 1H), 2.28-2.08 (m, 6H), 1.73-1.64 (m, 5H), 1.38 (t, J=7.0 Hz, 3H); HRMS (ESI) m/z 528.2494 ([M+Na$^+$], C$_{30}$H$_{35}$NO$_6$Na requires 528.2357.

Example 20

General Procedure for the Synthesis of Compounds 2-128

As depicted in Scheme 21, to a solution of pochonin D (2-85, X=Cl and R=Me) (25 mg, 71.2 μmol) in DMF (5 ml) TBSCl (53.6 mg, 356 μmol) and imidazole (23.6 mg, 356 μmol) were added and the mixture was stirred for 3 hours at room temperature. Purification by column chromatography (SiO$_2$ 0-30% EtOAc/cyclohexane gradient) afforded after evaporation 2-128 (40 mg, 98%). An illustrative example of compound 2-128 follows; its characterization data are in the text below the figure.

Illustrative Compound 2-128:

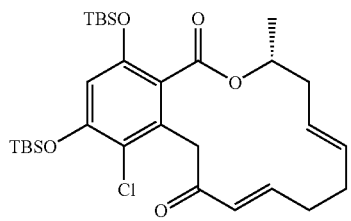

$^1$H NMR (CDCl$_3$, 400 MHz, 25° C.) δ 6.71 (dt, J=15.3, 7.3 Hz, 1H), 6.45 (s, 1H), 5.81 (d, J=15.3 Hz, 1H), 5.25 (s, 2H), 5.04-5.03 (m, 1H), 3.89 (d, J=17.4 Hz, 1H), 3.57 (d, J=17.4 Hz, 1H), 2.31-2.04 (m, 6H), 1.35 (d, J=6.4 Hz, 3H), 1.03 (s, 9H), 0.99 (s, 9H), 0.28-0.24 (m, 12H); $^{13}$C NMR (CDCl$_3$, 100 MHz, 25° C.) δ 195.8, 166.8, 152.9, 151.7, 146.5, 132.7, 131.9, 128.6, 126.8, 122.8, 119.7, 110.7, 71.9, 45.6, 38.5, 30.9, 25.7 (×4), 25.6 (×4), 18.7, 18.3, −4.1 (×2), −4.4 (×2); HRMS (ESI) m/z 601.2568 ([M+Na], C$_{30}$H$_{47}$ClO$_5$Si$_2$Na requires 601.2543).

Example 21

General Procedure for the Synthesis of Compounds 2-157

As depicted in Scheme 21, to a solution of compound 2-128 (1.0 equiv) in pyridine/AcOH (5/1, 250 μL) was added the corresponding hydroxylamine (5.0 equiv) and the mixture was heated up to 40° C. After stirring overnight the solvents were evaporated under reduced pressure, and filtration on SiO$_2$ with a mixture of 30% EtOAc/cyclohexane afforded after evaporation two isomers of 2-157 ~90%. An illustrative example of compound 2-157 follows; its characterization data are in the text below the figure.

Illustrative Compound 2-157:

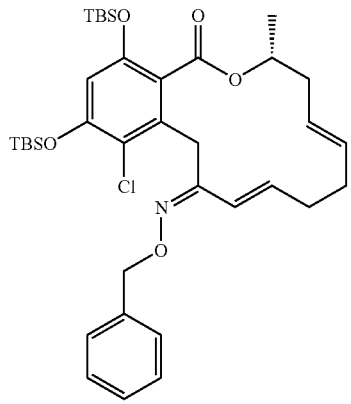

cis oxime $^1$H NMR (CDCl$_3$, 400 MHz) δ 7.42 (bd, J=6.4 Hz, 2H), 7.36 (bdd, J=7.5, 6.9 Hz, 2H), 7.34-7.32 (m, 1H), 6.52 (d, J=16.1 Hz, 1H), 6.38 (s, 1H), 6.18-6.10 (m, 1H), 5.36-5.32 (m, 2H), 5.16 (bs, 2H), 4.99-4.95 (m, 1H), 3.79-3.76 (m, 2H), 2.40-1.99 (m, 6H), 1.45 (d, J=6.2 Hz, 3H), 1.03 (s, 9H), 0.99 (s, 9H), 0.28 (s, 3H), 0.26 (s, 3H), 0.20 (s, 6H); trans oxime $^1$H NMR (CDCl$_3$, 400 MHz) δ 7.44 (bd, J=6.5 Hz, 2H), 7.37 (bdd, J=7.6, 6.9 Hz, 2H), 7.33-7.31 (m, 1H), 6.41 (s, 1H), 6.04-5.97 (m, 1H), 5.48 (bd, J=15.0 Hz, 1H), 5.29-5.27 (m, 1H), 5.22 (bs, 2H), 5.00-4.95 (m, 1H), 3.98-3.89 (m, 2H), 2.39-2.02 (m, 6H), 1.37 (d, J=5.9 Hz, 3H), 1.04 (s, 9H), 0.99 (s, 9H), 0.28 (s, 3H), 0.27 (s, 3H), 0.23 (s, 3H), 0.22 (s, 3H).

Example 22

General Procedure for the Synthesis of Compounds 2-158

As depicted in Scheme 21, to a solution of corresponding compound 2-157 (1.0 equiv) in THF was added TBAF (2.5 equiv, 1M solution in THF) and the mixture was stirred at room temperature for 2 hours. The solvents were then evaporated under reduced pressure, and filtration on SiO$_2$ with a mixture of 30% EtOAc/cyclohexane afforded after evaporation, compounds 2-158 in >85% yield. An illustrative example of compound 2-158 follows; its characterization data are in the text below the figure.

Illustrative Compound 2-158:

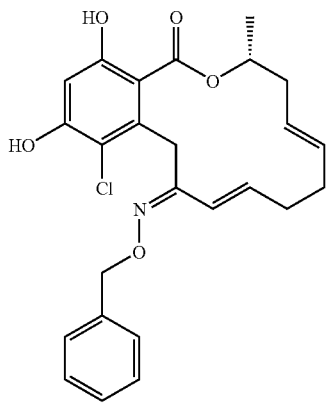

Cis: $^1$H NMR (CDCl$_3$, 400 MHz, 25° C.) δ 11.52 (s, 1H), 7.45-7.34 (m, 5H), 6.64 (s, 1H), 6.09-6.02 (m, 2H), 5.34-5.25 (m, 4H), 5.18-5.08 (m, 2H), 4.33 (d, J=17.0 Hz, 1H), 4.15 (d, J=17.6 Hz, 1H), 2.65-2.59 (m, 1H), 2.27-2.14 (m, 3H), 2.04-2.00 (m, 1H), 1.88-1.83 (m, 1H), 1.30 (t, J=6.4 Hz, 3H); HRMS (ESI) m/z 478.1372 ([M+Na$^+$], C$_{25}$H$_{26}$ClNO$_5$Na requires 478.1392).

Trans: $^1$H NMR (CDCl$_3$, 400 MHz, 25° C.) δ 11.73 (s, 1H), 7.32-7.26 (m, 5H), 6.64 (s, 1H), 6.50 (d, J=16.4 Hz, 1H), 6.06-5.98 (m, 2H), 5.43-5.24 (m, 3H), 4.91 (s, 2H), 4.22 (s, 2H), 2.61-2.55 (m, 1H), 2.46-2.33 (m, 2H), 2.20-2.02 (m, 3H), 0.98 (t, J=6.4 Hz, 3H); HRMS (ESI) m/z 478.1522 ([M+Na$^+$], C$_{25}$H$_{26}$ClNO$_5$Na requires 478.1392).

Example 23

General Procedure for the Synthesis of Compounds 2a-1 via Mitsunobu Cyclization

As depicted in Scheme 25, the preparation of compound 2a-1 begins with commercially available orcinol, 8. The description below is not intended to be limiting and alternate analogs may be prepared with the same general process.

Formylation of orcinol, synthesis of aldehyde 9. POCl$_3$ (54.9 mL, 600 mmol, 2.0 equiv) was added slowly to a flask containing DMF (100 mL) at 0° C. To this mixture was then added a solution of orcinol (42.65 g, 300 mmol, 1.0 equiv) as a solution in DMF (100 mL) and the reaction was allowed to warm up to 23° C. and stirred overnight. Then, the reaction was cooled to 0° C. and 200 mL of ice-water were added. The pH of the mixture was adjusted between 6 and 7 by addition of 10% of NaOH. The mixture was allowed to stand for 30 minutes and then the precipitates were filtered to afford the desired aldehyde 9 (29.2 g, 64%) as a white solid which was used in the subsequent step without further purification: Rf=0.31 (Hexane/EtOAc 3/1); $^1$H NMR ((CD$_3$)$_2$CO, 400 MHz, 25° C.) δ 12.48 (s, 1H), 10.10 (s, 1H), 9.53 (s, 1H), 6.30 (d, J=2.4 Hz, 1H), 6.17 (d, J=2.0 Hz, 1H), 2.54 (s, 3H); $^{13}$C NMR ((CD$_3$)$_2$CO, 100 MHz, 25° C.) δ 194.3, 167.3, 166.2, 146.1, 113.8, 111.5, 101.4, 18.2; HRMS (MALDI-TOF) m/z 175.0373 ([M+Na$^+$], C$_8$H$_8$O$_3$Na requires 175.0371).

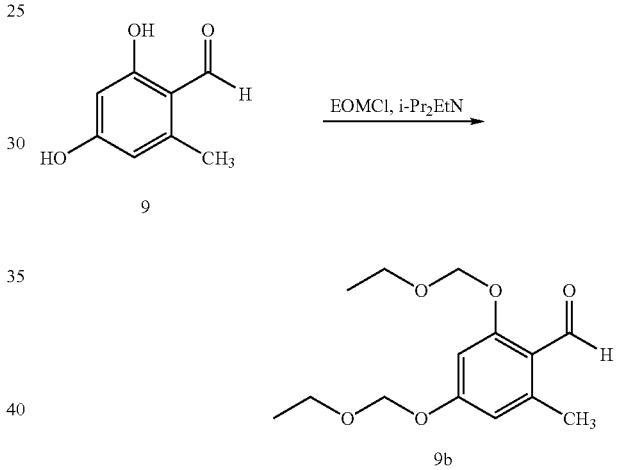

Bis-EOM-protection, synthesis of aldehyde 9b. To a solution of bis-phenol 9 (29.2 g, 191.9 mmol) in DMF (400 mL) at 0° C. were sequentially added iPr$_2$NEt (95.2 mL, 575.7 mmol, 3.0 equiv) and EOMCl (52.3 mL, 575.7 mmol, 3.0 equiv). The reaction was allowed to warm up to 23° C. and stirred overnight. Then, the reaction was quenched with sat. NH$_4$Cl$_{aq}$ (100 mL) and further diluted with CH$_2$Cl$_2$ (400 mL). The organic layer was separated and washed with sat. NH$_4$Cl$_{aq}$ (100 mL×2), brine (100 mL×2), and dried over anhydrous Na$_2$SO$_4$ (5.0 g). Filtration and evaporation of the solvents under reduced pressure followed by flash chromatography (SiO$_2$, Hexane/EtOAc 8/1) afforded protected aldehyde 9b as a colorless oil (46.5 g, 90%): Rf=0.51 (Hexane/EtOAc 3/1); $^1$H NMR (CDCl$_3$, 400 MHz, 25° C.) δ 10.48 (s, 1H), 6.71 (d, J=2 Hz, 1H), 6.49 (d, J=2 Hz, 1H), 5.27 (s, 2H), 5.22 (s, 2H), 3.72 (q, J=6.9 Hz, 2H), 3.69 (q, J=6.9 Hz, 2H), 2.54 (s, 3H), 1.20 (t, J=7.0 Hz, 3H), 1.19 (t, J=7.0 Hz, 3H); $^{13}$C NMR (CDCl$_3$, 100 MHz, 25° C.) δ 190.6, 163.0, 162.1, 144.2, 118.6, 112.3, 100.6, 93.6, 92.8, 64.8, 64.7, 22.2, 15.1 (×2); HRMS (MALDI-TOF) m/z 291.1224 ([M+Na$^+$], C$_{14}$H$_{20}$O$_5$Na requires 291.1209).

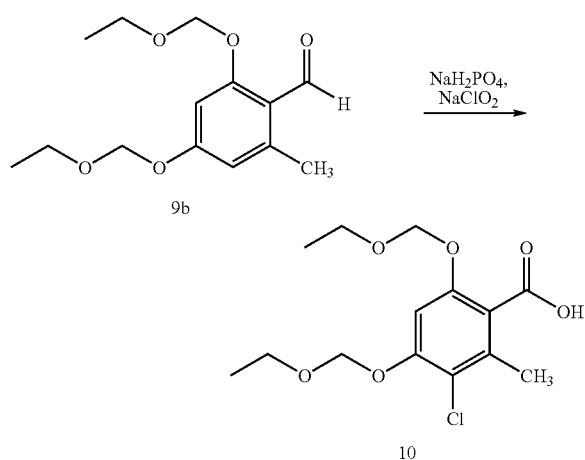

Oxidation-chlorination, synthesis of acid 10. To a solution of aldehyde 9b (46.5 g, 173 mmol) in THF (200 mL) was added a solution of NaH$_2$PO$_4$ (67.5 g, 433 mmol, 2.5 equiv) in H$_2$O (200 mL) and the mixture was cooled down to 0° C. Then a solution of NaClO$_2$ (48.9 g, 85%, 433 mmol, 2.5 equiv) in H$_2$O (200 mL) was added slowly to the reaction. After stirring overnight the mixture was diluted with EtOAc (500 mL), washed with brine (200 mL×3) and dried over Na$_2$SO$_4$ (5.0 g). Filtration and evaporation of the solvents under reduced pressure afforded acid 10 (49.6 g, 90%) as a white solid which was used in the next step without further purification: Rf=0.66 (CH$_2$Cl$_2$/MeOH 9/1); $^1$H NMR ((CD$_3$)$_2$CO, 400 MHz, 25° C.) δ 7.08 (s, 1H), 5.34 (s, 2H), 5.25 (s, 2H), 3.75 (q, J=7.1 Hz, 2H), 3.71 (q, J=7.1 Hz, 2H), 2.34 (s, 3H), 1.19 (t, J=7.1 Hz, 3H), 1.17 (t, J=7.1 Hz, 3H); $^{13}$C NMR ((CD$_3$)$_2$CO, 100 MHz, 25° C.) δ 168.1, 154.9, 153.9, 135.1, 121.8, 117.3, 102.8, 94.7, 94.6, 65.2, 65.0, 17.6, 15.4, 15.4; HRMS (MALDI-TOF) m/z 341.0713 ([M+Na$^+$], C$_{14}$H$_{19}$ClO$_6$Na requires 341.0768).

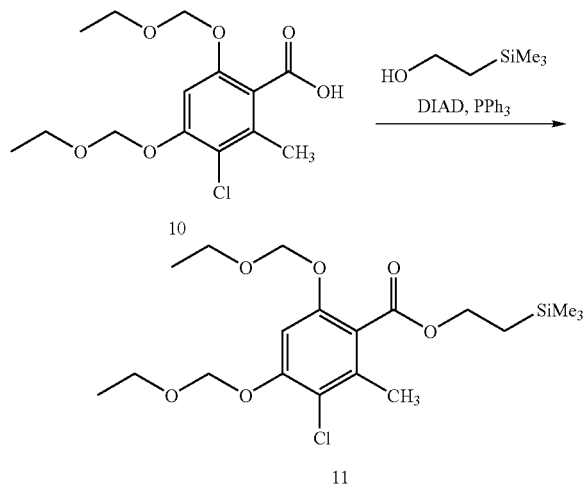

Mitsunobu esterification, synthesis of ester 11. To a solution of acid 10 (23.5 g, 73.7 mmol) in toluene (300 mL) at 0° C., were added sequentially trimethylsilylethanol (12.7 mL, 88.5 mmol, 1.2 equiv), PPh$_3$ (28.9 g, 110.5 mmol, 1.25 equiv) and DIAD (21.7 mL, 110.5 mmol, 1.25 equiv). The reaction was allowed to warm up to 23° C. and stirred for 3 hours. Evaporation of the solvents under reduced pressure followed by flash chromatography (SiO$_2$, Hexane/EtOAc 20/1 and 10/1) afforded ester 11 (24.7 g, 80%) as a white solid: Rf=0.60 (Hexane/EtOAc 3/1); $^1$H NMR (CDCl$_3$, 400 MHz, 25° C.) δ 6.98 (s, 1H), 5.28 (s, 2H), 5.18 (s, 2H), 4.41-4.36 (m, 2H), 3.75 (q, J=6.9 Hz, 2H), 3.70 (q, J=6.9 Hz, 2H), 2.32 (s, 3H), 1.21 (t, J=7.1 Hz, 3H), 1.20 (t, J=7.1 Hz, 3H), 1.12-1.07 (m, 2H), 0.06 (s, 3H); $^{13}$C NMR (CDCl$_3$, 100 MHz, 25° C.) δ 167.7, 154.2, 153.1, 135.0, 120.5, 117.3, 102.0, 94.0, 93.9, 64.7, 64.5, 63.8, 17.6, 15.1 (×2), -1.41 (×3); HRMS (MALDI-TOF) m/z 441.1487 ([M+Na$^+$], C$_{19}$H$_{31}$ClO$_6$SiNa requires 441.1476).

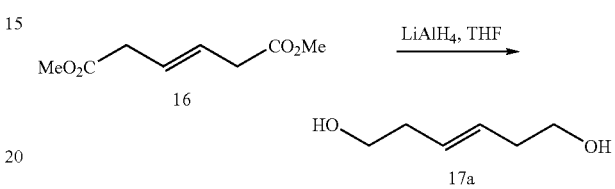

Reduction of diester 16, synthesis of diol 17a. To the suspension of LiAlH$_4$ (15.2 g, 400 mmol, 4 equiv) in THF (300 mL) at 0° C. was added drop wise a solution of trans-3-hexenedioic acid dimethyl ester (17.2 g, 100 mmol) in THF (100 mL). The reaction was stirred for 2 hours. After which, the reaction was quenched by addition of H$_2$O (15.2 mL), 15% of NaOH (15.2 mL), and H$_2$O again (45.6 mL). Then the mixture was poured into Et$_2$O (150 mL), stirred for 30 minutes, and filtered over Na$_2$SO$_4$ (5 g). Evaporation of the solvents under reduced pressure afforded diol 17a which was used without further purification (11.0 g, 95%): Rf=0.53 (CH$_2$Cl$_2$/MeOH 9/1); $^1$H NMR (CDCl$_3$, 400 MHz, 25° C.) δ 5.55-5.52 (m, 2H), 3.66 (dt, J=5.6, 5.2 Hz, 2H), 2.33-2.28 (m, 4H), the OH is not visible; $^{13}$C NMR (CDCl$_3$, 100 MHz, 25° C.) δ 129.8 (×2), 62.0 (×2), 36.16 (×2); HRMS (MALDI-TOF) m/z 139.0734 ([M+Na$^+$], C$_6$H$_{12}$O$_2$Na requires 139.0735).

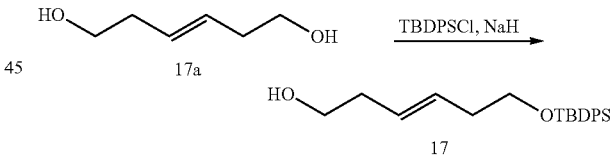

TBDPS-monoprotection of 17a, synthesis of alcohol 17. To a suspension of NaH (1.90 g, 47.4 mmol, 1.0 equiv) in THF (100 mL) at 0° C. a solution of diol 17a (5.5 g, 47.4 mmol, 1.0 equiv) in THF (20 mL) was added. After stirring for 45 minutes, TBDPSCl (12.4 ml, 47.4 mmol, 1.0 equiv) was added. The reaction mixture was allowed to warm up to 23° C. and stirred for 1 hour. Then, it was quenched with sat. NH$_4$Cl$_{aq}$ (200 mL) and extracted with EtOAc (150 mL×3), the combined organic layers were washed with brine (200 mL×2) and dried over Na$_2$SO$_4$ (10 g). Filtration and evaporation of the solvents under reduced pressure followed by flash chromatography (SiO$_2$, Hexane/EtOAc 20/1, 10/1 and 5/1) afforded desired alcohol 17 (11.5 g, 68%) as a colorless oil: Rf=0.46 (Hexane/EtOAc 3/1); $^1$H NMR (CDCl$_3$, 400 MHz, 25° C.) δ 7.68-7.65 (m, 4H), 7.43-7.36 (m, 6H), 5.56 (dt, J=15.2, 6.4 Hz, 1H), 5.44 (dt, J=15.2, 6.8 Hz, 1H), 3.69 (t, J=6.4 Hz, 2H), 3.62 (t, J=6.3 Hz, 2H), 2.31-2.24 (m, 4H), 1.05

(s, 9H), the OH is not visible; HRMS (MALDI-TOF) m/z 377.1927 ([M+Na⁺], $C_{22}H_{30}O_2SiNa$ requires 377.1913).

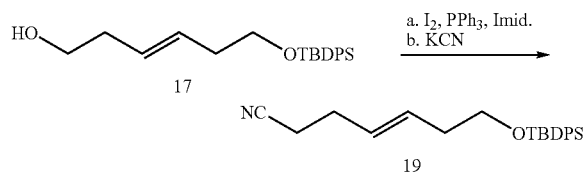

Synthesis of nitrile 19. To a solution of alcohol 17 (11.5 g, 32.4 mmol) in $CH_2Cl_2$ (150 mL) at 0° C. were added imidazole (4.30 g, 47.0 mmol, 1.45 equiv), triphenylphosphine (9.35 g, 35.7 mmol, 1.1 equi) and iodine (9.06 g, 35.7 mmol, 1.1 equiv) and the resulting solution was stirred at 0° C. for 6 hours. Then, the mixture was diluted with $Et_2O$/Hexane 1/1 (300 mL), washed with sat. $NaHCO_{3aq}$ (150 mL×2), sat. $Na_2S_2O_{5aq}$ (150 mL), brine (150 mL) and dried over $Na_2SO_4$ (5.0 g). The solvents were evaporated and resulting oily solids were triturated with hexanes (200 mL×2). Filtration and evaporation of the hexanes afforded the corresponding alkyl iodide 18 as a colorless oil which was directly used in the next step without further purification. Rf=0.46 (Hexane/EtOAc 3/1); $^1$H NMR ($CDCl_3$, 400 MHz, 25° C.) δ 7.70-7.67 (m, 4H), 7.45-7.36 (m, 6H), 5.58 (dt, J=15.2, 6.8 Hz, 1H), 5.44-5.37 (dt, J=15.2, 6.4 Hz, 1H), 3.69 (t, J=6.4 Hz, 2H), 3.11 (t, J=7.2 Hz, 2H), 2.54 (dt, J=7.2, 6.8 Hz, 2H), 2.26 (dt, J=6.4, 6.4 Hz, 2H), 1.05 (s, 9H); HRMS (MALDI-TOF) m/z 487.0923 ([M+H⁺], $C_{22}H_{29}IOSiH$ requires 487.0930).

To a solution of crude alkyl iodine 18 in DMSO (200 mL) was added KCN (21.0 g, 324 mmol, 1.0 equiv). The resulting mixture was stirred for 2 hours at 60° C. and then the reaction mixture was cooled down to 23° C., diluted with EtOAc (200 mL), washed with water (200 mL), brine (100 mL), and dried over $Na_2SO_4$ (5.0 g). Filtration and evaporation of the solvents under reduced pressure followed by flash chromatography ($SiO_2$, Hexane/EtOAc 20/1 and 10/1) afforded desired nitrile 19 (10.6 g, 90%) as a colorless oil: Rf=0.46 (Hexane/EtOAc 3/1); $^1$H NMR ($CDCl_3$, 400 MHz, 25° C.) δ 7.71-7.69 (m, 4H), 7.45-7.39 (m, 6H), 5.60 (dt, J=15.2, 6.4 Hz, 1H), 5.52-545 (m, 1H), 3.73 (t, J=6.4 Hz, 2H), 2.36-2.28 (m, 6H), 1.08 (s, 9H); $^{13}$C NMR ($CDCl_3$, 100 MHz, 25° C.) 135.7 (×4), 134.0 (×2), 130.5, 129.7 (×2), 127.8, 127.7 (×4), 119.4, 63.6, 35.9, 28.6, 27.0 (×3), 19.3, 17.6; HRMS (MALDI-TOF) m/z 386.1962 ([M+Na⁺], $C_{23}H_{29}OSiNNa$ requires 386.1916).

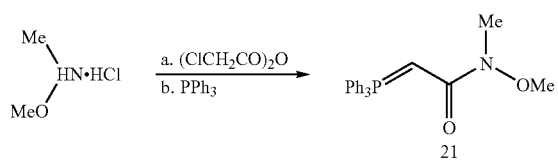

Synthesis of ylide 21. To a solution of N-methoxy-N-methylhydroxylamine hydrochloride (48.52 g, 500 mmol, 1.0 equiv) in $CH_2Cl_2$ (1.0 L) at 0° C. were added pyridine (80.63 mL, 1.0 mol) and chloroacetic anhydride (85.14 g, 500 mmol, 1.0 equiv). The resulting mixture was stirred for 15 min at 0° C., then warm up to 23° C. and stirred overnight. The reaction mixture was then poured carefully into sat. $NaHCO_{3aq}$ solution (1.0 L) and stirred 1 hour, after which the layers were separated, the aqueous phase was extracted with $CH_2Cl_2$ (400 mL) and the combined organic layers were washed with 1N HCl (200 mL×2), brine (200 mL×2), dried over $Na_2SO_4$ (10 g) and filtered. Evaporation of the solvents under reduced pressure afforded the corresponding acetamide (N-methoxy-N-methyl acetamide-2-chloride) as a green oil which was used in the next step without further purification. To a solution of this acetamide in $CH_3CN$ (800 mL) was added $Ph_3P$ (107.98 g, 411.7 mmol, 0.82 equiv) and the resulting mixture was refluxed for 18 hours. Then the solvents were removed under vacuum and the resulting viscous oil was dissolved in $CH_2Cl_2$ (1.0 L), washed with 2N KOH (400 mL×2), brine (400 mL) and dried over $Na_2SO_4$ (10.0 g). Filtration and evaporation of the solvents under reduced pressure afforded ylide 21 as a thick oil which solidified by standing (146.5 g, 80% over two steps). This compound was used in the next step without further purification. Rf=0.85 (Hexane/EtOAc 3/1); $^1$H NMR ($CDCl_3$, 400 MHz, 25° C.) δ 7.71-7.65 (m, 6H), 7.55-7.50 (m, 3H), 7.48-7.42 (m, 6H), 3.74 (s, 3H), 3.08 (s, 3H), 1.86 (s, 1H); $^{13}$C NMR ($CDCl_3$, 100 MHz, 25° C.) 133.3 (×3), 133.2 (×3), 131.9 (×3), 128.9 (×3), 128.8 (×3), 127.9, 61.3, 35.9.

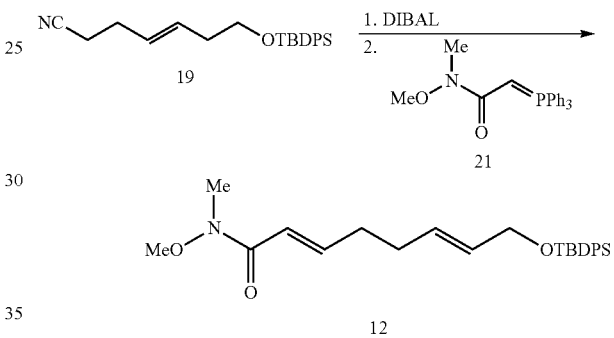

Synthesis of Weinreb amide 12. To a solution of nitrile 19 (22.94 g, 63.0 mmol, 1.0 equiv) in $CH_2Cl_2$ (250 mL) at −78° C., DIBAL (66.3 mL, 1M in toluene, 1.05 equiv) was added and the reaction was stirred for 30 min. To quench the reaction, a solution of sat. $K/Na(tartrate)_{aq}$ (300 mL) was added and the biphasic mixture was stirred until it became a clear biphasic system (over 2 h). The two phases were separated and the aqueous phase was further extracted with $CH_2Cl_2$ (200 mL×3). The combined organic layers were then washed with brine (200 mL) and dried over $Na_2SO_4$ (10 g). Filtration followed by evaporation of the solvents under reduced pressure afforded the corresponding aldehyde 20 which was used in the next step without further purification. Thus, the crude aldehyde 20 was dissolved in $CH_2Cl_2$ (200 mL) at 23° C. and ylide 21 was added (30 g, 81.9 mmol, 1.3 equiv). The reaction was then stirred overnight. Evaporation of the solvents under reduced pressure followed by flash chromatography ($SiO_2$, Hexane/EtOAc 20/1, 10/1 and 3/1) afforded desired Weinreb amide 12 (14.5 g, 61% over two steps) as a colorless oil: Rf=0.30 (Hexane/EtOAc 3/1); $^1$H NMR ($CDCl_3$, 400 MHz, 25° C.) δ 7.69-7.67 (m, 4H), 7.43-7.36 (m, 6H), 6.98 (dt, J=15.3, 7.1 Hz, 1H), 6.40 (d, J=15.3 Hz, 1H), 5.48-5.46 (m, 2H), 3.68 (t, J=6.6 Hz, 2H), 3.67 (s, 3H), 3.24 (s, 3H), 2.32-2.24 (m, 4H), 2.19-2.14 (m, 2H), 1.06 (s, 9H); $^{13}$C NMR ($CDCl_3$, 100 MHz, 25° C.) 167.1, 147.2, 135.7 (×4), 134.1, 131.0 (×2), 129.6 (×2), 127.8 (×4), 127.7, 119.0, 64.0, 61.7, 36.1, 32.6, 32.5, 31.5, 27.0 (×3), 19.3; HRMS (MALDI-TOF) m/z 474.2432 ([M+Na⁺], $C_{27}H_{37}NO_3SiNa$ requires 474.2440).

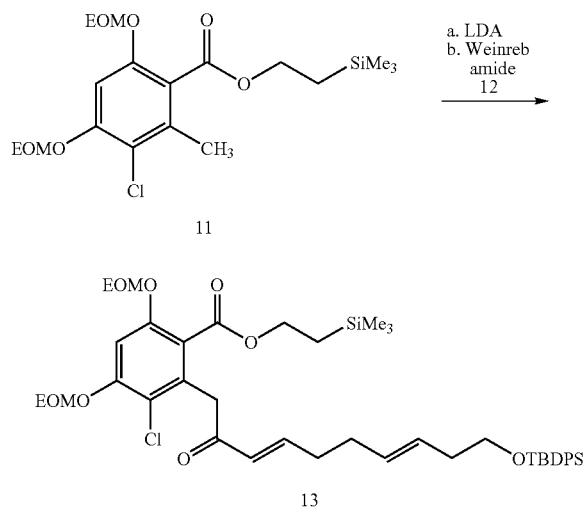

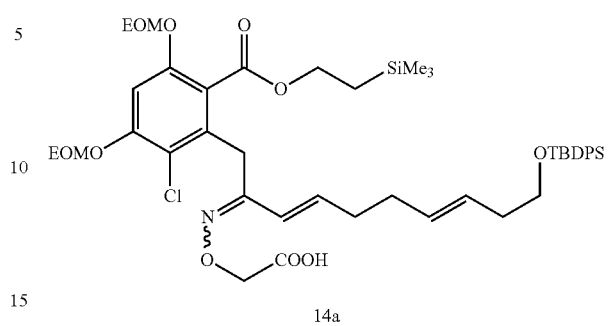

Coupling of toluate 11 and Weinreb amide 12, synthesis of ketone 13. A solution of compound 11 (8.38 g, 20.0 mmol, 1.0 equiv) in anhydrous THF (120 mL) at −78° C. was treated with freshly prepared LDA (71.4 mL, 0.56 M, 40.0 mmol, 2.0 equiv) added via cannula. Immediately after, a solution of Weinreb amide 12 (8.13 g, 18 mmol, 0.9 equiv) in THF (15 mL) at −78° C. was added via cannula. The resulting mixture was then stirred for 15 minutes and the reaction was quenched by addition of sat. $NH_4Cl_{aq}$ (20 mL). Upon warming to 23° C., the reaction mixture was extracted with EtOAc (200 mL×2), and the combined organic layers were then washed with brine (100 mL) and dried over $Na_2SO_4$ (5.0 g). Filtration and evaporation of the solvents under reduced pressure followed by flash chromatography ($SiO_2$, Hexane/EtOAc 20/1, 10/1 and 5/1) afforded desired ketone 13 (20.7 g, 65%): Rf=0.48 (Hexane/EtOAc 3/1); $^1H$ NMR ($CDCl_3$, 400 MHz, 25° C.) δ 7.70-7.68 (m, 4H), 7.42-7.38 (m, 6H), 7.10 (s, 1H), 6.94 (dt, J=15.8, 6.7 Hz, 1H), 6.19 (d, J=15.8 Hz, 1H), 5.49-5.46 (m, 2H), 5.30 (s, 2H), 5.22 (s, 2H), 4.36-4.32 (m, 2H), 4.06 (s, 2H), 3.79-3.68 (m, 6H), 2.30-2.25 (m, 4H), 2.18-2.13 (m, 2H), 1.23 (t×2, J=7.1 Hz, 6H), 1.07 (s, 9H), 1.08-1.03 (m, 2H), 0.06 (s, 9H); $^{13}C$ NMR ($CDCl_3$, 100 MHz, 25° C.) δ 194.5, 167.0, 154.6, 153.9, 147.1, 135.5 (×4), 133.9 (×2), 132.8, 130.5, 129.5 (×2), 129.1, 127.9, 127.6 (×4), 120.3, 117.7, 103.1, 93.9, 93.8, 64.6, 64.4, 63.8, 63.6, 60.3, 59.9, 43.0, 35.9, 32.4, 31.1, 26.8 (×3), 22.6, 22.0, 19.2, 17.4, 15.0, 14.2, 14.1, −1.40 (×3); HRMS (MALDI-TOF) m/z 831.3380 ([M+Na$^+$], $C_{44}H_{61}ClO_8Si_2Na$ requires 831.3491).

Synthesis of oximes 14a. To a solution of ketone 13 (18.6 g, 25.5 mmol) in pyridine (50 mL) at 40° C., carboxymethoxylamine hemihydrochloride (13.98 g, 127.5 mmol) was added and the reaction was stirred at such temperature for 24 hours. After evaporation of the pyridine, the residues were dissolved in $CH_2Cl_2$ (200 mL) and washed with sat. $NH_4Cl_{aq}$ (50 mL×2), brine (50 mL×2) and dried over anhydrous $Na_2SO_4$ (2.0 g). Filtration and evaporation of the solvents under reduced pressure followed by flash chromatography ($SiO_2$, Hexane/EtOAc 5/1 and 1/1) afforded desired oximes 14a (10.1 g, 50%) as a mixture of E/Z isomers in a 1/1 ratio: Rf=0.51 ($CH_2Cl_2$/MeOH 19/1); $^1H$ NMR ($CDCl_3$, 400 MHz, 25° C.) δ 7.69-7.65 (m, 8H), 7.42-7.35 (m, 12H), 7.07 (s, 1H), 7.05 (s, 1H), 6.74 (d, J=15.8 Hz, 1H), 6.36 (dt, J=15.8, 6.8 Hz, 1H), 6.07 (dt, J=15.8, 6.8 Hz, 1H), 5.79 (d, J=15.8 Hz, 1H), 5.48-5.43 (m, 2H), 5.39-5.34 (m, 2H), 5.30 (s, 2H), 5.28 (s, 2H), 5.21 (s, 2H), 5.19 (s, 2H), 4.63 (s, 2H), 4.46 (s, 2H), 4.35-4.29 (m, 4H), 4.03 (s, 2H), 3.88 (s, 2H), 3.80-3.60 (m, 12H), 2.31-2.25 (m, 6H), 2.17-2.15 (m, 2H), 2.10-2.06 (m, 2H), 2.00-1.97 (m, 2H), 1.27-1.21 (m, 12H), 1.08 (s, 9H), 1.07 (s, 9H), 1.07-1.05 (m, 4H), 0.09 (s, 9H), 0.08 (s, 9H), the OH from the acids are not visible; $^{13}C$ NMR ($CDCl_3$, 100 MHz, 25° C.) δ 172.0, 171.9, 167.9, 167.3, 157.0, 155.6, 154.6, 154.5, 153.7, 153.7, 141.4, 137.8, 135.7 (×8), 134.6, 134.1 (×4), 133.7, 131.2, 130.8, 129.7 (×4), 127.9, 127.7 (×8), 127.5, 124.2 (×2), 120.4, 119.1, 117.5, 117.4, 103.2, 102.8, 94.1, 94.0, 93.9, 93.8, 71.1, 70.5, 64.9, 64.9, 64.7, 64.6, 64.5, 64.0, 64.0, 63.9, 36.1 (×2), 33.5, 33.1, 32.9, 31.9, 31.9, 29.4, 27.0 (×6), 19.3 (×2), 17.5, 17.3, 15.1 (×4), −1.4 (×6).

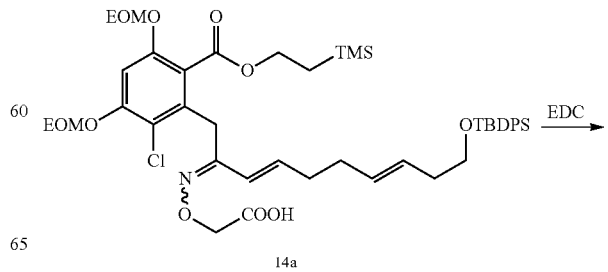

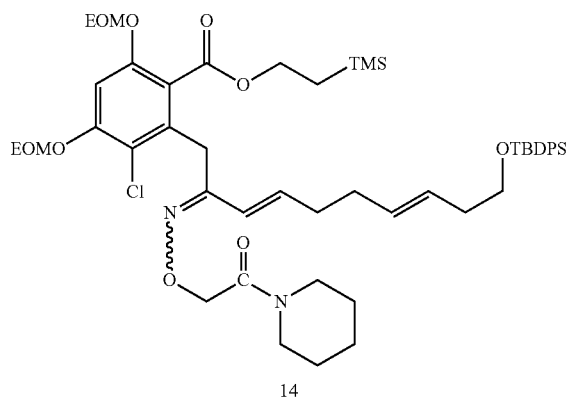

14

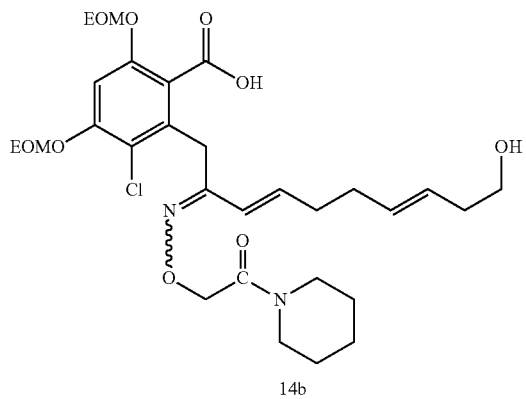

14b

Synthesis of amides 14. To the solution of acid 14a (10.0 g, 11.33 mmol, 1.0 equiv) in $CH_2Cl_2$ (60 mL) at 0° C., was added EDC.HCl (2.6 g, 13.6 mmol, 1.2 equiv) followed by a solution of piperidine (1.34 mL, 13.6 mmol, 1.2 equiv) in $CH_2Cl_2$ (10 mL). The reaction was allowed to warm up to 23° C., and stirred for 3 hours. The reaction mixture was then diluted with $CH_2Cl_2$ (200 mL), washed with sat. $NH_4Cl_{aq}$ (100 mL), brine (100 mL), and dried over anhydrous $Na_2SO_4$ (5 g). Filtration and evaporation of the solvents under reduced pressure followed by flash chromatography ($SiO_2$, Hexane/EtOAc 2/1 and 1/1) afforded desired amides 14 (6.60 g, 63%) as a mixture of two isomers in a 1/1 ratio: Rf=0.31 (Hexane/EtOAc 3/1); $^1H$ NMR ($CDCl_3$, 400 MHz, 25° C.) δ 7.68-7.64 (m, 8H), 7.41-7.33 (m, 12H), 7.04 (s×2, 2H), 6.71 (d, J=16.0 Hz, 1H), 6.21 (dt, J=16.0, 6.7 Hz, 1H), 6.07 (dt, J=16.0, 6.7 Hz, 1H), 5.73 (d, J=16.0 Hz, 1H), 5.45-5.39 (m, 2H), 5.37-5.32 (m, 2H), 5.28 (s, 2H), 5.25 (s, 2H), 5.19 (s, 4H), 4.73 (s, 2H), 4.60 (s, 2H), 4.37-4.27 (m, 4H), 3.95 (s, 2H), 3.87 (s, 2H), 3.80-3.60 (m, 12H), 3.55-3.52 (m, 2H), 3.51-3.48 (m, 2H), 3.38-3.35 (m, 2H), 3.32-3.29 (m, 2H), 2.26-2.16 (m, 6H), 2.09-2.06 (m, 2H), 2.01-1.98 (m, 2H), 1.95-1.91 (m, 2H), 1.61-1.46 (m, 12H), 1.28-1.17 (m, 12H), 1.05-1.01 (m, 4H), 1.04 (s, 9H), 1.03 (s, 9H), 0.05 (s, 9H), 0.04 (s, 9H); $^{13}C$ NMR ($CDCl_3$, 100 MHz, 25° C.) δ 167.1, 167.0 (×2), 166.8, 155.6, 154.3, 154.2, 153.5, 153.4, 153.1, 139.2, 136.5, 135.6 (×8), 134.7, 134.6, 134.1 (×4), 131.4, 131.1, 129.6 (×4), 127.6 (×8), 127.6, 127.1, 124.1, 121.0, 120.9, 119.5, 117.9, 117.7, 103.1, 102.9, 94.1, 94.0, 93.9, 73.1, 73.0, 64.8, 64.7, 64.6, 64.5, 64.0, 63.9, 63.9, 63.6, 60.4, 53.5, 46.4, 46.2, 43.0, 42.9, 36.1, 33.4, 33.0, 32.9, 32.0, 31.9, 30.0, 26.9 (×6), 26.6, 26.5, 25.6, 24.6, 19.3 (×2), 17.4, 17.3, 15.1 (×6), −1.42 (×6).

Silyl deprotection, synthesis of macrocyclization precursor 14b. To a solution of ester 14 (6.60 g, 6.9 mmol, 1.0 equiv) in THF (70 mL) at 23° C. TBAF (17.3 mL, 1M in THF, 2.5 equiv) was added dropwise and the resulting mixture was stirred for 3 hours. Then, EtOAc (100 mL) was added to the reaction, and the resulting mixture was washed with 1M HCl (60 mL×3), brine (60 mL), and dried over $Na_2SO_4$ (1.0 g). Filtration and evaporation of the solvents under reduced pressure followed by flash chromatography ($SiO_2$, EtOAc and EtOAc/MeOH 4/1) afforded desired acids 14b (3.78 g, 89%) as a mixture of two isomers in a 1/1 proportion: Rf=0.35 ($CH_2Cl_2$/MeOH 9/1); $^1H$ NMR ($CDCl_3$, 400 MHz, 25° C.) δ 7.03 (s, 1H), 6.99 (s, 1H), 6.62 (d, J=16.1 Hz, 1H), 6.23 (dt, J=16.1, 6.9 Hz, 1H), 6.11 (dt, J=16.1, 6.9 Hz, 1H), 5.95 (d, J=16.1 Hz, 1H), 5.55-5.30 (m, 4H), 5.26 (s×2, 4H), 5.21 (s, 2H), 5.20 (s, 2H), 4.72 (s, 2H), 4.63 (s, 2H), 4.05 (s, 2H), 4.00 (s, 2H), 3.81-3.66 (m, 8H), 3.65-3.57 (m, 4H), 3.54 (t, J=5.4 Hz, 2H), 3.44 (t, J=5.4 Hz, 2H), 3.31 (t, J=5.4 Hz, 2H), 3.24 (t, J=5.4 Hz, 2H), 2.23 (dt, J=6.5, 6.5 Hz, 4H), 2.18-2.04 (m, 8H), 1.67-1.49 (m, 10H), 1.42-1.40 (m, 2H), 1.25-1.16 (m, 12H), OH from the alcohols and the acids are not visible; $^{13}C$ NMR ($CDCl_3$, 100 MHz, 25° C.) δ 168.73, 168.03, 156.47, 154.19, 152.99, 152.94, 140.23, 136.77, 134.37, 134.18, 132.45, 132.11, 127.53, 127.23, 125.91, 122.46, 119.28, 116.76, 102.91, 102.80, 94.16, 94.02, 93.96, 71.51, 71.25, 64.92, 64.82, 64.54, 64.46, 62.11, 46.24, 45.60, 43.39, 43.27, 36.06, 35.98, 33.08, 32.80, 32.09, 31.86, 31.61, 29.20, 26.26, 26.18, 25.38, 25.30, 24.41, 24.30, 15.28, 15.16; HRMS (MALDI-TOF) m/z 633.2562 ([M+Na$^+$] $C_{30}H_{43}ClN_2O_9Na$ requires 633.2555).

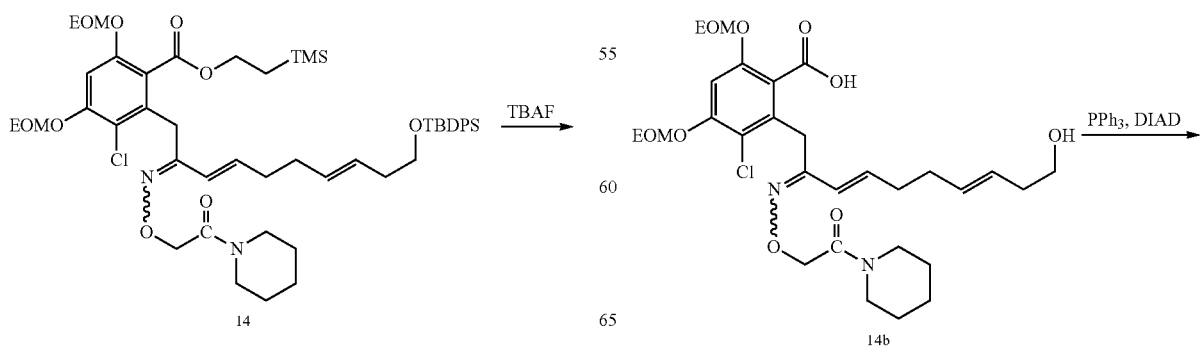

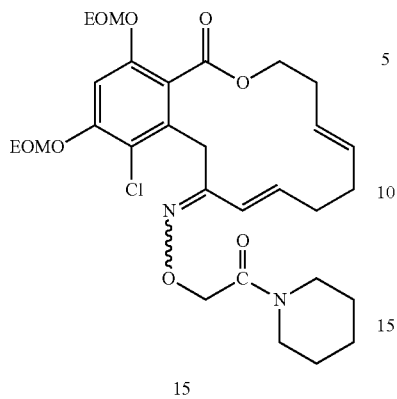

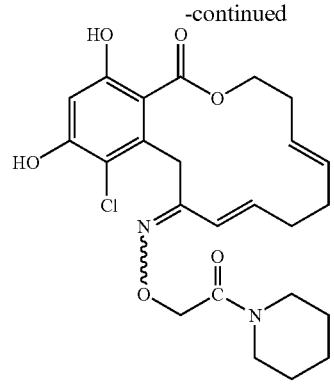

E/Z 2a-1

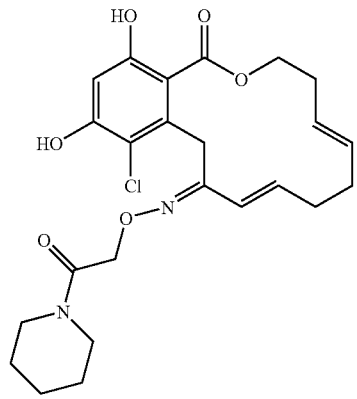

E = 2a-1

Macrocyclization of 14b, synthesis of compounds 15. To a solution of acid 14b (3.78 g, 6.18 mmol) in toluene (200 mL) at 0° C., was added PPh$_3$ (2.43 g, 9.27 mmol) followed by a slow addition of DIAD (1.83 mL, 9.3 mmol). The reaction was allowed to warm to 23° C. and stirred for 5 hours. Evaporation of the solvents under reduced pressure followed by flash chromatography (SiO$_2$, Hexane/EtOAc 4/1 and 1/1) afforded desired macrocycles 15 (2.09 g, 60%) as a mixture of two isomers in a 1/1 proportion: Rf=0.50 (Hexane/EtOAc 1/1); $^1$H NMR (CDCl$_3$, 400 MHz, 25° C.) δ 7.05 (s, 1H), 7.03 (s, 1H), 6.51 (d, J=16.0 Hz, 1H), 6.16 (dt, J=15.8, 6.5 Hz, 1H), 6.00 (dt, J=15.8, 7.7 Hz, 1H), 5.44 (d, J=16.0 Hz, 1H), 5.32 (m, 4H), 5.28 (s, 2H), 5.26 (s, 2H), 5.21 (s, 2H), 5.20 (s, 2H), 4.80 (s, 2H), 4.71 (s, 2H), 4.23 (t, J=5.1 Hz, 2H), 4.18 (t, J=5.1 Hz, 2H), 3.91 (bs, 2H), 3.80-3.66 (m, 10H), 3.60-3.51 (m, 4H), 3.48-3.46 (m, 2H), 3.41-3.38 (m, 2H), 2.40-2.32 (m, 4H), 2.19-2.16 (m, 1H), 2.11-2.00 (m, 7H), 1.67-1.51 (m, 12H), 1.23-1.19 (12H); $^{13}$C NMR (CDCl$_3$, 100 MHz, 25° C.) δ 167.5, 166.9, 154.8, 154.6, 154.4, 153.2, 141.0, 136.6, 134.1, 132.6, 128.5, 127.6; 124.6, 121.6, 119.5, 117.5, 102.94 (×2), 94.1 (×2), 93.8 (×2), 73.4, 73.2, 72.8, 72.7, 64.9, 64.8, 64.7 (×2), 64.3 (×2), 46.5, 46.3, 43.1 (×2), 35.7, 35.6, 32.5, 32.4, 32.2, 32.1, 31.9, 31.7, 30.2 (×2), 26.7 (×2), 26.6 (×2), 25.7 (×2), 24.7 (×4), 15.2 (×2), 15.1 (×2); HRMS (MALDI-TOF) m/z 615.2438 ([M+Na$^+$], C$_{30}$H$_{41}$ClN$_2$O$_8$Na requires 615.2450).

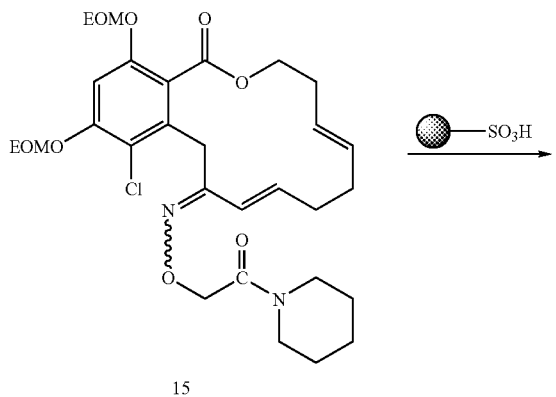

Deprotection, synthesis of 2a-1 as an E/Z mixture, isolation of the E isomer and isomerization of the Z isomer. To a solution of macrocycles 15 (2.8 g, 4.72 mmol) in MeOH (60 mL) at 40° C. sulfonic acid resin (7.87 g, 3.0 mmol/g, 23.6 mmol) was added, and the suspension was stirred for 2 hours. The mixture was diluted with CH$_2$Cl$_2$ (60 mL), filtered, and the resin was once rinsed with CH$_2$Cl$_2$ (20 mL×2). After removal of the solvent, the residue was re-dissolved in MeOH (50 mL) and sonicated. A precipitate began to form and the solution was allowed to stand for 12 h. The solution was filtered and rinsed with MeOH (30 mL). Evaporation of the combined solutions afforded 2a-1 (1.13 g, 9:1 E:Z as judged by LCMS). The remaining solid (pure Z-isomer, 900 mg) was dissolved in CH$_2$Cl$_2$ (180 mL) and treated with TFA (1.4 mL, 18.8 mmol) at 23° C. The mixture was stirred for 12 hours, after which toluene (50 mL) was added and the solvents were evaporated (LCMS of this crude indicated a 1:1 mixture of E/Z isomers). The residue obtained was re-dissolved in CH$_2$Cl$_2$ (30 mL). The insoluble precipitated was filtered and rinsed with MeOH (20 mL). Evaporation of the combined solutions afforded more of compound 2a-1 (450 mg) again as a 9:1 mixture in favor of the desired E isomer. The remaining solid (Z-isomer, 450 mg) was submitted to same isomerization conditions two more times. The combined batches of 8 were then purified by flash chromatography (70 g of C18, CH$_3$CN/H$_2$O 35/65 and 0.01% TFA, 50 mL/min) to afford the pure E isomer as a white powder (1.10 g, 51% overall yield); Rf=0.44 (Hexane/EtOAc 1/2); $^1$H NMR (CDCl$_3$, 400 MHz, 25° C.) δ 11.64 (s, 1H), 6.64 (s, 1H), 6.01 (td, J=15.5 7.5 Hz, 1H), 5.11 (d, J=15.5 Hz, 1H), 5.10-5.03 (m, 2H), 4.85 (s, 2H), 4.37 (t, J=4.8 Hz, 2H), 4.17 (s, 2H), 3.60 (t, J=5.0 Hz, 2H), 3.46 (t, J=5.0 Hz, 2H), 2.34 (q, J=5.4 Hz, 2H), 2.10-2.02 (m, 2H), 1.99-1.92 (m, 2H), 1.70-1.54 (m, 6H); $^{13}$C NMR (CDCl$_3$, 100 MHz, 25° C.) δ 170.27, 167.42, 163.21, 157.38, 155.18, 138.21, 135.62, 131.82, 129.13, 124.76, 115.55, 107.60, 103.47, 72.63, 65.03, 46.38, 43.31, 33.21, 32.76, 31.94, 31.84, 26.65, 25.64, 24.57; HRMS (MALDI-TOF) m/z 499.1638 ([M+H$^+$], C$_{24}$H$_{29}$ClN$_2$O$_6$H requires 499.1612).

Compound a2-13:

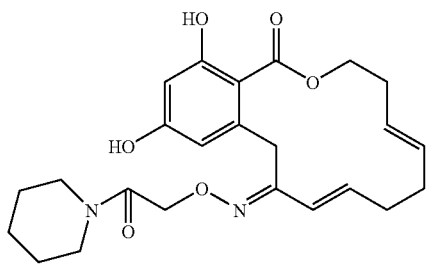

$^1$H NMR (CDCl$_3$, 400 MHz, 25° C.) δ 11.65 (s, 1H), 6.86 (d, J=1.8 Hz, 1H), 6.33 (d, J=1.8 Hz, 1H), 6.14 (td, J=15.8, 7.6 Hz, 1H), 5.82 (d, J=15.7 Hz, 1H), 5.33 (bs, 2H), 4.85 (s, 2H), 4.53 (bs, 2H), 4.33 (s, 2H), 3.57 (t, J=5.0 Hz, 2H), 3.39 (t, J=5.0 Hz, 2H), 2.50 (bs, 2H), 2.11-2.06 (m, 4H), 1.66-1.58 (m, 6H); $^{13}$C NMR (DMSO-d$_6$, 100 MHz, 25° C.) δ 168.5, 166.3, 159.3, 157.1, 156.2, 137.6, 136.0, 131.5, 129.5, 124.9, 113.1, 105.9, 100.9, 71.9, 63.7, 45.2, 42.1, 32.3, 31.8, 30.5, 28.1, 26.0, 25.3, 24.0; HRMS (MALDI-TOF) m/z 465.2054 ([M+Na$^+$], C$_{24}$H$_{30}$N$_2$O$_6$H requires 465.2002).

Example 24

Kinase Inhibition of Exemplary Compounds

A representative subset of the pochonin analogue library (84 compounds) was tested for its inhibition in a panel of 24 kinase (AKT1, ARK5, Aurora-A, Aurora-B, B-RAF-VE, CDK2/CycA, CDK4/CycD1, CK2-α1, FAK, EPHB4, ERB2, EGF-R, IGF1-R, SRC, VEGF-R2, VEGF-R3, FLT3, INS-R, MET, PDGFR-β, PLK1, SAK, TIE2, COT) at 10 μM using the procedure described below.

All protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was checked by SDS-PAGE/silver staining and the identity of each kinase was verified by western blot analysis with kinase specific antibodies or by mass spectroscopy.

Protein Kinase Assay

A radiometric protein kinase assay ($^{33}$PanQinase® Activity Assay) was used for measuring the kinase activity of the 24 protein kinases. All kinase assays were performed in 96-well FlashPlates™ from Perkin Elmer (Boston, Mass., USA) in a 50 μl reaction volume. The reaction cocktail was pipetted in 4 steps in the following order:

20 μl of assay buffer
5 μl of ATP solution (in H$_2$O)
5 μl of test compound (in 10% DMSO)
10 μl of substrate/10 μl of enzyme solution (premixed)

The assay for all enzymes contained 60 mM HEPES-NaOH, pH 7.5, 3 mM MgCl$_2$, 3 mM MnCl$_2$, 3 μM Na-orthovanadate, 1.2 mM DTT, 50 μg/ml PEG$_{20000}$, 1 μM [γ-$^{33}$P]-ATP (approx. 5×10$^{05}$ cpm per well).

For the 24 kinase assays, the following amounts of enzyme and substrate were used per well:

| # | Kinase | Kinase Lot # | Kinase ng/50 μl | Substrate | Substrate ng/50 μl |
|---|---|---|---|---|---|
| 1 | AKT1 | SP007 | 100 | GSK3(14-27), Lot 005 | 1000 |
| 2 | ARK5 | 002 | 100 | Autosphos. | — |
| 3 | Aurora-A | SP004 | 50 | tetra(LRRWSLG) | 500 |
| 4 | Aurora-B | SP007 | 100 | tetra(LRRWSLG) | 250 |
| 5 | B-RAF-VE | 001 | 20 | MEK1-KM(Lot 013) | 250 |
| 6 | CDK2/CycA | SP005 | 100 | Histone H1 | 125 |
| 7 | CDK4/CycD1 | 006 | 50 | Rb-CTF, Lot 010 | 500 |
| 8 | COT | 017 | 400 | Autophosphorylation | — |
| 9 | EGF-R | SP014 | 25 | Poly(Glu,Tyr)$_{4:1}$ | 125 |
| 10 | EPHB4 | SP006 | 10 | Poly(Glu,Tyr)$_{4:1}$ | 125 |
| 11 | ERBB2 | SP011 | 200 | Poly(Glu,Tyr)$_{4:1}$ | 125 |
| 12 | FAK | SP006 | 100 | Poly(Glu,Tyr)$_{4:1}$ | 125 |
| 13 | IGF1-R | 012 | 20 | Poly(Glu,Tyr)$_{4:1}$ | 125 |
| 14 | SRC | 004 | 10 | Poly(Glu,Tyr)$_{4:1}$ | 125 |
| 15 | VEGF-R2 | 011 | 50 | Poly(Glu,Tyr)$_{4:1}$ | 125 |
| 16 | VEGF-R3 | SP011 | 100 | Poly(Glu,Tyr)$_{4:1}$ | 125 |
| 17 | FLT3 | SP007 | 100 | Poly(Ala,Glu,Lys,Tyr)$_{6:2:5:1}$ | 125 |
| 18 | INS-R | SP005 | 25 | Poly(Ala,Glu,Lys,Tyr)$_{6:2:5:1}$ | 125 |
| 19 | MET | SP011 | 100 | Poly(Ala,Glu,Lys,Tyr)$_{6:2:5:1}$ | 125 |
| 20 | PDGFR-beta | SP012 | 50 | Poly(Ala,Glu,Lys,Tyr)$_{6:2:5:1}$ | 125 |
| 21 | PLK1 | 007 | 50 | Casein | 250 |
| 22 | SAK | 002 | 200 | Autophosphorylation | — |
| 23 | TIE2 | SP006 | 200 | Poly(Glu,Tyr)$_{4:1}$ | 250 |
| 24 | CK2-alpha1 | SP003 | 200 | Casein | 1000 |

The reaction cocktails were incubated at 30° C. for 80 minutes. The reaction was stopped with 50 μl of 2% (v/v) H$_3$PO$_4$, plates were aspirated and washed two times with 200 μl of 0.9% (w/v) NaCl or 200 μl H$_2$O. Incorporation of $^{33}$P$_i$ was determined with a microplate scintillation counter (Microbeta Trilux, Wallac).

All assays were performed with a BeckmanCoulter/Sagian robotic system.

Evaluation of Raw Data

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity.

As part of the data evaluation the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound $IC_{50}$ values were calculated using Quattro Workflow V2.1.0.0 (Quattro Research GmbH, Munich, Germany; www.quattro-research.com). The model used was "Sigmoidal response (variable slope)" with parameters "top" fixed at 100% and "bottom" at 0%.

Significantly, twelve compounds showed more than 50% inhibition, which represents a >14% hit rate for a kinase. Surprisingly, pochonin D, pochonin A and radicicol, though they had been shown to be powerful inhibitors of HSP90, showed no significant activity against this panel of kinases. Nine compounds were selected to calculate $IC_{50}$ against each of the 24 kinases (table 4). In this more detailed analysis, radicicol showed only very mild activity against VGFR-R2 with no inhibition for the twenty-three other kinases. Several pochonin analogues showed a well-defined pattern of activity against therapeutically relevant enzymes such as Src (8 μM for A2), Aurora A (12 μM for A3), IGF1-R (11 μM for A5). Importantly, the compounds that proved to be kinase inhibitors were not inhibitors of HSP90 and are not indiscriminate ATP-surrogates.

Another subset of the library was tested for HSP90 inhibition by measuring direct interaction in a competitive assay and measuring depletion of HSP90 client proteins in a cellular assay. HSP90's ATPase pocket has a specific fold that is present in a superfamily which includes functionally diverse proteins such as DNA topoisomerase II, helicase, MutL and histidine kinases (Bergerat fold). (A. Bergerat et al., *Nature*, 386:414 (1997); R. Dutta and M. Inouye, *Trends Biochem. Sci.*, 25:24 (2000)). In fact, it has been shown that radicicol does inhibit other members of this family albeit with lower affinity. (D. Gadelle et al., *Nucleic Acids Res.*, 33:2310 (2005); P. G. Besant et al., *Mol. Pharmacol.*, 62:289 (2002). Yet remarkably, the best HSP90 inhibitors of the invention were selective for HSP90 with respect to the panel of kinases. Sixteen compounds were found to have an IC50<1 μM.

Pochonin Analogs Selected for $IC_{50}$ Determination

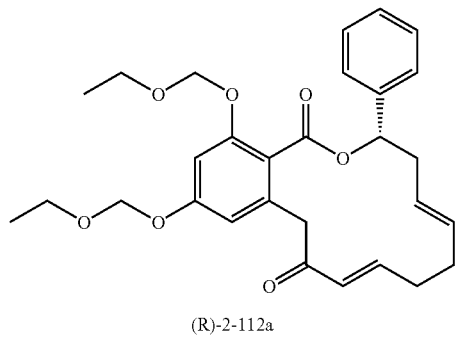

A-1

(R)-2-112a

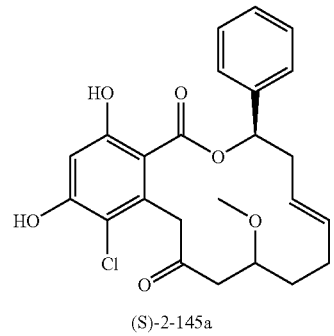

A-2

(S)-2-145a

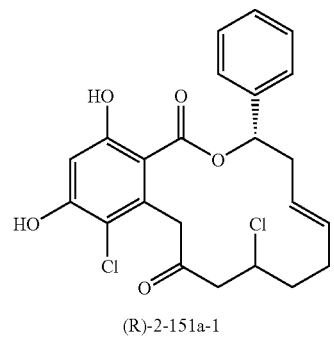

A-3

(R)-2-151a-1

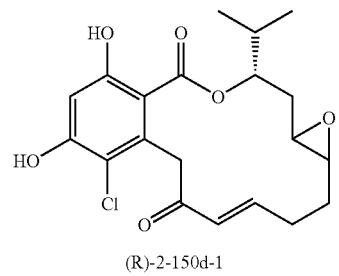

A-4

(R)-2-150d-1

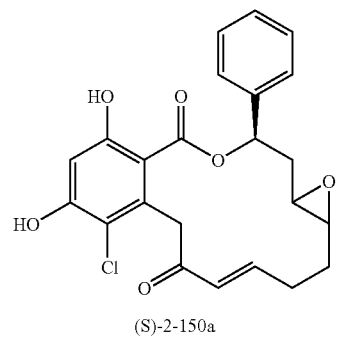

A-5

(S)-2-150a

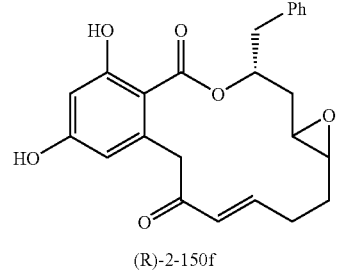

A-6

(R)-2-150f

167
-continued

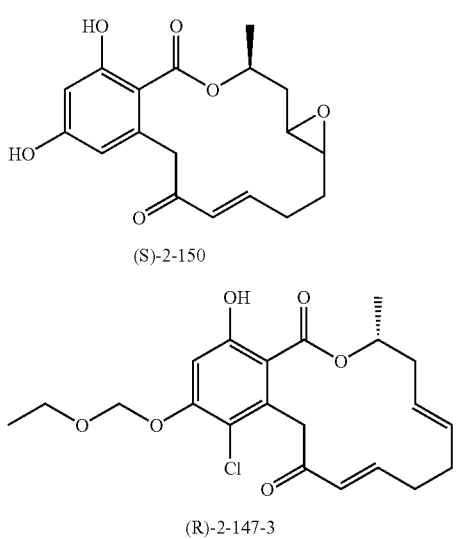

(S)-2-150

(R)-2-147-3

TABLE 4

Inhibitory activity (IC$_{50}$: μM) of selected pochonin analogs in a panel of 24 kinase assays (a blank represents an IC$_{50}$ >50 μM).

| Kinase | Radi-cicol | A1 | A2 | A3 | A4 | A5 | A6 | A7 | A8 |
|---|---|---|---|---|---|---|---|---|---|
| AKT1 | | | | | | | | | |
| ARK5 | | | | | | | | | |
| Aurora-A | | | 14 | 12 | 30 | 47 | | | |
| Aurora-B | | | 16 | 14 | 36 | | 16 | | |
| B-RAF-VE | | | | | | 50 | | | |
| CDK2/CycA | | | | | | | | | |
| CDK4/CycD1 | | | 50 | 30 | 48 | 45 | 37 | | |
| CK2-α1 | | | | | | | | | |
| FAK | | | 14 | 9 | 37 | 38 | 34 | | |
| EPHB4 | | | 16 | 40 | | 49 | 40 | | |
| ERBB2 | | | 16 | 24 | | | | | |
| EGF-R | | 33 | 10 | 14 | 22 | 16 | 32 | | |
| IGF1-R | | 23 | 16 | 19 | 13 | 11 | 21 | | |
| SRC | | 11 | 8 | 14 | 12 | 12 | 20 | | |
| VEGF-R2 | 49 | | 19 | 20 | 30 | 19 | 25 | | |
| VEGF-R3 | | | 40 | 19 | 31 | 31 | 34 | | |
| FLT3 | | | 23 | 23 | 45 | | 44 | | |
| INS-R | | | 36 | 44 | | | | | |
| MET | | | 32 | 29 | | | 36 | | |
| PDGFR-β | | | | | | | | | |
| PLK1 | | | | | | | | | |
| SAK | | | 17 | 25 | 19 | 20 | 17 | | |
| TIE2 | 72 | | 16 | 15 | | | 25 | | |
| COT | | | | | | | | | |

In this detailed analysis, radicicol showed only very mild activity against VGFR-R2 with no inhibition for the twenty three other kinases. Several pochonin analogs showed a well-defined pattern of activity against therapeutically relevant enzymes, such as Src (8 μM for A2), Aurora A (12 μM for A3), and IGF1-R (11 μM for A5). Importantly, the compounds that were found to be kinase inhibitors were not inhibitors of HSP90 (data not shown) and are not indiscriminate ATP-surrogates. The ATP-binding pocket of HSP90 targeted by radicicol and pochonin D has a specific fold that is present in a superfamily which includes functionally diverse proteins, such as DNA topoisomerase II, helicase, MutL, and histidine kinases (R. Dutta and M. Inouye, *Trends Biochem. Sci.*, 24:24 (2000)). In fact, it has been shown that radicicol does inhibit other members of this family albeit with lower affinity (D. Gadelle et al., *Nucleic Acids Res.*, 33:2310 (2005); P. G. Besant et al., *Mol. Pharmacol.*, 62:289 (2002)). While the pochonin library described above will certainly contain some compounds that are good inhibitors of enzymes bearing a Bergerat fold, we wished to evaluate whether modification around the pochonin scaffold could retune the selectivity of these compounds from HSP90 inhibitors to kinase inhibitors. The fact that more than fourteen percent of the compounds showed a kinase inhibition of greater than 50% at 10 mM clearly supports the hypothesis that RAL is a good scaffold for kinase inhibition.

Example 25

HSP 90 Inhibition Tests for Exemplary Compounds of the Library

Radicicol (2-1), pochonin D (2-85) and pochonin A (2-122), along with some closely related analogs such as monocillin II (2-103) or the diol analog of pochonin A (2-125) were first evaluated for HSP90 affinity in a competition assay with geldanamycin using a previously described method (V. Zhou et al., *Anal. Biochem.*, 331, 349 (2004)). The results are shown in below.

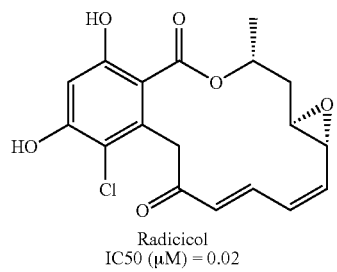

Radicicol
IC50 (μM) = 0.02

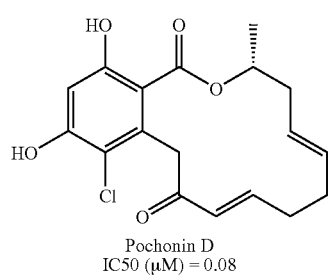

Pochonin D
IC50 (μM) = 0.08

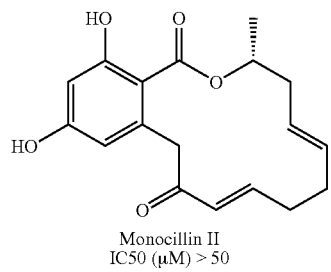

Monocillin II
IC50 (μM) > 50

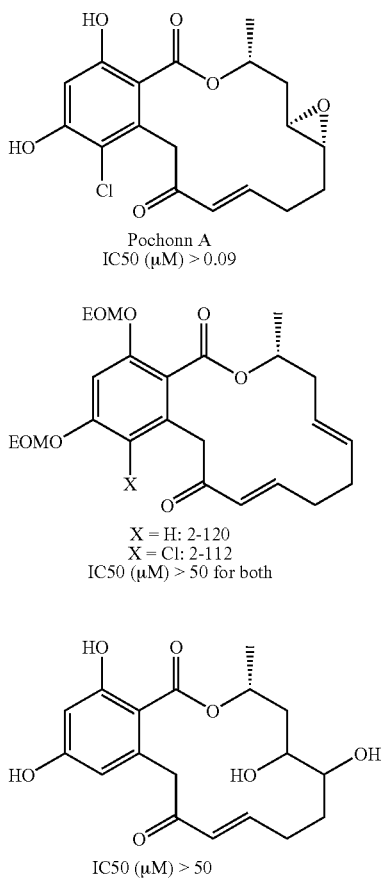

As aforementioned, pochonin D (2-85) was found to be a good ligand for HSP90 with an $IC_{50}$ of 80 nM, as compared to 20 nM for radicicol. This difference of activity is less than an order of magnitude, but without being bound by theory, it was rationalized by a molecular modelling study on pochonin D. The co-crystal structure of HSP90-radicicol reported by Pearl and co-workers showed a tightly bound water molecule making a hydrogen-bond bridge between the ortho-phenol, the ester, and Asp79 and a second water molecule making a bridge between the para-phenol and Leu34 (S. M. Roe et al., J. Med. Chem., 42:260 (1999). Consistent with this hypothesis, compounds 2-112 and 2-120 with protected phenols showed no affinity for HSP90. The importance of the chlorine atom is also evident from the comparison of pochonin D (2-85, 80 nM) and monocillin II (2-103, >50 μM). The bulky chlorine not only comes within van der Waals contact of Phe124 but fills a hydrophobic pocket. Notably, pochonin A (2-122) was a good ligand (90 nM), while analog 2-111 was inactive. The comparison between radicicol, pochonin D and pochonin A confirmed that the epoxide moiety is not essential for HSP90 inhibition and established that the γ,δ-conjugated olefin is not a prerequisite for potency. The ability of these natural products (2-1, 2-85, 2-122) to antagonize ATP in the N-terminal domain of HSP90 and to inhibit ATPase activity may be related to their inhibition of HSV (Herpes Simplex Virus) helicase. Similarly, compounds 2-164, 2-166 and 2-169 corresponding to bis-methylated analogs were evaluated for HSP90 inhibition.

Example 26

Cytotoxicity Against HCC1954 and SK-BR-3 Tumor Cells for Exemplary Compounds of the Library Tumor cells were grown as adherent monolayers at 37° C. in a humidified atmosphere (5% $CO_2$, 95% air). The culture medium was RPMI 1640 containing 2 mM L-glutamine (Ref BE12-702F, Cambrex, Verviers, Belgium) and supplemented with 10% fetal bovine serum (Ref DE14-801E, Cambrex). For experimental use, the adherent tumour cells were detached from the culture flask by a 5-minute treatment with trypsin-versene (Ref 02-007E, Cambrex), diluted in Hanks' medium without calcium or magnesium (Ref BE10-543F, Cambrex) and neutralized by addition of complete culture medium. Before use, cells were counted in a hemocytometer and their viability were assessed by 0.25% trypan blue exclusion. Mycoplasma detection was performed using the MycoAlert® Mycoplasma Detection Kit (Ref LT07-318, Cambrex) in accordance with the manufacturer instructions. The MycoAlert® Assay is a selective biochemical test that exploits the activity of mycoplasmal enzymes. The viable mycoplasma are lysed and the enzymes react with the MycoAlert® substrate catalyzing the conversion of ADP to ATP. By measuring the level of ATP in a sample both before and after the addition of the MycoAlert® substrate a ratio can be obtained which is indicative of the presence or absence of mycoplasma. The mycoplasma test was assayed in duplicate from the culture supernatants of the cell lines and compared to negative and positive controls (MycoAlert® Assay Control Set, Ref LT07-518, Cambrex) (Internal Standard Operating Procedure No TEC-007/002). Both HCC1954 and SK-BR-3 tumour cells (5,000 cells per well) were plated in 96-well flat-bottom microtitration plates (Ref 167008, Nunc, Dutscher, Brumath, France) and incubated at 37° C. for 24 hours before treatment in 190 μl of drug-free culture medium supplemented with 10% FBS. Both HCC1954 and SK-BR-3 tumour cell lines were incubated for 72 hours with 5 concentrations, in ¼ dilution steps, of the test substances (ranging from $10^{-6}$ to $10^{-11}$ M) to be tested as well as paclitaxel (ranging from $10^{-7}$ to $10^{-12}$ M). The cells (190 μl) will be incubated in a 200 μl final volume of culture medium supplemented with 10% FBS containing test substances at 37° C. under 5% $CO_2$. One experiment is performed, each concentration being issued from quadruplicate. Control cells are treated with corresponding vehicle alone. At the end of treatments, the cytotoxic activity is evaluated by a MTS assay. The in vitro cytotoxic activity of the test substances were revealed by a MTS assay using tetrazolium compound (MTS, 3-(4,5-dimethylthiazol-2-yl)-5-(3-carboxymethoxy phenyl)-2-(4-sulfophenyl)-2H-tetrazolium) and an electron coupling reagent named PMS (phenazine methosulfate). Like MTT, MTS is bioreduced by cells into a formazan product that is directly soluble in culture medium without processing, unlike MTT.

At the end of the cells treatment, 40 μl of a 0.22 μm filtered freshly combined solution of MTS (20 ml at 2 mg/ml, Ref G1111A, Promega, Charbonnières, France) and PMS (1 ml at 0.92 mg/ml, Ref P9625, Sigma) in Dulbecco's Phosphate Buffered Saline (DPBS, Ref 17-513F, Cambrex), were added in each well. Culture plates were incubated for 2 h at 37° C. Absorbency (OD) will be measured at 490 nm in each well using VICTOR$^{3TM}$ 1420 multilabeled counter (Wallac, PerkinElmer, Courtaboeuf, France).

TABLE 5
Cytotoxicity of selected pochonin analogs against HCC1954 and SK-BR-3 Tumor Cells
| | Structure | EC$_{50}$ HCC1954 | EC$_{50}$ SK-BR-3 |
|---|---|---|---|
| 2a-1 | 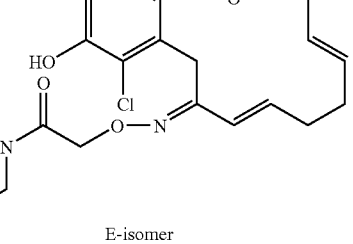 E-isomer | 320 nM | 125 nM |
| 2a-22 | 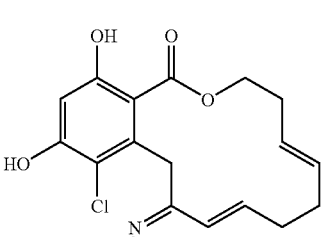 1:1 E:Z oxime mixture | 9.8 μM | 3.8 μM |
| 2a-3 | 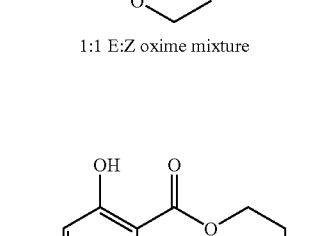 1:1 E:Z oxime mixture | 3.0 μM | 4.5 μM |
| 2a-4 | 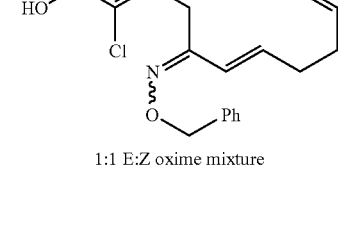 | >10 μM | 7.5 μM |

TABLE 5-continued

Cytotoxicity of selected pochonin analogs against HCC1954 and SK-BR-3 Tumor Cells

| | Structure | EC$_{50}$ HCC1954 | EC$_{50}$ SK-BR-3 |
|---|---|---|---|
| 2a-5 | 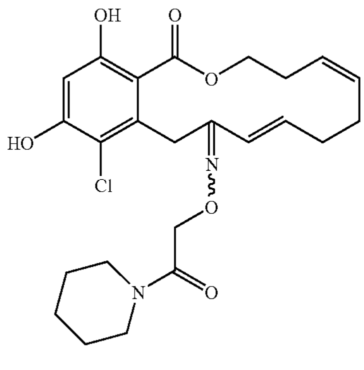 | 9.5 µM | 2.5 µM |
| 2a-6 | 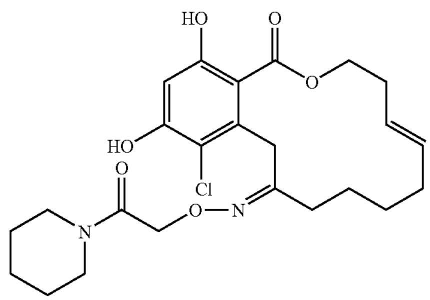 | 5.2 µM | >10 µM |
| 2a-7 | 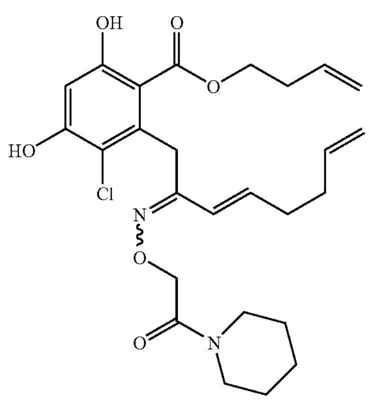 | >10 µM | >10 µM |
| 2a-8 | 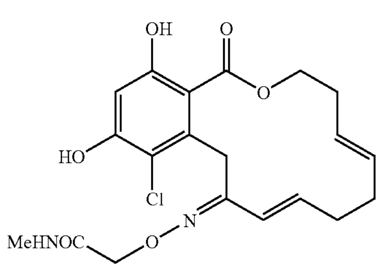 | >10 µM | >10 µM |

TABLE 5-continued
Cytotoxicity of selected pochonin analogs against HCC1954 and SK-BR-3 Tumor Cells
| | Structure | EC₅₀ HCC1954 | EC₅₀ SK-BR-3 |
|---|---|---|---|
| 2a-9 | 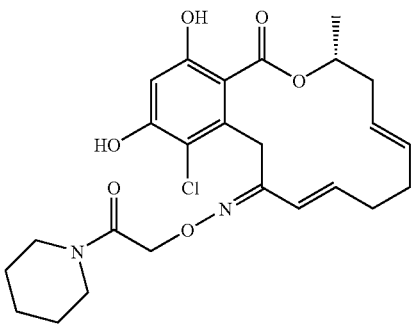 E isomer | 890 nM | 450 nM |
| 2a-10 | 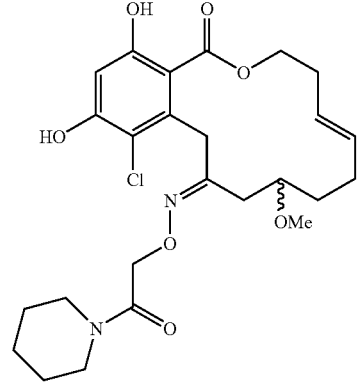 | >10 μM | >10 μM |
| 2a-11 | 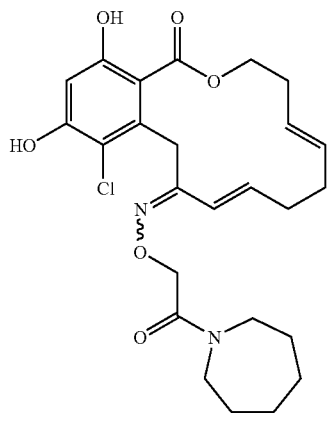 1:1 E:Z oxime mixture | 520 nM | 310 nM |
| 2a-12 | 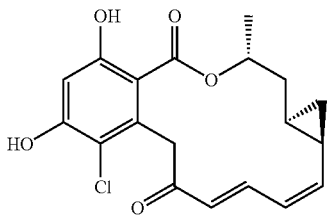 | >10 μM | 5.2 μM |

TABLE 5-continued
Cytotoxicity of selected pochonin analogs against HCC1954 and SK-BR-3 Tumor Cells
| | Structure | EC$_{50}$ HCC1954 | EC$_{50}$ SK-BR-3 |
|---|---|---|---|
| 2a-12 | 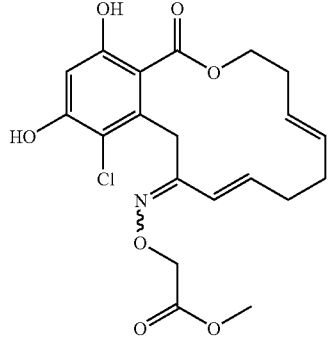<br>1:1 E:Z oxime mixture | >10 μM | >10 μM |
| 2a-13 | 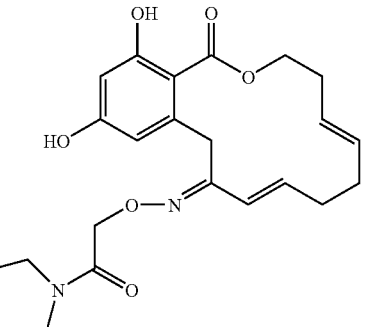<br>E isomer | 220 nM | 120 nM |
| 2a-14 | 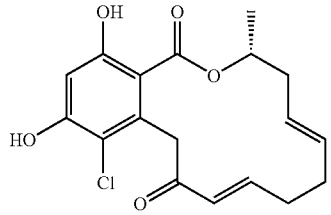 | 1.2 μM | 2.8 μM |
| 2a-15 | 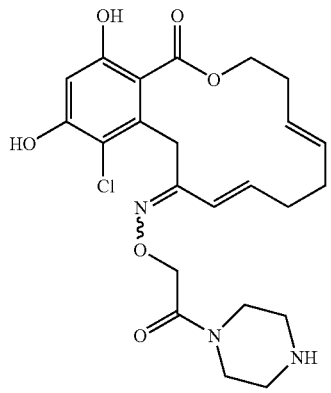<br>1:1 E:Z oxime mixture | >10 μM | >10 μM |

TABLE 5-continued
Cytotoxicity of selected pochonin analogs against HCC1954 and SK-BR-3 Tumor Cells
| | Structure | EC₅₀ HCC1954 | EC₅₀ SK-BR-3 |
|---|---|---|---|
| 2a-16 | 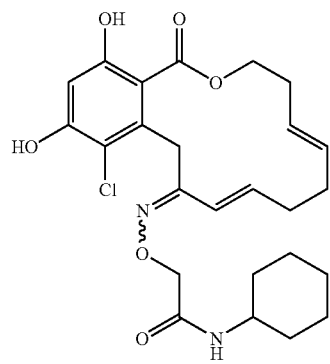<br>1:1 E:Z oxime mixture | 450 nM | 550 nM |
| 2a-17 | 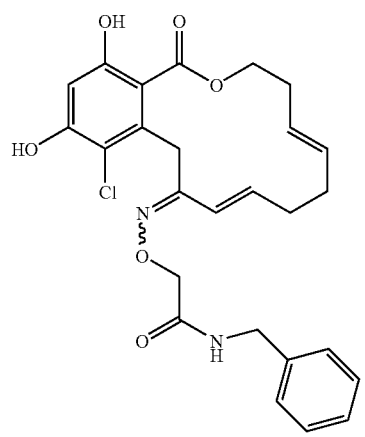<br>1:1 E:Z oxime mixture | 8.5 μM | 3.5 μM |
| 2a-18 | 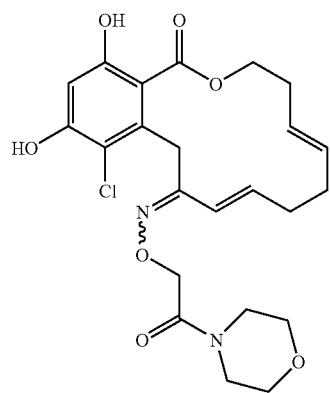<br>1:1 E:Z oxime mixture | >10 μM | >10 μM |

Experimental procedures and characterization data for exemplary compounds follows. The compounds and data described below are understood to be non-limiting.

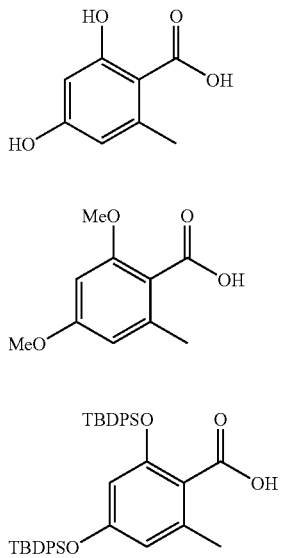

General procedure for oxidation using solvent system A: A solution of aldehyde 2-94 (1.0 equiv.) in $H_2O$/THF/DMSO (20:10:1, 0.03 M) was sequentially treated at 0° C. with sulfamic acid (3.5 equiv.) and a solution of sodium chlorite (3.25 equiv.) in $H_2O$. After 0.5-1 h stirring at this temperature, the reaction mixture was diluted with $Et_2O$, washed with saturated $NH_4Cl_{aq.}$ and dried over $MgSO_4$. Concentration under reduced pressure afforded the corresponding acid 2-95 which was used without any further purification in the next step.

2-95c: $^1$H NMR (400 MHz, $(CD_3)_2CO$, 25° C.): δ=6.48 (d, J=2.2 Hz, 1H), 6.45 (d, J=2.2 Hz, 1H), 3.84 (s, 3H), 3.83 (s, 3H), 2.33 (s, 3H).

2-94j: $^1$H NMR (400 MHz, $(CD_3)_2CO$, 25° C.): δ=7.58 (d, J=7.0 Hz, 4H), 7.47-7.35 (m, 10H), 7.31-7.21 (m, 6H), 6.31 (s, 1H), 5.89 (s, 1H), 2.35 (s, 3H), 1.05 (s, 9H), 0.93 (s, 9H).

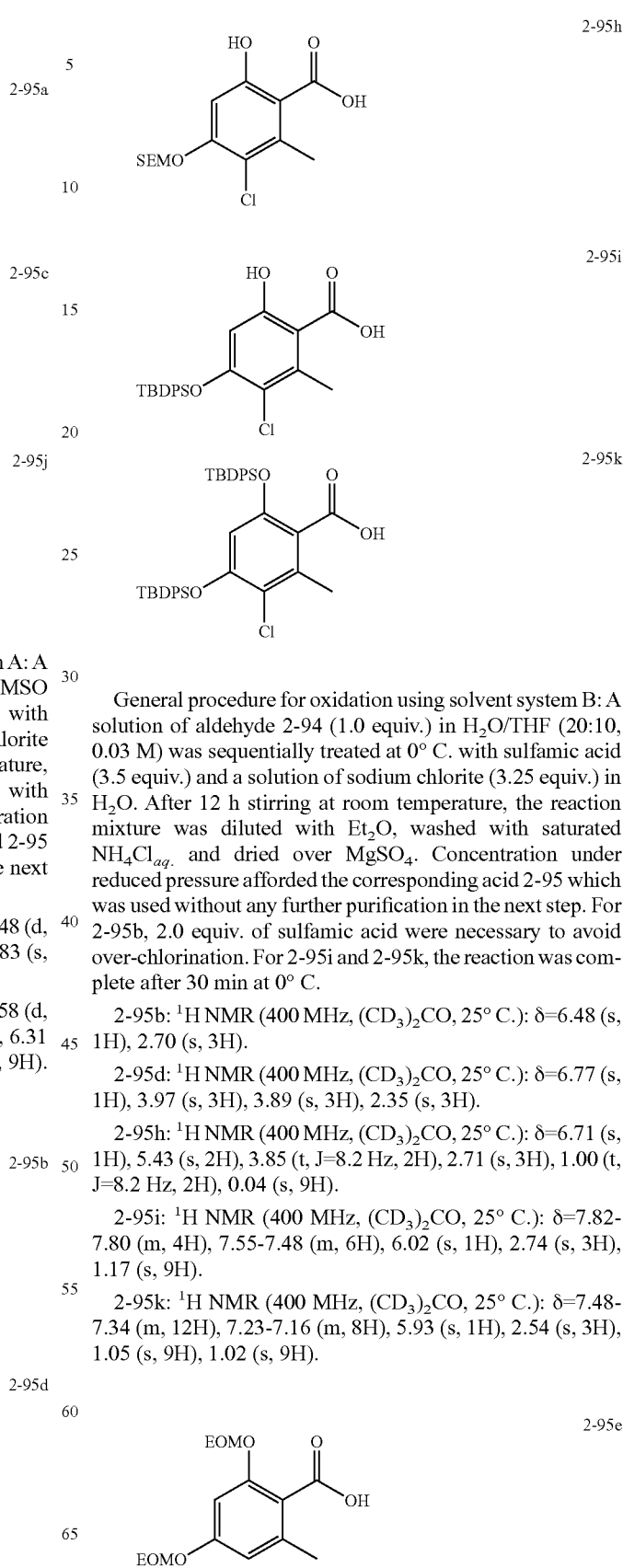

General procedure for oxidation using solvent system B: A solution of aldehyde 2-94 (1.0 equiv.) in $H_2O$/THF (20:10, 0.03 M) was sequentially treated at 0° C. with sulfamic acid (3.5 equiv.) and a solution of sodium chlorite (3.25 equiv.) in $H_2O$. After 12 h stirring at room temperature, the reaction mixture was diluted with $Et_2O$, washed with saturated $NH_4Cl_{aq.}$ and dried over $MgSO_4$. Concentration under reduced pressure afforded the corresponding acid 2-95 which was used without any further purification in the next step. For 2-95b, 2.0 equiv. of sulfamic acid were necessary to avoid over-chlorination. For 2-95i and 2-95k, the reaction was complete after 30 min at 0° C.

2-95b: $^1$H NMR (400 MHz, $(CD_3)_2CO$, 25° C.): δ=6.48 (s, 1H), 2.70 (s, 3H).

2-95d: $^1$H NMR (400 MHz, $(CD_3)_2CO$, 25° C.): δ=6.77 (s, 1H), 3.97 (s, 3H), 3.89 (s, 3H), 2.35 (s, 3H).

2-95h: $^1$H NMR (400 MHz, $(CD_3)_2CO$, 25° C.): δ=6.71 (s, 1H), 5.43 (s, 2H), 3.85 (t, J=8.2 Hz, 2H), 2.71 (s, 3H), 1.00 (t, J=8.2 Hz, 2H), 0.04 (s, 9H).

2-95i: $^1$H NMR (400 MHz, $(CD_3)_2CO$, 25° C.): δ=7.82-7.80 (m, 4H), 7.55-7.48 (m, 6H), 6.02 (s, 1H), 2.74 (s, 3H), 1.17 (s, 9H).

2-95k: $^1$H NMR (400 MHz, $(CD_3)_2CO$, 25° C.): δ=7.48-7.34 (m, 12H), 7.23-7.16 (m, 8H), 5.93 (s, 1H), 2.54 (s, 3H), 1.05 (s, 9H), 1.02 (s, 9H).

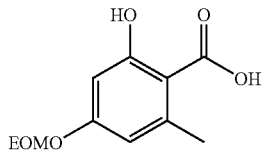

2-95g

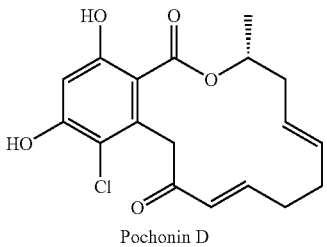

Pochonin D 2-85

General procedure for oxidation using solvent system C: To a solution of aldehyde 2-94 (1.0 equiv.) in DMSO (0.4 M) at 0° C., were added slowly in a sequential fashion, NaH$_2$PO$_4$.H$_2$O (5.0 equiv.) dissolved in H$_2$O (3 M) and NaClO$_2$ (5.0 equiv.) dissolved in H$_2$O (3 M). After stirring for 12 h, the reaction was diluted with Et$_2$O, washed with saturated NH$_4$Cl$_{aq.}$ and dried over MgSO$_4$. Concentration under reduced pressure resulted into the corresponding acid 2-95 used without further purification in the next step.

2-95e: $^1$H NMR (400 MHz, (CD$_3$)$_2$CO, 25° C.): δ=6.76 (d, J=1.9 Hz, 1H), 6.60 (d, J=1.6 Hz, 1H), 5.25 (s, 4H), 3.75-3.69 (m, 4H), 2.31 (s, 3H), 1.18 (t, J=7.0 Hz, 6H).

2-95g: $^1$H NMR (400 MHz, (CD$_3$)$_2$CO, 25° C.): δ=12.13 (bs, 1H), 6.46 (s, 2H), 5.30 (s, 2H), 3.73 (q, J=7.0 Hz, 4H), 2.58 (s, 3H), 1.19 (t, J=7.0 Hz, 3H).

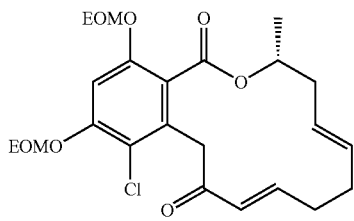

2-112

1-Chloro-2,4-bis-ethoxymethoxy-7-methyl-7,8,11,12-tetrahydro-16H-6-oxa-benzocyclotetradecene-5,15-dione (2-112): A 2 mM solution of compound 2-111 (200 mg, 0.38 mmol) in anhydrous toluene (190 mL) was treated with 10% mol of catalyst Grubbs' II (30 mg, 0.038 mmol) and heated at 80° C. overnight. The reaction mixture was then passed through a pad of silica, which was washed with CH$_2$Cl$_2$. The combined filtrates were concentrated under reduced pressure. Purification by flash chromatography (silica gel, 0-25% EtOAc/hexane gradient) afforded pure macrocycle 2-112 (167 mg, 94%). $^1$H NMR (400 MHz, C$_6$D$_6$, 25° C.): δ=7.27 (s, 1H), 6.85 (dt, J=15.2, 7.6 Hz, 1H), 6.15 (d, J=15.8 Hz, 1H), 5.16-4.94 (m, 7H), 4.41 (d, J=17.0 Hz, 1H), 4.13 (d, J=17.0 Hz, 1H), 3.61-3.45 (m, 4H), 2.18-2.07 (m, 2H), 1.86-1.62 (m, 4H), 1.38 (d, J=5.8 Hz, 3H), 1.11 (t, J=7.0 Hz, 3H), 1.04 (t, J=7.0 Hz, 3H); $^{13}$C NMR (100 MHz, C$_6$D$_6$, 25° C.): δ=193.5, 166.4, 155.0, 154.1, 146.0, 133.7, 131.5, 128.8, 127.7, 121.2, 118.1, 102.9, 93.7, 93.6, 71.6, 64.4, 64.4, 45.0, 39.2, 30.7, 30.4, 19.3, 14.9, 14.8; I.R. (film): ν$_{max}$=2917, 1720, 1690, 1622, 1591, 1320, 1255, 1120, 1037 cm$^{-1}$; HRMS (ESI-TOF): m/z: calculated for C$_{24}$H$_{31}$O$_7$ClNa: 489.1651, found 489.1737 [M+Na$^+$]. (−)-(2R): [α]$^{25}_D$=−24.0 (c 0.59, CHCl$_3$).

Pochonin D (2-85): Compound 2-112 (50 mg, 0.1 mmol) was stirred for 2 h in a 5:1 mixture of CH$_2$Cl$_2$/TFA (3 mL). Concentration under reduced pressure, followed by flash chromatography (silica gel, 0-33% EtOAc/hexane gradient) afforded synthetic pochonin D 2-85 (25 mg, 72%). Synthetic pochonin D was found to have identical $^1$H NMR as natural pochonin D. $^1$H NMR (400 MHz, C$_6$D$_6$, 25° C.): δ=12.42 (s, 1H), 6.89 (s, 1H), 6.67-6.62 (m, 1H), 5.82 (d, J=15.6 Hz, 1H), 5.17-5.12 (m, 1H), 5.00-4.92 (m, 1H), 4.76-4.69 (m, 1H), 4.28 (d, J=17.2 Hz, 1H), 4.18 (d, J=17.7 Hz, 1H), 2.54-2.47 (m, 1H), 1.93-1.77 (m, 5H), 0.98 (d, J=6.4 Hz, 3H); $^1$H NMR (400 MHz, CDCl$_3$, 25° C.): δ=11.73 (s, 1H), 6.76-6.69 (m+s, 2H), 6.19 (s, 1H), 5.82 (d, J=15.2 Hz, 1H), 5.46-5.40 (m, 1H), 5.31-5.15 (m, 2H), 4.37 (d, J=17.6 Hz, 1H), 4.09 (d, J=17.0 Hz, 1H), 2.68-2.61 (m, 1H), 2.39-2.03 (m, 5H), 1.34 (d, J=7.0 Hz, 3H); $^1$H NMR (400 MHz, CD$_3$OD, 25° C.): δ=6.74 (dt, J=15.5, 7.6 Hz, 1H), 6.51 (s, 1H), 5.83 (d, J=15.5 Hz, 1H), 5.36-5.22 (m, 3H), 4.25 (d, J=17.7 Hz, 1H), 4.13 (d, J=17.7 Hz, 1H), 2.54-2.47 (ddd, J=14.5, 8.0, 4.0 Hz, 1H), 2.31-2.15 (m, 5H), 1.31 (d, J=6.6 Hz, 3H); $^{13}$C NMR (100 MHz, C$_6$D$_6$, 25° C.): δ=194.2, 169.9, 164.3, 157.3, 146.1, 137.1, 131.9, 128.1, 126.2, 115.5, 107.5, 103.6, 72.4, 45.0, 36.4, 31.0, 30.8, 17.2; I.R. (KBr): ν$_{max}$=2936, 1654, 1603, 1347, 1313, 1239 cm$^{-1}$; HRMS (ESI-TOF): m/z: calculated for C$_{18}$H$_{19}$O$_5$ClNa: 373.0813, found 373.0903 [M+Na$^+$]. (+)-(2R): [α]$^{25}_D$=+11.1 (c 0.72, CHCl$_3$).

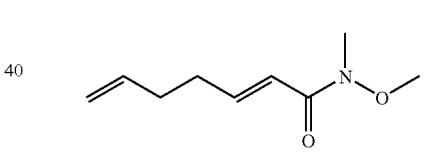

2-114

Hepta-2,6-dienoic acid methoxy-methyl-amide (2-114): To a solution of 2-chloro-N-methoxy-N-methylacetamide (6.0 g, 48.8 mmol) in dry DMF (20 mL) at 23° C. was added 3-mercaptophenol (4.44 mL, 48.8 mmol) and K$_2$CO$_3$ (6.7 g, 48.8 mmol). The resulting suspension was stirred at 23° C. overnight. After this period of time, Merrifield resin (24 g, <2 mmol.g$^{-1}$, <48.8 mmol) was added to the mixture followed by K$_2$CO$_3$ (11.4 g, 83.0 mmol) as well as TBAI (catalytic amount), and the suspension was heated up to 50° C. After 12 hours at this temperature, the resin was filtered and washed several times: HCl$_{aq.}$ (50 mL), MeOH (50 mL), CH$_2$Cl$_2$ (50 mL) and Et$_2$O (50 mL). The resin was dried under reduced pressure to constant mass of 29.2 g. The final mass gain (5.2 g, 27.3 mmol) indicated an estimate loading of 0.81 mmol.g$^{-1}$. Resin 2-49 (10 g, 0.81 mmol.g$^{-1}$) was suspended in a 1:1 mixture of HFIP/CH$_2$Cl$_2$ (50 mL). To this suspension, H$_2$O$_2$ (3 mL, 16.0 mmol) was added at 23° C. and the resulting mixture was shaken for 12 h. Resin 2-113 was then filtered, washed using MeOH (50 mL), CH$_2$Cl$_2$ (50 mL) and Et$_2$O (50 mL) and dried under reduced pressure to constant mass before subsequent use. Resin 2-113 (4.0 g, <0.81 mmol.g$^{-1}$) was suspended in DMSO (40 mL) followed by the addition of tBuOK (336 mg, 3.0 mmol). After shaking the reaction for 1 h at room temperature, 5-iodo-1-pentene (588 mg, 3.0 mmol) was added to the suspension and the mixture was shaken for 3 h. The resin was filtered, washed and dried as before. Then, it was suspended in toluene and heated at 80° C. After 8 h at this temperature, the resin was filtered and washed several times with more toluene. The combined toluene solutions were evaporated giving pure compound 2-114 as a colourless oil (321 mg, 77%) of 95% purity judged by NMR. $^1$H NMR (400 MHz, CDCl$_3$, 25° C.): δ=6.94 (dt, J=15.7, 6.7 Hz, 1H), 6.39 (d, J=15.2 Hz, 1H), 5.84-5.74 (m, 1H), 5.02 (dd, J=17.4, 1.7 Hz, 1H), 4.97 (d, J=10.1 Hz, 1H), 3.67 (s, 3H), 3.21 (s, 3H), 2.34-2.29 (m, 2H), 2.23-2.18 (m, 2H); $^{13}$C NMR (100 MHz, CDCl$_3$, 25° C.): δ=166.8, 146.7, 137.3, 119.1, 115.3, 61.6, 32.3, 31.7, (one carbon is not detected); I.R. (film): ν$_{max}$=2934, 1681, 1638, 1378, 1179 cm$^{-1}$.

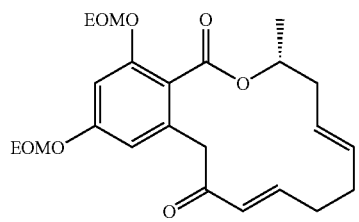

2-120

2,4-Bis-ethoxymethoxy-7-methyl-7,8,11,12-tetrahydro-16H-6-oxa-benzocyclotetradecene-5,15-dione (2-120). A 2 mM solution of crude 2-119 (1.5 mmol) in anhydrous toluene (750 mL) was treated with 10% mol of catalyst Grubbs' II (139 mg, 0.15 mmol), and heated at 80° C. overnight. The crude reaction mixture was then passed through a pad of silica, which was washed with CH$_2$Cl$_2$. The combined filtrates were concentrated under reduced pressure. Purification by flash chromatography (silica gel, 0-25% EtOAc/cyclohexane gradient) afforded pure 2-120 (260 mg, 40% over two steps). $^1$H NMR (400 MHz, C$_6$D$_6$, 25° C.): δ=7.08 (d, J=2.2 Hz, 1H), 7.01 (d, J=2.2 Hz, 1H), 6.93-6.86 (m, 1H), 6.17 (d, J=16.1 Hz, 1H), 5.34-4.90 (m, 7H), 4.41 (d, J=14.5 Hz, 1H), 3.75 (d, J=14.5 Hz, 1H), 3.59-3.45 (m, 4H), 2.27-2.12 (m, 2H), 1.95-1.61 (m, 4H), 1.45 (d, J=6.2 Hz, 3H), 1.07 (t, J=7.0 Hz, 3H), 1.07 (t, J=7.0 Hz, 3H); $^{13}$C NMR (100 MHz, C$_6$D$_6$, 25° C.): δ=196.0, 167.2, 159.5, 156.6, 147.6, 135.8, 131.5, 130.2, 128.5, 119.1, 109.7, 102.3, 93.3, 92.9, 71.0, 64.2, 64.0, 44.5, 39.6, 30.9, 30.2, 20.1, 14.8, 14.8; I.R. (film): ν$_{max}$=2976, 1717, 1602, 1438, 1284, 1155, 1110, 1036, 1018 cm$^{-1}$; HRMS (ESI-TOF): nm/z: calculated for C$_{24}$H$_{32}$O$_7$Na: 455.2040, found 455.2135 [M+Na$^+$]. (−)-(2R): [α]$^{25}$$_D$=−50.3 (c 1.00, CHCl$_3$).

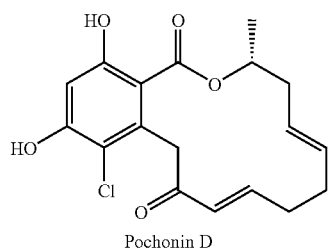

2-85

Pochonin D

Pochonin D (2-85) using polymer-bound reagents: PS-TsOH (300 mg, 3.2 mmol.g$^{-1}$) was added to a solution of compound 2-112 (50 mg, 0.1 mmol) in MeOH (3 mL) of and the suspension was shaken at 40° C. for 4 h. The reaction mixture was then filtered and the methanolic solution concentrated under reduced pressure. Purification by flash chromatography (silica gel, 0-20% EtOAc/cyclohexane gradient) afforded synthetic pochonin D 2-85 (32 mg, 90%).

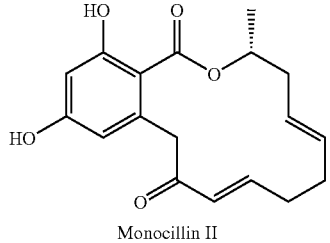

2-103

Monocillin II

Monocillin II (2-103) using polymer-bound reagents: PS-TsOH (145 mg, 3.2 mmol.g$^{-1}$) was added to a solution of compound 2-120 (20 mg, 0.05 mmol) in MeOH (1.5 mL) and the suspension was shaken at 40° C. for 4 h. The reaction mixture was then filtered and the methanolic solution concentrated under reduced pressure. Purification by flash chromatography (silica gel, 0-20% EtOAc/cyclohexane gradient) afforded synthetic monocillin II 2-103 (14 mg, 92%). $^1$H NMR (400 MHz, C$_6$D$_6$, 25° C.): δ=12.49 (s, 1H), 6.70-6.62 (m, 1H), 6.49 (d, J=2.9 Hz, 1H), 6.09 (d, J=2.4 Hz, 1H), 5.86 (d, J=15.2 Hz, 1H), 5.08-4.95 (m, 2H), 4.82-4.75 (m, 1H), 4.14 (d, J=16.8 Hz, 1H), 3.71 (d, J=17.0 Hz, 1H), 2.64-2.57 (m, 1H), 1.83-1.76 (m, 3H), 1.74-1.66 (m, 2H), 0.97 (d, J=6.4 Hz, 3H); $^{13}$C NMR (100 MHz, C$_6$D$_6$, 25° C.): δ=195.7, 170.3, 166.5, 161.3, 146.1, 140.5, 131.7, 129.9, 126.5, 112.4, 102.8, 72.2, 49.1, 36.6, 31.0, 30.6, 17.5, (one carbon is not detected); I.R. (KBr): ν$_{max}$=2936, 1654, 1603, 1347, 1313, 1239 cm$^{-1}$; HRMS (ESI-TOF): m/z: calculated for C$_{18}$H$_{21}$O$_5$ requires 317.3980, found 317.3978 [M+H$^+$]. (+)-(2R): [α]$^{25}$$_D$=+40.6 (c 0.18, CHCl$_3$).

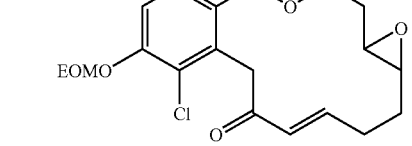

2-123

Macrocycle 2-122: To a solution of compound 2-112 (50 mg, 0.11 mmol) in CH$_3$CN (5 mL) at 0° C. was added freshly made DMDO (275 µL, 0.11 mmol, 0.04 M in acetone) and the mixture was stirred for 1.5 h. After evaporation of the solvents under reduced pressure, purification by flash chromatography (silica gel, 0-70% Et$_2$O/hexane gradient) afforded compound 2-122 (41 mg, 79%) as a 1:1 mixture of two diastereoisomers. $^1$H NMR (400 MHz, CDCl$_3$, 25° C.): δ=7.12 (s, 1H), 7.11 (s, 1H), 6.90-6.76 (m, 2H), 6.11 (d, J=15.6 Hz, 1H), 6.05 (d, J=15.8 Hz, 1H), 5.37-5.27 (m, 6H), 5.26-5.21 (m, 4H), 4.14 (d, J=16.9 Hz, 1H), 4.12 (d, J=17.4 Hz, 1H), 4.04 (d, J=17.2 Hz, 1H), 3.82-3.70 (m, 9H), 2.81-2.78 (m, 1H), 2.74-2.72 (m, 1H), 2.67-2.62 (m, 2H), 2.38-2.11 (m, 8H), 2.05-2.03 (m, 1H), 2.03-2.00 (m, 1H), 1.74-1.60 (m, 2H), 1.41 (d, J=7.2 Hz, 3H), 1.39 (d, J=6.2 Hz, 3H), 1.27-1.22 (m, 12H); $^{13}$C NMR (100 MHz, CDCl$_3$, 25° C.): δ=195.1 (×2), 166.7, 166.3, 154.9, 154.8, 154.0, 153.5, 147.8, 147.4, 132.9, 132.4, 129.1, 129.0, 119.7 (×2), 118.0, 117.9, 102.9, 102.8, 93.9 (×2), 93.6 (×2), 71.1, 70.4, 64.8 (×2), 64.6 (×2), 58.4, 57.6, 56.9, 55.1, 43.4 (×2), 39.0, 37.9, 29.9, 29.7, 27.9 (×2), 18.4, 18.0, 15.0 (×4); HRMS (ESI-TOF): m/z: calculated for $C_{24}H_{32}ClO_8$: 483.1780, found 483.1814 [M+H$^+$].

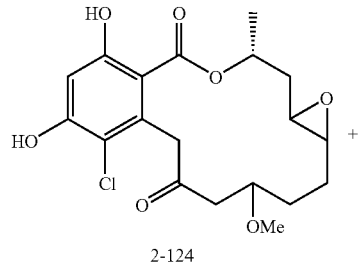

2-124

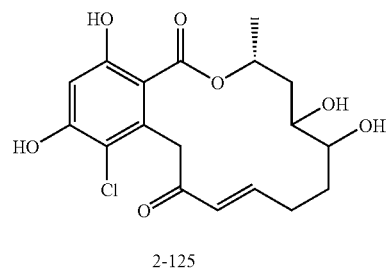

2-125

Macrocycles 2-124 and 2-125: PS-TsOH (264 mg, 3.2 mmol.g$^{-1}$) was added to a solution of compound 2-123 (41 mg, 85 mmol) in MeOH (3 mL) and the suspension was shaken at 40° C. until consumption of all starting material (~1 h). The reaction mixture was filtered and the methanolic solution concentrated under reduced pressure. L.C./M.S. analysis of the crude mixture showed clearly 2 peaks corresponding to methanol addition on the conjugated olefin (2-124) and opening of the epoxide as a diol (2-125).

2-125: $^1$H NMR (400 MHz, CD$_3$OD, 25° C.): δ=7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 1H), 2.39-2.30 (m, 2H), 2.27-2.18 (m, 1H), 2.08-2.00 (m, 2H), 2.00-1.85 (m, 4H), 1.44 (d, J=6.4 Hz, 6H); HRMS (ESI-TOF): m/z: calculated for $C_{18}H_{22}ClO_7$: 385.1054, found 385.0944 [M+H$^+$].

2-124: compound 2-124 which was characterized as the MeOH-addition on the α,β-conjugated system based on the loose of olefinic protons in the NMR (a detailed assignment is not possible as product 2-124 represents a mixture of 4 compounds); HRMS (ESI-TOF): m/z: calculated for $C_{19}H_{24}ClO_7$: 399.1211, found 399.1030 [M+H$^+$].

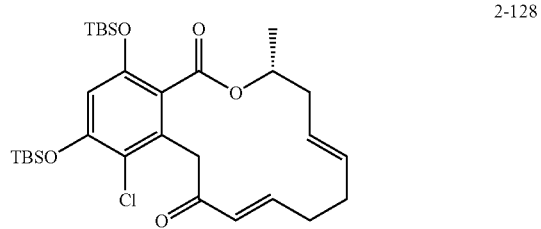

2-128

Macrocycle 2-128: A 2 mM solution of compound 2-127 (140 mg, 0.23 mmol) in anhydrous toluene (115 mL) was treated with 10% mol of catalyst Grubbs' II (18.4 mg, 0.023 mmol) and heated up to 80° C. for 12 h. The reaction mixture was then filtered through a pad of silica, which was washed with CH$_2$Cl$_2$. The combined filtrates were concentrated under reduced pressure. Purification by flash chromatography (silica gel, 0-25% EtOAc/hexane gradient) afforded macrocycle 2-128 (116 mg, 87%). $^1$H NMR (400 MHz, CDCl$_3$, 25° C.): δ=6.71 (dt, J=15.3, 7.3 Hz, 1H), 6.45 (s, 1H), 5.81 (d, J=15.3 Hz, 1H), 5.25 (s, 2H), 5.04-5.03 (m, 1H), 3.89 (d, J=17.4 Hz, 1H), 3.57 (d, J=17.4 Hz, 1H), 2.31-2.04 (m, 6H), 1.35 (d, J=6.4 Hz, 3H), 1.03 (s, 9H), 0.99 (s, 9H), 0.28-0.24 (m, 12H); $^{13}$C NMR (100 MHz, CDCl$_3$, 25° C.): δ=195.8, 166.8, 152.9, 151.7, 146.5, 132.7, 131.9, 128.6, 126.8, 122.8, 119.7, 110.7, 71.9, 45.6, 38.5, 30.9, 25.7 (×4), 25.6 (×4), 18.7, 18.3, −4.1 (×2), −4.4 (×2); HRMS (ESI-TOF): m/z: calculated for $C_{30}H_{47}ClO_5Si_2Na$: 601.2543, found 601.2568 [M+Na$^+$].

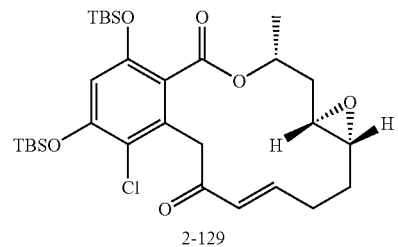

2-129

Macrocycle 2-129: An aqueous Na$_2$.EDTA solution (700 μL, 4×10$^{-4}$M) was added to a solution of compound 2-128 (80 mg, 0.14 mmol) in a 2:1 mixture of dimethoxymethane/acetonitrile (2.1 mL). The resulting mixture was cooled to 0° C. and treated with trifluoroacetone (150 μL) added via a precooled syringe. A mixture of sodium bicarbonate (88 mg, 1.05 mmol) and Oxone (430 mg, 0.70 mmol) was added in portions over a period of ~1 h to this homogeneous solution. The reaction was followed by TLC and found to be complete in 2 h. The reaction mixture was then poured into water (10 mL), extracted with CH$_2$Cl$_2$ (20 mL) and dried over Na$_2$SO$_4$. Removal of the solvent under reduced pressure afforded pure compound 2-129 (66 mg, 93%) as a mixture of 2 diastereoisomers in a 3:1 ratio. $^1$H NMR (400 MHz, CDCl$_3$, 25° C.): δ=6.90-6.77 (m, 1.33H), 6.45 (s, 1.33H), 6.06 (d, J=15.8 Hz, 1.33H), 5.31-5.29 (m, 1H), 5.29-5.21 (m, 0.33H), 4.03 (d, J=18.1 Hz, 1.33H), 3.63 (d, J=17.6 Hz, 1H), 2.82-2.80 (m, 1.33H), 2.74-2.71 (m, 1.33H), 2.62-2.60 (m, 1.33H), 2.41-2.11 (m, 4.6H), 2.02-1.95 (m, 0.33H), 1.80-1.78 (m; 1H), 1.78-1.68 (m, 0.7H), 1.41 (d, J=6.4 Hz, 3.9H), 1.05 (s, 12H), 0.97 (s, 12H), 0.26 (s, 16H); $^{13}$C NMR (100 MHz, CDCl$_3$, 25° C.): δ=195.4, 195.1, 167.0, 166.2, 153.1 (×2), 152.1, 151.5, 147.8, 146.9, 132.9, 132.2, 129.0, 128.3, 122.2, 121.4, 120.0, 119.7, 110.6, 110.3, 71.3, 70.1, 58.2, 57.9, 56.6, 55.2, 44.7, 43.9, 38.7, 37.6, 30.1, 29.4, 28.3, 27.5, 25.7 (×4), 25.6 (×4), 25.5 (×4), 25.4 (×4), 20.8, 17.8, −3.9, −4.0, −4.3 (×3), −4.4 (×3); HRMS (ESI-TOF): m/z: calculated for $C_{30}H_{48}O_6ClSi_2$: 595.2672, found 595.2698 [M+H$^+$].

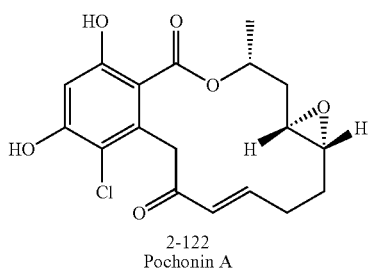

2-122
Pochonin A

Pochonin A (2-122): TBAF (244 µL, 1M solution in hexane, 0.24 mmol) was added to a solution of compound 2-129 (66 mg, 0.11 mmol) in THF (2 mL) and the mixture was stirred at room temperature for 20 min. The reaction was then quenched with saturated $NH_4Cl_{aq.}$ (8 mL), extracted several times with EtOAc (10 mL) and dried over $Na_2SO_4$. Concentration under reduced pressure followed by purification by flash chromatography (silica gel, 0-70% $Et_2O$/hexane) afforded two different diastereoisomers pochonin A (2-122) and its diastereoisomer 2-122b as a 3:1 mixture (80% yield) The isomers were separated by preparative TLC with a 3:1 mixture of $Et_2O$/hexane. $^1$H NMR (400 MHz, [$D_6$]DMSO, 25° C.): δ=10.81 (s, 1H), 10.74 (s, 1H), 6.97-6.89 (m, 1H), 6.53 (s, 1H), 6.08 (d, J=15.8 Hz, 1H), 5.15-5.13 (m, 1H), 4.19 (d, J=17.5 Hz, 1H), 4.09 (d, J=17.5 Hz, 1H), 2.81 (s, 1H), 2.60 (m, 1H), 2.44-2.40 (m, 2H), 2.30-2.22 (m, 2H), 1.80-1.78 (m, 2H), 1.32 (d, J=6.4 Hz, 3H); $^1$H NMR (400 MHz, CDCl$_3$, 25° C.): δ=11.85 (s, 1H), 6.94-6.87 (m, 1H), 6.70 (s, 1H), 6.14 (s, 1H), 6.12 (d, J=16.4 Hz, 1H), 5.32-5.31 (m, 1H), 4.53 (d, J=18.1 Hz, 1H), 4.27 (d, J=18.1 Hz, 1H), 2.77 (s, 1H), 2.58-2.56 (m, 2H), 2.47-2.43 (m, 1H), 2.35-2.28 (m, 1H), 2.11-2.07 (m, 1H), 1.93-1.86 (m, 1H), 1.51 (d, J=6.4 Hz, 3H), 0.94-0.90 (m, 1H); $^{13}$C NMR (100 MHz, CDCl$_3$, 25° C.): δ=195.0, 170.0, 164.1, 156.4, 147.5, 135.7, 129.9, 115.0, 107.3, 103.8, 72.2, 57.0, 55.5, 45.1, 36.3, 30.9, 29.1, 17.9; HRMS (ESI-TOF): m/z: calculated for $C_{18}H_{19}ClO_6Na$: 389.0762, found 389.0724 [M+Na$^+$]. (−)-(2R,4R, SR): [α]$^{25}_D$=−7.0 (c 0.11, CHCl$_3$).

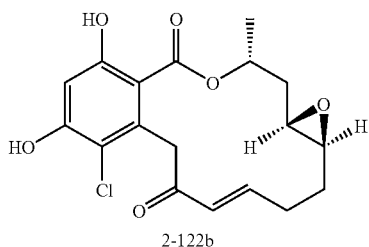

2-122b

Compound 2-122b: $^1$H NMR (400 MHz, [$D_6$]DMSO, 25° C.): δ=10.74 (s, 1H), 10.39 (s, 1H), 6.94-6.89 (m, 1H), 6.52 (s, 1H), 6.02 (d, J=16.4 Hz, 1H), 5.18 (m, 1H), 4.32 (d, J=17.5 Hz, 1H), 3.96 (d, J=17.5 Hz, 1H), 2.82 (s, 1H), 2.68 (s, 1H), 2.34-2.26 (m, 3H), 1.86-1.83 (m, 1H), 1.70-1.63 (m, 1H), 1.22 (d, J=5.8 Hz, 3H), 1H masked by the solvent peak; $^1$H NMR (400 MHz, CDCl$_3$, 25° C.): δ=11.37 (s, 1H), 6.90-6.83 (m, 1H), 6.67 (s, 1H), 6.24 (d, J=16.4 Hz, 1H), 6.08 (s, 1H), 5.39-5.37 (m, 1H), 4.52-4.36 (m, 2H), 2.72-2.62 (m, 2H), 2.56-2.52 (m, 1H), 2.45-2.40 (m, 1H), 2.40-2.37 (m, 1H), 2.08-2.04 (m, 1H), 1.91-1.86 (m, 1H), 1.35 (d, J=6.4 Hz, 3H), 1H masked by the solvent peak; HRMS (ESI-TOF): m/z: calculated for $C_{18}H_{19}ClO_6Na$: 389.0762; found 389.0796 [M+Na$^+$]. (+)-(2R,4S,5S): [α]$^{25}_D$=+13.8 (c 0.13, CHCl$_3$).

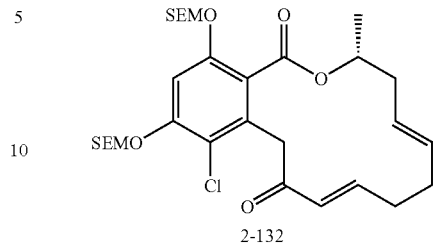

2-132

Macrocycle 2-132: A 2 mM solution of compound 2-131 (166 mg, 0.26 mmol) in anhydrous toluene (130 mL) was treated with 10% mol of Grubbs' II (20.8 mg, 0.026 mmol) and heated up to 80° C. for 12 h. The reaction mixture was then filtered through a pad of silica, which was washed with $CH_2Cl_2$. The combined filtrates were concentrated under reduced pressure. Purification by flash chromatography (silica gel, 0-25% EtOAc/hexane gradient) afforded macrocycle 2-132 (136 mg, 87%). $^1$H NMR (400 MHz, CDCl$_3$, 25° C.): δ=7.08 (s, 1H), 6.77-6.71 (m, 1H), 5.89 (d, J=15.2 Hz, 1H), 5.35-5.24 (m, 6H), 5.09-5.05 (m, 1H), 4.02 (d, J=17.0 Hz, 1H), 3.85-3.78 (m, 5H), 2.37-2.08 (m, 6H), 1.39 (d, J=5.8 Hz, 3H), 1.02-0.97 (m, 4H), 0.04 (s, 18H); $^{13}$C NMR (100 MHz, CDCl$_3$, 25° C.): δ=195.7, 166.8, 154.6, 153.9, 147.0, 132.8, 131.7, 128.6, 127.5, 120.6, 117.8, 102.7, 93.7, 93.3, 71.9, 66.9, 66.6, 44.7, 39.2, 30.8 (×2), 19.5, 18.0, 17.9, −1.4 (×6); HRMS (ESI-TOF): m/z: calculated for $C_{30}H_{47}O_7ClSi_2H_2O$: 628.2649, found 628.2870 [M+H$_2$O]. (−)-(2R): [α]$^{25}_D$=−16.3 (c 0.85, CHCl$_3$).

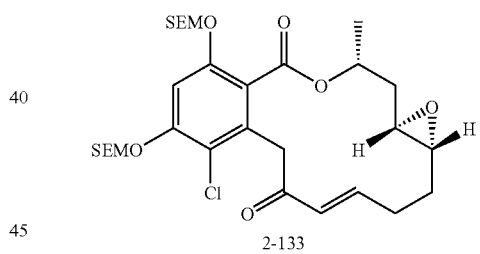

2-133

Macrocycle 2-133: An aqueous $Na_2$.EDTA solution (350 µL, 4×10$^{-4}$M) was added to a solution of compound 2-132 (40 mg, 65 µmol) in a 2:1 mixture of dimethoxymethane/acetonitrile (1.1 mL). The resulting solution was cooled to 0° C. and trifluoroacetone (75 µL) was added via a precooled syringe. A mixture of sodium bicarbonate (44 mg, 0.5 mmol) and Oxone (215 mg, 0.35 mmol) was then added in portions over a period of ~1 h to this homogeneous solution. The reaction was followed by TLC and found to be complete in 2 h. The reaction mixture was then poured into water (5 mL), extracted with $CH_2Cl_2$ (10 mL) and dried over $Na_2SO_4$. Removal of the solvent under reduced pressure afforded pure compound 2-133 (34 mg, 82%) as a 1:1 mixture of two diastereoisomers. $^1$H NMR (400 MHz, CDCl$_3$, 25° C.): δ=7.11 (s, 1H), 7.09 (s, 1H), 6.91-6.76 (m, 2H), 6.12 (d, J=15.8 Hz, 1H), 6.06 (d, J=15.8 Hz, 1H), 5.36-5.31 (m, 6H), 5.23-5.22 (m, 4H), 4.15 (d, J=16.9 Hz, 1H), 4.13 (d, J=16.0 Hz, 1H), 4.05 (d, J=17.5 Hz, 1H), 3.85-3.75 (m, 9H), 2.81-2.79 (m, 1H), 2.75-2.73 (m, 1H), 2.68-2.62 (m, 2H), 2.42-2.29 (m, 10H), 1.72-1.60 (m, 2H), 1.41 (d, J=7.6 Hz, 3H), 1.39 (d, J=6.4 Hz, 3H), 1.02-0.96 (m, 8H), 0.03 (s, 36H); $^{13}$C NMR (100 MHz, CDCl$_3$, 25° C.): δ=195.1 (×2), 166.8, 166.3, 154.9 (×2), 154.2, 153.7, 147.8, 147.4, 132.9, 132.4, 129.1, 129.0, 119.8, 119.6, 117.9, 117.8, 102.8, 102.7, 93.7 (×2), 93.4 (×2), 71.1, 70.3, 66.9, 66.8, 66.6, 66.5, 58.4, 57.6, 56.9, 55.1, 43.5 (×2), 38.9, 37.9, 29.9, 29.7, 27.9 (×2), 20.7 (×2), 18.4, 18.0, 17.9 (×2), −1.40 (×12); HRMS (ESI-TOF): m/z: calculated for C$_{30}$H$_{48}$O$_8$ClSi$_2$: 627.2571, found 627.2551 [M+H$^+$].

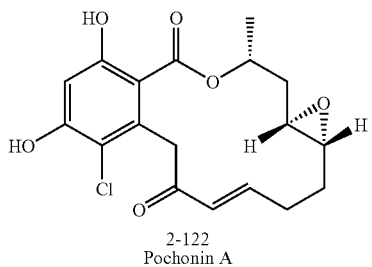

2-122
Pochonin A

Pochonin A (2-122) from macrocycle 2-133: A solution of compound 2-133 (21 mg, 33 µmol) in CH$_2$Cl$_2$ (2.5 mL) was treated at room temperature with MgBr$_2$.Et$_2$O (69 mg, 0.27 mmol). The reaction was followed by L.C./M.S. until bromohydrine started appearing (~1 h). The reaction was then diluted with EtOAc (5 mL), washed with saturated NH$_4$Cl$_{aq.}$ (5 mL) and dried over MgSO$_4$. After concentration under reduced pressure, purification by flash chromatography (silica gel, 0-70% Et$_2$O/hexane gradient) afforded pochonin A (2-122) (8.6 mg, 70%) as a 1:1 mixture of diastereoisomers.

General procedure for the synthesis of compounds 2-110a-g and 2-117a-g: A solution of acid 2-95a or 2-95b (1.0 equiv.), homoallylic alcohol (R)-120a-g or (S)-120a-g (1.0 equiv.) and tris-(3-chlorophenyl)phosphine (2.0 equiv.) in anhydrous toluene (0.05 M) was treated at room temperature with PS-DEAD (2.5 equiv., 1.3 mmol.g$^{-1}$). After stirring for 30 min, the reaction mixture was filtered on silica and washed with hexane/EtOAc (10:1, 100 mL) and hexane/EtOAc (3:1, 100 mL). The 3:1 mixture was concentrated under reduced pressure to yield compound 2-115a-g or 2-116a-g (60-80%). Without further purification, compound 2-115a-g or 2-116a-g (1.0 equiv.) and TBAI (catalytic amount) were dissolved in DMF (0.15 M) and treated with diisopropylethylamine (4.0 equiv.) and chloromethylethyl ether (4.0 equiv.). After stirring overnight at 80° C., the reaction mixture was diluted with EtOAc and washed several times with a saturated NH$_4$Cl$_{aq.}$ solution. The organic phase was dried over MgSO$_4$ and concentrated under reduced pressure to yield compounds 2-110a-g and 2-117a-g (80-90%).

General procedure for the synthesis of compounds 2-119a-g and 2-140a-g: A solution of compound 2-110a-g or 2-117a-g (1.0 equiv.) in anhydrous THF (0.2 M) cooled at −78° C. was treated with freshly prepared LDA (2.0 equiv.). Immediately after, the α,β-unsaturated Weinreb amide 2-114 was added to the cooled solution (1.0 equiv.). The resulting mixture was then stirred for 10 min at −78° C. and quenched by addition of Amberlite resin (20 equiv.). Upon warming up to room temperature, the reaction was filtered on a pad of silica and washed with EtOAc. Concentration under reduced pressure afforded the desired compound 2-118a-g or 2-119a-g. This compound was used directly in the metathesis reaction without any further purification. When X=H, 20% of the corresponding 1,4-addition compound was observed and a fraction of the mixture was purified for characterization of compounds 2-119a-g and 2-140a-g (silica gel, 0-20% EtOAc/ hexane gradient).

General procedure for the metathesis reaction: A solution of crude 2-118a-g or 2-119a-g (or mixture 2-119a-g or 2-140a-g when X=H) in anhydrous toluene (2 mM) was treated with Grubbs' II (0.10 equiv.) and heated at 80° C. for 12 h. The reaction was cooled down to room temperature and the mixture was filtered through a pad of silica gel, washed with CH$_2$Cl$_2$ followed by a mixture EtOAc/cyclohexane 1:1, and concentrated under reduced pressure. Purification by flash chromatography (silica gel, 0-25% EtOAc/cyclohexane gradient) afforded compound 2-112a-g or 2-120a-g (and 2-121a-g) (38-70% over two steps).

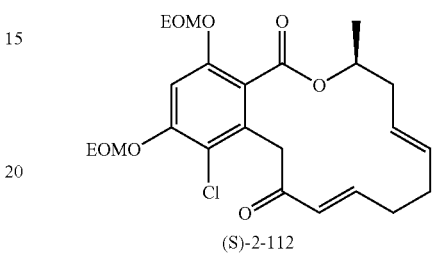

(S)-2-112

Compound (S)-2-112: $^1$H NMR (400 MHz, CDCl$_3$, 25° C.): δ=7.10 (s, 1H), 6.75-6.71 (m, 1H), 5.88 (d, J=15.8 Hz, 1H), 5.32 (s, 2H), 5.27-5.20 (m, 2H), 5.25 (s, 2H), 5.08-5.04 (m, 1H), 4.01 (d, J=17.0 Hz, 1H), 3.82-3.73 (m, 5H), 2.36-2.32 (m, 2H), 2.26-2.20 (m, 3H), 2.12-2.05 (m, 2H), 1.38 (d, J=5.8 Hz, 3H), 1.25 (t, J=7.0 Hz, 3H), 1.24 (t, J=7.0 Hz, 3H); $^{13}$C NMR (100 MHz, CDCl$_3$, 25° C.): δ=195.5, 166.7, 154.6, 153.8, 147.1, 132.8, 131.6, 128.6, 127.5, 120.7, 117.8, 103.0, 94.0, 93.7, 72.0, 64.8, 64.6, 44.7, 39.1, 30.8, 19.4, 15.0, 2C missing; HRMS (ESI-TOF): m/z: calculated for C$_{24}$H$_{31}$O$_7$ClNa: 489.1551, found 489.1651 [M+Na$^+$]. (+)-(2S): [α]$^{25}_D$=+25.0 (c 1.00, CHCl$_3$).

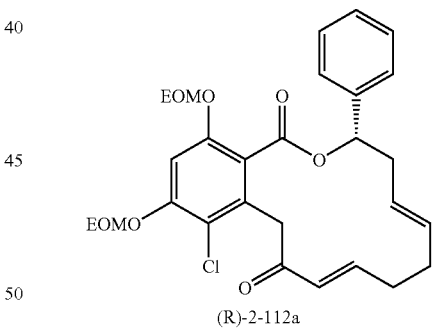

(R)-2-112a

Compound (R)-2-112a: $^1$H NMR (400 MHz, CDCl$_3$, 25° C.): δ=7.49-7.47 (m, 2H), 7.40-7.29 (m, 3H), 7.10 (s, 1H), 6.84-6.77 (m, 1H), 5.98 (d, J=15.2 Hz, 1H), 5.78 (d, J=8.8 Hz, 1H), 5.44-5.30 (m, 4H), 5.15 (d, J=7.0 Hz, 1H), 5.05 (d, J=6.8 Hz, 1H), 4.07 (d, J=17.0 Hz, 1H), 3.90 (d, J=17.0 Hz, 1H), 3.80 (d, J=7.0 Hz, 2H), 3.60-3.51 (m, 2H), 2.68-2.62 (m, 1H), 2.50-2.47 (m, 1H), 2.38-2.29 (m, 2H), 2.14-2.02 (m, 2H), 1.25 (t, J=7.0 Hz, 3H), 1.17 (t, J=7.0 Hz, 3H); $^{13}$C NMR (100 MHz, CDCl$_3$, 25° C.): δ=195.7, 166.7, 154.8, 154.2, 147.3, 140.7, 133.3, 132.1, 128.5, 128.3 (×2), 128.2, 127.9, 127.7, 126.7 (×2), 120.1, 118.1, 102.9, 93.9, 93.4, 77.4, 64.8, 64.4, 44.5, 40.5, 30.7, 15.0, 14.9; HRMS (ESI-TOF): m/z: calculated for C$_{29}$H$_{33}$O$_7$ClNa: 551.1680, found 551.1807 [M+Na$^+$]. [α]$^{25}_D$=−40.4 (c 0.79, CHCl$_3$).

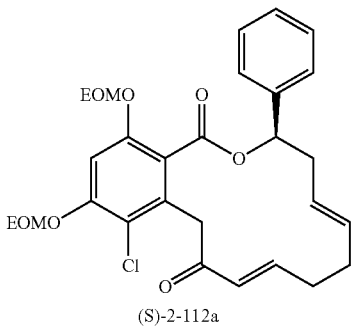

(S)-2-112a

Compound (S)-2-112a: $^1$H NMR (400 MHz, CDCl$_3$, 25° C.): δ=7.53-7.51 (m, 2H), 7.44-7.33 (m, 3H), 7.14 (s, 1H), 6.88-6.81 (m, 1H), 6.02 (d, J=15.2 Hz, 1H), 5.78 (dd, J=10.5, 1.8 Hz, 1H), 5.46-5.33 (m, 4H), 5.19 (d, J=7.0 Hz, 1H), 5.09 (d, J=7.6 Hz, 1H), 4.10 (d, J=17.0 Hz, 1H), 3.94 (d, J=17.5 Hz, 1H), 3.83 (d, J=7.0 Hz, 2H), 3.64-3.55 (m, 2H), 2.70-2.64 (m, 1H), 2.54-2.50 (m, 1H), 2.37-2.33 (m, 2H), 2.15-2.08 (m, 2H), 1.29 (t, J=7.3 Hz, 3H), 1.21 (t, J=7.0 Hz, 3H); $^{13}$C NMR (100 MHz, CDCl$_3$, 25° C.): δ=195.7, 166.7, 154.8, 154.2, 147.3, 140.7, 133.2, 132.1, 128.5, 128.2, 127.9, 127.7, 126.7, 120.1, 118.0, 102.8, 93.9, 93.5, 77.4, 64.8, 64.4, 44.5, 40.5, 30.7, 15.0, 14.9, (one carbon is not detected); HRMS (ESI-TOF): m/z: calculated for C$_{29}$H$_{33}$O$_7$ClNa: 551.1680, found 551.1704 [M+Na$^+$]. [α]$^{25}_D$=+48.8 (c 1.00, CHCl$_3$).

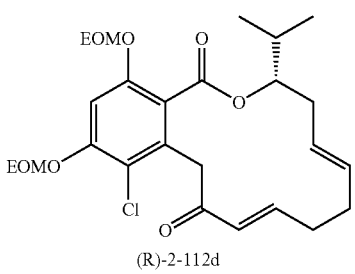

(R)-2-112d

Compound (R)-2-112d: $^1$H NMR (400 MHz, CDCl$_3$, 25° C.): δ=7.14 (s, 1H), 6.72-6.66 (m, 1H), 5.88 (d, J=15.2 Hz, 1H), 5.33-5.17 (m, 6H), 4.92-4.88 (m, 1H), 4.21 (d, J=17.0 Hz, 1H), 3.92 (d, J=17.0 Hz, 1H), 3.79-3.67 (m, 4H), 2.33-2.17 (m, 5H), 2.07-1.96 (m, 2H), 1.23 (t, J=7.0 Hz, 3H), 1.21 (t, J=7.0 Hz, 3H), 1.00 (d, J=5.8 Hz, 6H); $^{13}$C NMR (100 MHz, CDCl$_3$, 25° C.): δ=195.7, 167.1, 154.7, 154.4, 147.4, 133.7, 131.2, 128.8, 128.4, 119.7, 118.0, 102.7, 93.9, 93.5, 80.0, 64.8, 64.5, 44.1, 32.3, 31.2, 30.7, 30.6, 18.3, 17.2, 15.0, 14.9; HRMS (ESI-TOF): m/z: calculated for C$_{26}$H$_{35}$O$_7$ClNa: 517.1964, found 517.1844 [M+Na$^+$]. [α]$^{25}_D$=+21.3 (c 1.00, CHCl$_3$).

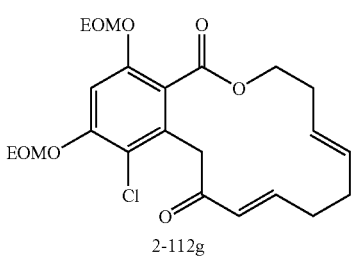

2-112g

Compound 2-112g: $^1$H NMR (400 MHz, CDCl$_3$, 25° C.): δ=7.12 (s, 1H), 6.76-6.70 (m, 1H), 5.87 (d, J=15.0 Hz, 1H), 5.33 (s, 2H), 5.26 (s, 2H), 5.24-5.16 (m, 2H), 4.25 (t, J=5.1 Hz, 2H), 3.82-3.73 (m, 6H), 2.40-2.36 (m, 2H), 2.16-2.13 (m, 4H), 1.27-1.23 (m, 6H); $^{13}$C NMR (100 MHz, CDCl$_3$, 25° C.): δ=195.2, 167.2, 154.6, 153.4, 146.8, 132.3, 131.3, 128.9, 128.5, 121.0, 117.8, 103.0, 94.0, 93.7, 64.8, 64.7, 64.6, 45.4, 31.9, 31.0, 30.7, 15.0, 15.0; HRMS (ESI-TOF): m/z: calculated for C$_{23}$H$_{30}$O$_7$Cl: 453.1675, found 453.1672 [M+H$^+$].

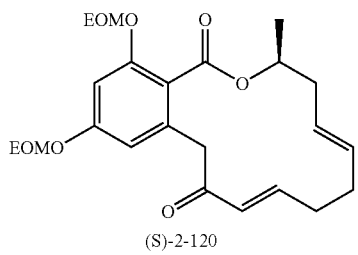

(S)-2-120

Compound (S)-2-120: $^1$H NMR (400 MHz, CDCl$_3$, 25° C.): δ=6.81-6.72 (m, 1H), 6.74 (d, J=1.8 Hz, 1H), 6.56 (d, J=1.8 Hz, 1H), 5.98 (d, J=15.8 Hz, 1H), 5.38-5.33 (m, 2H), 5.22-5.13 (m, 5H), 4.06 (d, J=14.6 Hz, 1H), 3.75-3.65 (m, 4H), 3.46 (d, J=14.6 Hz, 1H), 2.37-2.22 (m, 4H), 2.18-2.02 (m, 2H), 1.39 (d, J=5.8 Hz, 3H), 1.22 (t, J=7.0 Hz, 3H), 1.18 (t, J=7.0 Hz, 3H); $^{13}$C NMR (100 MHz, CDCl$_3$, 25° C.): δ=197.4, 167.7, 159.0, 156.1, 148.9, 135.0, 131.7, 129.8, 128.5, 118.5, 109.7, 102.2, 93.4, 93.0, 71.5, 64.5, 64.4, 44.3, 39.5, 30.9, 30.6, 20.2, 15.0 (×2); HRMS (ESI-TOF): m/z: calculated for C$_{24}$H$_{32}$O$_7$Na: 455.2040, found 455.1901 [M+Na$^+$]. (+)-(2S): [α]$^{25}_D$=+59.5 (c 1.00, CHCl$_3$).

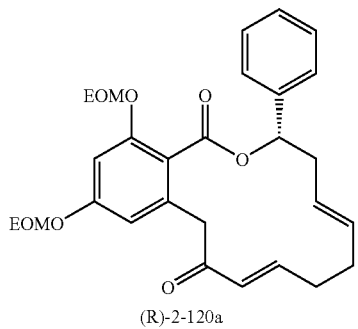

(R)-2-120a

Compound (R)-2-120a: $^1$H NMR (400 MHz, CDCl$_3$, 25° C.): δ=7.56-7.54 (m, 2H), 7.41-7.29 (m, 3H), 6.89-6.82 (m, 1H), 6.78 (d, J=2.3 Hz, 1H), 6.61 (d, J=1.8 Hz, 1H), 6.06 (d, J=16.4 Hz, 1H), 5.98 (dd, J=11.7, 2.4 Hz, 1H), 5.53-5.51 (m, 2H), 5.20 (d, J=7.0 Hz, 1H), 5.17 (d, J=6.4 Hz, 1H), 5.07 (d, J=7.0 Hz, 1H), 4.96 (d, J=7.0 Hz, 1H), 4.20 (d, J=14.6 Hz, 1H), 3.73-3.68 (m, 2H), 3.54-3.45 (m, 3H), 2.71-2.66 (m, 1H), 2.55-2.51 (m, 1H), 2.38-2.32 (m, 2H), 2.23-2.06 (m, 2H), 1.22 (t, J=7.0 Hz, 3H), 1.14 (t, J=7.0 Hz, 3H); $^{13}$C NMR (100 MHz, CDCl$_3$, 25° C.): δ=197.6, 167.4, 159.3, 156.6, 149.0, 140.8, 135.6, 132.2, 129.9, 128.5, 128.2 (×2), 127.9, 126.9 (×2), 117.9, 109.7, 102.3, 93.2, 93.0, 76.6, 64.4, 64.3, 44.4, 40.5, 31.0, 30.6, 15.0, 14.9; HRMS (ESI-TOF): m/z: calculated for C$_{29}$H$_{34}$O$_7$Na: 517.2197, found 517.2062 [M+Na$^+$]. [α]$^{25}_D$=−108.3 (c 1.00, CHCl$_3$).

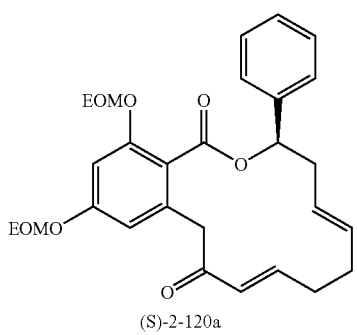

(S)-2-120a

Compound (S)-2-120a: $^1$H NMR (400 MHz, CDCl$_3$, 25° C.): δ=7.56-7.54 (m, 2H), 7.41-7.29 (m, 3H), 6.90-6.82 (m, 1H), 6.78 (d, J=2.4 Hz, 1H), 6.61 (d, J=1.8 Hz, 1H), 6.07 (d, J=16.4 Hz, 1H), 5.98 (dd, J=11.4, 2.0 Hz, 1H), 5.53-5.51 (m, 2H), 5.20 (d, J=7.0 Hz, 1H), 5.18 (d, J=7.0 Hz, 1H), 5.07 (d, J=7.0 Hz, 1H), 4.97 (d, J=7.0 Hz, 1H), 4.20 (d, J=14.6 Hz, 1H), 3.74-3.69 (m, 2H), 3.55-3.46 (m, 3H), 2.71-2.66 (m, 1H), 2.55-2.52 (m, 1H), 2.38-2.33 (m, 2H), 2.23-2.09 (m, 2H), 1.22 (t, J=7.0 Hz, 3H), 1.15 (t, J=7.0 Hz, 3H); $^{13}$C NMR (100 MHz, CDCl$_3$, 25° C.): δ=197.6, 167.5, 159.3, 156.6, 149.0, 140.8, 135.6, 132.2, 129.9, 128.5, 128.2 (×2), 127.9, 126.9 (×2), 117.9, 110.0, 102.3, 93.2, 93.0, 76.6, 64.4, 64.3, 44.4, 40.5, 31.0, 30.6, 15.0, 14.9; HRMS (ESI-TOF): m/z: calculated for C$_{29}$H$_{34}$O$_7$Na: 517.2197, found 517.2049 [M+Na$^+$]. [α]$^{25}_D$=+81.6 (c 1.00, CHCl$_3$).

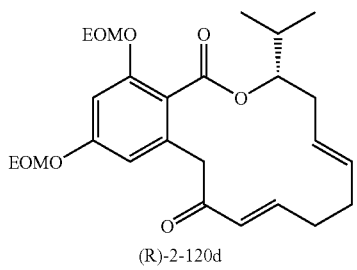

(R)-2-120d

Compound (R)-2-120d: $^1$H NMR (400 MHz, CDCl$_3$, 25° C.): δ=6.83 (d, J=1.7 Hz, 1H), 6.79-6.72 (m, 1H), 6.61 (d, J=1.2 Hz, 1H), 6.00 (d, J=16.4 Hz, 1H), 5.38-5.36 (m, 2H), 5.26-5.09 (m, 5H), 4.30 (d, J=14.6 Hz, 1H), 3.74-3.67 (m, 4H), 3.46 (d, J=14.6 Hz, 1H), 2.33-2.26 (m, 4H), 2.18-2.14 (m, 2H), 2.06-2.01 (m, 1H), 1.23 (t, J=7.0 Hz, 3H), 1.21 (t, J=7.0 Hz, 3H), 1.06 (d, J=6.6 Hz, 3H), 1.05 (d, J=7.0 Hz, 3H); $^{13}$C NMR (100 MHz, CDCl$_3$, 25° C.): δ=197.9, 167.6, 159.2, 156.9, 149.2, 136.4, 131.5, 129.9, 129.2, 117.4, 109.8, 102.0, 93.3, 93.0, 78.9, 64.4 (×2), 44.2, 33.0, 32.0, 31.0, 30.4, 18.3, 17.2, 15.0 (×2); HRMS (ESI-TOF): m/z: calculated for C$_{26}$H$_{36}$O$_7$Na: 483.2353, found 483.2215 [M+Na$^+$]. [α]$^{25}_D$=+52.8 (c 1.00, CHCl$_3$).

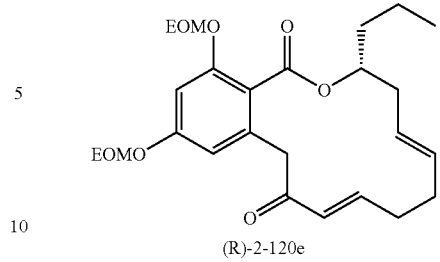

(R)-2-120e

Compound (R)-2-120e: $^1$H NMR (400 MHz, CDCl$_3$, 25° C.): δ=6.77 (d, J=1.8 Hz, 1H), 6.77-6.70 (m, 1H), 6.57 (d, J=1.7 Hz, 1H), 5.97 (d, J=16.4 Hz, 1H), 5.37-5.32 (m, 2H), 5.21-5.14 (m, 5H), 4.17 (d, J=14.6 Hz, 1H), 3.73-3.65 (m, 4H), 3.45 (d, J=14.6 Hz, 1H), 2.39-2.20 (m, 4H), 2.17-2.00 (m, 2H), 1.78-1.72 (m, 1H), 1.69-1.60 (m, 1H), 1.54-1.44 (m, 2H), 1.22 (t, J=7.0 Hz, 3H), 1.18 (t, J=7.0 Hz, 3H), 0.97 (d, J=7.3 Hz, 3H); $^{13}$C NMR (100 MHz, CDCl$_3$, 25° C.): δ=197.7, 167.6, 159.1, 156.6, 149.0, 135.8, 131.5, 129.9, 128.7, 117.9, 109.8, 102.1, 93.3, 93.0, 74.5, 64.4, 64.3, 44.2, 37.3, 37.0, 31.0, 30.5, 18.2, 15.0, 14.9, 14.2. [α]$^{25}_D$=−1.3 (c 1.00, CHCl$_3$).

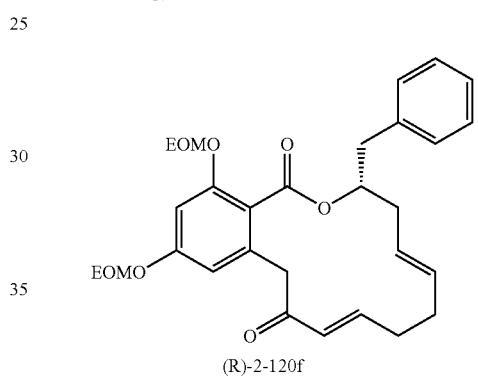

(R)-2-120f

Compound (R)-2-120f: $^1$H NMR (400 MHz, CDCl$_3$, 25° C.): δ=7.39-7.33 (m, 4H), 7.31-7.27 (m, 1H), 6.82 (s, 1H), 6.82-6.75 (m, 1H), 6.63 (s, 1H), 6.02 (d, J=16.4 Hz, 1H), 5.35-5.29 (m, 2H), 5.27-5.20 (m, 5H), 4.16 (d, J=14.6 Hz, 1H), 3.79-3.70 (m, 4H), 3.52 (d, J=14.6 Hz, 1H), 3.37 (dd, J=13.4, 4.1 Hz, 1H), 2.78 (dd, J=13.5, 9.4 Hz, 1H), 2.37-2.12 (m, 5H), 2.06-2.02 (m, 1H), 1.26 (t, J=7.0 Hz, 3H), 1.24 (t, J=7.0 Hz, 3H); $^{13}$C NMR (100 MHz, CDCl$_3$, 25° C.): δ=197.6, 167.8, 159.2, 156.5, 149.0, 137.3, 135.5, 131.8, 129.9, 129.5 (×2), 128.6 (×2), 128.4, 126.7, 118.1, 109.9, 102.3, 93.5, 93.1, 75.8, 64.6, 64.4, 44.4, 41.0, 36.2, 31.0, 30.6, 15.0 (×2); HRMS (ESI-TOF): m/z: calculated for C$_{30}$H$_{36}$O$_7$Na: 531.2359, found 531.2350 [M+Na$^+$]. [α]$^{25}_D$=−24.1 (c 0.33, CHCl$_3$).

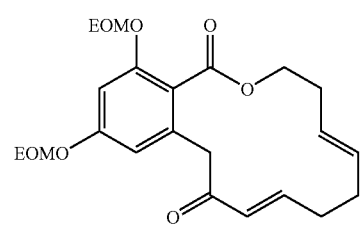

2-120g

Compound 2-120g: ¹H NMR (400 MHz, CDCl₃, 25° C.): δ=6.85-6.78 (m+s, 2H), 6.56 (d, J=2.1 Hz, 1H), 6.00 (d, J=16.1 Hz, 1H), 5.38-5.34 (m, 2H), 5.23 (s, 2H), 5.19 (s, 2H), 4.33 (t, J=5.4 Hz, 2H), 3.75-3.70 (m, 6H), 2.45-2.41 (m, 2H), 2.19 (bs, 4H), 1.27-1.20 (m, 6H); ¹³C NMR (100 MHz, CDCl₃, 25° C.): δ=197.2, 168.1, 159.1, 155.8, 148.6, 134.5, 131.7, 129.8, 129.1, 118.9, 109.9, 102.4, 93.6, 93.1, 64.5, 64.5, 64.4, 45.4, 31.9, 31.1, 30.8, 15.0, 15.0; HRMS (ESI-TOF): m/z: calculated for C₂₃H₃₀O₇Na: 441.1884, found 441.1888 [M+Na⁺].

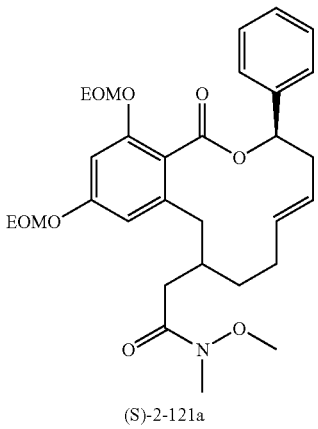

(S)-2-121a

Compound (S)-2-121a: Mixture of four diastereoisomers; ¹H NMR (400 MHz, CDCl₃, 25° C.): δ=7.51-7.42 (m, 2H), 7.38-7.29 (m, 3H), 6.73-6.70 (m, 1H), 6.60-6.49 (m, 1H), 6.45-6.31 (m, 1H), 5.73-5.42 (m, 2H), 5.25-5.01 (m, 4H), 3.76-3.69 (m, 2H), 3.62-3.34 (m, 6H), 3.20-3.09 (m, 3H), 2.66-2.50 (m, 2H), 2.22-2.12 (m, 4H), 1.72-1.66 (m, 2H), 1.31-1.19 (m, 5H), 1.10-1.04 (m, 3H); HRMS (ESI-TOF): m/z: calculated for C₃₁H₄₁O₈NNa: 578.2724, found 578.2720 [M+Na⁺].

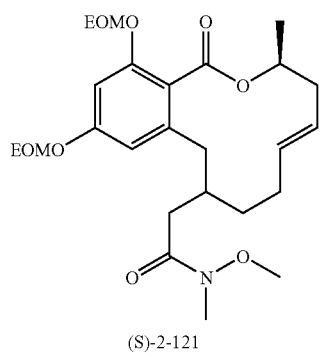

(S)-2-121

Compound (S)-2-121: Mixture of four diastereoisomers; ¹H NMR (400 MHz, CDCl₃, 25° C.): δ=6.77-6.72 (m, 1H), 6.57-6.47 (m, 1H), 5.62-5.35 (m, 3H), 5.24-5.16 (m, 4H), 3.77-3.70 (m, 4H), 3.62-3.60 (m, 1.5H), 3.53-3.49 (m, 1.5H), 3.17-3.11 (m, 3H), 3.04-2.97 (m, 1H), 2.57-2.44 (m, 2H), 2.36-1.99 (m, 6H), 1.37-1.33 (m, 3H), 1.28-1.21 (m, 8H); HRMS (ESI-TOF): m/z: calculated for C₂₆H₃₉O₈NNa: 516.2568, found 516.2596 [M+Na⁺].

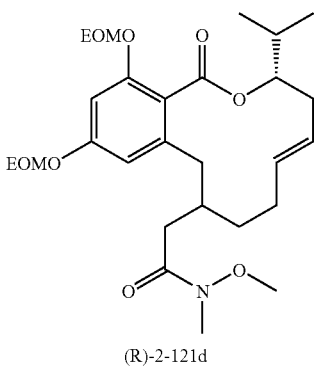

(R)-2-121d

Compound (R)-2-121d: Mixture of four diastereoisomers; ¹H NMR (400 MHz, CDCl₃, 25° C.): δ=6.77 (s, 1H), 6.52 (s, 0.5H), 6.46 (s, 0.5H), 5.59-5.37 (m, 2H), 5.21-5.18 (m, 4H), 5.09-4.92 (m, 1H), 3.75-3.70 (m, 4H), 3.53-3.48 (m, 3H), 3.38-3.34 (m, 1H), 3.19-3.10 (m, 3H), 2.65-2.47 (m, 3H), 2.29-2.04 (m, 6H), 1.89-1.72 (m, 2H), 1.31-1.20 (m, 6H), 1.06-0.96 (m, 6H); HRMS (ESI-TOF): m/z: calculated for C₂₈H₄₃O₈NNa: 544.2881, found 544.2907 [M+Na⁺].

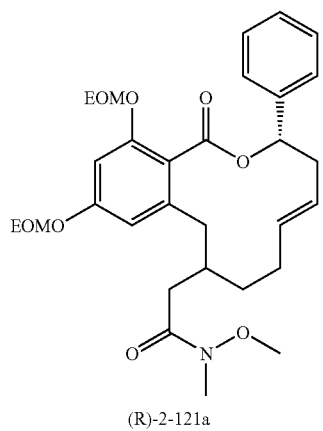

(R)-2-121a

Compound (R)-2-121a: Mixture of four diastereoisomers; ¹H NMR (400 MHz, CDCl₃, 25° C.): δ=7.51-7.42 (m, 2H), 7.38-7.31 (m, 3H), 6.73-6.70 (m, 1H), 6.60-6.49 (m, 1H), 6.45-6.31 (m, 1H), 5.73-5.39 (m, 2H), 5.23-5.00 (m, 4H), 3.75-3.69 (m, 2H), 3.56-3.34 (m, 6H), 3.19-3.09 (m, 3H), 2.66-2.08 (m, 8H), 1.31-1.19 (m, 5H), 1.10-1.04 (m, 3H); HRMS (ESI-TOF): m/z: calculated for C₃₁H₄₁O₈NNa: 578.2724, found 578.2715 [M+Na⁺].

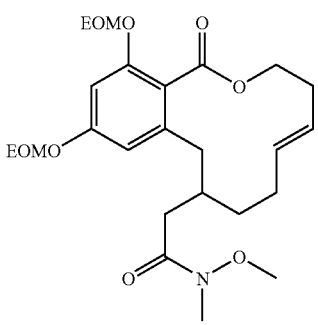

2-121g

Compound 2-121g: Mixture of two diastereoisomers; ¹H NMR (400 MHz, CDCl₃, 25° C.): δ=6.74-6.72 (m, 1H), 6.54

(d, J=1.8 Hz, 0.6H), 6.50 (d, J=1.7 Hz, 0.4H), 5.52-5.41 (m, 2H), 5.21 (s, 2H), 5.19 (s, 2H), 4.69-4.65 (m, 1H), 4.58-4.47 (m, 1H), 3.74-3.68 (m, 4H), 3.55 (s, 3H), 3.13 (s, 3H), 2.97-2.94 (m, 1H), 2.52-2.40 (m, 2H), 2.26-1.98 (m, 6H), 1.72-1.58 (m, 2H), 1.24-1.20 (m, 6H); HRMS (ESI-TOF): m/z: calculated for $C_{25}H_{38}O_8N$: 480.2567, found 480.2592 [M+H$^+$].

General procedure for the EOM deprotection to generate compounds deprotected-2-121a-g, 2-85a-g and 2-103a-g: PS-TsOH (10.0 equiv., 3.2 mmol.g$^{-1}$) was added to a solution of the corresponding compound 2-121a-g or 2-112a-g or 2-120a-g (1.0 equiv.) in MeOH (0.03 M) and the resulting suspension was shaken at 40° C. for 1 to 4 h. After this time, the reaction mixture was filtered and the methanolic solution concentrated under reduced pressure. Purification by flash chromatography (silica gel, 0-33% EtOAc/cyclohexane gradient) afforded the corresponding compound deprotected-2-121a-g or 2-85a-g or 2-103a-g (>90%).

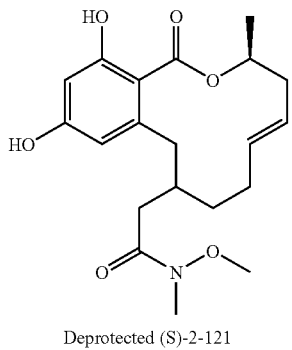

Deprotected (S)-2-121

Deprotected compound (S)-2-121: Mixture of four diastereoisomers; $^1$H NMR (400 MHz, CDCl$_3$, 25° C.): δ=12.90 (s, 0.5H), 12.83 (s, 0.5H), 12.12 (s, 0.5H), 12.02 (s, 0.5H), 6.92 (s, 0.5H), 6.84 (s, 0.5H), 6.83 (s, 1H), 6.79 (s, 0.5H), 6.60 (s, 1H), 6.54 (s, 0.5H), 5.60-5.29 (m, 4H), 5.17-4.99 (m, 2H), 4.14-3.99 (m, 2H), 2.98-2.72 (m, 12H), 2.60-1.92 (m, 16H), 1.31 (d, J=6.4 Hz, 1.5H), 1.22 (d, J=8.7 Hz, 1.5H), 1.13-1.02 (m, 7H); HRMS (ESI-TOF): m/z: calculated for $C_{20}H_{27}O_6NNa$: 400.1851, found 400.1731 [M+Na$^+$].

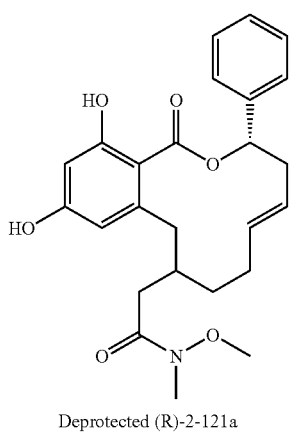

Deprotected (R)-2-121a

Deprotected compound (R)-2-121a: Mixture of four diastereoisomers; $^1$H NMR (400 MHz, CDCl$_3$, 25° C.): δ=11.90 (s, 0.25H), 11.08 (s, 0.5H), 10.98 (s, 0.25H), 7.38-7.29 (m, 5H), 6.39 (s, 0.25H), 6.33 (s, 0.25H), 6.29 (s, 1.25H), 6.26 (s, 0.25H), 6.05-5.95 (m, 1H), 5.70-5.52 (m, 2H), 4.18-4.03 (m, 1H), 3.51-3.49 (m, 3H), 3.16-3.14 (m, 3H), 2.75-2.62 (m, 2H), 2.36-2.29 (m, 2H), 2.12-1.96 (m, 4H), 1.81-1.73 (m, 2H), para-phenol not detected; HRMS (ESI-TOF): m/z: calculated for $C_{25}H_{30}O_6N$, 440.2068. found 440.2103 [M+H$^+$].

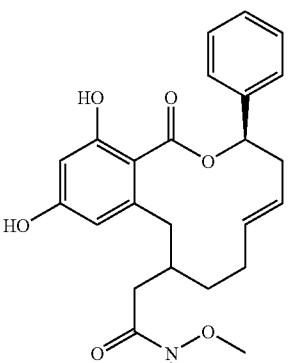

Deprotected (S)-2-121a

Deprotected compound (S)-2-121a: Mixture of four diastereoisomers; $^1$H NMR (400 MHz, CDCl$_3$, 25° C.): δ=11.90 (s, 0.25H), 11.08 (s, 0.5H), 10.98 (s, 0.25H), 7.38-7.31 (m, 5H), 6.38 (s, 0.25H), 6.33 (s, 0.25H), 6.29 (s, 1.25H), 6.26 (s, 0.25H), 6.05-5.95 (m, 1H), 5.71-5.54 (m, 2H), 4.13-4.04 (m, 1H), 3.53-3.50 (m, 3H), 3.19-3.14 (m, 3H), 2.78-2.63 (m, 2H), 2.33-2.29 (m, 2H), 2.16-2.04 (m, 4H), 1.81-1.68 (m, 2H), para-phenol not detected; HRMS (ESI-TOF): m/z: calculated for $C_{25}H_{29}O_6NNa$: 462.1887, found 462.2080 [M+Na$^+$].

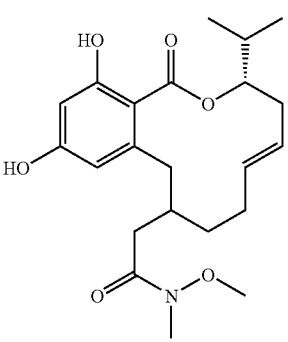

Deprotected (R)-2-121d

Deprotected compound (R)-2-121d: Mixture of four diastereoisomers; $^1$H NMR (400 MHz, CDCl$_3$, 25° C.): δ=11.54 (s, 1H), 6.33 (d, J=2.3 Hz, 1H), 6.25 (s, 1H), 5.53-5.51 (m, 1H), 5.44-5.41 (m, 1H), 5.11-5.08 (m, 1H), 4.01 (d, J=11.7 Hz, 2H), 3.45 (s, 3H), 3.11 (s, 3H), 2.83-2.73 (m, 1H), 2.68-2.59 (m, 1H), 2.27-2.20 (m, 1H), 2.10-1.87 (m, 6H), 1.82-1.72 (m, 1H), 1.01-0.94 (m, 6H), para-phenol not detected; HRMS (ESI-TOF): m/z: calculated for $C_{22}H_{31}O_6NNa$: 428.2044, found 428.2109 [M+Na$^+$].

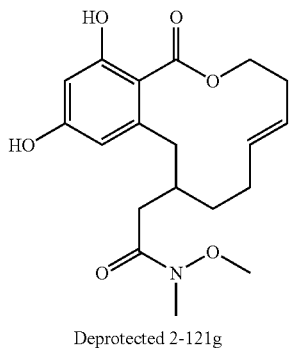

Deprotected 2-121g

Deprotected compound 2-121g: Mixture of two diastereoisomers; $^1$H NMR (400 MHz, CDCl$_3$, 25° C.): δ=12.33 (s, 0.5H), 11.85 (s, 0.5H), 6.34-6.32 (m, 1H), 6.25-6.22 (m, 1H), 5.62-5.45 (m, 2H), 4.54-4.37 (m, 1H), 4.29-4.21 (m, 1H), 3.53-3.49 (m, 3H), 3.15-3.12 (m, 3.5H), 2.95-2.86 (m, 0.5H), 2.67-2.52 (m, 2H), 2.39-1.96 (m, 8H), para-phenol not detected; HRMS (ESI-TOF): m/z: calculated for C$_{19}$H$_{26}$O$_6$N, 364.1755. found 364.1715 [M+H$^+$].

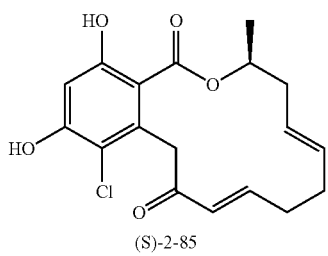

(S)-2-85

Compound (S)-2-85: $^1$H NMR (400 MHz, C$_6$D$_6$, 25° C.): δ=12.40 (s, 1H), 6.83 (s, 1H), 6.66-6.61 (m, 1H), 5.96 (bs, 1H), 5.80 (d, J=15.2 Hz, 1H), 5.16-5.12 (m, 1H), 4.99-4.91 (m, 1H), 4.75-4.68 (m, 1H), 4.26 (d, J=17.5 Hz, 1H), 4.13 (d, J=17.5 Hz, 1H), 2.52-2.45 (m, 1H), 1.86-1.79 (m, 3H), 1.75-1.67 (m, 1H), 1.54-1.49 (m, 1H), 0.97 (d, J=7.0 Hz, 3H); $^{13}$C NMR (100 MHz, C$_6$D$_6$, 25° C.): δ=193.8, 169.8, 164.3, 156.8, 146.0, 137.1, 131.9, 128.1, 126.2, 115.2, 107.6, 103.6, 72.4, 46.2, 36.3, 31.0, 30.8, 17.2. (−)-(2S): [α]$^{25}_D$=−21.9 (c 0.62, CHCl$_3$).

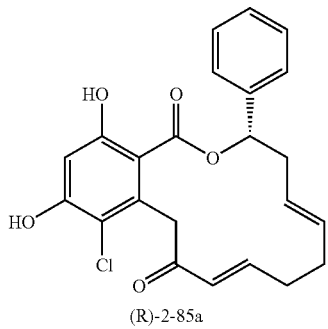

(R)-2-85a

Compound (R)-2-85a: $^1$H NMR (400 MHz, C$_6$D$_6$, 25° C.): δ=12.25 (bs, 1H), 7.32-7.29 (m, 2H), 7.19-7.15 (m, 3H), 6.80 (s, 1H), 6.81-6.75 (m, 1H), 6.29-6.26 (m, 1H), 5.92 (d, J=15.8 Hz, 1H), 5.80 (s, 1H), 5.05-4.99 (m, 1H), 4.81-4.75 (m, 1H), 4.56 (d, J=17.6 Hz, 1H), 4.12 (d, J=17.5 Hz, 1H), 2.73-2.66 (m, 1H), 2.39-2.35 (m, 1H), 1.86-1.76 (m, 2H), 1.64-1.49 (m, 2H); $^{13}$C NMR (100 MHz, C$_6$D$_6$, 25° C.): δ=194.2, 169.8, 164.4, 156.8, 145.5, 138.3, 137.0, 132.9, 129.9 (×2), 128.6, 127.3, 126.6 (×2), 125.8, 115.2, 107.5, 103.6, 77.6, 46.6, 38.3, 31.0, 30.6; HRMS (ESI-TOF): m/z: calculated for C$_{23}$H$_{21}$O$_5$ClNa: 435.0970, found 435.0914 [M+Na$^+$]. [α]$^{25}_D$=−12.0 (c 0.55, CHCl$_3$).

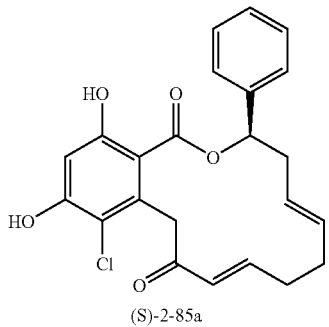

(S)-2-85a

Compound (S)-2-85a: $^1$H NMR (400 MHz, C$_6$D$_6$, 25° C.): δ=12.20 (bs, 1H), 7.15-7.09 (m, 3H), 6.75 (s, 1H), 6.77-6.71 (m, 1H), 6.25-6.22 (m, 1H), 5.88 (d, J=15.2 Hz, 1H), 5.72 (s, 1H), 5.00-4.95 (m, 1H), 4.77-4.73 (m, 1H), 4.52 (d, J=17.6 Hz, 1H), 4.08 (d, J=17.5 Hz, 1H), 2.68-2.62 (m, 1H), 2.35-2.31 (m, 1H), 1.81-1.78 (m, 2H), 1.56-1.49 (m, 2H), 2H masked by the solvent peak; $^{13}$C NMR (100 MHz, C$_6$D$_6$, 25° C.): δ=194.2, 169.8, 164.4, 156.8, 145.5, 138.3, 137.0, 132.2, 129.9 (×2), 128.5, 127.3, 126.5 (×2), 125.8, 115.2, 107.5, 103.6, 77.5, 46.6, 38.2, 31.0, 30.6; HRMS (ESI-TOF): m/z: calculated for C$_{23}$H$_{21}$O$_5$ClNa: 435.0970, found 435.0885 [M+Na$^+$]. [α]$^{25}_D$=+11.6 (c 0.51, CHCl$_3$).

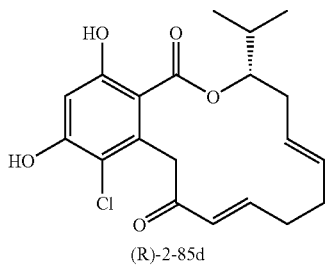

(R)-2-85d

Compound (R)-2-85d: $^1$H NMR (400 MHz, C$_6$D$_6$, 25° C.): δ=12.31 (s, 1H), 6.83 (s, 1H), 6.74-6.67 (m, 1H), 5.84 (bs, 1H), 5.82 (d, J=15.8 Hz, 1H), 5.03-4.95 (m, 1H), 4.88-4.86 (m, 1H), 4.76-4.70 (m, 1H), 4.40 (d, J=17.6 Hz, 1H), 4.15 (d, J=17.5 Hz, 1H), 2.40-2.34 (m, 1H), 2.22-2.18 (m, 1H), 1.87-1.65 (m, 4H), 1.53-1.48 (m, 1H), 0.92 (d, J=6.4 Hz, 3H), 0.66 (d, J=7.0 Hz, 3H); $^{13}$C NMR (100 MHz, C$_6$D$_6$, 25° C.): δ=193.7, 164.2, 156.8, 145.8, 137.2, 131.8, 129.3, 126.3, 115.3, 107.9, 103.6, 82.1, 46.4, 33.3, 30.9, 30.7, 28.8, 20.1, 18.5, 18.3; HRMS (ESI-TOF): m/z: calculated for C$_{20}$H$_{23}$ClO$_5$Na: 401.1126, found 401.1170 [M+Na$^+$]. [α]$^{25}_D$=−35.6 (c 0.52, CHCl$_3$).

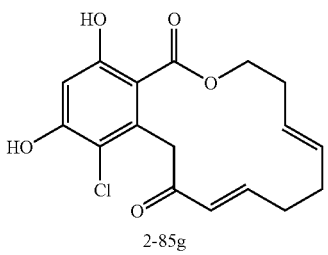

2-85g

Compound 2-85g: $^1$H NMR (400 MHz, CD$_3$OD, 25° C.): δ=6.74-6.68 (m, 1H), 6.48 (s, 1H), 5.86 (d, J=15.2 Hz, 1H), 5.31-5.25 (m, 2H), 4.39 (t, J=5.3 Hz, 2H), 4.27 (s, 2H), 2.43-2.40 (m, 2H), 2.25 (m, 4H), phenols not detected; $^{13}$C NMR (100 MHz, CD$_3$OD, 25° C.): δ=196.9, 170.1, 161.9, 158.1, 147.8, 135.9, 130.9, 130.2, 129.9, 115.2, 107.3, 102.4, 65.9, 46.2, 31.3, 30.9, 30.5; HRMS (ESI-TOF): m/z: calculated for C$_{17}$H$_{18}$O$_5$Cl: 337.0837, found 337.0797 [M+H$^+$].

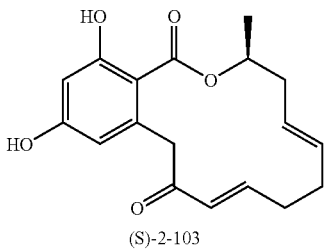

(S)-2-103

Compound (S)-2-103: $^1$H NMR (400 MHz, CD$_3$OD, 25° C.): δ=6.78-6.71 (m, 1H), 6.29 (d, J=2.4 Hz, 1H), 6.22 (d, J=2.0 Hz, 1H), 5.87 (d, J=15.5 Hz, 1H), 5.37-5.23 (m, 3H), 4.01 (d, J=17.2 Hz, 1H), 3.92 (d, J=17.0 Hz, 1H), 2.67-2.61 (m, 1H), 2.29-2.15 (m, 5H), 1.31 (d, J=6.4 Hz, 3H), phenols not detected; $^{13}$C NMR (100 MHz, CD$_3$OD, 25° C.): δ=198.5, 169.8, 164.2, 162.3, 148.4, 139.1, 131.6, 129.6, 127.3, 111.7, 101.7, 72.0, 47.7, 36.8, 30.8, 30.7, 17.4, (one quartenary carbon is not detected); HRMS (ESI-TOF): m/z: calculated for C$_{18}$H$_{20}$O$_5$Na: 339.1203, found 339.1141 [M+Na$^+$]. (−)-(2S): [α]$^{25}_D$=−45.1 (c 0.27, CHCl$_3$).

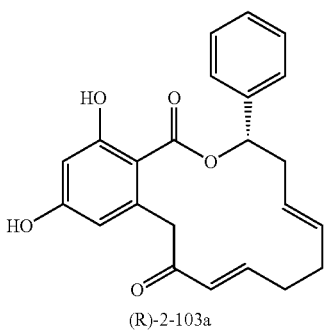

(R)-2-103a

Compound (R)-2-103a: $^1$H NMR (400 MHz, C$_6$D$_6$, 25° C.): δ=12.0 (bs, 1H), 7.32-7.29 (m, 3H), 7.19-7.15 (m, 2H), 6.86-6.79 (m, 1H), 6.51 (d, J=2.4 Hz, 1H), 6.27-6.25 (m, 1H), 6.11 (d, J=2.4 Hz, 1H), 6.02 (d, J=15.8 Hz, 1H), 5.49 (s, 1H), 5.17-5.10 (m, 1H), 4.97-4.90 (m, 1H), 4.40 (d, J=16.4 Hz, 1H), 3.97 (d, J=17.2 Hz, 1H), 2.83-2.76 (m, 1H), 2.45-2.38 (m, 1H), 1.89-1.78 (m, 2H), 1.67-1.58 (m, 2H); $^{13}$C NMR (100 MHz, C$_6$D$_6$, 25° C.): δ=196.5, 169.6, 166.1, 161.3, 146.0, 140.5, 138.8, 132.1, 130.0, 128.6 (×2), 127.3, 126.6 (×2), 126.3, 112.2, 105.9, 103.0, 77.1, 48.6, 38.4, 30.9, 30.3; HRMS (ESI-TOF): m/z: calculated for C$_{23}$H$_{22}$O$_5$Na: 401.1359, found 401.1271 [M+Na$^+$]. [α]$^{25}_D$=−10.3 (c 0.25, CHCl$_3$).

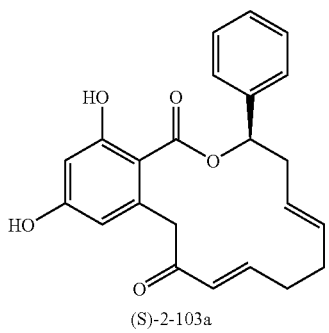

(S)-2-103a

Compound (S)-2-103a: $^1$H NMR (400 MHz, C$_6$D$_6$, 25° C.): δ=12.0 (bs, 1H), 7.27-7.21 (m, 3H), 7.17-7.13 (m, 2H), 6.87-6.79 (m, 1H), 6.55 (d, J=2.3 Hz, 1H), 6.29-6.26 (m, 1H), 6.16 (d, J=2.3 Hz, 1H), 6.03 (d, J=15.8 Hz, 1H), 5.74 (s, 1H), 5.18-5.12 (m, 1H), 4.98-4.91 (m, 1H), 4.41 (d, J=15.8 Hz, 1H), 3.99 (d, J=16.9 Hz, 1H), 2.84-2.77 (m, 1H), 2.46-2.43 (m, 1H), 1.85-1.79 (m, 2H), 1.70-1.58 (m, 2H); $^{13}$C NMR (100 MHz, C$_6$D$_6$, 25° C.): δ=196.9, 169.6, 166.2, 161.5, 146.3, 140.5, 138.9, 132.1, 130.0, 128.6 (×2), 127.3, 126.6 (×2), 126.3, 112.2, 105.8, 103.0, 77.1, 48.6, 38.4, 30.9, 30.4; HRMS (ESI-TOF): m/z: calculated for C$_{23}$H$_{22}$O$_5$Na: 401.1359, found 401.1264 [M+Na$^+$]. [α]$^{25}_D$=+11.9 (c 0.51, CHCl$_3$).

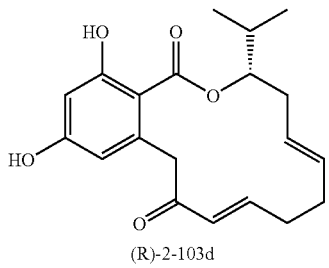

(R)-2-103d

Compound (R)-2-103d: $^1$H NMR (400 MHz, C$_6$D$_6$, 25° C.): δ=12.10 (s, 1H), 6.79 (dt, J=15.2, 7.6 Hz, 1H), 6.59 (d, J=2.4 Hz, 1H), 6.22 (d, J=2.3 Hz, 1H), 5.96 (d, J=15.8 Hz, 1H), 5.88 (bs, 1H), 5.13-5.05 (m, 1H), 4.92-4.85 (m, 2H), 4.27 (d, J=15.8 Hz, 1H), 4.03 (d, J=15.8 Hz, 1H), 2.50-2.44 (m, 1H), 2.24-2.20 (m, 1H), 1.96-1.71 (m, 4H), 1.63-1.56 (m, 1H), 0.91 (d, J=6.3 Hz, 3H), 0.71 (d, J=6.4 Hz, 3H); $^{13}$C NMR (100 MHz, C$_6$D$_6$, 25° C.): δ=196.5, 169.7, 166.0, 161.4, 146.8, 140.8, 131.7, 129.5, 126.9, 112.3, 106.0, 103.0, 81.3, 48.5, 33.7, 30.9, 30.4, 29.6, 19.7, 18.4; HRMS (ESI-TOF): m/z: calculated for C$_{20}$H$_{24}$O$_5$Na: 367.1516, found 367.1424 [M+Na$^+$]. [α]$^{25}_D$=−31.9 (c 0.50, CHCl$_3$).

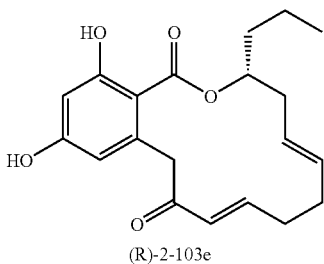

(R)-2-103e

Compound (R)-2-103e: $^1$H NMR (400 MHz, CDCl$_3$, 25° C.): δ=12.43 (s, 1H), 6.74 (d, J=1.7 Hz, 1H), 6.73-6.65 (m, 1H), 6.48 (d, J=1.7 Hz, 1H), 5.92 (d, J=15.8 Hz, 1H), 5.12-5.00 (m, 2H), 4.91-4.80 (m, 1H), 4.19 (d, J=17.0 Hz, 1H), 3.84 (d, J=16.4 Hz, 1H), 2.77 (m, 1H), 2.64-2.57 (m, 1H), 2.01-1.97 (m, 1H), 1.89-1.70 (m, 3H), 1.61-1.56 (m, 2H), 1.30-1.21 (m, 2H), 0.90 (t, J=6.7 Hz, 3H), para-phenol not detected; $^{13}$C NMR (100 MHz, CDCl$_3$, 25° C.): δ=197.5, 169.9, 165.6, 160.6, 147.5, 140.2, 131.9, 129.5, 127.0, 112.8, 106.1, 102.9, 76.2, 48.7, 35.7, 34.3, 31.1, 29.7, 19.4, 13.8; HRMS (ESI-TOF): m/z: calculated for C$_{20}$H$_{25}$O$_5$: 345.1697, found 345.1739 [M+H$^+$]. [α]$^{25}_D$=+21.6 (c 0.36, CHCl$_3$).

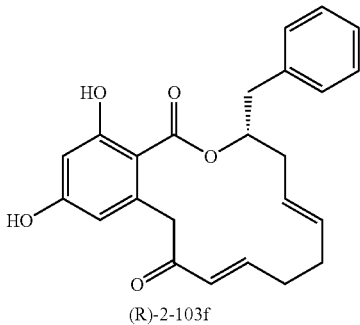

(R)-2-103f

Compound (R)-2-103f: $^1$H NMR (400 MHz, CDCl$_3$, 25° C.): δ=12.31 (s, 1H), 7.19-7.13 (m, 5H), 6.80-6.72 (m, 1H), 6.53 (d, J=1.8 Hz, 1H), 6.05 (s, 1H), 5.89 (d, J=15.8 Hz, 1H), 5.47-5.44 (m, 1H), 5.11-5.05 (m, 1H), 4.85-4.81 (m, 1H), 4.10 (d, J=17.0 Hz, 1H), 3.62 (d, J=17.0 Hz, 1H), 2.89-2.84 (m, 1H), 2.67-2.60 (m, 2H), 2.08-2.04 (m, 1H), 1.90-1.69 (m, 3H), 1.52-1.44 (m, 1H), para-phenol not detected; $^{13}$C NMR (100 MHz, CDCl$_3$, 25° C.): δ=197.7, 169.9, 165.7, 160.7, 147.4, 140.2, 137.2, 132.2, 129.5, 128.8 (×2), 128.7 (×3), 126.8, 112.4, 105.9, 102.9, 48.9, 38.5, 35.3, 31.1 (×2), 29.7; HRMS (ESI-TOF): m/z: calculated for C$_{24}$H$_{25}$O$_5$: 393.1697, found 393.1765 [M+H$^+$]. [α]$^{25}_D$=+25.4 (c 0.41, CHCl$_3$).

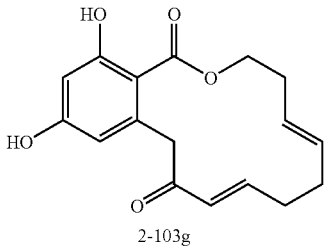

2-103g

Compound 2-103g: $^1$H NMR (400 MHz, CD$_3$OD, 25° C.): δ=6.75-6.69 (m, 1H), 6.29 (s, 1H), 6.29 (d, J=2.3 Hz, 1H), 5.90 (d, J=15.8 Hz, 1H), 5.30-5.28 (m, 2H), 4.39 (t, J=5.2 Hz, 2H), 4.02 (s, 2H), 2.45-2.41 (m, 2H), 2.28-2.24 (m, 4H), phenols not detected; $^{13}$C NMR (100 MHz, CD$_3$OD, 25° C.): δ=198.4, 170.6, 164.9, 162.5, 148.1, 139.2, 130.7, 130.6, 130.2, 112.2, 105.0, 101.6, 65.7, 47.7, 31.4, 30.9, 30.5; HRMS (ESI-TOF): m/z: calculated for C$_{17}$H$_{19}$O$_5$: 303.1227, found 303.1179 [M+H$^+$].

General procedure for the synthesis of compounds 2-141: BER-resin (Borohydride on Amberlite, 1.0 equiv., 2.5 mmol.g$^{-1}$) was added to a solution of corresponding compound 2-112a-g or 2-120a-g (1.0 equiv.) in MeOH (0.03 M) at 0° C. and the reaction was stirred for 12 h. The reaction mixture was then filtered and concentrated under reduced pressure. Purification by flash chromatography (silica gel, 0-20% EtOAc/cyclohexane gradient) afforded 2-141 (~60% yield) as a mixture of two diastereoisomers 1:1.

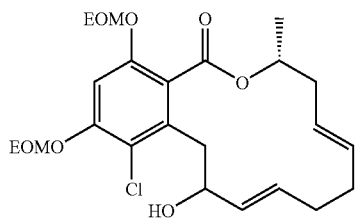

Selected example of compounds 2-141: $^1$H NMR (400 MHz, CDCl$_3$, 25° C.): δ=7.05 (s, 1H), 6.99 (s, 1H), 5.64-5.57 (m, 2H), 5.54-5.53 (m, 2H), 5.49-5.35 (m, 7H), 5.31-5.28 (m, 4H), 5.24-5.16 (m, 4H), 5.13-5.08 (m, 1H), 4.68 (m, 1H), 4.56 (m, 1H), 3.81-3.69 (m, 8H), 3.25 (dd, J=13.9, 8.0 Hz, 1H), 3.19 (dd, J=13.7, 4.8 Hz, 1H), 3.11 (dd, J=13.5, 10.1 Hz, 1H), 2.90 (dd, J=13.9, 5.1 Hz, 1H), 2.35 (m, 9H), 2.09-1.95 (m, 1H), 1.80-1.70 (m, 2H), 1.39 (d, J=2.9 Hz, 3H), 1.37 (d, J=3.2 Hz, 3H), 1.24 (2×q, J=6.9, 5.0 Hz, 12H); HRMS (ESI-TOF): m/z: calculated for C$_{24}$H$_{33}$ClO$_7$Na: 491.1807, found 491.1729 [M+Na$^+$].

General procedure for the synthesis of compounds 2-142: PS-TsOH (10.0 equiv., 3.2 mmol.g$^{-1}$) was added to a solution of the corresponding compound 2-141 (1.0 equiv.) in MeOH (0.02 M) and the suspension was shaken at 40° C. for 4 h. The reaction mixture was then filtered and the methanolic solution concentrated under reduced pressure. Purification by preparative TLC (silica gel, 25% EtOAc/cyclohexane) afforded 2-142 (~90% yield) as a mixture of two diastereoisomers 1:1.

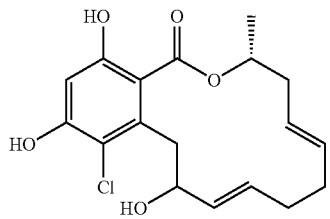

Selected example of compounds 2-142: $^1$H NMR (400 MHz, (CD$_3$)$_2$CO, 25° C.): δ=12.30 (s, 2H), 11.43 (s, 2H), 6.75 (s, 2H), 6.00 (bdd, J=6.4, 6.2 Hz, 1H), 5.97 (bdd, J=6.4, 6.2 Hz, 1H), 5.97 (bd, J=6.7 Hz, 1H), 5.77 (bd, J=6.7 Hz, 1H), 5.57-5.48 (m, 4H), 5.18-5.14 (m, 2H), 3.38-3.28 (m, 3H), 3.02 (dd, J=16.1, 10.5 Hz, 1H), 2.41-2.09 (m, 12H), 1.11 (d, J=6.2 Hz, 6H), alcohols not detected; HRMS (ESI-TOF): m/z: calculated for C$_{18}$H$_{21}$ClO$_5$Na: 375.0970, found 375.1029 [M+Na$^+$].

General procedure for the synthesis of compounds 2-143: Ac$_2$O (1.2 equiv.), morpholinomethyl polystyrene (1.2 equiv., 3.2 mmol.g$^{-1}$) and DMAP (0.05 equiv.) were added to a solution of the corresponding compound 2-141 (1.0 equiv.) in DMF (0.02 M) at 23° C. and the mixture was stirred for 30 min, followed by TLC until consumption of the starting material. The resin was then filtered and the organic phase was concentrated under reduced pressure. Purification by preparative TLC (silica gel, 20% EtOAc/cyclohexane) afforded corresponding compound 2-143 (~80% yield) as a mixture of two diastereoisomers 1:1.

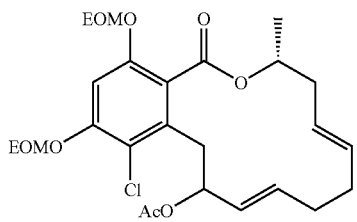

Selected example of compounds 2-143: $^1$H NMR (400 MHz, CDCl$_3$, 25° C.): δ=7.04 (s, 1H), 7.01 (s, 1H), 5.86 (dd, J=15.0, 6.9 Hz, 1H), 5.67 (dd, J=12.4, 6.2 Hz, 1H), 5.60-5.54 (m, 4H), 5.48 (dd, J=7.2, 7.2 Hz, 1H), 5.41-5.34 (m, 3H), 5.32-5.30 (m, 4H), 5.28-5.23 (m, 2H), 5.21 (dd, J=11.0, 6.7 Hz, 2H), 5.17 (dd, J=11.8, 6.9 Hz, 2H), 3.81-3.69 (m, 8H), 3.43 (dd, J=14.2, 7.5 Hz, 1H), 3.23-3.15 (m, 2H), 2.85 (dd, J=13.9, 5.4 Hz, 1H), 2.30-2.17 (m, 8H), 2.12 (s, 3H), 2.06 (s, 3H), 2.00-1.95 (m, 4H), 1.39 (2xd, J=5.6 Hz, 6H), 1.24 (m, 12H); HRMS (ESI-TOF): m/z: calculated for C$_{26}$H$_{35}$ClO$_8$Na: 533.1913, found 533.1864 [M+Na$^+$].

General procedure for the synthesis of compounds 2-144: PS-TsOH (10.0 equiv., 3.2 mmol.g$^{-1}$) was added to a solution of corresponding compound 2-143 (1.0 equiv.) in MeOH (0.02 M) and the suspension was shaken at 40° C. for 4 h. After this time, the reaction mixture was filtered and the methanolic solution concentrated under reduced pressure. Purification by preparative TLC (silica gel, 20% EtOAc/cyclohexane) afforded compound 2-144 (~60% yield).

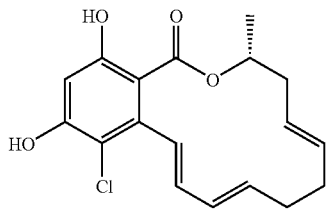

Selected example of compounds 2-144: Mixture of diastereoisomers 2:1; $^1$H NMR (400 MHz, CDCl$_3$, 25° C.): δ=12.60 (s, 1H), 12.12 (s, 0.5H), 6.93 (d, J=8.7 Hz, 0.5H), 6.66 (s, 1H), 6.64 (s, 0.5H), 6.62-6.60 (m, 1H), 6.10-6.05 (m, 3H), 5.47-5.33 (m, 6H), 2.60-2.53 (m, 1.5H), 2.26-2.02 (m, 7.5H), 1.44 (d, J=6.2 Hz, 1.5H), 1.43 (d, J=6.4 Hz, 3H), para-phenol not detected; HRMS (ESI-TOF): m/z: calculated for C$_{18}$H$_{19}$ClO$_4$Na: 357.0864, found 357.0898 [M+Na$^+$].

General procedure for the preparation of compounds 2-145: PS-TsOH (10.0 equiv.) was added to a solution of corresponding compound 2-85a-g (1.0 equiv.) in methanol (0.03 M) and the suspension was stirred for 15 h at 40° C. The reaction was then filtered and the resin washed several times with CH$_2$Cl$_2$. Concentration under reduced pressure followed by purification on preparative TLC (silica gel, 50% hexane/EtOAc) afforded desired compound 2-145 as a mixture of diastereoisomers 2:1.

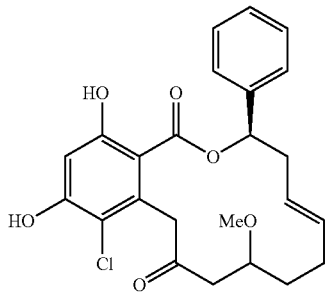

Selected example of compounds 2-145: $^1$H NMR (400 MHz, C$_6$D$_6$, 25° C.): δ=12.28 (s, 0.4H), 11.91 (s, 0.6H), 7.21-7.11 (m, 5H), 6.62 (s, 1H), 6.03-6.01 (m, 1H), 5.58 (bs, 1H), 5.38-5.33 (m, 1H), 5.27-5.20 (m, 1H), 4.76 (d, J=17.5 Hz, 0.6H), 4.02 (d, J=17.0 Hz, 0.4H), 4.18 (d, J=18.1 Hz, 0.6H), 4.09 (d, J=17.0 Hz, 0.4H), 3.87 (bs, 0.4H), 3.81 (bs, 0.6H), 3.15 (s, 1.8H), 3.12 (s, 1.2H), 2.83-2.78 (m, 1H), 2.45-2.30 (m, 2H), 2.18-2.16 (m, 1H), 2.02-1.97 (m, 2H), 1.79-1.72 (m, 2H); HRMS (ESI-TOF): m/z: calculated for C$_{24}$H$_{25}$O$_6$ClNa: 467.1232, found 467.1366 [M+Na$^+$].

General procedure for the synthesis of compounds 2-146: (Polystyrylmethyl)trimethyl-ammonium cyanoborohydride (2.0 equiv., 3.5 mmol.g$^{-1}$) was added to a solution of corresponding compound 2-85a-g or 2-103a-g (1.0 equiv.) in CH$_2$Cl$_2$/AcOH 10:1 (0.08 M) at 23° C. and the reaction was monitored by TLC until consumption of the starting material (4 h). The resin was then filtered and the organic phase was concentrated under reduced pressure. Purification by preparative TLC (silica gel, 30% EtOAc/cyclohexane) afforded compound 2-146 (50-60% yield).

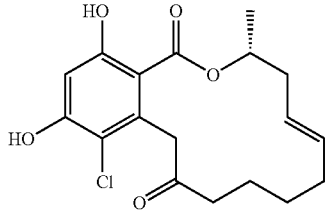

Selected example of compounds 2-146: $^1$H NMR (400 MHz, CDCl$_3$, 25° C.): δ=11.75 (s, 1H), 6.65 (s, 1H), 5.48 (m, 2H), 5.49 (ddt, J=6.1, 3.5, 2.9 Hz, 1H), 4.53 (d, J=17.5 Hz, 1H), 4.04 (d, J=17.7 Hz, 1H), 2.61-2.54 (m, 2H), 2.48-2.28 (m, 3H), 2.19-2.14 (m, 1H), 2.08-1.99 (m, 1H), 1.72-1.61 (m, 3H), 1.41 (d, J=6.4 Hz, 3H), para-phenol not detected; HRMS (ESI-TOF): m/z: calculated for C$_{18}$H$_{21}$ClO$_5$Na: 375.0970, found 375.1050 [M+Na$^+$].

General procedure for the synthesis of compounds 2-147: The corresponding alcohol R$^2$OH (2.0 equiv.), triphenylphosphine (2.0 equiv.) and PS-DEAD (2.0 equiv., 1.3 mmol.g$^{-1}$) were added to a solution of corresponding compound 2-85a-g or 2-103a-g (1.0 equiv.) in THF (0.05 M) in a sequential manner. The reaction mixture was shaken at room temperature for 8 h, and then the resin was filtered and the filtrates were directly purified by preparative TLC (silica gel, 10% EtOAc/cyclohexane) to afford a mixture of compound 2-147 along with the bis-alkylated product (78% yield).

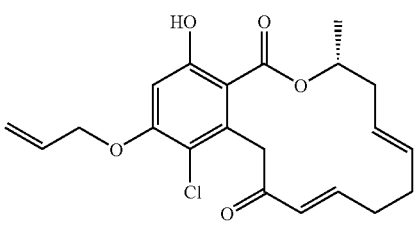

Selected example of compounds 2-147: Mixture with the corresponding bis-allylated compound 1:1; $^1$H NMR (400 MHz, CDCl$_3$, 25° C.): δ=11.83 (s, 1H), 6.82 (ddd, J=15.7, 8.2, 4.6 Hz, 1H), 6.72-6.65 (m, 1H), 6.46 (s, 1H), 6.41 (s, 1H), 6.09-5.98 (m, 3H), 5.82 (d, J=15.7 Hz, 1H), 5.46-5.16 (m, 8H), 4.57-4.54 (m, 3H), 4.51-4.49 (m, 3H), 4.19 (d, J=17.5 Hz, 1H), 4.11 (d, J=14.6 Hz, 1H), 3.78 (d, J=17.0 Hz, 1H), 3.51 (d, J=14.2 Hz, 1H), 2.76-2.69 (m, 1H), 2.38-2.05 (m, 11H), 1.42 (d, J=6.2 Hz, 3H), 1.35 (d, J=6.3 Hz, 3H); mono-allylated compound: HRMS (ESI-TOF): m/z: calculated for C$_{21}$H$_{23}$ClO$_5$Na: 413.1132, found 413.1103 [M+Na$^+$]; bis-allylated compound: HRMS (ESI-TOF): m/z: calculated for C$_{24}$H$_{27}$ClO$_5$Na: 453.1449, found 453.1422 [M+Na$^+$].

General procedure for the synthesis of compounds 2-148: TBD-methyl polystyrene (2.0 equiv., 2.9 mmol.g$^{-1}$) and the corresponding alkyl bromide or chloride (BrCH$_2$COO$^t$Bu, EOMCl, 0.9 equiv.) were added to a solution of the corresponding compound 2-85a-g or 2-103a-g (1.0 equiv.) in CH$_2$Cl$_2$ (0.05 M) at 23° C. and the mixture was shaken for 3 h. The resin was then filtered and the filtrates were concentrated under reduced pressure. Purification by preparative TLC (silica gel, 30% EtOAc/cyclohexane) afforded corresponding compound 2-148 (>90% yield).

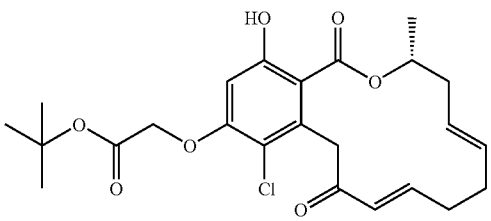

Selected examples of compounds 2-148: $^1$H NMR (400 MHz, CDCl$_3$, 25° C.): δ=11.84 (s, 1H), 6.69 (m, 1H), 6.41 (s, 1H), 5.76 (d, J=15.0 Hz, 1H), 5.43 (m, 1H), 5.26 (ddd, J=15.0, 9.1, 4.8 Hz, 1H), 5.18-5.11 (m, 1H), 4.65 (s, 2H), 4.33 (d, J=17.7 Hz, 1H), 4.16 (d, J=17.5 Hz, 1H), 2.65-2.58 (m, 1H), 2.37-2.34 (m, 2H), 2.25-2.21 (m, 1H), 2.12-2.01 (m, 2H), 1.53 (s, 9H), 1.34 (d, J=6.5 Hz, 3H); HRMS (ESI-TOF): m/z: calculated for C$_{24}$H$_{29}$ClO$_7$Na: 487.1494, found 487.1498 [M+Na$^+$].

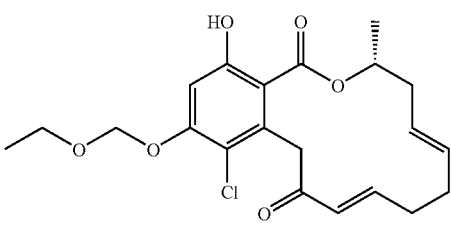

$^1$H NMR (400 MHz, C$_6$D$_6$, 25° C.): δ=11.76 (s, 1H), 6.86 (s, 1H), 6.70 (dt, J=14.9, 7.3 Hz, 1H), 5.77 (d, J=15.8 Hz, 1H), 5.46-5.42 (m, 1H), 5.37 (s, 2H), 5.30-5.19 (m, 2H), 4.34 (d, J=17.6 Hz, 1H), 4.16 (d, J=18.1 Hz, 1H), 3.80 (q, J=7.0 Hz, 2H), 2.66-2.59 (m, 1H), 2.37-2.34 (m, 2H), 2.26-2.21 (m, 1H), 2.13-2.06 (m, 2H), 1.34 (d, J=6.4 Hz, 3H), 1.27 (t, J=7.0 Hz, 3H); HRMS (ESI-TOF): m/z: calculated for C$_{21}$H$_{25}$O$_6$ClNa: 431.1237, found 431.1257 [M+Na$^+$].

General procedure for the synthesis of compounds 2-149: OsO$_4$ (0.1 equiv.) and NMO (1.0 equiv.) were added to a solution of compound 2-85a-g or 2-103a-g (1.0 equiv.) in acetone/H$_2$O 10:1 (0.05 M) at 23° C. and the mixture was stirred for 1 h. The crude mixture was filtered through a pad of silica, concentrated and purified by preparative TLC (silica gel, 30% EtOAc/cyclohexane) to afford 2-149 as a mixture of two diastereoisomers 1:1 (>70% yield).

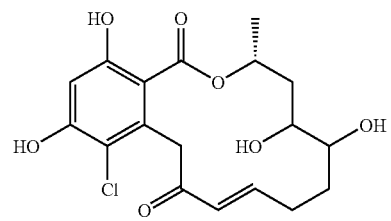

Selected example of compounds 2-149: $^1$H NMR (400 MHz, CD$_3$OD, 25° C.): δ=7.19 (m, 1H), 6.89-6.81 (m, 1H), 6.52 (s, 1H), 6.47 (s, 1H), 6.20 (d, J=16.1 Hz, 1H), 6.04 (d, J=15.6 Hz, 1H), 5.54-5.49 (m, 1H), 5.43-5.36 (m, 1H), 4.50 (d, J=17.7 Hz, 1H), 4.46 (d, J=17.7 Hz, 1H), 4.39 (d, J=17.2 Hz, 1H), 4.07 (d, J=17.2 Hz, 1H), 3.80-3.64 (m, 2H), 3.51-3.46 (m, 2H), 2.62-2.58 (m, 2H), 2.39-2.30 (m, 2H), 2.27-2.18 (m, 2H), 2.08-1.98 (m, 2H), 2.00-1.85 (m, 4H), 1.44 (d, J=6.4 Hz, 6H), phenols and alcohols not detected; HRMS (ESI-TOF): m/z: calculated for C$_{18}$H$_{21}$ClO$_7$Na: 407.0868, found 407.1031 [M+Na$^+$].

General procedure for the synthesis of compounds 2-150: Freshly prepared DMDO (1.2 equiv., 0.04 M in acetone) was added to a solution of compound 2-85a-g or 2-103a-g (1.0 equiv.) in CH$_3$CN (0.03 M) at 0° C. and the mixture was stirred for 30 min. After evaporation of the solvents under reduced pressure, purification by preparative TLC (silica gel, 30% EtOAc/cyclohexane) afforded epoxides 2-150 (>90% yield) as a mixture of two diastereoisomers (1:1 to 3:1).

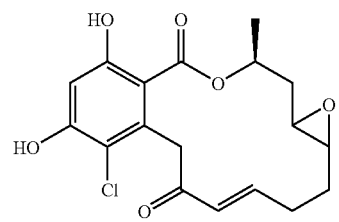

Selected examples of compounds 2-150: $^1$H NMR (400 MHz, C$_6$D$_6$, 25° C.): δ=11.85 (s, 1H), 6.94-6.87 (m, 2H), 6.69 (s, 1H), 6.65 (s, 1H), 6.24 (bd, J=15.2 Hz, 2H), 6.12 (d, J=15.8 Hz, 1H), 5.41-5.37 (m, 1H), 5.33-5.30 (m, 1H), 4.54 (bd, J=18.1 Hz, 2H), 4.52-4.48 (m, 1H), 4.40-4.34 (m, 1H), 4.27 (d, J=17.5 Hz, 1H), 2.78-2.72 (m, 2H), 2.58-2.55 (m, 4H), 2.47-2.28 (m, 5H), 2.07 (m, 2H), 1.92-1.86 (m, 3H), 1.51 (d, J=6.4 Hz, 3H), 1.35 (d, J=6.4 Hz, 3H), para-phenol not detected; HRMS (ESI-TOF): mm/z: calculated for C$_{18}$H$_{19}$O$_6$ClNa: 389.0762, found 389.0844 [M+Na$^+$].

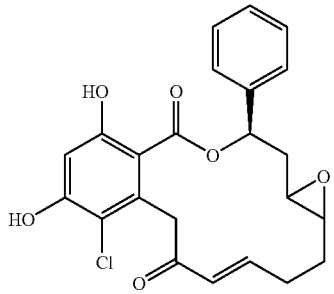

$^1$H NMR (400 MHz, C$_6$D$_6$, 25° C.): δ=11.80 (2×s, 2H), 7.43-7.18 (m, 10H), 7.03-6.95 (m, 2H), 6.69 (s, 1H), 6.61 (s, 1H), 6.30 (d, J=16.4 Hz, 1H), 6.21 (d, J=15.8 Hz, 1H), 6.15-6.10 (m, 1H), 6.03 (d, J=11.1 Hz, 1H), 4.84 (2×d, J=18.1 Hz, 2H), 4.41 (2×d, J=17.6 Hz, 2H), 2.68-2.60 (m, 4H), 2.41-2.27 (m, 8H), 1.83-1.76 (m, 4H), para-phenol not detected; HRMS (ESI-TOF): m/z: calculated for C$_{23}$H$_{21}$O$_6$ClNa: 451.0919, found 451.1028 [M+Na$^+$].

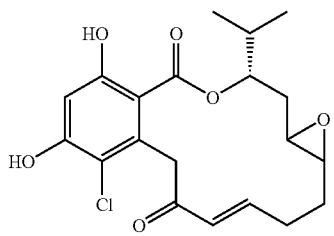

$^1$H NMR (400 MHz, C$_6$D$_6$, 25° C.): δ=11.56 (2×s, 2H), 6.92-6.82 (m, 2H), 6.71 (s, 1H), 6.67 (s, 1H), 6.20 (m, 3H), 6.06 (d, J=15.8 Hz, 1H), 5.11 (bs, 1H), 5.94 (m, 1H), 4.46 (2×d, J=18.1 Hz, 2H), 4.20 (2×d, J=18.1 Hz, 2H), 2.72-2.70 (m, 2H), 2.53-2.48 (m, 4H), 2.38-2.35 (m, 3H), 2.25-2.13 (m, 5H), 1.84-1.77 (m, 2H), 1.05-1.01 (m, 6H), 0.91-0.88 (m, 3H), 0.86-0.84 (m, 3H), para-phenol not detected; HRMS (ESI-TOF): m/z: calculated for C$_{20}$H$_{23}$O$_6$ClNa: 417.1075, found 417.1128 [M+Na$^+$].

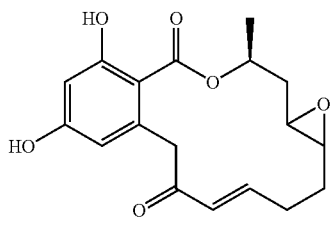

$^1$H NMR (400 MHz, C$_6$D$_6$, 25° C.): δ=11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (m, 2H), 2.57-2.52 (m, 2H), 2.46-2.27 (m, 2H), 2.14-2.10 (m, 1H), 1.93-1.88 (m, 1H), 1.48 (d, J=6.4 Hz, 3H); other isomer: $^1$H NMR (400 MHz, C$_6$D$_6$, 25° C.): δ=11.67 (s, 1H), 6.89-6.83 (m, 1H), 6.40 (d, J=2.4 Hz, 1H), 6.24 (d, J=2.9 Hz, 1H), 6.21 (d, J=16.4 Hz, 1H), 5.37 (bs, 1H), 5.22 (m, 1H), 4.20 (d, J=17.0 Hz, 1H), 4.06 (d, J=17.0 Hz, 1H), 2.74 (m, 2H), 2.57-2.20 (m, 4H), 1.80-1.76 (m, 1H), 1.68-1.60 (m, 1H), 1.37 (d, J=6.4 Hz, 3H), para-phenol not detected; HRMS (ESI-TOF): m/z: calculated for C$_{18}$H$_{20}$O$_6$Na: 355.1152, found 355.1249 [M+Na$^+$].

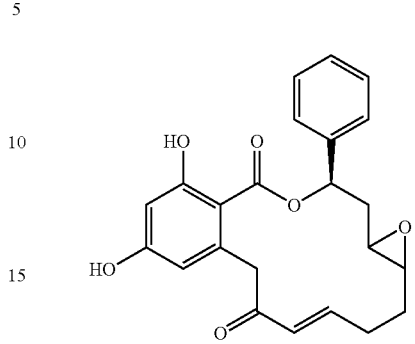

$^1$H NMR (400 MHz, C$_6$D$_6$, 25° C.): δ=11.98 (s, 1H), 6.91-6.83 (m, 1H), 6.43 (d, J=2.3 Hz, 1H), 6.24 (d, J=2.4 Hz, 1H), 6.11 (d, J=15.8 Hz, 1H), 5.35 (bs, 1H), 5.29 (m, 1H), 4.52 (d, J=17.5 Hz, 1H), 3.63 (d, J=17.5 Hz, 1H), 2.77 (bs, 1H), 2.57-2.52 (m, 2H), 2.46-2.27 (m, 2H), 2.14-2.10 (m, 1H), 1.93-1.88 (m, 1H), 1.48 (d, J=6.4 Hz, 3H).

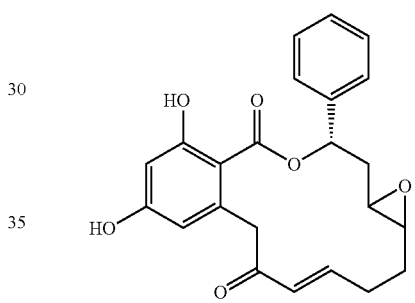

Major isomer: $^1$H NMR (400 MHz, C$_6$D$_6$, 25° C.): δ=11.90 (s, 1H), 7.41-7.23 (m, 5H), 6.95-6.89 (m, 1H), 6.42 (d, J=2.8 Hz, 1H), 6.27 (d, J=2.9 Hz, 1H), 6.20 (d, J=15.8 Hz, 1H), 6.13 (d, J=4.1 Hz, 1H), 5.51 (m, 1H), 4.79 (d, J=17.5 Hz, 1H), 3.79 (d, J=17.0 Hz, 1H), 2.68-2.55 (m, 3H), 2.44-2.25 (m, 4H), para-phenol not detected; HRMS (ESI-TOF): m/z: calculated for C$_{23}$H$_{22}$O$_6$Na: 417.1309, found 417.1399 [M+Na$^+$].

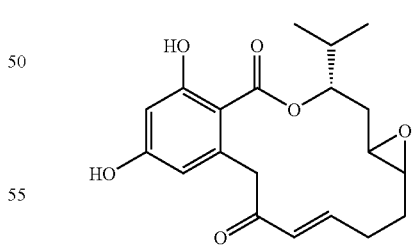

$^1$H NMR (400 MHz, C$_6$D$_6$, 25° C.): δ=11.77 (s, 1H), 6.92-6.82 (m, 1H), 6.44 (d, J=2.3 Hz, 1H), 6.28 (d, J=2.4 Hz, 1H), 6.09 (d, J=15.8 Hz, 1H), 5.40 (bs, 1H), 4.92 (m, 1H), 4.50 (d, J=17.5 Hz, 1H), 3.61 (d, J=17.5 Hz, 1H), 2.72-2.70 (m, 1H), 2.56-2.45 (m, 2H), 2.38-2.15 (m, 4H), 1.91-1.85 (m, 1H), 1.05-1.01 (m, 6H), para-phenol not detected; other isomer: $^1$H NMR (400 MHz, C$_6$D$_6$, 25° C.): δ=11.55 (s, 1H), 6.86-6.79 (m, 1H), 6.42 (s, 1H), 6.29 (s, 1H), 6.20 (d, J=15.8 Hz, 1H), 5.40 (m, 1H), 5.16 (m, 1H), 4.14 (s, 1H), 4.12 (s, 1H), 2.72-2.70 (m, 1H), 2.53-2.37 (m, 4H), 2.18-2.10 (m, 2H), 1.92-1.86 (m, 1H), 0.91-0.85 (m, 6H), para-phenol not detected; HRMS (ESI-TOF): m/z: calculated for $C_{20}H_{24}O_6Na$: 383.1465, found 383.1574 [M+Na$^+$].

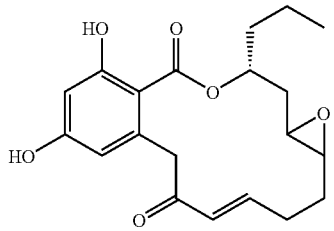

$^1$H NMR (400 MHz, $C_6D_6$, 25° C.): δ=11.87 (s, 1H), 6.90-6.82 (m, 1H), 6.43 (s, 1H), 6.26 (s, 1H), 6.10 (d, J=15.2 Hz, 1H), 5.31 (bs, 1H), 5.18 (bs, 1H), 4.46 (d, J=17.5 Hz, 1H), 3.60 (d, J=17.6 Hz, 1H), 2.74 (bs, 1H), 2.57-2.38 (m, 3H), 2.32-2.22 (m, 1H), 2.08-1.82 (m, 2H), 1.73-1.67 (m, 1H), 1.42-1.37 (m, 2H), 1.33-1.28 (m, 2H), 1.01 (t, J=7.3 Hz, 3H); other isomer: $^1$H NMR (400 MHz, $C_6D_6$, 25° C.): δ=11.72 (s, 1H), 6.86-6.80 (m, 1H), 6.41 (s, 1H), 6.27 (s, 1H), 6.21 (d, J=16.4 Hz, 1H), 5.37 (m, 1H), 5.22 (m, 1H), 4.25 (d, J=16.4 Hz, 1H), 3.96 (d, J=16.4 Hz, 1H), 2.74 (bs, 1H), 2.60-2.37 (m, 4H), 1.87-1.78 (m, 2H), 1.70-1.58 (m, 3H), 1.38-1.22 (m, 2H), 0.95 (t, J=7.3 Hz, 3H); HRMS (ESI-TOF): m/z: calculated for $C_{20}H_{24}O_6Na$: 383.1465, found 383.1492 [M+Na$^+$].

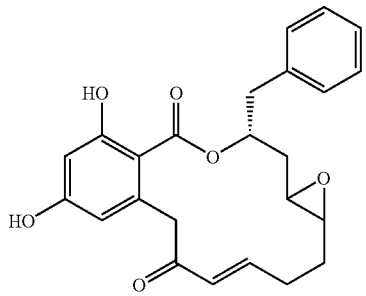

Major isomer: $^1$H NMR (400 MHz, $C_6D_6$, 25° C.): δ=11.94 (s, 1H), 7.36-7.28 (m, 5H), 6.95-6.88 (m, 1H), 6.42 (s, 1H), 6.22 (s, 1H), 6.11 (d, J=15.8 Hz, 1H), 5.47 (m, 1H), 5.41 (bs, 1H), 4.43 (d, J=17.5 Hz, 1H), 3.56 (d, J=17.6 Hz, 1H), 3.19 (dd, J=13.7, 6.0 Hz, 1H), 3.03 (dd, J=13.7, 7.9 Hz, 1H), 2.87 (bs, 1H), 2.70-2.28 (m, 4H), 2.03-1.93 (m, 2H), para-phenol not detected; HRMS (ESI-TOF): nm/z: calculated for $C_{24}H_{24}O_6Na$: 431.1465, found 431.1578 [M+Na$^+$].

General procedure for the preparation of macrocycles 2-151: HCl$_{conc.}$ (20.0 equiv.) was added to a solution of compound 2-120 (1.0 equiv.) in dioxane (0.05 M) at 23° C., and the mixture was stirred for 3 h. After this time, the reaction was filtered through a pad of silica, the solvents evaporated under reduced pressure, and purification by preparative TLC (silica gel, 30% EtOAc/cyclohexane) afforded compound 2-151 (>75% yield) as a mixture of two diastereoisomers 1:1.

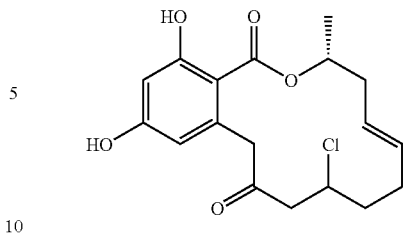

Selected examples of compounds 2-151: $^1$H NMR (400 MHz, CDCl$_3$, 25° C.): δ=12.11 (s, 1H), 11.78 (s, 1H), 6.51 (s, 1H), 6.43 (s, 1H), 6.41 (d, J=2.4 Hz, 1H), 6.37 (d, J=2.7 Hz, 1H), 6.21 (d, J=2.4 Hz, 1H), 6.11 (d, J=2.4 Hz, 1H), 5.59-5.51 (m, 3H), 5.40-5.32 (m, 3H), 4.54 (d, J=17.2 Hz, 1H), 4.42 (d, J=17.2 Hz, 1H), 3.60 (d, J=17.2 Hz, 1H), 3.45 (d, J=17.0 Hz, 1H), 3.28 (dd, J=18.5, 9.4 Hz, 1H), 3.11 (dd, J=13.7, 6.2 Hz, 1H), 3.07 (dd, J=13.4, 4.6 Hz, 1H), 2.76 (dd, J=19.0, 6.2 Hz, 1H), 2.62 (ddd, J=15.5, 8.8, 4.0 Hz, 1H), 2.54 (ddd, J=15.3, 6.2, 3.2 Hz, 1H), 2.40-2.26 (m, 4H), 2.25-2.13 (m, 4H), 2.03-1.91 (m, 2H), 1.42 (d, J=6.4 Hz, 3H), 1.40 (d, J=6.4 Hz, 3H), para-phenol not detected; HRMS (ESI-TOF): m/z: calculated for $C_{18}H_{21}ClO_5Na$: 375.0970, found 375.0928 [M+Na$^+$].

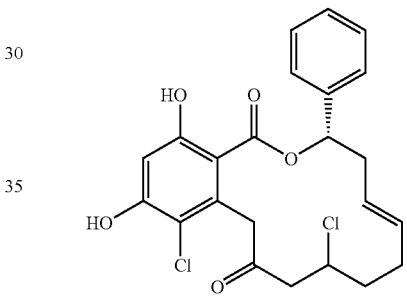

$^1$H NMR (400 MHz, $C_6D_6$, 25° C.): δ=11.76 (s, 0.5H), 11.36 (s, 0.5H), 7.40-7.29 (m, 5H), 6.65 (s, 0.5H), 6.62 (s, 0.5H), 6.18 (t, J=5.8 Hz, 1H), 6.14 (s, 0.5H), 6.12 (s, 0.5H), 5.67-5.62 (m, 1H), 5.55-5.49 (m, 1H), 4.93 (d, J=18.1 Hz, 0.5H), 4.80 (d, J=17.1 Hz, 0.5H), 4.58-4.56 (m, 1H), 4.38 (d, J=18.1 Hz, 0.5H), 4.18 (d, J=17.1 Hz, 0.5H), 3.33-3.27 (m, 1H), 3.10 (dd, J=18.4, 3.8 Hz, 0.5H), 2.84-2.68 (m, 2.5H), 2.42-2.32 (m, 2H), 2.23-2.17 (m, 1H), 2.13-2.04 (m, 1H), para-phenol not detected; HRMS (ESI-TOF): m/z: calculated for $C_{23}H_{22}O_5Cl_2Na$: 471.0737, found 471.0754 [M+Na$^+$].

Elimination of β-Cl from compound 2-151: PS-TBD (51 mg, 2.6 mmol.g$^{-1}$) was added to a solution of compound 2-151 (95 mg, 270 μmol) in CH$_2$Cl$_2$ (5 mL) at 23° C., and the mixture was stirred for 8 h. After this time, the reaction was filtered, the solvents were evaporated under reduced pressure, and the remaining residue was purified by flash chromatography (silica gel, 0-30% EtOAc/cyclohexane gradient) to afford 2-103 (84 mg, 98%).

General procedure for the synthesis of compounds 2-152: Compound 2-120a or 2-112a (1.0 equiv.) was dissolved in a 1:5 mixture of TFA/CH$_2$Cl$_2$ and stirred for 2 h at room temperature. Evaporation of the solvents; followed by flash chromatography (silica gel, 0-50% Et$_2$O/hexane), afforded compound 2-152 (~70% yield).

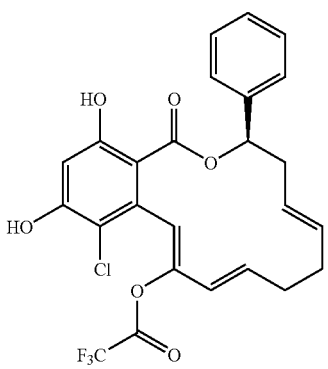

Selected example of compounds 2-152: $^1$H NMR (400 MHz, C$_6$D$_6$, 25° C.): δ=11.74 (s, 1H), 7.22-7.14 (m, 5H), 6.52 (s, 1H), 6.46 (dt, J=15.2, 7.3 Hz, 1H), 6.28 (s, 1H), 5.89 (t, J=7.0 Hz, 1H), 5.76 (s, 1H), 5.59 (d, J=15.2 Hz, 1H), 5.37 (ddd, J=15.2, 6.9, 6.9 Hz, 1H), 5.24 (ddd, J=15.2, 7.3, 7.0 Hz, 1H), 2.56-2.49 (m, 1H), 2.44-2.39 (m, 1H), 2.01-1.92 (m, 4H); $^{13}$C NMR (100 MHz, C$_6$D$_6$, 25° C.): δ=164.8, 162.8, 158.7, 153.1, 137.6, 136.9, 136.1, 133.9, 128.7 (×2), 126.5 (×2), 124.2, 122.0, 102.4, 100.8, 79.9, 39.0, 32.3, 31.4, four quaternary carbons are not detected; HRMS (ESI-TOF): m/z: calculated for C$_{25}$H$_{20}$ClF$_3$O$_6$Na: 531.0793, found 531.0992 [M+Na$^+$].

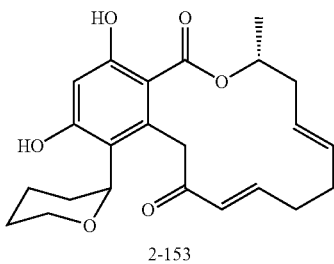

2-153

Macrocycle 2-153: DHP (3.7 μL, 40.8 μmol) and PS-TsOH (12.7 mg, 40.8 μmol, 3.2 mmol.g$^{-1}$) were added to a solution of compound 2-103 (12.9 mg, 40.8 μmol) in CH$_2$Cl$_2$ (1 mL) at 23° C., and the mixture was stirred for 5 h. After this time, the reaction was filtered and the solvents were evaporated under reduced pressure. Purification by preparative TLC (silica gel, 30% EtOAc/cyclohexane) afforded 2-153 (13.8 mg, 85%) as a mixture of two diastereoisomers. $^1$H NMR (400 MHz, CDCl$_3$, 25° C.): δ=12.33 (s, 1H), 12.11 (s, 1H), 9.45 (s, 1H), 9.40 (s, 1H), 6.67, (m, 2H), 6.28 (2×s, 2H), 5.83 (d, J=13.2 Hz, 1H), 5.79 (d, J=12.9 Hz, 1H), 5.35-5.30 (m, 3H), 5.27-5.22 (m, 3H), 5.06 (bd, J=8.2 Hz, 2H), 4.10 (d, J=17.5 Hz, 2H), 3.90-3.85 (m, 1H), 3.80-3.76 (m, 1H), 3.65 (d, J=17.7 Hz, 2H), 3.57-3.52 (m, 2H), 3.46-3.41 (m, 2H), 2.77-2.71 (m, 3H), 2.53-2.49 (m, 3H), 2.36-2.29 (m, 4H), 2.24-1.56 (m, 12H), 1.31 (d, J=6.4 Hz, 3H), 1.28 (d, J=6.4 Hz, 3H); HRMS (ESI-TOF): m/z: calculated for C$_{23}$H$_{28}$O$_6$Na: 423.1778, found 423.1778 [M+Na$^+$].

General procedure for the synthesis of compounds 2-154: The hydroxylamine R$^2$ONH$_2$ (5.0 equiv.) was added to a solution of compound 2-120 (1.0 equiv.) in pyridine/AcOH (5:1, 0.03 M) and the mixture was heated up to 40° C. After stirring overnight, the solvents were evaporated under reduced pressure with silica gel. Purification over a short pad of silica gel with a mixture of 30% EtOAc/cyclohexane afforded compound 2-154 (~99%) as a mixture of two diastereoisomers cis/trans.

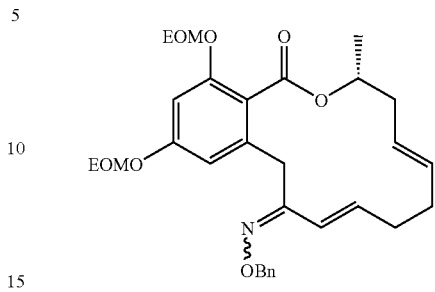

Selected example of compounds 2-154: $^1$H NMR (400 MHz, CDCl$_3$, 25° C.): δ=7.50-7.25 (m, 10H), 6.82 (s, 1H), 6.75 (s, 1H), 6.66 (s, 1H), 6.48 (s, 1H), 6.24-6.11 (m, 2H), 6.11-6.05 (m, 2H), 5.45-5.38 (m, 4H), 5.34-5.31 (m, 14H), 4.50 (d, J=17.2 Hz, 1H), 3.65-3.38 (m, 8H), 3.60 (d, J=17.1 Hz, 1H), 3.54 (d, J=17.1 Hz, 1H), 3.24 (d, J=17.2 Hz, 1H), 2.48-2.36 (m, 4H), 2.21-2.17 (m, 2H), 2.11-2.04 (m, 2H), 1.95-1.83 (m, 2H), 1.62-1.51 (m, 2H), 1.49 (d, J=6.4 Hz, 6H), 1.32-1.20 (m, 12H); $^{13}$C NMR (100 MHz, CDCl$_3$, 25° C.): δ=168.1, 167.9, 159.1, 158.8, 157.2, 155.6, 155.4, 154.2, 140.8, 138.2, 138.2, 137.8, 136.9, 136.7, 132.3, 132.3, 128.3 (×2), 128.3 (×2), 128.2, 128.1 (×2), 128.0 (×2), 127.7, 127.6, 125.5, 118.8, 118.6, 118.3, 108.8, 108.5, 101.7, 101.7, 93.5, 93.4, 93.1 (×2), 77.2, 76.0, 75.9, 71.2, 71.0, 64.5, 64.5, 64.3, 64.3, 40.0, 40.0, 34.9, 32.4, 32.3, 31.6, 31.1, 28.9, 20.3, 20.2, 15.0 (×2), 15.0 (×2); HRMS (ESI-TOF): m/z: calculated for C$_{31}$H$_{39}$NO$_7$Na: 560.2619, found 560.2627 [M+Na$^+$].

General procedure for the synthesis of compounds 2-155: PS-TsOH (10.0 equiv., 3.2 mmol.g$^{-1}$) was added to a solution of compound 2-154 (1.0 equiv.) in MeOH (0.02 M) and the suspension was shaken at 40° C. for 4 h. After this time, the reaction mixture was filtered and the methanolic solution concentrated under reduced pressure. The crude product obtained was submitted without further purification to the next step. Thus, DHP (1.0 equiv.) and PS-TsOH (catalytic amount, 3.2 mmol.g$^{-1}$) were added to a solution of this crude in CH$_2$Cl$_2$ (0.02 M) at 23° C., and the mixture was stirred for 5 h. After this time, the mixture was filtered, the solvents were evaporated under reduced pressure, and the remaining residue was purified by preparative TLC (silica gel, 30% EtOAc/cyclohexane) to afford two different diastereoisomers 1:1 of 2-155 (~65% yield).

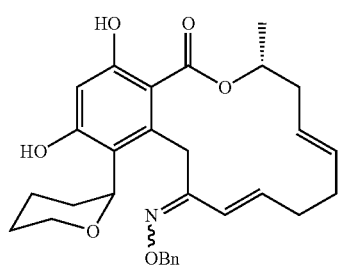

Selected example of compounds 2-155: Less polar diastereoisomer: $^1$H NMR (400 MHz, CDCl$_3$, 25° C.): δ=9.25 (s, 1H), 9.24 (s, 1H), 7.46-7.33 (m, 10H), 6.29 (s, 1H), 6.26 (s, 1H), 6.07-6.02 (m, 2H), 5.75 (d, J=15.8 Hz, 1H), 5.69 (d, J=15.8 Hz, 1H), 5.44-5.38 (m, 6H), 5.23 (s, 4H), 5.03 (d, J=8.8 Hz, 2H), 4.34-4.13 (m, 6H), 3.69-3.63 (m, 2H), 2.70-

2.67 (m, 2H), 2.30-2.16 (m, 6H), 2.08-1.94 (m, 8H), 1.73-1.65 (m, 8H), 1.42 (t, J=6.4 Hz, 3H), 1.39 (t, J=7.0 Hz, 3H); HRMS (ESI-TOF): m/z: calculated for $C_{30}H_{35}NO_6Na$: 528.2357, found 528.2562 [M+Na$^+$].

More polar diastereoisomer: $^1$H NMR (400 MHz, CDCl$_3$, 25° C.): δ=11.61 (s, 1H), 9.27 (s, 1H), 7.41-7.33 (m, 5H), 6.62 (d, J=16.4 Hz, 1H), 6.47 (s, 1H), 6.15-6.07 (m, 1H), 5.50-5.38 (m, 3H), 5.16 (s, 2H), 5.04 (d, J=10.5 Hz, 1H), 4.30 (d, J=15.2 Hz, 1H), 4.24 (d, J=10.5 Hz, 1H), 3.84 (d, J=15.2 Hz, 1H), 3.66 (t, J=11.4 Hz, 1H), 2.71-2.65 (m, 1H), 2.28-2.08 (m, 6H), 1.73-1.64 (m, 5H), 1.38 (t, J=7.0 Hz, 3H); HRMS (ESI-TOF): m/z: calculated for $C_{30}H_{35}NO_6Na$: 528.2357, found 528.2494 [M+Na$^+$].

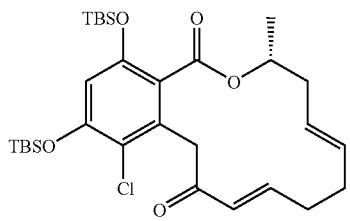

2-128

Macrocycle 2-128 from pochonin D (2-85): TBSCl (53.6 mg, 356 μmol) and imidazole (23.6 mg, 356 μmol) were added to a solution of pochonin D (2-85, 25 mg, 71.2 μmol) in DMF (5 mL) and the mixture was stirred for 3 h at room temperature. Purification by column chromatography (silica gel, 0-30% EtOAc/cyclohexane gradient) afforded compound 2-128 (40 mg, 98%).

General procedure for compounds 2-157: The hydroxylamine RONH$_2$ (5.0 equiv.) was added to a solution of compound 2-128 (1.0 equiv.) in pyridine/AcOH (5:1, 250 μL) and the mixture was heated up to 40° C. After stirring overnight, the solvents were evaporated under reduced pressure, and filtration on silica gel with a mixture of 30% EtOAc/cyclohexane afforded two isomers of 2-157 (~90% yield).

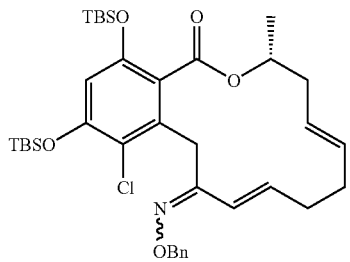

Selected example of compounds 2-157: cis oxime: $^1$H NMR (400 MHz, CDCl$_3$, 25° C.): δ=7.42 (bd, J=6.4 Hz, 2H), 7.36 (bdd, J=7.5, 6.9 Hz, 2H), 7.34-7.32 (m, 1H), 6.52 (d, J=16.1 Hz, 1H), 6.38 (s, 1H), 6.18-6.10 (m, 1H), 5.36-5.32 (m, 2H), 5.16 (bs, 2H), 4.99-4.95 (m, 1H), 3.79-3.76 (m, 2H), 2.40-1.99 (m, 6H), 1.45 (d, J=6.2 Hz, 3H), 1.03 (s, 9H), 0.99 (s, 9H), 0.28 (s, 3H), 0.26 (s, 3H), 0.20 (s, 6H); trans oxime: $^1$H NMR (400 MHz, CDCl$_3$, 25° C.): δ=7.44 (bd, J=6.5 Hz, 2H), 7.37 (bdd, J=7.6, 6.9 Hz, 2H), 7.33-7.31 (m, 1H), 6.41 (s, 1H), 6.04-5.97 (m, 1H), 5.48 (bd, J=15.0 Hz, 1H), 5.29-5.27 (m, 1H), 5.22 (bs, 2H), 5.00-4.95 (m, 1H), 3.98-3.89 (m, 2H), 2.39-2.02 (m, 6H), 1.37 (d, J=5.9 Hz, 3H), 1.04 (s, 9H), 0.99 (s, 9H), 0.28 (s, 3H), 0.27 (s, 3H), 0.23 (s, 3H), 0.22 (s, 3H).

General procedure for compounds 2-158: To a solution of corresponding compound 2-157 (1.0 equiv) in THF was added TBAF (2.5 equiv, 1M solution in THF) and the mixture was stirred at room temperature for 2 h. The solvents were then evaporated under reduced pressure, and filtration on silica gel with a mixture of 30% EtOAc/cyclohexane afforded compound 2-158 in >85% yield.

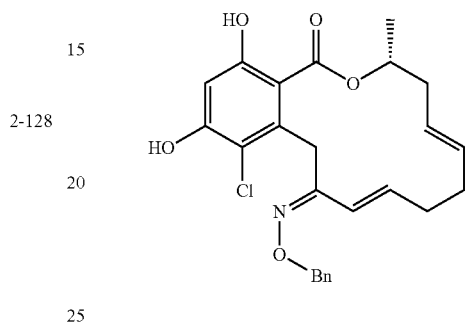

Selected example of compounds 2-158: cis oxime: $^1$H NMR (400 MHz, CDCl$_3$, 25° C.): δ=11.52 (s, 1H), 7.45-7.34 (m, 5H), 6.64 (s, 1H), 6.09-6.02 (m, 2H), 5.34-5.25 (m, 4H), 5.18-5.08 (m, 2H), 4.33 (d, J=17.0 Hz, 1H), 4.15 (d, J=17.6 Hz, 1H), 2.65-2.59 (m, 1H), 2.27-2.14 (m, 3H), 2.04-2.00 (m, 1H), 1.88-1.83 (m, 1H), 1.30 (t, J=6.4 Hz, 3H); HRMS (ESI-TOF): m/z: calculated for $C_{25}H_{26}ClNO_5Na$: 478.1392, found 478.1372 [M+Na$^+$].

trans oxime: $^1$H NMR (400 MHz, CDCl$_3$, 25° C.): δ=11.73 (s, 1H), 7.32-7.26 (m, 5H), 6.64 (s, 1H), 6.50 (d, J=16.4 Hz, 1H), 6.06-5.98 (m, 2H), 5.43-5.24 (m, 3H), 4.91 (s, 2H), 4.22 (s, 2H), 2.61-2.55 (m, 1H), 2.46-2.33 (m, 2H), 2.20-2.02 (m, 3H), 0.98 (t, J=6.4 Hz, 3H); HRMS (ESI-TOF): m/z: calculated for $C_{25}H_{26}ClNO_5Na$: 478.1392, found 478.1522 [M+Na$^+$].

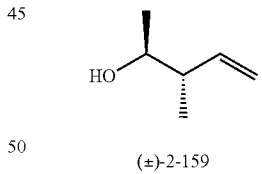

(±)-2-159

Compound (±)-2-159: A solution of cis-butene oxide (1.75 mL, 20 mmol) in Et$_2$O (10 mL) was cooled to −30° C. Copper iodide (1.14 g, 6 mmol) was added to this solution and then, vinyl magnesium bromide (40 mL, 1M solution in THF, 40 mmol) was added dropwise over a period of 1 h. The reaction mixture was then warmed up to room temperature over 12 h and the reaction turned black. The reaction mixture was quenched slowly with saturated NH$_4$Cl$_{aq.}$ (20 mL), stirred for 2 h, extracted with Et$_2$O (20 mL) and dried over MgSO$_4$. Concentration under reduced pressure afforded compound (+)-2-159 (1.3 g, 65%). $^1$H NMR (400 MHz, CDCl$_3$, 25° C.): δ=5.81-5.72 (m, 1H), 5.15 (d, J=13.2 Hz, 2H), 3.59 (m, 1H), 2.23-2.10 (m, 1H), 1.21 (d, J=6.4 Hz, 3H), 1.05 (d, J=7.0 Hz, 3H).

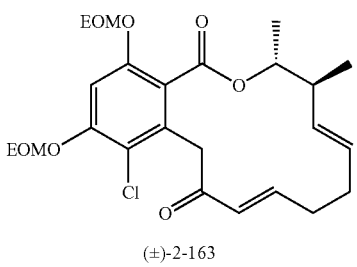

(±)-2-163

Compound (±)-2-163: In a similar manner as that described for compound 2-112, compound (±)-2-163 was prepared with a 57% yield from (±)-2-162. $^1$H NMR (400 MHz, CDCl$_3$, 25° C.): δ=7.10 (s, 1H), 6.76-6.71 (m, 1H), 5.87 (d, J=15.8 Hz, 1H), 5.32 (s, 2H), 5.25-5.18 (s+m, 4H), 4.87-4.80 (m, 1H), 3.99 (d, J=16.9 Hz, 1H), 3.80-3.71 (m, 5H), 2.32-2.26 (m, 2H), 2.20-2.11 (m, 3H), 1.36 (d, J=6.4 Hz, 3H), 1.25 (t, J=7.0 Hz, 6H), 1.04 (d, J=7.0 Hz, 3H); $^{13}$C NMR (100 MHz, CDCl$_3$, 25° C.): δ=195.7, 166.6, 154.6, 153.8, 147.1, 133.3, 132.8, 120.7, 117.7, 102.9, 93.9, 93.6, 76.2, 64.8, 64.6, 45.1, 41.6, 30.7, 30.7, 18.2, 16.9, 15.0, 15.0.

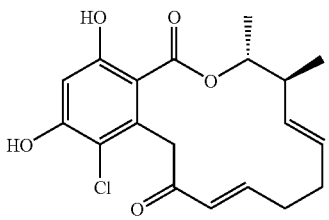

(±)-2-164

Compound (±)-2-164: In a similar manner as that described for compound 2-85 using PS-TsOH, compound (±)-2-164 was prepared with a 40% yield from (±)-2-163. $^1$H NMR (400 MHz, CDCl$_3$, 25° C.): δ=11.52 (s, 1H), 6.78-6.69 (m, 1H), 6.67 (s, 1H), 6.05 (s, 1H), 5.93 (d, J=16.4 Hz, 1H), 5.47-5.45 (m, 1H), 5.37-5.33 (m, 1H), 5.16 (dd, J=15.8, 7.0 Hz, 1H), 4.48 (bs, 1H), 4.35 (d, J=17.6 Hz, 1H), 2.45-2.26 (m, 5H), 1.27 (d, J=6.4 Hz, 3H), 1.10 (d, J=7.0 Hz, 3H); ESI: m/z: calculated for C$_{18}$H$_{21}$ClO$_5$: 365.12, found 365.22 [M+H$^+$].

The description and examples provided herein are merely illustrative, and the invention is not so limited. Numerous variations, permutations and derivatives of these compounds, procedures and uses will occur to those of ordinary skill in the art, and are contemplated within the scope of the invention.

What is claimed is:

1. A compound of formula 1, tautomers thereof, or a pharmaceutically acceptable salt, solvate, or ester thereof:

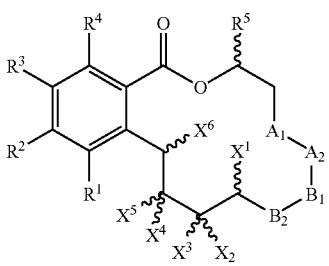

I wherein:

R$^1$, R$^2$, R$^3$, R$^4$ and R$^5$ are independently hydrogen, halogen, nitro, cyano, alkyl, substituted alkyl, alkenyl, alkynyl, alkylaryl, aralkyl, aryl, heteroalkyl, alkylheteroaryl, heterocyclyl, heteroaryl, OH, OR, NH$_2$, N(R)$_2$, SR, S(O)R, S(O)$_2$R, —SO$_2$N(R)$_2$, —N(R)SO$_2$R, —N(CO)R, —N(CO)N(R)$_2$, —N(CO)OR, —O(CO)R, —(CO)R, —(CO)OR, —(CO)N(R)$_2$, —O(CO)OR, or —O(CO)N(R)$_2$, wherein each R can be the same or different;

when B$_1$ and B$_2$ together are —CH$_2$—CH$_2$—, then A$_1$ and A$_2$ together are —CH$_2$—CH$_2$—, or —CH═CH—; or when B$_1$ and B$_2$ together represent a covalent bond, then A$_1$ and A$_2$ together are —CH$_2$—CH$_2$—, —CH═CH—, —CH(OH)—CH(OH)—, —CH(OH)—CH(halogen)-, —CH(halogen)-CH(OH)—, 1,2-cyclopropadiyl;

X$^1$ is hydrogen, halogen, OH, OR, NH$_2$, N(R)$_2$, NH—OR, SR, S(O)R, S(O)$_2$R, —NH—O—(CH$_2$)$_n$—CO$_2$—R, —NH—O—(CH$_2$)$_n$—CON(R)$_2$; or X$_1$ together with X$_2$ or X$_3$ represents a covalent bond, wherein each R can be the same or different;

X$^2$ and X$^3$ are both hydrogen, or one of X$_2$ and X$_3$ is hydrogen and the other together with X$_1$ represents a covalent bond;

X$^4$ and X$^5$ together are ═N—OR, ═N—O—(CH$_2$)$_n$COOR, ═N—O—(CH$_2$)$_n$CON(R)$_2$, ═N—N(R)$_2$, ═N—N—SOR or ═N—N—SO$_2$R; or one of X$^4$ and X$^5$ is hydrogen and the other is OH, OR, O(CO)R, O(CO)OR, O(CO)N(R)$_2$, —(CH$_2$)$_n$C(O)OR, or —(CH$_2$)C(O)N(R)$_2$, and n is 0, 1, 2, or 3; or one of X$^4$ and X$^5$ together with X$^6$ represents a covalent bond and the other of X$^4$ and X$^5$ is OH, OR, O(CO)R, O(CO)OR, —N(R)$_2$ or O(CO)N(R)$_2$, wherein each R can be the same or different;

X$^6$ is hydrogen or X$^6$ together with one of X$^4$ and X$^5$ represents a covalent bond; and R is hydrogen, alkyl, acyl, aryl, alkaryl, arylalkyl including benzyl, heteroalkyl, heteroaryl, heterocyclyl, a protecting group; or two R on the same nitrogen are taken together with the nitrogen to form a 5-8 membered heterocyclic or heteroaryl ring; and n is 0, 1, 2 or 3.

2. The compound of claim 1, wherein the compound has the structure of formula II:

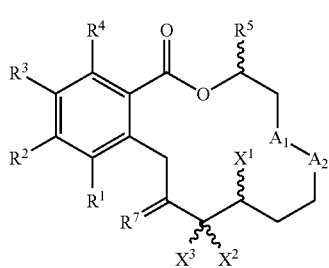

II wherein, R$^7$ is ═N—OR, ═N—O—(CH$_2$)$_n$COOR, ═N—O—(CH$_2$)$_n$CON(R)$_2$, ═N—N(R)$_2$, ═N—N—SOR or ═N—N—SO$_2$R; and wherein each R can be the same or different.

3. The compound of claim 2, wherein R$^1$ is H, halogen or heterocyclyl.

4. The compound of claim 2, wherein R$^5$ is hydrogen, alkyl, aryl, heteroaryl or arylalkyl.

5. The compound of claim 2, wherein A$_1$ and A$_2$ together are —CH═CH—.

6. The compound of claim 2, wherein A$_1$ and A$_2$ together are —CH(OH)—CH(OH)—, —CH(OH)—CH(halogen)- or —CH(halogen)- CH(OH)—.

7. The compound of claim 2, wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH— or —C(OH)—C(OH)—;
$X^1$ is hydrogen, halogen or NH—OR; and
$R^7$ is =N—OR, =N—O—$(CH_2)_n$COOR, =N—O—$(CH_2)_n$CON(R)$_2$, =N—N(R)$_2$, =N—N—SOR, =N—N—SO$_2$R.

8. The compound of claim 2, wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are 1,2-oxirane;
$X^1$ is hydrogen, halogen or NH—OR; and
$R^7$ is =N—OR, =N—O—$(CH_2)_n$COOR, =N—O—$(CH_2)_n$CON(R)$_2$, =N—N(R)$_2$, =N—N—SOR, =N—N—SO$_2$R.

9. The compound of claim 2, wherein:
$R^1$ is H, Cl or heterocyclyl;
$R^2$ and $R^4$ are independently OH or OR;
$R^5$ is hydrogen, alkyl, aryl or aralkyl;
$A_1$ and $A_2$ together are —CH=CH— or —C(OH)—C(OH)—;
$X^1$ together with $X^2$ represent a bond; and
$R^7$ is =N—OR, =N—O—$(CH_2)_n$COOR, =N—O—$(CH_2)_n$CON(R)$_2$, =N—N(R)$_2$, =N—N—SOR, =N—N—SO$_2$R.

10. The compound of claim 2, wherein:
$R^1$ is Cl or heterocyclyl;
$R^2$ and $R^4$ are independently OH or OR;
$R^5$ is hydrogen, alkyl, aryl or aralkyl;
$A_1$ and $A_2$ together are 1,2-oxirane;
$X^1$ together with $X^2$ represent a bond; and
$R^7$ is =N—OR, =N—O—$(CH_2)_n$COOR, =N—O—$(CH_2)_n$CON(R)$_2$, =N—N(R)$_2$, =N—N—SOR, =N—N—SO$_2$R.

11. The compound of claim 9, wherein:
$R^1$ is H or Cl;
$R^5$ is hydrogen, methyl, propyl, isopropyl or phenyl; and
$R^7$ is =N—OR, =N—O—$(CH_2)_n$COOR, or =N—O—$(CH_2)_n$CON(R)$_2$.

12. The compound of claim 11, wherein $R^1$ is Cl and $R^5$ is hydrogen.

13. The compound of claim 11, wherein $R^7$ is =N—O—$(CH_2)_n$COOR, or =N—O—$(CH_2)_n$CON(R)$_2$; and n is 1.

14. The compound of claim 11, wherein $R^5$ is hydrogen and $R^7$ is =N—O—$(CH_2)_n$COOR, or =N—O—$(CH_2)_n$CON(R)$_2$.

15. The compound of claim 11, wherein $R^5$ is hydrogen and $R^7$ is =N—OR.

16. The compound of claim 7, wherein $R_7$ is =N—OR, =N—O—$(CH_2)_n$COOR, or =N—O—$(CH_2)_n$CON(R)$_2$.

17. The compound of claim 10, wherein $R_7$ is =N—OR, =N—O—$(CH_2)_n$COOR, or =N—O—$(CH_2)_n$CON(R)$_2$.

18. The compound of claim 1, wherein the compound has the formula IV:

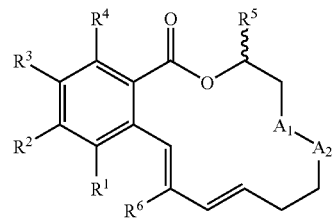

IV wherein $R^6$ is hydrogen, or N(R)$_2$.

19. The compound of claim 18, wherein $R^1$ is H, halogen or heterocyclyl.

20. The compound of claim 18, wherein $R^5$ is hydrogen, alkyl, aryl, heteroaryl or arylalkyl.

21. The compound of claim 18, wherein $A_1$ and $A_2$ together are —CH=CH—.

22. The compound of claim 1, wherein the compound has the formula V:

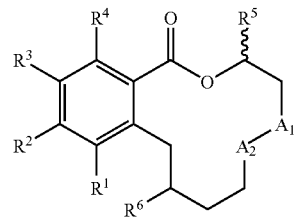

V wherein $R^6$ is $(CH_2)_n$C(O)OR, or —$(CH_2)_n$C(O)N(R)$_2$; and
n is 0, 1, 2 or 3.

23. The compound of claim 22, wherein $R^6$ is —CH$_2$C(O)N(Me)OMe.

24. The compound of claim 22, wherein $R^1$ is H, halogen or heterocyclyl.

25. The compound of claim 22, wherein $R^5$ is hydrogen, alkyl, aryl, heteroaryl or arylalkyl.

26. The compound of claim 22, wherein $A_1$ and $A_2$ together are —CH=CH—.

27. The compound of claim 22, wherein $A_1$ and $A_2$ together are —CH(OH)—CH(OH)—, —CH(OH)—CH(halogen)- or —CH(halogen)-CH(OH)—.

28. The compound of claim 22, wherein $A_1$ and $A_2$ together are 1,2-oxirane.

29. The compound of claim 1, wherein the compound is selected from the group consisting of

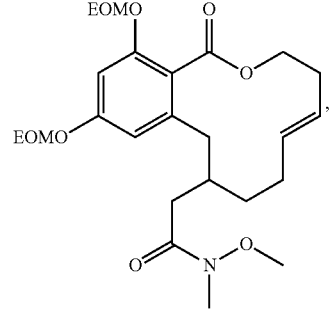

223
-continued
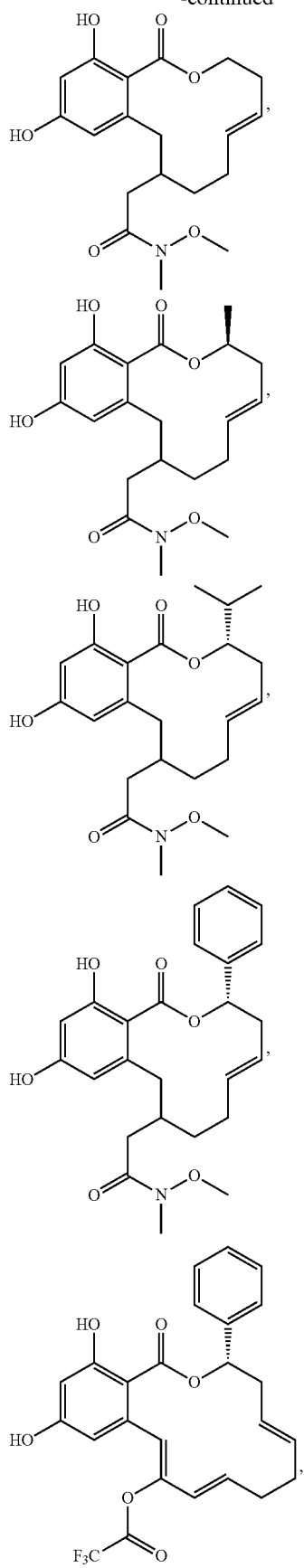
224
-continued
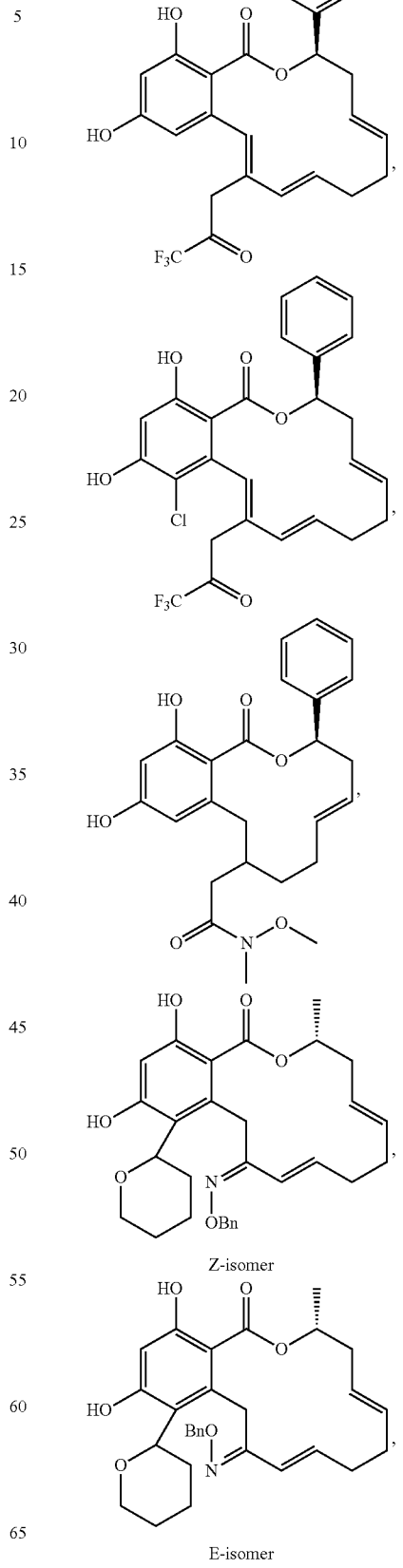

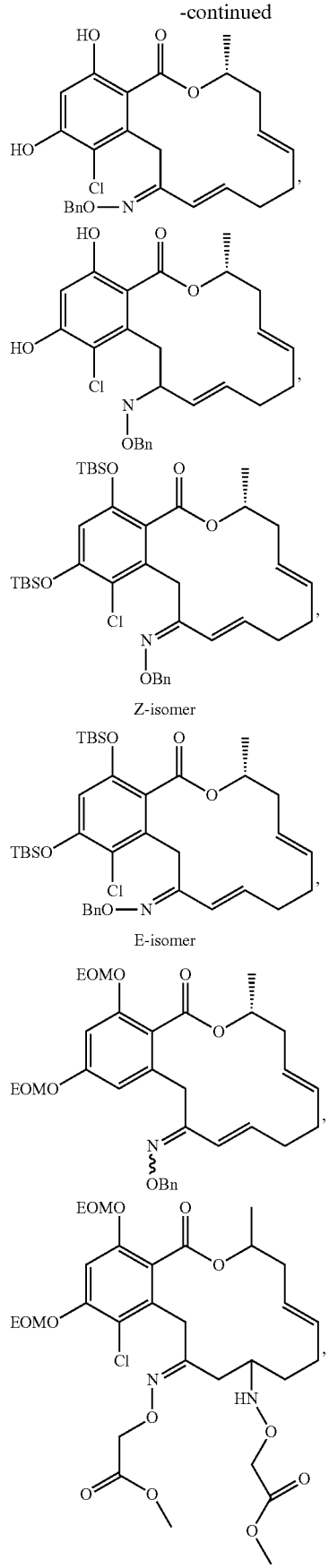

227
-continued
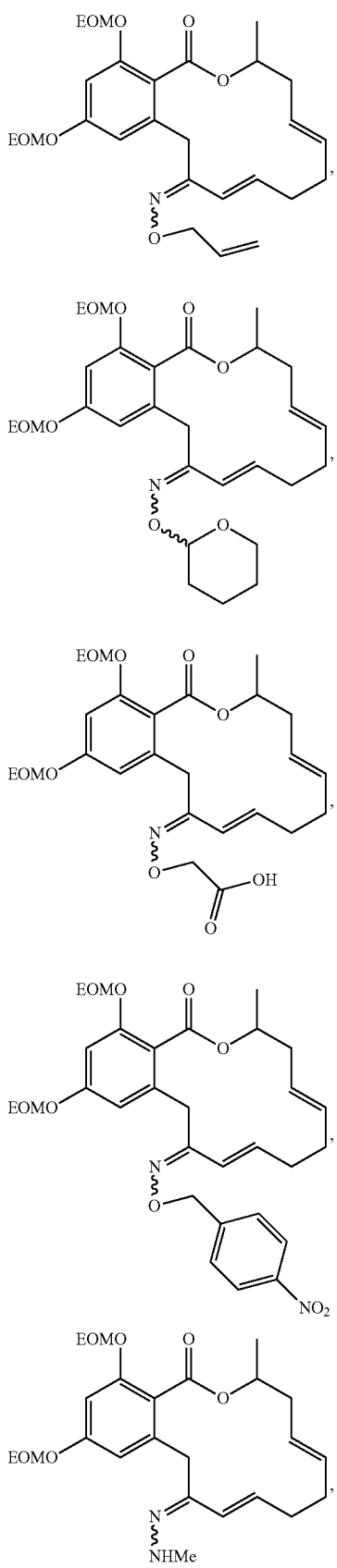
228
-continued
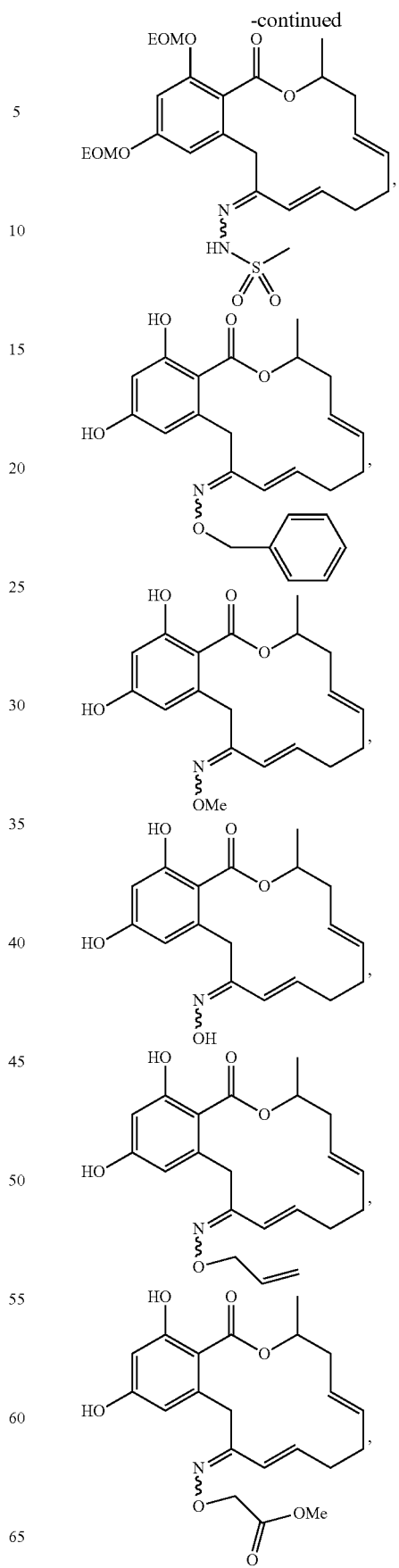

229
-continued
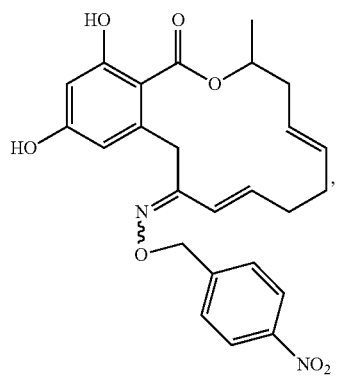
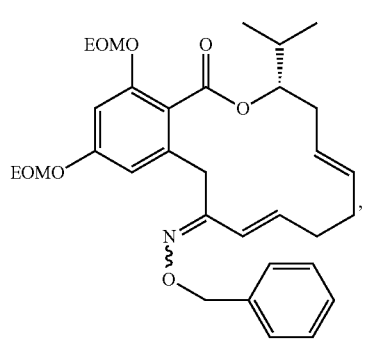
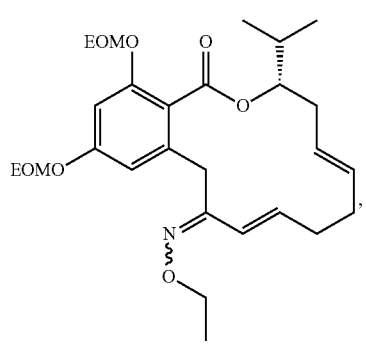
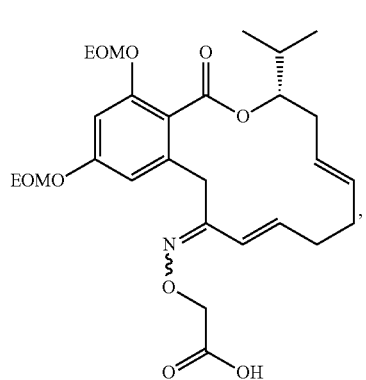
230
-continued
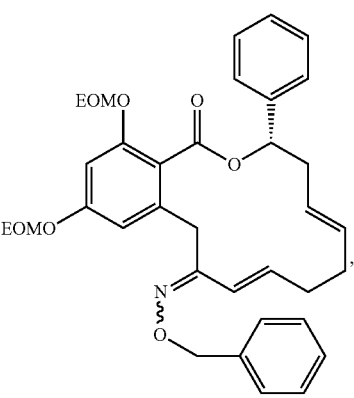
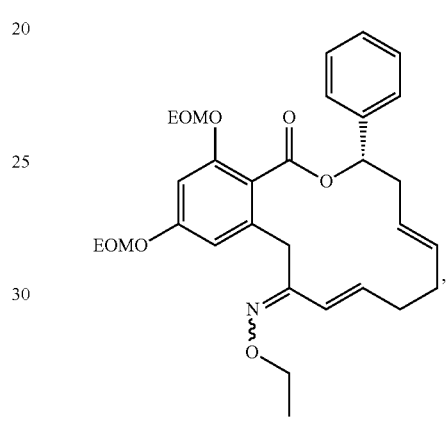
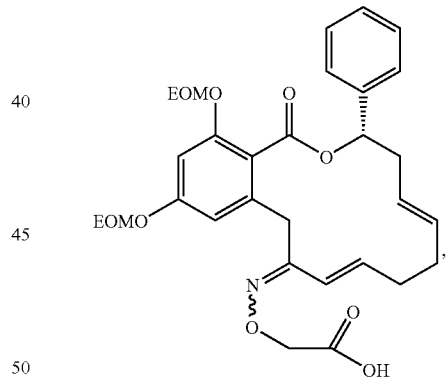
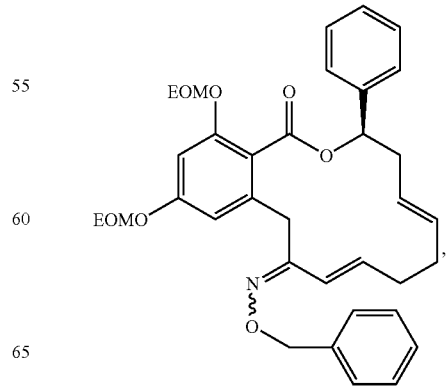
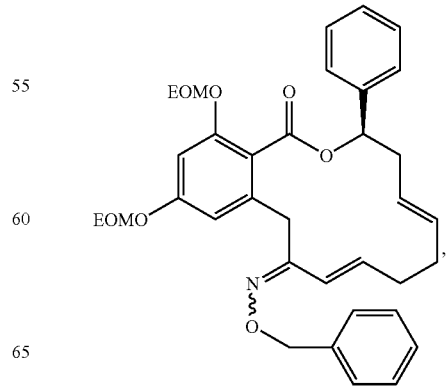

231
-continued
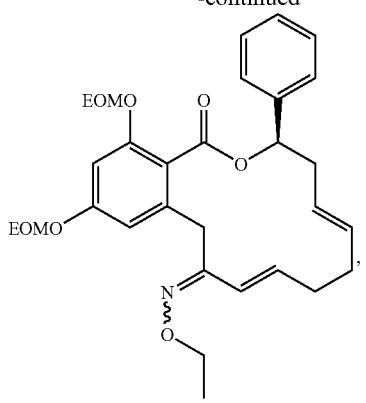
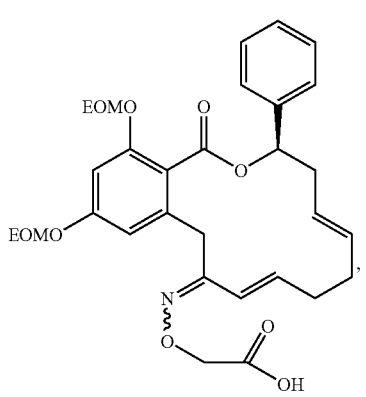
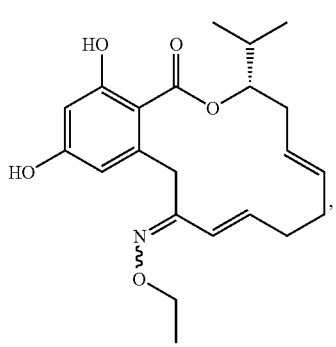
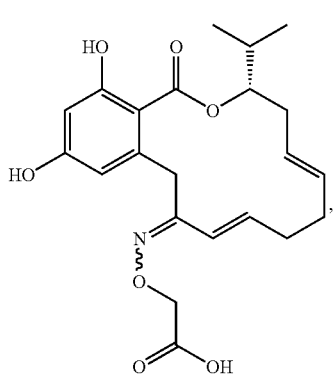
232
-continued
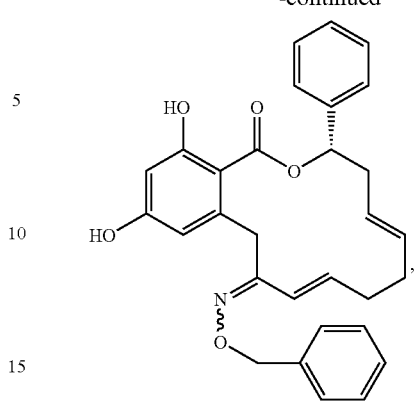
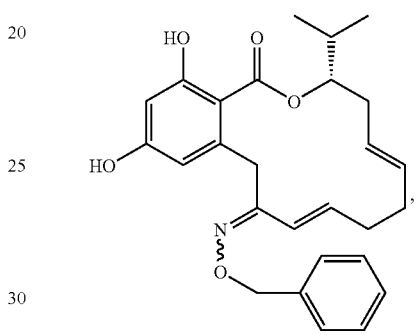
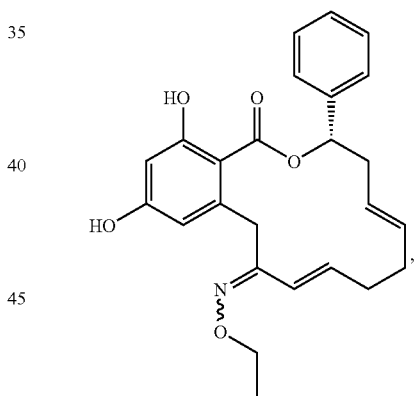
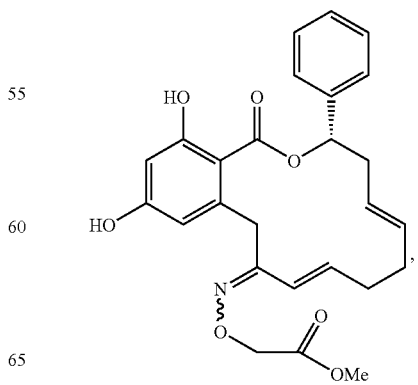

233
-continued
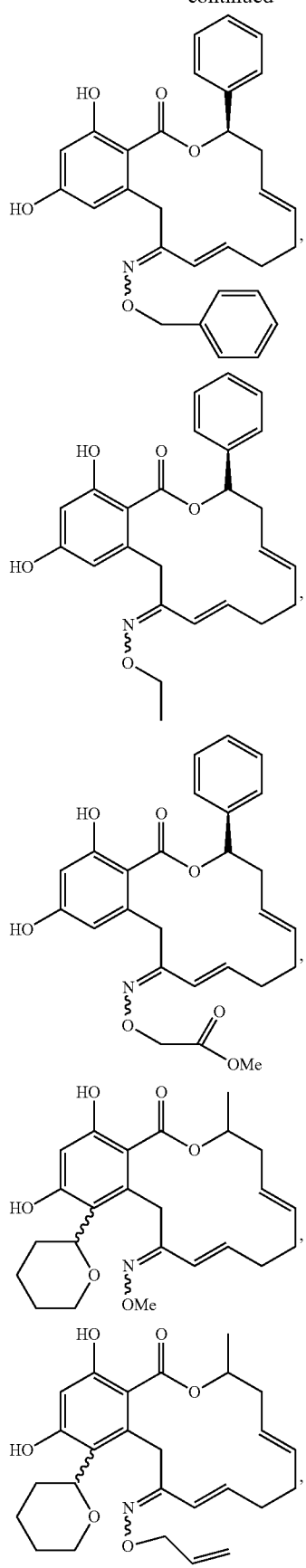
234
-continued
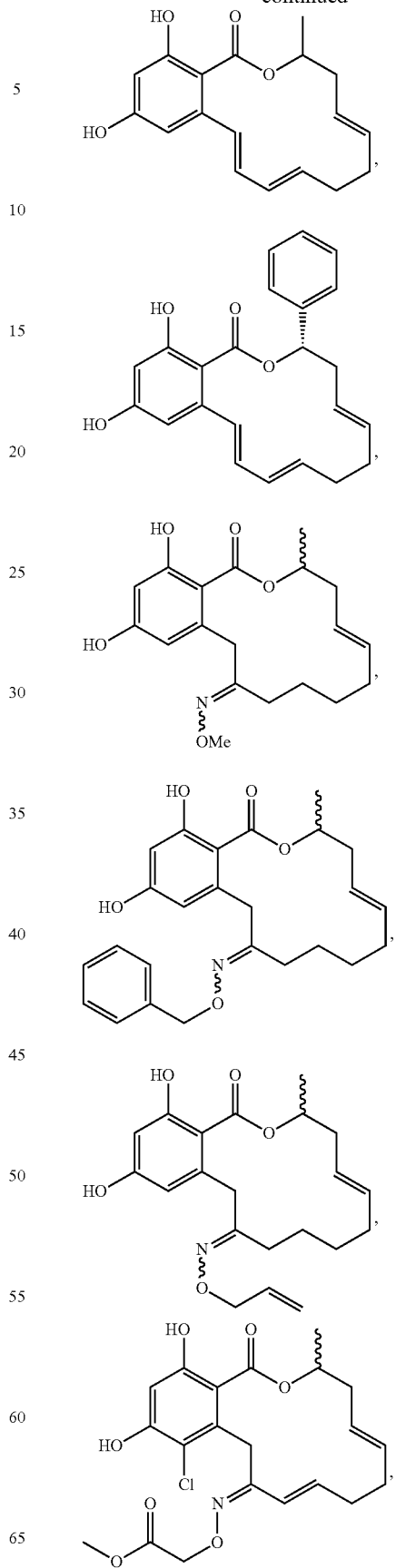

235
-continued
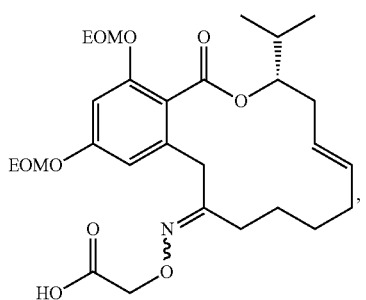
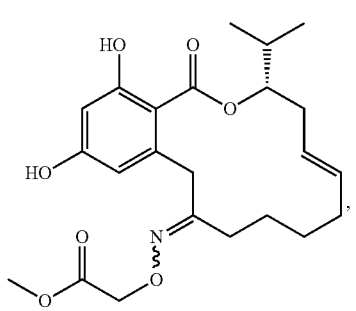
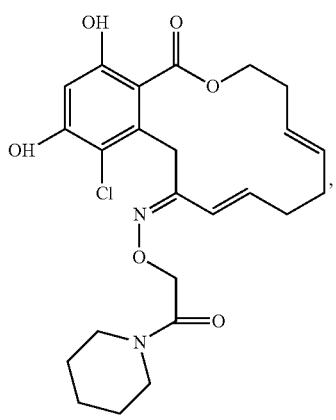
Z-isomer
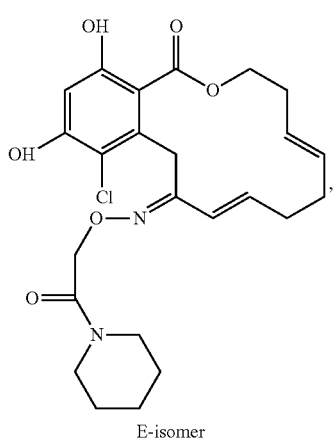
E-isomer
236
-continued
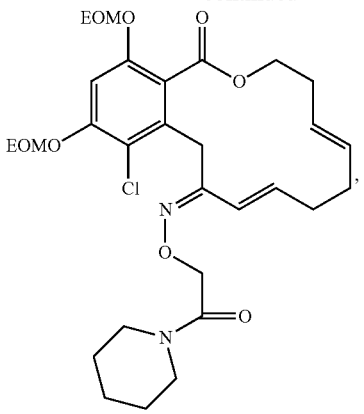
Z-isomer
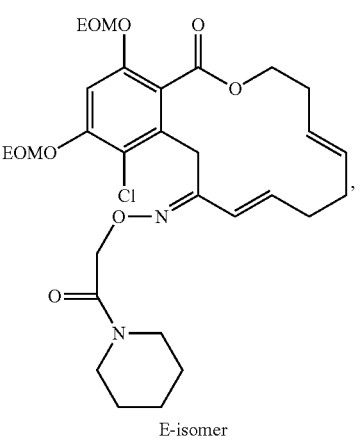
E-isomer
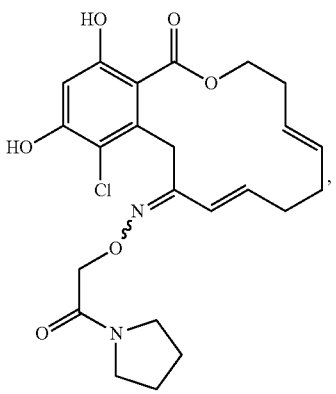
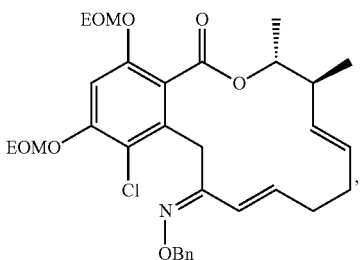

237
-continued
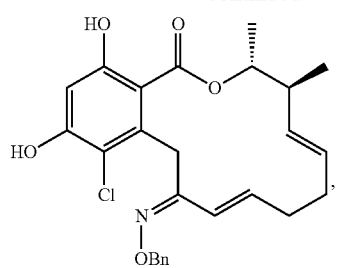
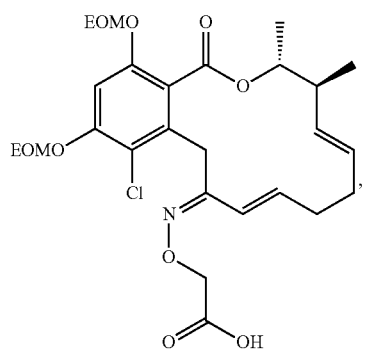
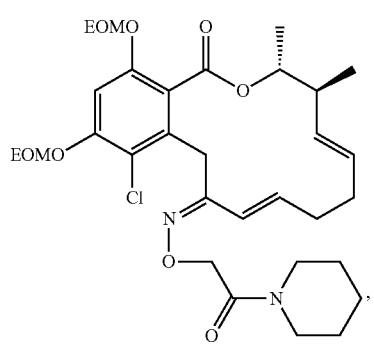
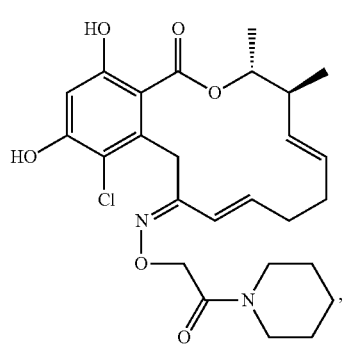
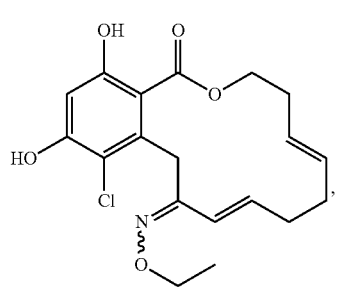
238
-continued
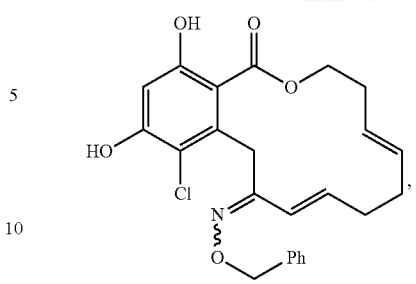
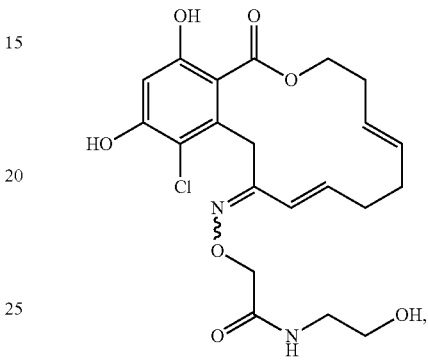
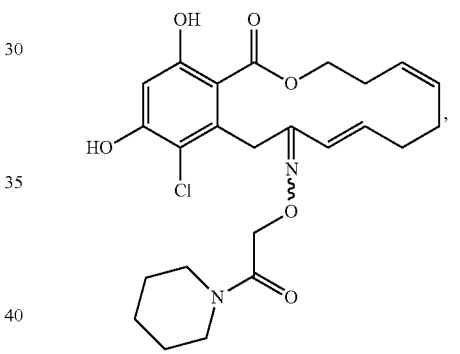
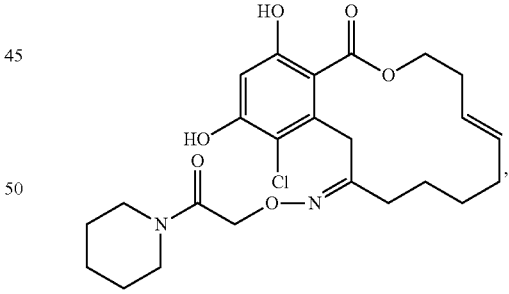
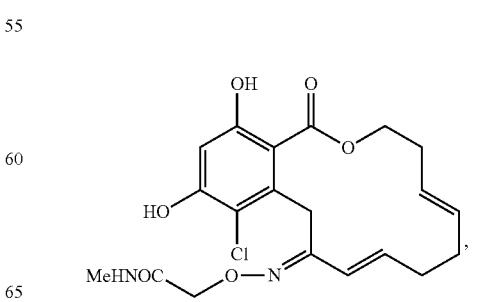

239
-continued
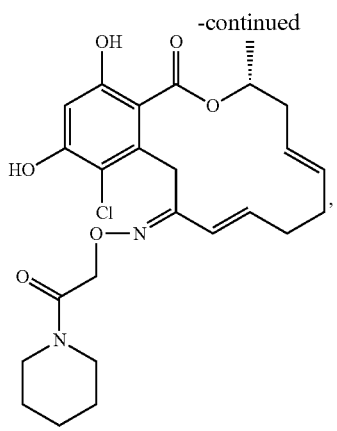
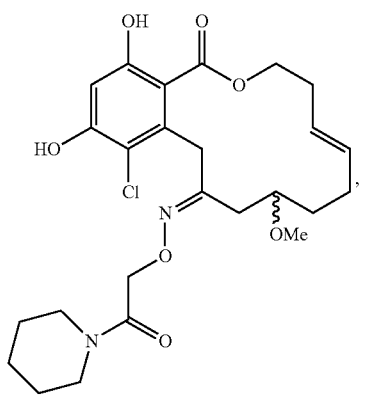
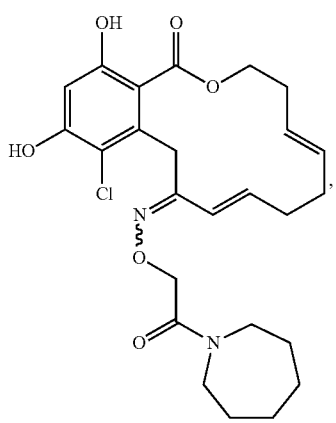
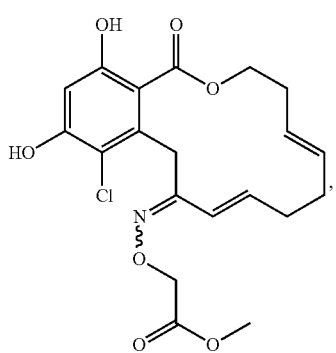
240
-continued
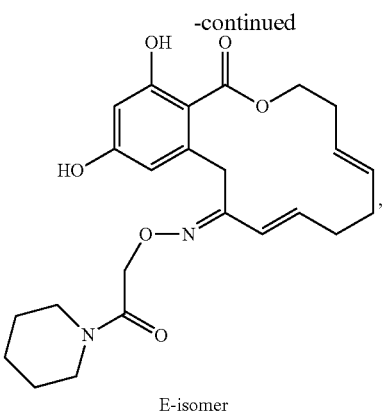
E-isomer
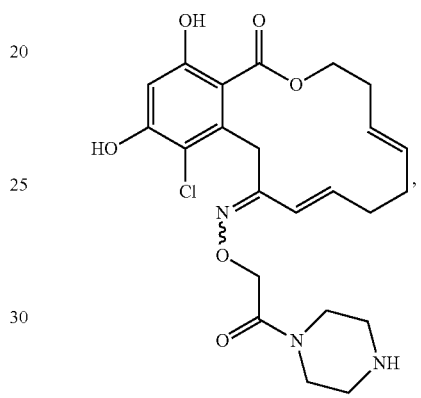
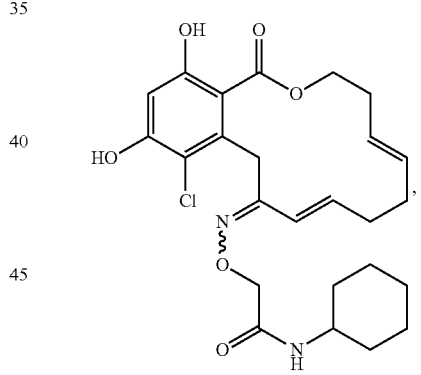
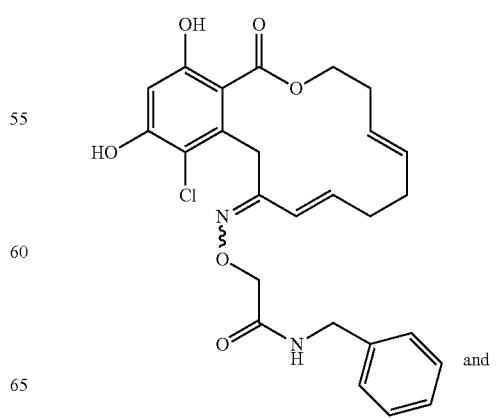
and -continued

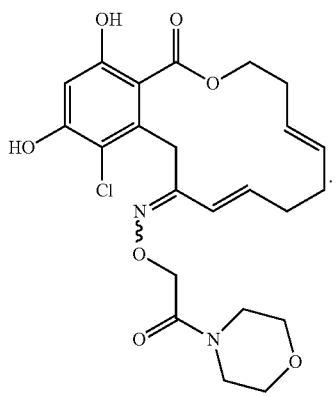

30. A pharmaceutical composition comprising an effective kinase-inhibiting amount of a compound of any of claim 1, 2, 18, 22 or 29 in combination with a pharmaceutically acceptable carrier.

31. A pharmaceutical composition comprising an effective HSP 90-inhibiting amount of a compound of any of claim 1, 2, 18, 22 or 29 in combination with a pharmaceutically acceptable carrier.

32. The composition of claim 31, wherein the composition comprises particles that are less than about 2 microns average particle size.

33. The composition of claim 31, wherein the composition is incorporated into a biodegradable or non-biodegradable polymer.

34. The composition of claim 31, further comprising an additive.

35. The composition of claim 34, wherein the additive is selected from an anti-oxidant, a buffer, a bacteriostat, a liquid carrier, a solute, a suspending agent, a thickening agent, a flavoring agent, a gelatin, glycerin, a binder, a lubricant, an inert diluent, a preservative, a surface active agent, a dispersing agent, a biodegradable polymer, or any combination thereof.

36. The composition of claim 31, wherein the carrier is suitable for oral, parenteral, inhalation, topical, or intradermal administration.

* * * * *